(12) United States Patent
Bourque et al.

(10) Patent No.: US 10,759,796 B2
(45) Date of Patent: Sep. 1, 2020

(54) CXCR4 INHIBITORS AND USES THEREOF

(71) Applicant: X4 Pharmaceuticals, Inc., Cambridge, MA (US)

(72) Inventors: Elyse Marie Josee Bourque, Bellingham, WA (US); Renato Skerlj, West Newton, MA (US)

(73) Assignee: X4 PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 16/311,020

(22) PCT Filed: Jun. 21, 2017

(86) PCT No.: PCT/US2017/038609
§ 371 (c)(1),
(2) Date: Dec. 18, 2018

(87) PCT Pub. No.: WO2017/223239
PCT Pub. Date: Dec. 28, 2017

(65) Prior Publication Data
US 2020/0123150 A1    Apr. 23, 2020

Related U.S. Application Data

(60) Provisional application No. 62/352,820, filed on Jun. 21, 2016, provisional application No. 62/456,526, filed on Feb. 8, 2017.

(51) Int. Cl.
*C07D 471/04*     (2006.01)
*C07D 519/00*     (2006.01)

(52) U.S. Cl.
CPC ......... *C07D 471/04* (2013.01); *C07D 519/00* (2013.01)

(58) Field of Classification Search
CPC .................... C07D 471/04; C07D 519/00
See application file for complete search history.

(56) References Cited

U.S. PATENT DOCUMENTS

| | | | |
|---|---|---|---|
| 4,933,447 A | 6/1990 | Konno et al. |
| 5,021,409 A | 6/1991 | Murrer et al. |
| 5,235,056 A | 8/1993 | Cunkle et al. |
| 5,563,151 A | 10/1996 | Bowles et al. |
| 5,582,823 A | 12/1996 | Souza et al. |
| 5,583,131 A | 12/1996 | Bridger et al. |
| 5,698,546 A | 12/1997 | Bridger et al. |
| 5,817,807 A | 10/1998 | Bridger et al. |
| 5,932,749 A | 8/1999 | Li et al. |
| 6,001,826 A | 12/1999 | Murrer et al. |
| 6,245,799 B1 | 6/2001 | Asseslin et al. |
| 6,268,354 B1 | 7/2001 | Nishimura et al. |
| 6,365,583 B1 | 4/2002 | MacFarland et al. |
| 6,506,770 B1 | 1/2003 | Bridger et al. |
| 6,552,065 B2 | 4/2003 | Remiszewski et al. |
| 6,635,278 B1 | 10/2003 | Dahl et al. |
| 6,683,192 B2 | 1/2004 | Baxter et al. |
| 6,734,191 B2 | 5/2004 | Bridger et al. |
| 6,734,194 B2 | 5/2004 | End et al. |
| 6,794,379 B2 | 9/2004 | Medina et al. |
| 6,825,351 B2 | 11/2004 | McEachern et al. |
| 6,835,731 B2 | 12/2004 | Bridger et al. |
| 6,864,265 B2 | 3/2005 | Bridger et al. |
| 6,878,714 B2 | 4/2005 | Askew et al. |
| 6,987,102 B2 | 1/2006 | Bridger et al. |
| 7,053,215 B2 | 5/2006 | Medina et al. |
| 7,091,217 B2 | 8/2006 | Bridger et al. |
| 7,135,570 B2 | 11/2006 | McEachern et al. |
| 7,169,750 B2 | 1/2007 | Bridger et al. |
| 7,291,631 B2 | 11/2007 | Bridger et al. |
| 7,332,605 B2 | 2/2008 | Crawford et al. |
| 7,354,932 B2 | 4/2008 | Bridger et al. |
| 7,354,934 B2 | 4/2008 | Bridger et al. |
| 7,452,994 B2 | 11/2008 | McEachern et al. |
| 7,491,544 B2 | 2/2009 | Canary et al. |
| 7,501,518 B2 | 3/2009 | Chen et al. |
| 7,550,484 B2 | 6/2009 | Bridger et al. |
| 7,592,351 B2 | 9/2009 | Sundermann et al. |
| 7,723,525 B2 | 5/2010 | Crawford et al. |
| 7,863,293 B2 | 1/2011 | Bridger et al. |
| 7,897,590 B2 | 3/2011 | Bridger et al. |
| 7,935,692 B2 | 5/2011 | Bridger et al. |
| 8,168,783 B2 | 5/2012 | Kokubo et al. |
| 8,178,123 B2 | 5/2012 | Pauletti et al. |
| 8,778,967 B2 | 7/2014 | Bridger et al. |
| 8,889,159 B2 | 11/2014 | Cleary et al. |
| 8,906,682 B2 | 12/2014 | June et al. |
| 9,119,790 B2 | 9/2015 | Crowley et al. |

(Continued)

FOREIGN PATENT DOCUMENTS

EP           0434385        6/1991
WO    WO-1997009976    3/1997

(Continued)

OTHER PUBLICATIONS

"Common Terminology Criteria for Adverse Events (CTCAE), Version 4.0," U.S. Department of Health and Human Services, National Institutes of Health, National Cancer Institute, NIH Publication No. Sep. 5410, May 28, 2009, revised Jun. 2010 (196 pages).
"European Medicines Agency, Background Review for Sodium Laurilsulfate Used as an Excipient," Jul. 23, 2015, http://www.ema.europa.eu/docs/en_GB/document_library/Report/2015/08/WC500191475.pdf. p. 5, table 1. Date Accessed Jan. 23, 2017 (18 pages).
"Nivolumab," Drugbank, http://www.drugbank.ca/drugs/DB09035. Date Accessed, Nov. 30, 2018 (14 pages).
"Q3C—Tables and Lists, Guidance for Industry," U.S. Department of Health and Human Services, Food and Drug Adminstration, Center for Drug Evaluation and Research, Center for Biologics Evaluation and Research, Aug. 2018, https://www.fda.gov/downloads/Drugs/GuidanceComplianceRegulatoryInformation/Guidances/UCM073395.pdf. Date Accessed Jan. 22, 2019 (10 pages).

(Continued)

*Primary Examiner* — Joseph R Kosack
(74) *Attorney, Agent, or Firm* — Andrea L.C. Reid; Joseph W. Arico; Dechert LLP

(57) ABSTRACT

The present invention provides compounds, compositions thereof, and methods of using the same.

26 Claims, No Drawings

(56) References Cited

U.S. PATENT DOCUMENTS

| | | | |
|---|---|---|---|
| 9,155,723 | B2 | 10/2015 | Jain et al. |
| 9,267,934 | B2 | 2/2016 | Singh et al. |
| 9,314,468 | B2 | 4/2016 | Clark et al. |
| 2003/0220341 | A1 | 11/2003 | Bridger et al. |
| 2003/0232808 | A1 | 12/2003 | Kobayashi et al. |
| 2005/0154201 | A1 | 7/2005 | Chen et al. |
| 2005/0227958 | A1* | 10/2005 | Wang ............... C09B 57/10 514/185 |
| 2007/0123538 | A1 | 5/2007 | Dunkle et al. |
| 2007/0167459 | A1 | 7/2007 | Habashita et al. |
| 2007/0232615 | A1 | 10/2007 | Gudmundsson et al. |
| 2008/0045537 | A1 | 2/2008 | Gudmundsson et al. |
| 2008/0058353 | A1 | 3/2008 | Banks |
| 2008/0096861 | A1 | 4/2008 | Gudmundsson et al. |
| 2008/0167341 | A1 | 7/2008 | Bridger et al. |
| 2008/0171740 | A1 | 7/2008 | Gudmundsson et al. |
| 2009/0203533 | A1 | 8/2009 | Munnes et al. |
| 2009/0247570 | A1 | 10/2009 | Mayer |
| 2009/0325877 | A1 | 12/2009 | Grunt et al. |
| 2010/0002272 | A1 | 1/2010 | Sato et al. |
| 2010/0022724 | A1 | 1/2010 | Jacobsen et al. |
| 2010/0143301 | A1 | 6/2010 | Desai et al. |
| 2011/0206607 | A1 | 8/2011 | Olsson et al. |
| 2011/0293521 | A1 | 12/2011 | Hyde et al. |
| 2012/0041028 | A1 | 2/2012 | Cooper et al. |
| 2012/0141471 | A1 | 6/2012 | Salvino et al. |
| 2013/0216531 | A1 | 8/2013 | Jain et al. |
| 2014/0275260 | A1 | 9/2014 | Kawale, Sr. et al. |
| 2015/0004239 | A1 | 1/2015 | Cullen et al. |
| 2015/0030561 | A1 | 1/2015 | Dale et al. |
| 2015/0246019 | A1 | 9/2015 | Bridger et al. |
| 2015/0301058 | A1 | 10/2015 | Schettini et al. |
| 2016/0089385 | A1 | 3/2016 | Sherman et al. |
| 2017/0090658 | A1 | 3/2017 | Park et al. |
| 2017/0166591 | A1 | 6/2017 | Ojima et al. |
| 2018/0228894 | A1 | 8/2018 | Fearon |
| 2018/0369167 | A1 | 12/2018 | Arbeit et al. |
| 2018/0369229 | A1 | 12/2018 | Ragan et al. |
| 2019/0030023 | A1 | 1/2019 | Arbeit et al. |
| 2019/0083485 | A1 | 3/2019 | Arbeit et al. |
| 2019/0160051 | A1 | 5/2019 | Arbeit et al. |

FOREIGN PATENT DOCUMENTS

| | | |
|---|---|---|
| WO | WO-1999004794 | 2/1999 |
| WO | WO-1999031264 | 6/1999 |
| WO | WO-2000002870 | 1/2000 |
| WO | WO-2000022599 | 4/2000 |
| WO | WO-2000045814 | 8/2000 |
| WO | WO-2000056729 | 9/2000 |
| WO | WO-2002022600 | 3/2002 |
| WO | WO-2002034745 | 5/2002 |
| WO | WO-2002076948 | 10/2002 |
| WO | WO-2003011277 | 2/2003 |
| WO | WO-2003055876 | 7/2003 |
| WO | WO-2004019973 | 3/2004 |
| WO | WO-2004093817 | 11/2004 |
| WO | WO-2004106493 | 12/2004 |
| WO | WO-2006026703 | 3/2006 |
| WO | WO-2006036816 | 4/2006 |
| WO | WO-2006096444 | 9/2006 |
| WO | WO-2006138259 | 12/2006 |
| WO | WO-2007008539 | 1/2007 |
| WO | WO-2007027999 | 3/2007 |
| WO | WO-2007087548 | 8/2007 |
| WO | WO-2007087549 | 8/2007 |
| WO | WO-2009026251 | 2/2009 |
| WO | WO-2011147026 | 12/2011 |
| WO | WO-2012049277 | 4/2012 |
| WO | WO-2012075362 | 6/2012 |
| WO | WO-2012094703 | 7/2012 |
| WO | WO-2015030853 | 3/2015 |
| WO | WO-2015038887 | 3/2015 |
| WO | WO-2015069770 | 5/2015 |
| WO | WO-2015143012 | 9/2015 |
| WO | WO-2015200341 | 12/2015 |
| WO | WO-2016008976 | 1/2016 |
| WO | WO-2016146261 | 9/2016 |
| WO | WO-2016201425 | 12/2016 |
| WO | WO-2017048702 | 3/2017 |
| WO | WO-2017106328 | 6/2017 |
| WO | WO-2017106332 | 6/2017 |
| WO | WO-2017112894 | 6/2017 |
| WO | WO-2017127811 | 7/2017 |
| WO | WO-2017177230 | 10/2017 |
| WO | WO-2017181073 | 10/2017 |
| WO | WO-2017223229 | 12/2017 |
| WO | WO-2017223239 | 12/2017 |
| WO | WO-2017223243 | 12/2017 |
| WO | WO-2018237158 | 12/2018 |
| WO | WO-2019094392 | 5/2019 |
| WO | WO-2019126106 | 6/2019 |
| WO | WO-2019200223 | 10/2019 |

OTHER PUBLICATIONS

"Therapeutics," Encyclopedia Britannica Online, 2018, https://www.britannica.com/science/therapeutics. Date Accessed, Nov. 6, 2018 (1 page).

"WMA Declaration of Helsinki—Ethical Principles for Medical Research Involving Human Subjects," amended Oct. 2013, http://www.wma.net/en/30publications/10policies/b3/. Date Accessed Apr. 6, 2015 (4 Pages).

Abi-Younes et al., "The Stromal Cell-Derived Factor-1 Chemokine Is a Potent Platelet Agonist Highly Expressed in Atherosclerotic Plaques," Circulation Research, vol. 86, Feb. 4, 2000 (pp. 131-138).

Acharyya et al.,"CXCL1 paracrine network links cancer chemoresistance and metastasis." Cell, vol. 150, No. 1, 2012 (pp. 165-178).

Aduro Biotech, Inc., "Safety and Efficacy of MIW815 (ADU-S100) +/− Ipilimumab in Patients With Advanced/Metastatic Solid Tumors or Lymphomas," ClinicalTrials.gov: NCT02675439, First Posted: Feb. 5, 2016, Last Update: Sep. 26, 2018, https://clinicaltrials.gov/ct2/show/study/NCT02675439. Date Accessed, Mar. 18, 2019 (6 pages).

Aeglea Biotherapeutics, "A Multiple Dose, Dose Escalation Trial of AEB1102 in Patients With Advanced Solid Tumors," ClinicalTrials.gov: NCT02561234, First Posted: Sep. 28, 2015, Last Update: Mar. 22, 2019, https://clinicaltrials.gov/ct2/show/study/NCT02561234. Date Accessed, Mar. 25, 2019 (6 pages).

Aeglea Biotherapeutics, "A Multiple Dose, Dose Escalation Trial of AEB1102 in Patients With AML or MDS," ClinicalTrials.gov: NCT02732184, First Posted: Apr. 8, 2016, Last Update: Oct. 17, 2018, https://clinicaltrials.gov/ct2/show/study/NCT02732184. Date Accessed, Mar. 25, 2019 (6 pages).

Agenus Inc., "AGEN-1884, an Anti-CTLA-4 Antibody, in Advanced Solid Cancers," ClinicalTrials.gov: NCT02694822, First Posted: Mar. 1, 2016, Last Update: Jun. 27, 2017, https://clinicaltrials.gov/ct2/show/study/NCT02694822. Date Accessed, Mar. 25, 2019 (7 pages).

Aileron Therapeutics, "ALRN-6924 in Patients With Advanced Solid Tumors or Lymphomas," ClinicalTrials.gov: NCT02264613, First Posted: Oct. 15, 2014, Last Update: Jun. 27, 2017, https://clinicaltrials.gov/ct2/show/study/NCT02264613. Date Accessed, Mar. 25, 2019 (7 pages).

Aileron Therapeutics, "Safety Study of ALRN-6924 in Patients With Acute Myeloid Leukemia or Advanced Myelodysplastic Syndrome," ClinicalTrials.gov: NCT02909972, First Posted: Sep. 21, 2016, Last Update: Jun. 27, 2017, https://clinicaltrials.gov/ct2/show/study/NCT02909972. Date Accessed, Mar. 25, 2019 (7 pages).

ALX Oncology Inc., "A Study of ALX148 in Patients With Advanced Solid Tumors and Lymphoma," ClinicalTrials.gov: NCT03013218, First Posted: Jan. 6, 2017, Last Update: Aug. 8, 2018, https://clinicaltrials.gov/ct2/show/study/NCT03013218. Date Accessed, Mar. 18, 2019 (6 pages).

Ami and Horui, "Lipase-catalyzed Kinetic Resolution of (±)-trans and cis-2-Azidocycloalkanols," Bioscience, Biotechnology, Biochemistry, vol. 63, No. 12, 1999 (pp. 2150-2156).

(56) References Cited

OTHER PUBLICATIONS

An et al., "Solution phase combinatorial chemistry. Discovery of 13- and 15-membered polyazapyridinocyclophane libraries with antibacterial activity," Tetrahedron, vol. 54, (pp. 3999-4012).
Andtbacka et al., "X4P-001, an Orally Bioavailable CXCR4 Antagonist, Increases T Cell Infiltration in Human Metastatic Melanoma," The Society for Immunotherapy of Cancer Annual Meeting, National Harbor, Maryland, Nov. 8-12, 2017 (1 page).
AnorMed, "X4P-001 Product Page," Adis Insight, Latest Information Update: Mar. 20, 2019, https://adisinsight.springer.com/drugs/800017499, Date Accessed, Apr. 1, 2019 (5 pages).
Arenburg et al., "The role of CXC chemokines in the regulation of angiogenesis in non-small cell lung cancer," Journal of Leukocyte Biology, vol. 62, 1997 (pp. 554-562).
Auiti et al., "The Chemokine SDF-1 Is a Chemoattractant for Human CD34+ Hematopoietic Progenitor Cells and Provides a New Mechanism to Explain the Mobilization of CD34+ Progenitors to Peripheral Blood," Journal of Experimental Medicine, vol. 185, No. 1, Jan. 6, 1997 (pp. 111-120).
Ayers et al., "IFN-γ-related mRNA profile predicts clinical response to PD-1 blockade," The Journal of Clinical Investigation, vol. 127, No. 8, 2017 (pp. 2930-2940).
Baggiolini, "Chemokines and leukocyte traffic," Nature, vol. 392, Apr. 9, 1998 (pp. 565-568).
Balabanian, et al., "Proper desensitization of CXCR4 is required for lymphocyte development and peripheral compartmentalization in mice," Blood, vol. 119, No. 24, Mar. 2012 (pp. 5722-5730).
Balabanian, et al., "WHIM syndromes with different genetic anomalies are accounted for by impaired CXCR4 desensitization to CXCL12," Blood, vol. 105, No. 6, Mar. 15, 2005 (pp. 2449-2457).
Bayer, "Phase I Study of BAY1436032 in IDH1-mutant Advanced Solid Tumors," ClinicalTrials.gov: NCT02746081, First Posted: Apr. 21, 2016, Last Update: Mar. 19, 2019, https://clinicaltrials.gov/ct2/show/study/NCT02746081. Date Accessed, Mar. 25, 2019 (8 pages).
Beaussant-Cohen, et al., "Description and outcome of a cohort of 8 patients with WHIM syndrome from the French Severe Chronic Neutropenia Registry," Orphanet Journal of Rare Diseases, vol. 7, No. 71, Jun. 14, 2012 (pp. 5722-5730).
Berge et al., "Pharmaceutical Salts," Journal of Pharmaceutical Sciences, vol. 66, No. 1, Jan. 1977 (pp. 1-19).
Black et al., "In vivo HIV-1 infection of CD45RA+CD4+ T cells is established primarily by syncytium-inducing variants and correlates with the rate of CD4+ T cell decline," Proceedings of the National Academy of Sciences of the United States of America, vol. 97, No. 3, 2000 (pp. 1269-1274).
Blanchette, S., "NCT02823405: X4P-001 and Prembrolizumab in Patents With Advanced Melanoma (X4P-001-MELA)," Jul. 6, 2016, https://clinicaltrials.gov/ct2/show/NCT02823405> Date Accessed Oct. 5, 2018 (7 pages).
Blanco et al. "The CXCR4 Antagonist AMD3100 Efficiently Inhibits Cell-Surface-Expressed Human Immunodeficiency Virus Type 1 Envelope-Induced Apoptosis," Antimicrobial Agents and Chemotherapy, vol. 44, No. 1., Jan. 2000 (pp. 51-56).
Bleul et al., "B Lymphocyte Chemotaxis Regulated in Association with Microanatomic Localization, Differentiation State, and B Cell Receptor Engagement," Journal of Experimental Medicine, vol. 187, No. 5, Mar. 2, 1998 (pp. 753-762).
Bohinjec, "Myelokathexis: chronic neutropenia with hyperplastic bone marrow and hypersegmented neutrophils in two siblings," Blut, vol. 42, 1981 (pp. 191-196).
Boutsikou et al., "Tumour necrosis factor, interferon-gamma and interleukins as predictive markers of antiprogrammed cell-death protein-1 treatment in advanced non-small cell lung cancer: a pragmatic approach in clinical practice," Therapeutic Advances in Medical Oncology, vol. 10, 2018 (pp. 1-8).
Bristol-Myers Squibb, "A Phase I Open Label Study of the Safety and Tolerability of Elotuzumab (BMS-901608) Administered in Combination With Either Lirilumab (BMS-986015) or Urelumab (BMS-663513) in Subjects With Multiple Myeloma," ClinicalTrials.gov: NCT02252263, First Posted: Sep. 30, 2014, Last Update: Nov. 1, 2017, https://clinicaltrials.gov/ct2/show/study/NCT02252263. Date Accessed, Mar. 18, 2019 (7 pages).
Bristol-Myers Squibb, "An Investigational Immuno-therapy Study of Experimental Medication BMS-986178 by Itself or in Combination With Nivolumab and/or Ipilimumab in Patients With Solid Cancers That Are Advanced or Have Spread," ClinicalTrials.gov: NCT02737475, First Posted: Apr. 14, 2016, Last Update Jan. 31, 2019, https://clinicaltrials.gov/ct2/show/study/NCT02737475. Date Accessed, Mar. 18, 2019 (11 pages).
Bristol-Myers Squibb, "An Investigational Immuno-therapy Study of Experimental Medication BMS-986179 Given Alone and in Combination With Nivolumab," ClinicalTrials.gov: NCT02754141, First Posted: Apr. 28, 2016, Last Update: Feb. 1, 2019, https://clinicaltrials.gov/ct2/show/study/NCT02754141. Date Accessed, Mar. 18, 2019 (8 pages).
Bristol-Myers Squibb, "An Investigational Immuno-Therapy Study to Determine the Safety and Effectiveness of Nivolumab and Daratumumab in Patients With Multiple Myeloma," ClinicalTrials.gov: NCT01592370, First Posted: May 7, 2012, Last Update: Jan. 15, 2019, https://clinicaltrials.gov/ct2/show/study/NCT01592370. Date Accessed, Mar. 18, 2019 (9 pages).
Bristol-Myers Squibb, "An Investigational Immuno-therapy Study to Evaluate the Safety and Effectiveness of Experimental Medication BMS-986207 by Itself and in Combination With Nivolumab in Solid Cancers That Are Advanced or Have Spread," ClinicalTrials.gov: NCT02913313, First Posted: Sep. 23, 2016, Last Update Jan. 31, 2019, https://clinicaltrials.gov/ct2/show/study/NCT02913313. Date Accessed, Mar. 25, 2019 (9 pages).
Bristol-Myers Squibb, "Safety and Efficacy Study of Ulocuplumab and Nivolumab in Subjects With Solid Tumors (CXCessoR4)," ClinicalTrials.gov: NCT02472977, First Posted: Jun. 16, 2015, Last Update: Nov. 1, 2018, https://clinicaltrials.gov/ct2/show/study/NCT02472977. Date Accessed, Aug. 20, 2019 (7 pages).
Bristol-Myers Squibb, "An Investigational Immuno-therapy Study to Investigate the Safety and Effectiveness of Nivolumab, and Nivolumab Combination Therapy in Virus-associated Tumors (CheckMate358)," ClinicalTrials.gov: NCT02488759, First Posted: Jul. 2, 2015, Last Update: Oct. 19, 2018, https://clinicaltrials.gov/ct2/show/study/NCT02488759. Date Accessed Nov. 29, 2018 (7 pages).
Broxmeyer et al., "Effects of in vivo treatment with PIXY321 (GM-CSF/IL-3 fusion protein) on proliferation kinetics of bone marrow and blood myeloid progenitor cells in patients with sarcoma," Experimental Hematology, vol. 23, 1995 (pp. 335-340).
Broxmeyer, "A WHIM satisfactorily addressed," Blood, vol. 123, No. 15, 2014 (pp. 2286-2288).
Burger et al., "Chronic Lymphocytic Leukemia B Cells Express Functional CXCR4 Chemokine Receptors That Mediate Spontaneous Migration Beneath Bone Marrow Stromal Cells," Blood, vol. 94, No. 11, Dec. 1, 1999 (pp. 3658-3667).
Canadian Cancer Trials Group, "Reolysin Combined With Docetaxel and Prednisone or Docetaxel and Prednisone Alone in Metastatic Castration Resistant Prostate Cancer," ClinicalTrials.gov: NCT01619813, First Posted: Jun. 14, 2012, Last Update: Jan. 23, 2019, https://clinicaltrials.gov/ct2/show/study/NCT01619813. Date Accessed, Mar. 25, 2019 (8 pages).
Canadian Cancer Trials Group, "Reolysin in Combination With FOLFOX6 and Bevacizumab or FOLFOX6 and Bevacizumab Alone in Metastatic Colorectal Cancer," ClinicalTrials.gov: NCT01622543 First Posted: Jun. 19, 2012, Last Update: Feb. 1, 2018, https://clinicaltrials.gov/ct2/show/study/NCT01622543. Date Accessed, Mar. 25, 2019 (8 pages).
Cao, et al., "Effect of Low-Dose Ritonavir on the Pharmacokinetics of the CXCR4 Antagonist AMD070 in Healthy Volunteers," Antimicrobial Agents and Chemotherpy, vol. 52, No. 5, 2008 (pp. 1630-1634).
Catalano, J. G. et al., "Synthesis of a novel tricyclic 1, 2,3,4, 4a, 5,, 10b-octahydro-1, 10-phenanthroline ring system and CXCR4 antagonists with potent activity against HIV-1," Bioorganic & Medicinal Chemistry Letters, vol. 20, 2010 (pp. 2186-2190).
Celgene, "A Safety and Efficacy Study of Oral AG-120 Plus Subcutaneous Azacitidine and Oral AG-221 Plus Subcutaneous

(56) References Cited

OTHER PUBLICATIONS

Azacitidine in Subjects With Newly Diagnosed Acute Myeloid Leukemia (AML)," ClinicalTrials.gov: NCT02677922, First Posted: Feb. 9, 2016, Last Update: Feb. 21, 2019, https://clinicaltrials.gov/ct2/show/study/NCT02677922. Date Accessed, Mar. 20, 2019 (11 pages).

Celgene, "A Study of CC-90002 in Subjects With Acute Myeloid Leukemia (AML) and High-risk Myelodysplastic Syndrome (MDS)," ClinicalTrials.gov: NCT02641002, First Posted: Dec. 29, 2015, Last Update: Oct. 18, 2018, https://clinicaltrials.gov/ct2/show/study/NCT02641002. Date Accessed, Mar. 18, 2019 (7 pages).

Celgene, "An Efficacy and Safety Study of AG-221 (CC-90007) Versus Conventional Care Regimens in Older Subjects With Late Stage Acute Myeloid Leukemia Harboring an Isocitrate Dehydrogenase 2 Mutation (IDHENTIFY)," ClinicalTrials.gov: NCT02577406, First Posted: Oct. 16, 2015, Last Update: Feb. 21, 2019, https://clinicaltrials.gov/ct2/show/study/NCT02577406. Date Accessed, Mar. 25, 2019 (12 pages).

Celldex Therapeutics, "A Dose Escalation and Cohort Expansion Study of Anti-CD27 (Varlilumab) and Anti-PD-1 (Nivolumab) in Advanced Refractory Solid Tumors," ClinicalTrials.gov: NCT02335918, First Posted: Jan. 12, 2015, Last Update. Jan. 7, 2019, https://clinicaltrials.gov/ct2/show/study/NCT02335918. Date Accessed, Mar. 18, 2019 (9 pages).

Celldex Therapeutics, "A Study of CDX-1127 (Varlilumab) in Patients With Select Solid Tumor Types or Hematologic Cancers," ClinicalTrials.gov: NCT01460134, First Posted: Oct. 26, 2011, Last Update. Jan. 31, 2018, https://clinicaltrials.gov/ct2/show/study/NCT01460134. Date Accessed, Mar. 18, 2019 (9 pages).

Centre Leon Berard, "Evaluation of Safety and Activity of an Anti-PDL1 Antibody (Durvalumab) Combined With CSF-1R TKI (Pexidartinib) in Patients With Metastatic/Advanced Pancreatic or Colorectal Cancers (Mediplex)," ClinicalTrials.gov: NCT02777710, First Posted: May 19, 2016, Last Update Jan. 17, 2019, https://clinicaltrials.gov/ct2/show/study/NCT02777710. Date Accessed, Mar. 18, 2019 (10 pages).

Chen et al., "CXCR4 inhibition in tumor microenvironmental facilitates anti-programmed death receptor-1 immunotherapy in sorafenib-treated hepatocellular carcinoma in mice," Hepatology, vol. 61, No. 5, May 2015, (pp. 1591-1602).

Clark, PE., "Rationale for targeted therapies and potential role of pazopanib in advanced renal cell carcinoma," Biologics: Targets and Therapy, vol. 4, Jun. 26, 2010 (pp. 187-197).

Cold Genesys, Inc., "Safety and Efficacy of CG0070 Oncolytic Virus Regimen for High Grade NMIBC After BCG Failure (BOND2)," ClinicalTrials.gov: NCT02365818, First Posted: Feb. 19, 2015, Last Update: Mar. 20, 2019, https://clinicaltrials.gov/ct2/show/study/NCT02365818. Date Accessed, Mar. 25, 2019 (9 pages).

Comba et al., "Catalytic Aziridination of Styrene with Copper Complexes for Substituted 3,7-Diazabicyclo[3.3.1]nonanones," European Journal of Inorganic Chemistry, vol. 9, 2003 (pp. 1711-1718).

Connolly et al., "Complexities of TGF-β Targeted Cancer Therapy," (2012) International Journal of Biological Sciences vol. 8, No. 7, Jul. 2012 (pp. 964-978).

Connor et al., "Human Immunodeficiency Virus Type 1 Variants with Increased Replicative Capacity Develop during the Asymptomatic Stage before Disease Progression," Journal of Virology, vol. 68, No. 7, 1994 (pp. 4400-4408).

Courtney et al., "Optimizing recent advances in metastatic renal cell carincoma," Current Onocology Reports, vol. 11, No. 3, May 1, 2009 (pp. 218-226).

Crawford et al., "AMD070, a CXCR4 Chemokine Receptor Antagonist: Practical Large-Scale Laboratory Synthesis," Organic Process Research and Development, vol. 12, No. 5, 2008 (pp. 823-830).

Crump et al., "Solution structure and basis for functional activity of stromal cell derived factor-1; dissociation of CXCR4 activation from binding and inhibition of HIV-1," The EMBO Journal, vol. 16, No. 23, 1997 (pp. 6996-7007).

D' Alterio, et al., "Inhibition of stromal CXCR4 impairs development of lung metastases," Cancer Immunology, Immunotherapy, vol. 61, 2012 (pp. 1713-1720).

Dale et al., "Effects of Granulocyte-Macrophage Colony-Stimulating Factor (GM-CSF) on Neutrophil Kinetics and Function in Normal Human Volunteers," American Journal of Hematology, (1998), vol. 57, 1998 (pp. 7-15).

Dale et al., "The CXCR4 antagonist plerixafor is a potential therapy for myelokathexis, WHIM syndrome," Blood, vol. 118, No. 18, Nov. 3, 2011 (pp. 4963-4966).

Dale et al., "The Severe Chronic Neutropenia International Registry: 10-Year Follow-up Report," Supportive Cancer Therapy. vol. 3, No. 4, 2006 (pp. 220-231).

Dana-Farber Cancer Institute, "LY3022855 With BRAF/MEK Inhibition in Patients With Melanoma," ClinicalTrials.gov: NCT03101254, First Posted: Apr. 5, 2017, Last Update: Feb. 4, 2019, https://clinicaltrials.gov/ct2/show/study/NCT03101254. Date Accessed, Mar. 18, 2019 (9 pages).

Debnath et al., "Small molecule inhibitors of CXCR4," Theranostics, vol. 3, No. 1, Jan. 15, 2013 (pp. 47-75).

DePrimo et al., "Circulating protein biomarkers of pharmacodynamic activity of sunitinib in patients with metastatic renal cell carcinoma: modulation of VEGF and VEGF-related proteins," Journal of Translational Medicine, vol. 5, No. 32, Jul. 2, 2007 (11 pages).

Doranz, "Chemokine receptors as fusion cofactors for human immunodeficiency virus type 1 (HIV-1)," Immunologic Research, vol. 16, 1997 (pp. 15-28).

Dorwald, "Side Reactions in Organic Synthesis," Wiley: VCH, Weinheim, 2005 (p. IX of preface and pp. 1-15, 41).

Dotta et al., "Clinical and genetic features of warts, hypogammaglobulinemia, infections and myelokathexis (WHIM) syndrome," Current Molecular Medicine, vol. 11, 2011 (pp. 317-325).

Duda et al., "CXCL12 (SDF1a)-CXCR4/CXCR7 Pathway Inhibition: An Emerging Sensitizer for Anticancer Therapies?," Clinical Cancer Research, vol. 17, No. 8, 2011 (pp. 2074-2080).

Egberink et al., "Bicyclams, Selective Antagonists of the Human Chemokine Receptor CXCR4, Potently Inhibit Feline Immunodeficiency Virus Replication," Journal of Virology, vol. 73, No. 8, 1999 (pp. 6346-6352).

Eli Lilly and Company, "A Study of LY3022855 in Combination With Durvalumab or Tremelimumab in Participants With Advanced Solid Tumors," ClinicalTrials.gov: NCT02718911, First Posted: Mar. 24, 2016, Last Update Jan. 15, 2019, https://clinicaltrials.gov/ct2/show/study/NCT02718911. Date Accessed, Mar. 18, 2019 (7 pages).

Eli Lilly and Company, "A Study of LY3321367 Alone or With LY3300054 in Participants With Advanced Relapsed/Refractory Solid Tumors," ClinicalTrials.gov: NCT03099109, First Posted: Apr. 4, 2017, Last Update: Mar. 5, 2019, https://clinicaltrials.gov/ct2/show/study/NCT03099109. Date Accessed, Mar. 25, 2019 (10 pages).

EMD Serono Research & Development Institute, Inc., "MSB0011359C (M7824) in Metastatic or Locally Advanced Solid Tumors," ClinicalTrials.gov: NCT02517398, First Posted: Aug. 7, 2015, Last Update: Nov. 19, 2018, https://clinicaltrials.gov/ct2/show/study/NCT02517398. Date Accessed, Mar. 25, 2019 (8 pages).

Facciabene et al., "Tumour hypoxia promotes tolerance and angiogenesis via CCL28 and Treg cells," Nature, vol. 475, 2011 (pp. 226-230).

Fedyk et al., "Maturation decreases responsiveness of human bone marrow B lineage cells to stromal-derived factor 1 (SDF-1)," Journal of Leukocyte Biology, vol. 66, Oct. 1999 (pp. 667-673).

Feig et al., "Targeting CXCL12 from FAP-expressing carcinoma-associated fibroblasts synergizes with anti-PD-L1 immunotherapy in pancreatic cancer," PNAS, vol. 110, No. 50, 2013 (pp. 20212-20217).

Finke J. et al., "MDSC as a mechanism of tumor escape from sunitinib mediated anti-angiogenic therapy," International Immunopharmacology, vol. 11, No. 7, Jul. 2011 (pp. 856-861).

Forty Seven, Inc., "CAMELLIA: Anti-CD47 Antibody Therapy in Haematological Malignancies," ClinicalTrials.gov: NCT02678338, First Posted: Feb. 9, 2016, Last Update: Feb. 21, 2019, https://clinicaltrials.gov/ct2/show/study/NCT02678338. Date Accessed, Mar. 18, 2019 (5 pages).

(56) References Cited

OTHER PUBLICATIONS

Forty Seven, Inc., "Trial of Hu5F9-G4 in Combination With Cetuximab in Patients With Solid Tumors and Advanced Colorectal Cancer," ClinicalTrials.gov: NCT02953782, First Posted: Nov. 3, 2016, Last Update: Aug. 1, 2018, https://clinicaltrials.gov/ct2/show/study/NCT02953782. Date Accessed, Mar. 18, 2019 (7 pages).

Forty Seven, Inc., "Trial of Hu5F9-G4 in Combination With Rituximab in Relapsed/Refractory B-cell Non-Hodgkin's Lymphoma," ClinicalTrials.gov: NCT02953509, First Posted: Nov. 2, 2016, Last Update: Feb. 8, 2019, https://clinicaltrials.gov/ct2/show/study/NCT02953509. Date Accessed, Mar. 18, 2019 (8 pages).

Gacche, RN. "Compensatory angiogenesis and tumor refractoriness," Oncogenesis, vol. 4, e153, Jun. 1 2015 (8 pages).

Gale et al., "Chemokines: extracellular messengers for all occasions?," BioEssays, vol. 21, 1999 (pp. 17-28).

Galsky et al., "A Phase I Trial of LY2510924, a CXCR4 Peptide Antagonist, in Patients with Advanced Cancer," Clinical Cancer Research, vol. 20, No. 16, Aug. 15, 2014 (pp. 3581-3588; 4414).

Genelux Corporation, "GL-ONC1 Oncolytic Immunotherapy in Patients With Recurrent or Refractory Ovarian Cancer," ClinicalTrials.gov: NCT02759588, First Posted: May 3, 2016, Last Update: Nov. 8, 2018, https://clinicaltrials.gov/ct2/show/study/NCT02759588. Date Accessed, Mar. 25, 2019 (8 pages).

Genelux GmbH, "A Study of GL-ONC1, an Oncolytic Vaccinia Virus, in Patients With Advanced Peritoneal Carcinomatosis," ClinicalTrials.gov: NCT01443260, First Posted: Sep. 29, 2011, Last Update: Mar. 10, 2015, https://clinicaltrials.gov/ct2/show/study/NCT01443260. Date Accessed, Mar. 25, 2019 (6 pages).

Genzyme, a Sanofi Company, "Safety and Efficacy Study of GC1008 to Treat Renal Cell Carcinoma or Malignant Melanoma," ClinicalTrials.gov: NCT00356460, First Posted: Jul. 26, 2006, Last Update: Mar. 19, 2014, https://clinicaltrials.gov/ct2/show/study/NCT00356460. Date Accessed, Mar. 25, 2019 (10 pages).

Glaspy et al., "Peripheral Blood Progenitor Cell Mobilization Using Stem Cell Factor in Combination With Filgrastim in Breast Cancer Patients," Blood, vol. 90, 1997 (pp. 2939-2951).

GlaxoSmithKline, "Dose Escalation and Expansion Study of GSK3359609 in Subjects With Selected Advanced Solid Tumors (INDUCE-1)," ClinicalTrials.gov: NCT02723955, First Posted: Mar. 31, 2016, Last Update: Feb. 25, 2019, https://clinicaltrials.gov/ct2/show/study/NCT02723955. Date Accessed, Mar. 18, 2019 (25 pages).

GlaxoSmithKline, "GSK3174998 Alone or With Pembrolizumab in Subjects With Advanced Solid Tumors (ENGAGE-1)," ClinicalTrials.gov: NCT02528357, First Posted: Aug. 19, 2015, Last Update: Jun. 1, 2018, https://clinicaltrials.gov/ct2/show/study/NCT02528357. Date Accessed, Mar. 18, 2019 (11 pages).

Gonzalo et al., "Critical Involvement of the Chemotactic Axis CXCR4/Stromal Cell-Derived Factor-1α in the Inflammatory Component of Allergic Airway Disease," Journal of Immunology, vol. 165, No. 1, Jul. 1, 2000 (pp. 499-508).

Gudmundsson, K.S., "Amine sustituted N-(1H-benzimidazol-2ylmethyl)-5,6,7,8-tetrahydro-8-quino-linamines as CXCR4 antagonists with potent activity against HIV-1," Bioorganic & Medicinal Chemistry Letters, 2009 (pp. 1-5).

Gulino et al., "Altered leukocyte response to CXCL12 in patients with warts hypogammaglobulinemia, infections, myelokathexis (WHIM) syndrome," Blood, vol. 104, No. 2, 2014 (pp. 444-452).

H. Lee Moffitt Cancer Center and Research Institute, "Combining PD-1 Blockade, CD137 Agonism and Adoptive Cell Therapy for Metastatic Melanoma," ClinicalTrials.gov: NCT02652455, First Posted. Jan. 11, 2016, Last Update: Dec. 4, 2018, https://clinicaltrials.gov/ct2/show/study/NCT02652455. Date Accessed, Mar. 18, 2019 (9 pages).

Hamid et al., "Safety and Tumor Responses with Lambrolizumab (Anti-PD-1) in Melanoma," New England Journal of Medicine, vol. 369, No. 2, 2013 (pp. 134-144).

Hendrix et al., "Pharmacokinetics and safety of AMD-3100, a novel antagonist of the CXCR-4 chemokine receptor, in human volunteers," Antimicrobial Agents and Chemotherapy, vol. 44, No. 6, Jun. 2000 (pp. 1667-1673).

Hendrix, et al., "Safety, Pharmacokinetics, and Antiviral Activity of AMD3100, a Selective CXCR4 Receptor Inhibitor, in HIV-1 Infection," Journal of Acquired Immune Deficiency Syndrome, vol. 37, No. 2. Oct. 1, 2004 (pp. 1253-1262).

Hernandez et al., "Mutations in the chemokine receptor gene CXCR4 are associated with Whim syndrome, a combined immunodeficiency disease," Nature Genetics, vol. 34, No. 1., May 31, 2003 (pp. 70-74).

Hesselgesser et al., "CD-4-independent association between HIV-1 gp120 and CXCR4: functional chemokine receptors are expressed in human neurons," Current Biology, vol. 7, No. 2, Jan. 21, 1997 (pp. 112-121).

Hesselgesser et al., "Neuronal apoptosis inducted by HIV-1 gp120 and chemokine SDF-1α is mediated by the chemokine receptor CXCR4," Current Biology, vol. 8, No. 10, Apr. 27, 1998 (pp. 595-598).

Highfill et al., "Disruption of CXCR2-mediated MDSC tumor trafficking enhances anti-PD1 efficacy," Science Translational Medicine, vol. 6, No. 237, May 21, 2014 (pp. 1-13).

Husain Z. et al., "Tumor-derived lactate modifies antitumor immune response: Effect on myeloid-derived suppressor cells and NK cells," Journal of Immunology, vol. 191, 2013 (pp. 1486-1495).

Immutep Australia Pty. Ltd., "Phase 1 Study of IMP321 (Eftilagimod Alpha) Adjuvant to Anti-PD-1 Therapy in Unresectable or Metastatic Melanoma (TACTI-mel)," ClinicalTrials.gov: NCT02676869, First Posted: Feb. 8, 2016, Last Update. Jan. 11, 2019, https://clinicaltrials.gov/ct2/show/study/NCT02676869. Date Accessed, Mar. 25, 2019 (6 pages).

Immutep S.A., "IMP321 (Eftilagimod Alpha) as Adjunctive to a Standard Chemotherapy Paclitaxel Metastatic Breast Carcinoma," ClinicalTrials.gov: NCT02614833, First Posted: Nov. 25, 2015, Last Update: Mar. 18, 2019, https://clinicaltrials.gov/ct2/show/study/NCT02614833. Date Accessed, Mar. 25, 2019 (9 pages).

Immutep S.A., "IMP321 Plus First-line Paclitaxel in Metastatic Breast Carcinoma," ClinicalTrials.gov: NCT00349934, First Posted: Jul. 10, 2006, Last Update Jan. 7, 2010, https://clinicaltrials.gov/ct2/show/study/NCT00349934. Date Accessed, Mar. 25, 2019 (7 pages).

Incyte Biosciences International Sàrl, "An Open-Label, Dose-Escalation, Safety Study of INCAGN01876 in Subjects With Advanced or Metastatic Solid Tumors," ClinicalTrials.gov: NCT02697591, First Posted: Mar. 3, 2016, Last Update: Oct. 31, 2018, https://clinicaltrials.gov/ct2/show/study/NCT02697591. Date Accessed, Mar. 18, 2019 (6 pages).

Incyte Biosciences International Sàrl, "Phase 1/2 Study Exploring the Safety, Tolerability, and Efficacy of INCAGN01876 Combined With Immune Therapies in Advanced or Metastatic Malignancies," ClinicalTrials.gov: NCT03126110, First Posted: Apr. 24, 2017, Last Update: Dec. 10, 2018, https://clinicaltrials.gov/ct2/show/study/NCT03126110. Date Accessed, Mar. 18, 2019 (7 pages).

Innate Pharma, "Combination Study of IPH2201 With Ibrutinib in Patients With Relapsed, Refractory or Previously Untreated Chronic Lymphocytic Leukemia," ClinicalTrials.gov: NCT02557516, First Posted: Sep. 23, 2015, Last Update: Apr. 24, 2018, https://clinicaltrials.gov/ct2/show/study/NCT02557516. Date Accessed, Mar. 20, 2019 (6 pages).

Innate Pharma, "Efficacy Study of Anti-KIR Monoclonal Antibody as Maintenance Treatment in Acute Myeloid Leukemia (EFFIKIR) (EFFIKIR)," ClinicalTrials.gov: NCT01687387, First Posted: Sep. 18, 2012, Last Update: Feb. 8, 2019, https://clinicaltrials.gov/ct2/show/study/NCT01687387. Date Accessed, Mar. 18, 2019 (9 pages).

Innate Pharma, "Study of IPH4102 in Patients With Relapsed/Refractory Cutaneous T-cell Lymphomas (CTCL)," ClinicalTrials.gov: NCT02593045, First Posted: Oct. 30, 2015, Last Update: Feb. 12, 2019, https://clinicaltrials.gov/ct2/show/study/NCT02593045. Date Accessed, Mar. 18, 2019 (6 pages).

Innate Pharma, "Study of Monalizumab and Cetuximab in Patients With Recurrent or Metastatic Squamous Cell Carcinoma of the Head and Neck," ClinicalTrials.gov: NCT02643550, First Posted: Dec. 31, 2015, Last Update: Sep. 13, 2018, https://clinicaltrials.gov/ct2/show/study/NCT02643550. Date Accessed, Mar. 20, 2019 (9 pages).

(56) References Cited

OTHER PUBLICATIONS

Innate Pharma, "Study on the Anti-tumor Activity, Safety and Pharmacology of IPH2101 in Patients With Smoldering Multiple Myeloma (KIRMONO)," ClinicalTrials.gov: NCT01222286, First Posted: Oct. 18, 2010, Last Update: May 9, 2014, https://clinicaltrials.gov/ct2/show/study/NCT01222286. Date Accessed, Mar. 18, 2019 (7 pages).

Innate Pharma, "Study on the Safety, Anti-tumor Activity and Pharmacology of IPH2101 Combined With Lenalidomide in Patients With Multiple Myeloma Experiencing a First or Second Relapse (KIRIMID)," ClinicalTrials.gov: NCT01217203, First Posted: Oct. 8, 2010, Last Update: Feb. 28, 2014, https://clinicaltrials.gov/ct2/show/study/NCT01217203. Date Accessed, Mar. 18, 2019 (7 pages).

International Preliminary Examination Report for PCT/US2002/041407, titled "Chemokine Receptor Binding Heterocyclic Compounds with Enhanced Efficacy," dated Aug. 1, 2003 (4 pages).

International Preliminary Report on Patentability for PCT/US2004/015977, titled "Chemokine Receptor Binding Heterocyclic Compounds with Enhanced Efficacy," dated May 2, 2006 (4 pages).

International Search Report and Written Opinion issued by the United States Patent and Trademark Office as International Searching Authority for International Patent Application No. PCT/US2016/066634, dated Feb. 16, 2017 (15 pages).

International Search Report and Written Opinion issued by the United States Patent and Trademark Office as International Searching Authority for International Patent Application No. PCT/US2016/066639, dated Feb. 16, 2017 (11 pages).

International Search Report and Written Opinion issued by the United States Patent and Trademark Office as International Searching Authority for International Patent Application No. PCT/US2016/068394, dated Mar. 3, 2017 (10 pages).

International Search Report and Written Opinion issued by the United States Patent and Trademark Office as International Searching Authority for International Patent Application No. PCT/US2017/014578, dated Apr. 4, 2017 (12 pages).

International Search Report and Written Opinion issued by the United States Patent and Trademark Office as International Searching Authority for International Patent Application No. PCT/US2018/066141, dated Mar. 8, 2019 (8 pages).

International Search Report and Written Opinion issued by the United States Patent and Trademark Office as International Searching Authority for International Patent Application No. PCT/US2019/049065, dated Nov. 15, 2019 (10 pages).

International Search Report issued by the United States Patent and Trademark Office as International Searching Authority for International Patent Application No. PCT/US05/34491, dated Apr. 11, 2006 (2 pages).

International Search Report issued by the United States Patent and Trademark Office as International Searching Authority for International Patent Application No. PCT/US05/34950, dated Oct. 4, 2006 (4 pages).

International Search Report issued by the United States Patent and Trademark Office as International Searching Authority for International Patent Application No. PCT/US2002/029372, dated Aug. 10, 2004 (4 pages).

International Search Report issued by the United States Patent and Trademark Office as International Searching Authority for International Patent Application No. PCT/US2004/011328, dated Oct. 20, 2004 (2 pages).

International Search Report issued by the United States Patent and Trademark Office as International Searching Authority for International Patent Application No. PCT/US2004/012627, dated Jan. 13, 2005 (3 pages).

International Search Report issued by the United States Patent and Trademark Office as International Searching Authority for International Patent Application No. PCT/US2004/015977, dated Jul. 15, 2005 (3 pages).

International Search Report issued by the United States Patent and Trademark Office as International Searching Authority for International Patent Application No. PCT/US2005/08268, dated May 26, 2005 (3 pages).

Ishii et al., "Expression of Stromal Cell-Derived Factor-1/Pre-B Cell Growth-Stimulating Factor Receptor, CXC Chemokine Receptor 4, on CD34+ Human Bone Marrow Cells Is a Phenotypic Alteration for Committed Lymphoid Progenitors," The Journal of Immunology, vol. 163, 1999 (pp. 3612-3620).

Iwakura et al., "AMD-3100, a CXCR4 Antagonist, Augments Incorporation of Bone Marrow-Derived Eendothelial Progenitor Cells into Sites of Myocardial Neovascularization," Abstract # 1127, Poster Board #-Session: 293I, Blood, vol. 100, No. 11, Nov. 16, 2002 (pp. 293A-294A).

Jackson et al., "Regeneration of ischemic cardiac muscle and vascular endothelium by adult stem cells," The Journal of Clinical Investigation, vol. 107, No. 1, Jun. 2011 (pp. 1395-1402).

Jennerex Biotherapeutics, "A Study of Recombinant Vaccinia Virus to Treat Malignant Melanoma," ClinicalTrials.gov: NCT00429312, First Posted: Jan. 31, 2007, Last Update. Jan. 15, 2015, https://clinicaltrials.gov/ct2/show/study/NCT00429312. Date Accessed, Mar. 25, 2019 (7 pages).

Jounce Therapeutics, Inc., "JTX-2011 Alone and in Combination With Anti-PD-1 or Anti-CTLA-4 in Subjects With Advanced and/or Refractory Solid Tumors (ICONIC)," ClinicalTrials.gov: NCT02904226, First Posted: Sep. 16, 2016, Last Update: Jun. 28, 2018, https://clinicaltrials.gov/ct2/show/study/NCT02904226. Date Accessed, Mar. 18, 2019 (11 pages).

Kawai et al., "Enhanced function with decreased internalization of carboxy-terminus truncated CXCR4 responsible for WHIM syndrome," Experimental Hematology, vol. 33, 2005 (pp. 460-468).

Kawai et al., "WHIM syndrome myelokathexis reproduced in the NOD/SCID mouse xenotransplant model engrafted with healthy human stem cells transduced with C-terminus-truncated CXCR4," Blood, vol. 109, No. 1, Jan. 1, 2007 (pp. 78-84), Epub Aug. 31, 2006.

Kawai et al., "WHIM syndrome: congenital immune deficiency disease," Current Opinion in Hematology, vol. 16, No. 1, Jan. 2009 (pp. 20-26).

Kim, et al., "CXCR4 signaling regulates metastasis of chemoresistant melanoma cells by a lymphatic metastatic niche," Cancer Research, vol. 70, No. 24, 2010 (pp. 10411-10421).

King, A. G. et al. "Rapid Mobilization of Murine Hematopoietic Stem Cells With Enhanced Engraftment Properties and Evaluation of Hematopoietic Progenitor Cell Mobilization in Rhesus Monkeys by a Single Injection of SB-251353, a Specific Truncated Form of the Human CXC Chemokine GROI3," Blood, vol. 97, No. 6, 2001 (pp. 1534-1542).

Kirkland et al., "Quantitation of Mafosfamide-Resistant Pre-Colony-Forming Units in Allogeneic Bone Marrow Transplantation: Relationship With Rate of Engraftment and Evidence for Long-Lasting Reduction in Stem Cell Numbers," Blood, vol. 87, No. 9, 1996 (pp. 3963-3969).

Kocher et al. "Neovascularization of ischemic myocardium by human bone-marrow-derived angioblasts prevents cardiomyocyte apoptosis, reduces remodeling and improves cardiac function," Nature Medicine, vol. 7, 2001 (pp. 430-436).

Lagane et al., "CXCR4 dimerization and beta-arrestin-mediated signaling account for the enhanced chemotaxis to CXCL12 in WHIM syndrome," Blood, vol. 112, No. 1, Jul. 1, 2008 (pp. 34-44).

Langan et al., "Liver Directed Therapy for Renal Cell Carcinoma," Journal of Cancer, vol. 3, 2012 (pp. 184-190).

Lapidot et al., "Current understanding of stem cell mobilization the roles of chemokines, proteolytic enzymes, adhesion molecules, cytokines, and stromal cells," Experimental Hematology, vol. 30, 2002, (pp. 973-981).

Lapidot et al., "The essential roles of the chemokine SDF-1 and its receptor CXCR4 in human stem cell homing and repopulation of transplanted immune-deficient NOD/SCID and NOD/SCID/B2m(null) mice," Leukemia, vol. 16, 2002 (pp. 1992-2003).

Lataillade et al., "Chemokine SDF-1 enhances circulating CD341 cell proliferation in synergy with cytokines: possible role in progenitor survival," Blood, vol. 95, No. 3., 1999 (pp. 756-768).

(56) References Cited

OTHER PUBLICATIONS

Leap Therapeutics, Inc., "Phase 1 Open-label Study of TRX518 Monotherapy and TRX518 in Combination With Gemcitabine, Pembrolizumab, or Nivolumab," ClinicalTrials.gov: NCT02628574, First Posted: Dec. 11, 2015, Last Update. Jan. 17, 2018, https://clinicaltrials.gov/ct2/show/study/NCT02628574. Date Accessed, Mar. 18, 2019 (8 pages).

Leap Therapeutics, Inc., "Trial of TRX518 (Anti-Gitr mAb) in Stage III or IV Malignant Melanoma or Other Solid Tumors (TRX518-001)," ClinicalTrials.gov: NCT01239134, First Posted: Nov. 11, 2010, Last Update: Aug. 14, 2018, https://clinicaltrials.gov/ct2/show/study/NCT01239134. Date Accessed, Mar. 18, 2019 (8 pages).

Lee et al., "Coreceptor/Chemokine Receptor Expression on Human Hematopoietic Cells: Biological Implications for Human Immunodeficiency Virus—Type 1 Infection," Blood, vol. 93, No. 4, 1999 (pp. 1145-1156).

Liu et al., "Homozygous defect in HIV-1 coreceptor accounts for resistance of some multiply-exposed individuals to HIV-1 infection," Cell, vol. 86, No. 3, 1996 (pp. 367-377).

Lord, B. I. et al "Mobilization of Early Hematopoietic Progenitor Cells with BB-1001-: A Genetically Engineered Variant of Human Macrophage Inflammatory Protein-1 alpha," Blood, vol. 85, No. 12, 1995 (pp. 3412-3415).

Ludwig Institute for Cancer Research, "A Phase 1/2 Study of Motolimod (VTX-2337) and MEDI4736 in Subjects With Recurrent, Platinum-Resistant Ovarian Cancer for Whom Pegylated Liposomal Doxorubicin (PLD) is Indicated," ClinicalTrials.gov: NCT02431559, First Posted: May 1, 2015, Last Update: Aug. 7, 2018, https://clinicaltrials.gov/ct2/show/study/NCT02431559. Date Accessed, Mar. 25, 2019 (9 pages).

Ludwig Institute for Cancer Research, "A Phase 1/2 Study to Investigate the Safety, Biologic and Anti-tumor Activity of ONCOS-102 in Combination With Durvalumab in Subjects With Advanced Peritoneal Malignancies," ClinicalTrials.gov: NCT02963831, First Posted: Nov. 15, 2016, Last Update: Mar. 18, 2019, https://clinicaltrials.gov/ct2/show/study/NCT02963831. Date Accessed, Mar. 25, 2019 (8 pages).

Lukacs et al., "AMD3100, a CxCR4 Antagonist, Attenuates Allergic Lung Inflammation and Airway Hyperreactivity," American Journal of Pathology, vol. 16, No. 4, 2002 (pp. 1353-1360).

Lycera Corp., "Study of LYC-55716 in Adult Subjects With Locally Advanced or Metastatic Cancer," ClinicalTrials.gov: NCT02929862, First Posted: Oct. 11, 2016, Last Update: May 7, 2018, https://clinicaltrials.gov/ct2/show/study/NCT02929862. Date Accessed, Mar. 25, 2019 (6 pages).

M.D. Anderson Cancer Center, "Lirilumab and Azacitidine in Treating Patients With Refractory or Relapsed Acute Myeloid Leukemia," ClinicalTrials.gov: NCT02399917, First Posted: Mar. 26, 2015, Last Update: Nov. 30, 2018, https://clinicaltrials.gov/ct2/show/study/NCT02399917. Date Accessed, Mar. 18, 2019 (8 pages).

M.D. Anderson Cancer Center, "Lirilumab and Nivolumab With 5-Azacitidine in Patients With Myelodysplastic Syndromes (MDS)," ClinicalTrials.gov: NCT02599649, First Posted: Nov. 6, 2015, Last Update: Feb. 1, 2019, https://clinicaltrials.gov/ct2/show/study/NCT02599649. Date Accessed, Mar. 18, 2019 (8 pages).

M.D. Anderson Cancer Center, "Lirilumab With Rituximab for Relapsed, Refractory or High-risk Untreated Chronic Lymphocytic Leukemia (CLL) Patients," ClinicalTrials.gov: NCT02481297, First Posted: Jun. 25, 2015, Last Update: Jul. 3, 2018, https://clinicaltrials.gov/ct2/show/study/NCT02481297. Date Accessed, Mar. 18, 2019 (7 pages).

M.D. Anderson Cancer Center, "Nivolumab and HPV-16 Vaccination in Patients With HPV-16 Positive Incurable Solid Tumors," ClinicalTrials.gov: NCT02426892, First Posted: Apr. 27, 2015, Last Update: Aug. 6, 2018, https://clinicaltrials.gov/ct2/show/NCT02426892. Date Accessed Nov. 29, 2018 (8 pages).

Ma et al., "The chemokine receptor CXCR4 is required for retention of B lineage and granulocytic precursors in the bone marrow microenvironment," Immunity, vol. 10, Apr. 1999 (pp. 463-471).

Maciejweski-Duval et al., "Altered chemotactic response to CXCL12 in patients carrying GATA2 mutations," Journal of Leukocyte Biology, vol. 99, No. 6. Epub Dec. 28, 2015 (pp. 1065-1076).

Maekawa et al., "Chemokine/Receptor Dynamics in the Regulation of Hematopoiesis," Internal Medicine, vol. 39, No. 2., 2000 (pp. 90-100).

Matthys et al., "AMD3100, a potent and specific antagonist of the stromal cell-derived factor-1 chemokine receptor CXCR4, inhibits autoimmune joint inflammation in IFN-gamma receptor-deficient mice," Journal of Immunology, vol. 167, No. 8, 2001 (p. 4686-4692).

Maximilian Diehn, "SABR-ATAC: A Trial of TGF-beta Inhibition and Stereotactic Ablative Radiotherapy for Early Stage Non-small Cell Lung Cancer," ClinicalTrials.gov: NCT02581787, First Posted: Oct. 21, 2015, Last Update: Feb. 5, 2019, https://clinicaltrials.gov/ct2/show/study/NCT02581787. Date Accessed, Mar. 25, 2019 (7 pages).

McCormick et al., "Impaired recruitment of Grk6 and beta-Arrestin 2 causes delayed internalization and desensitization of a WHIM syndrome-associated CXCR4 mutant receptor," PLoS One, vol. 4, 2009, (e8102).

McDermott et al., "A phase 1 clinical trial of long-term, low-dose treatment of WHIM syndrome with the CXCR4 antagonist plerixafor," Blood, vol. 123, No. 15, Apr. 10, 2014 (pp. 2308-2316).

McDermott et al., "The CXCR4 antagonist plerixafor corrects panleukopenia in patients with WHIM syndrome," Blood, vol. 118, No. 18, Sep. 2, 2011 (pp. 4957-4962).

McDermott et al.,"Severe congenital neutropenia resulting from G6PC3 deficiency with increased neutrophil CXCR4 expression and myelokathexis," Blood Journal, vol. 116, 2010 (pp. 2793-2802).

McDermott, D. "Whim Syndrome," National Organization for Rare Disorders, 2013, 2016, https://rarediseases.org/rare-diseases/whim-syndrome. Date Accessed Sep. 27, 2018 (10 pages).

MedImmune LLC, "A Phase 1 Study of MEDI0562 in Adult Subjects With Selected Advanced Solid Tumors," ClinicalTrials.gov: NCT02318394, First Posted: Dec. 17, 2014, Last Update. Jan. 29, 2018, https://clinicaltrials.gov/ct2/show/study/NCT02318394. Date Accessed, Mar. 18, 2019 (7 pages).

MedImmune LLC, "A Study in Adult Subjects With Select Advanced Solid Tumors," ClinicalTrials.gov: NCT02583165, First Posted: Oct. 22, 2015, Last Update. Jan. 8, 2019, https://clinicaltrials.gov/ct2/show/study/NCT02583165. Date Accessed, Mar. 18, 2019 (7 pages).

MedImmune LLC, "A Study to Evaluate MEDI0562 in Combination With Immune Therapeutic Agents in Adult Subjects With Advanced Solid Tumors," ClinicalTrials.gov: NCT02705482, First Posted: Mar. 10, 2016, Last Update: Feb. 19, 2019, https://clinicaltrials.gov/ct2/show/study/NCT02705482. Date Accessed, Mar. 18, 2019 (10 pages).

MedImmune LLC, "MEDI9447 Alone and in Combination With MEDI4736 in Adult Subjects With Select Advanced Solid Tumors," ClinicalTrials.gov: NCT02503774, First Posted: Jul. 21, 2015, Last Update: Mar. 11, 2019, https://clinicaltrials.gov/ct2/show/study/NCT02503774. Date Accessed, Mar. 18, 2019 (8 pages).

Merck KGaA, Darmstadt, Germany, ""MSB0011359C (M7824) in Subjects With Metastatic or Locally Advanced Solid Tumors.""

Merck Sharp & Dohme Corp., "Study of MK-1454 Alone or in Combination With Pembrolizumab in Participants With Advanced/Metastatic Solid Tumors or Lymphomas (MK-1454-001)," ClinicalTrials.gov: NCT03010176, First Posted. Jan. 4, 2017, Last Update: Mar. 15, 2019, https://clinicaltrials.gov/ct2/show/study/NCT03010176. Date Accessed, Mar. 18, 2019 (11 pages).

Merck Sharp & Dohme Corp., "Study of MK-4166 and MK-4166 in Combination With Pembrolizumab (MK-3475) in Participants With Advanced Solid Tumors (MK-4166-001)," ClinicalTrials.gov: NCT02132754, First Posted: May 7, 2014, Last Update: Sep. 24, 2018, https://clinicaltrials.gov/ct2/show/study/NCT02132754. Date Accessed, Mar. 18, 2019 (6 pages).

Michael et al., "Exclusive and Persistent Use of the Entry Coreceptor CXCR4 by Human Immunodeficiency Virus Type 1 from a Subject Homozygous for CCR5 Δ32," Journal of Virology, vol. 72, No. 7, Jul. 1998 (pp. 6040-6047).

(56) References Cited

OTHER PUBLICATIONS

Miller, J. et al, "Synthesis and Sar of novel isoquinoline CXCR4 antagonists with potent anti-HIV activity," vol. 20, 2010 (pp. 3026-3030).
Montane et al., "Prevention of murine autoimmune diabetes by CCL22-mediated Treg recruitment to pancreatic islets," Journal of Clinical Investigation, vol. 121, No. 8, Aug. 2011 (pp. 3024-3028).
Mosi R. M. et al., "The molecular pharmacology of AMD11070: An orally bioavailable CXCR4 HIV entry inhibitor," Biochemical Pharmacology, vol. 83, 2012 (pp. 472-479).
Moskovits N. et al., "p53 attenuates cancer cell migration and invasion through repression of SDF-1/CXCL12 expression in stromal fibroblasts," Cancer Research, vol. 66, No. 22, Nov. 15, 2006 (pp. 10671-10676).
Motzer et al., "Nivolumab for Metastatic Renal Cell Carcinoma: Results of a Randomized Phase II Trial," Journal of Clinical Oncology, vol. 33, No. 13, 2015 (pp. 1430-1437).
Motzer et al. (2015), "Nivolumab versus Everolimus in Advanced Renal-Cell Carcinoma," New England Journal of Medicine, vol. 373, No. 19, (pp. 1803-1813).
Moyle, et al., "Proof of Activity with AMD11070, an Orally Bioavailable Inhibitor of CXCR4-Tropic HIV Type 1," Clinical Infectious Diseases, vol. 48, 2009 (pp. 798-805).
Murdoch et al., "Chemokine receptors and their role in inflammation and infectious diseases," Blood, vol. 95, 2000 (pp. 3032-3043).
Nagaraj S. et al., "Altered recognition of antigen is a mechanism of CD8+ T cell tolerance in cancer," Natural Medicine, vol. 13, No. 7, Jul. 2007 (pp. 828-835).
Nagase et al., "Expression of CXCR4 in Eosinophils: Functional Analyses and Cytokine-Mediated Regulation," The Journal of Immunology, vol. 164, No. 11, 2000 (pp. 5935-5943).
Nanki et al., "Cutting Edge: Stromal Cell-Derived Factor-1 Is a Costimulator for CD4+ T Cell Activation," The Journal of Immunology, vol. 164, No. 10, 2000 (pp. 5010-5014).
Nash et al., "Allogeneic HSCT for autoimmune diseases: conventional conditioning regimens," Bone Marrow Transplantation, vol. 32, 2003 (pp. S77-S80).
National Cancer Institute (NCI), "A Phase I Study of Intravenous Recombinant Human IL-15 in Adults With Refractory Metastatic Malignant Melanoma and Metastatic Renal Cell Cancer," ClinicalTrials.gov: NCT01021059, First Posted: Nov. 26, 2009, Last Update: Feb. 26, 2019, https://clinicaltrials.gov/ct2/show/study/NCT01021059. Date Accessed, Mar. 20, 2019 (9 pages).
National Cancer Institute (NCI), "Anti-ICOS Monoclonal Antibody MEDI-570 in Treating Patients With Relapsed or Refractory Peripheral T-cell Lymphoma Follicular Variant or Angioimmunoblastic T-cell Lymphoma," ClinicalTrials.gov: NCT02520791, First Posted: Aug. 13, 2015, Last Update: Feb. 6, 2019, https://clinicaltrials.gov/ct2/show/study/NCT02520791. Date Accessed, Mar. 18, 2019 (13 pages).
National Cancer Institute (NCI), "Part 2 of Phase 1 Study of GC1008 to Treat Advanced Melanoma (Part 2 Will Only Accept and Treat Patients With Advanced Malignant Melanoma)," ClinicalTrials.gov: NCT00923169, First Posted: Jun. 18, 2009, Last Update: Mar. 12, 2019, https://clinicaltrials.gov/ct2/show/study/NCT00923169. Date Accessed, Mar. 25, 2019 (8 pages).
National Cancer Institute (NCI), "Subcutaneous Recombinant Human IL-15 (s.c. rhIL-15) and Alemtuzumab for People With Refractory or Relapsed Chronic and Acute Adult T-cell Leukemia (ATL)," ClinicalTrials.gov: NCT02689453, First Posted: Feb. 24, 2016, Last Update: Mar. 20, 2019, https://clinicaltrials.gov/ct2/show/study/NCT02689453. Date Accessed, Mar. 20, 2019 (9 pages).
National Cancer Institute (NCI), "Trametinib and Navitoclax in Treating Patients With Advanced or Metastatic Solid Tumors," ClinicalTrials.gov: NCT02079740, First Posted: Mar. 6, 2014, Last Update: Feb. 6, 2019, https://clinicaltrials.gov/ct2/show/study/NCT02079740. Date Accessed, Mar. 25, 2019 (12 pages).
National Cancer Institute (NCI), "Use of IL-15 After Chemotherapy and Lymphocyte Transfer in Metastatic Melanoma," ClinicalTrials.gov: NCT01369888, First Posted: Jun. 9, 2011, Last Update. Jan. 27, 2015, https://clinicaltrials.gov/ct2/show/study/NCT01369888. Date Accessed, Mar. 20, 2019 (9 pages).
National Cancer Institute, "Nivolumab and Ipilimumab in Treating Patients With HIV Associated Relapsed or Refractory Classical Hodgkin Lymphoma or Solid Tumors That Are Metastatic or Cannot Be Removed by Surgery," ClinicalTrials.gov: NCT02408861, First Posted: Apr. 6, 2016, Last Update: Jun. 12, 2018, https://clinicaltrials.gov/ct2/show/study/NCT02408861. Date Accessed, Nov. 29, 2018 (13 pages).
National Cancer Institute, "Nivolumab in Treating Patients With HTLV-Associated T-Cell Leukemia/Lymphoma," ClinicalTrials.gov: NCT02631746, First Posted: Dec. 16, 2015, Last Update: Aug. 28, 2018, https://clinicaltrials.gov/ct2/show/study/NCT02631746. Date Accessed, Nov. 29, 2018 (9 pages).
Neumedicines Inc., "NM-IL-12 (rHuIL-12) in Relapsed/Refractory Diffuse Large B-Cell Lymphoma (DLBCL) Undergoing Salvage Chemotherapy," ClinicalTrials.gov: NCT02544724, First Posted: Sep. 9, 2015, Last Update: Aug. 3, 2016, https://clinicaltrials.gov/ct2/show/study/NCT02544724. Date Accessed, Mar. 20, 2019 (8 pages).
Neumedicines Inc., "NM-IL-12 in Cutaneous T-Cell Lymphoma (CTCL) Undergoing Total Skin Electron Beam Therapy (TSEBT)," ClinicalTrials.gov: NCT02542124, First Posted: Sep. 4, 2015, Last Update: Nov. 16, 2018, https://clinicaltrials.gov/ct2/show/study/NCT02542124. Date Accessed, Mar. 20, 2019 (8 pages).
Neves, M. et al., Ligand-guided optimization of CXCR4 homology models for virtual screening using a multiple chemotype approach, Journal of Computer-Aided Molecular Design, vol. 24, No. 12, Oct. 20, 2010 (pp. 1023-1033).
Nicholas Butowski, "A Study of Varlilumab and IMA950 Vaccine Plus Poly-ICLC in Patients With WHO Grade II Low-Grade Glioma (LGG)," ClinicalTrials.gov: NCT02924038, First Posted: Oct. 5, 2016, Last Update: Mar. 6, 2019, https://clinicaltrials.gov/ct2/show/study/NCT02924038. Date Accessed, Mar. 18, 2019 (9 pages).
No author listed, SciFinder Search Results, No month listed, 2015 (39 pages).
No author listed, SciFinder Search Results, No month listed, 2015 (9 pages).
Novartis Pharmaceuticals, "A Phase I/Ib Study of NIZ985 in Combination With PDR001 in Adults With Metastatic Cancers," ClinicalTrials.gov: NCT02452268, First Posted: May 22, 2015, Last Update: Oct. 2, 2018, https://clinicaltrials.gov/ct2/show/study/NCT02452268. Date Accessed, Mar. 20, 2019 (7 pages).
Novartis Pharmaceuticals, "Phase I/Ib Study of GWN323 Alone and in Combination With PDR001 in Patients With Advanced Malignancies and Lymphomas," ClinicalTrials.gov: NCT02740270, First Posted: Apr. 15, 2016, Last Update: Feb. 18, 2019, https://clinicaltrials.gov/ct2/show/study/NCT02740270. Date Accessed, Mar. 28, 2019 (6 pages).
Novartis Pharmaceuticals, "Phase I/Ib Study of NIS793 in Combination With PDR001 in Patients With Advanced Malignancies.," ClinicalTrials.gov: NCT02947165, First Posted: Oct. 27, 2016, Last Update: Nov. 6, 2018, https://clinicaltrials.gov/ct2/show/study/NCT02947165. Date Accessed, Mar. 25, 2019 (9 pages).
Novartis Pharmaceuticals, "Phase I/II Study of BLZ945 Single Agent or BLZ945 in Combination With PDR001 in Advanced Solid Tumors," ClinicalTrials.gov: NCT02829723, First Posted: Jul. 12, 2016, Last Update: Jul. 12, 2018, https://clinicaltrials.gov/ct2/show/study/NCT02829723. Date Accessed, Mar. 18, 2019 (7 pages).
Novartis Pharmaceuticals, "Safety and Efficacy of MBG453 as Single Agent and in Combination With PDR001 in Patients With Advanced Malignancies," ClinicalTrials.gov: NCT02608268, First Posted: Nov. 18, 2015, Last Update: Oct. 2, 2018, https://clinicaltrials.gov/ct2/show/study/NCT02608268. Date Accessed, Mar. 25, 2019 (10 pages).
Novartis Pharmaceuticals, "Study of the Safety and Efficacy of MIW815 With PDR001 to Patients With Advanced/Metastatic Solid Tumors or Lymphomas," ClinicalTrials.gov: NCT03172936, First Posted: Jun. 1, 2017, Last Update: Feb. 18, 2019, https://clinicaltrials.gov/ct2/show/study/NCT03172936. Date Accessed, Mar. 18, 2019 (9 pages).
Nyunt, et al., "Pharmacokinetic Effect of AMD070, an Oral CXCR4 Antagonist, on CYP3A4 and CYP2D6 Substrates Midazolam and

(56) References Cited

OTHER PUBLICATIONS

Dextromethorphan in Healthy Volunteers," Journal of Acquired Immune Deficiency Syndrome, vol. 47, 2008 (pp. 559-565).
O'Hagen et al., "Apoptosis Induced by Infection of Primary Brian Cultures with Diverse Human Immunodeficiency Virus Type 1 Isolates: Evidence for a Role of the Envelope," Journal of Virology, vol. 73, No. 2, Feb. 1999 (pp. 897-906).
O'Boyle et al., "Inhibition of CXCR4-CXCL12 chemotaxis in melanoma by AMD11070," British Journal of Cancer, vol. 108, No. 8, Apr. 2013 (pp. 1634-1640).
Okazaki, T et al., "A rheostat for immune responses: the unique properties of PD1 and their advantages for clinical application," Nature Immunology, vol. 14, No. 12, Dec. 2013 (pp. 1212-1218).
Oncolytics Biotech, "A Study of Reolysin® in Combination With Gemcitabine in Patients With Advanced Pancreatic Adenocarcinoma," ClinicalTrials.gov: NCT00998322, First Posted: Oct. 20, 2009, Last Update: Apr. 10, 2015, https://clinicaltrials.gov/ct2/show/study/NCT00998322. Date Accessed, Mar. 25, 2019 (6 pages).
Oncolytics Biotech, "Efficacy Study of Reolysin® in Combination With Paclitaxel and Carboplatin in Platinum-Refractory Head and Neck Cancers," ClinicalTrials.gov: NCT01166542, First Posted: Jul. 21, 2010, Last Update: Nov. 5, 2014, https://clinicaltrials.gov/ct2/show/study/NCT01166542. Date Accessed, Mar. 25, 2019 (7 pages).
Oncolytics Biotech, "Phase 2 Study of Reolysin® in Combination With Paclitaxel and Carboplatin for Non-Small Cell Lung Cancer With KRAS or EGFR Activation," ClinicalTrials.gov: NCT00861627, First Posted: Mar. 13, 2009, Last Update: Dec. 2, 2015, https://clinicaltrials.gov/ct2/show/study/NCT00861627. Date Accessed, Mar. 25, 2019 (7 pages).
OncoMed Pharmaceuticals, Inc., "A Study of OMP-313M32 in Subjects With Locally Advanced or Metastatic Solid Tumors," ClinicalTrials.gov: NCT03119428, First Posted: Apr. 18, 2017, Last Update: Dec. 7, 2018, https://clinicaltrials.gov/ct2/show/study/NCT03119428. Date Accessed, Mar. 25, 2019 (7 pages).
Panka, DJ. et al., "HDM2 antagonism delays the development of sunitinib resistance in RCC xenografts: Effects of MI-319 on sunitinib-induced p53 activation, SDF-1 induction, and tumor infiltration by CD11b+/Gr-1+ myeloid suppressor cells," Molecular Cancer, vol. 12, No. 17, 2013 (pp. 1-12).
Parameswaran et al., "Combination of drug therapy in acute lymphblastic leukemia with CXCR4 antagonist," Leukemia, vol. 25, No. 8, Aug. 1, 2011 (pp. 1314-1323).
Peled et al., "The chemokine SDF-1 activates the integrins LFA-1, VLA-and VLA-5 on immature human CD34(+) cells: role in transendothelial/stromal migration and engraftment of NOD/SCID mice," Blood, vol. 95, No. 11, 2000 (pp. 3289-3296).
Pfizer, "A Study of Avelumab in Combination With Other Cancer Immunotherapies in Advanced Malignancies (JAVELIN Medley)," ClinicalTrials.gov: NCT02554812, First Posted: Sep. 18, 2015, Last Update: Mar. 13, 2019, https://clinicaltrials.gov/ct2/show/study/NCT02554812. Date Accessed, Mar. 18, 2019 (13 pages).
Pfizer, "Avelumab in Combination Regimens That Include an Immune Agonist, Epigenetic Modulator, CD20 Antagonist and/or Conventional Chemotherapy in Patients With Relapsed or Refractory Diffuse Large B-cell Lymphoma (R/R DLBCL) (Javelin DLBCL)," ClinicalTrials.gov: NCT02951156, First Posted: Nov. 1, 2016, Last Update. Jan. 29, 2019, https://clinicaltrials.gov/ct2/show/study/NCT02951156. Date Accessed, Mar. 18, 2019 (11 pages).
Pike et al., "Nutrition: an Integrated Approach," Third Edition, John Wiley & Sons, 1984 (pp. 538-539).
Plexxikon, "A Combination Clinical Study of PLX3397 and Pembrolizumab to Treat Advanced Melanoma and Other Solid Tumors," ClinicalTrials.gov: NCT02452424, First Posted: May 22, 2015, Last Update: Nov. 15, 2018, https://clinicaltrials.gov/ct2/show/study/NCT02452424. Date Accessed, Mar. 18, 2019 (9 pages).
Ponath et al., "Chemokine receptor antagonists: novel therapeutics for inflammation and AIDS," Expert Opinion on Investigational Drugs, vol. 7, No. 1, 1998 (pp. 1-18).
Providence Health & Services, "Anti-OX40 Antibody (MEDI6469) in Patients With Metastatic Colorectal Cancer," ClinicalTrials.gov: NCT02559024, First Posted: Sep. 24, 2015, Last Update: Oct. 10, 2018, https://clinicaltrials.gov/ct2/show/study/NCT02559024. Date Accessed, Mar. 18, 2019 (6 pages).
Providence Health & Services, "Anti-OX40 Antibody in Head and Neck Cancer Patients," ClinicalTrials.gov: NCT02274155, First Posted: Oct. 24, 2014, Last Update: Nov. 26, 2018, https://clinicaltrials.gov/ct2/show/study/NCT02274155. Date Accessed, Mar. 18, 2019 (6 pages).
Providence Health & Services, "Anti-OX40, Cyclophosphamide (CTX) and Radiation in Patients With Progressive Metastatic Prostate Cancer," ClinicalTrials.gov: NCT01303705, First Posted: Feb. 25, 2011, Last Update: Aug. 29, 2018, https://clinicaltrials.gov/ct2/show/study/NCT01303705. Date Accessed, Mar. 18, 2019 (10 pages).
Providence Health & Services, "Stereotactic Body Radiation and Monoclonal Antibody to OX40 (MEDI6469) in Breast Cancer Patients With Metastatic Lesions (OX40 Breast)," ClinicalTrials.gov: NCT01862900, First Posted: May 27, 2013, Last Update: Mar. 6, 2019, https://clinicaltrials.gov/ct2/show/study/NCT01862900. Date Accessed, Mar. 18, 2019 (7 pages).
PsiOxus Therapeutics Ltd, "Phase I / Dose Expansion Study of Enadenotucirev in Ovarian Cancer Patients (OCTAVE)," ClinicalTrials.gov: NCT02028117, First Posted. Jan. 6, 2014, Last Update: Feb. 26, 2019, https://clinicaltrials.gov/ct2/show/study/NCT02028117. Date Accessed, Mar. 25, 2019 (8 pages).
PsiOxus Therapeutics Ltd, "Phase I Study of Enadenotucirev and PD-1 Inhibitor in Subjects With Metastatic or Advanced Epithelial Tumors (SPICE)," ClinicalTrials.gov: PsiOxus Therapeutics Ltd, First Posted: Dec. 21, 2015, Last Update: Mar. 4, 2019, https://clinicaltrials.gov/ct2/show/study/NCT02636036. Date Accessed, Mar. 25, 2019 (9 pages).
PubChem Open Chemistry Database, Compound Summary for CID 10890081, created Oct. 25, 2006 (14 pages).
PubChem Open Chemistry Database, Compound Summary for CID 12087079, created Feb. 7, 2007 (14 pages).
PubChem Open Chemistry Database, Compound Summary for SID 219642471, created Oct. 21, 2014 (12 pages).
PubChem Open Chemistry Database, Compound Summary for CID 19046926, created Dec. 4, 2017 (11 pages).
PubChem Open Chemistry Database, Compound Summary for CID 70962830, created Mar. 21, 2013 (12 pages).
Raman et al., "Immunotherapy in Metastatic Renal Cell Carcinoma: A Comprehensive Review," Biomed Research International, vol. 2015, 2015 (pp. 1-9).
Rana et al., "Role of CCR5 in infection of primary macrophages and lymphocytes by macrophage-tropic strains of human immunodeficiency virus: resistance to patient-derived and prototype isolates resulting from the delta ccr5 mutation," Journal of Virology, vol. 71, No. 4, 1997 (pp. 3219-3227).
Ratajczak, et al., "The pleotropic effects of the SDF-1—CXCR4 axis in organogenesis, regeneration, and tumorigenesis," Leukemia, vol. 20, 2006 (pp. 1915-1924).
Reagen-Shaw et al., "Dose translation from animal to human studies revisited," The FASEB Journal, vol. 22, Mar. 2007 (pp. 659-661).
Reetz et al., "Highly Efficient Lipase-Catalyzed Kinetic Resolution of Chiral Amines" Chimia International Journal for Chemistry, vol. 48, No. 12, 1994 (p. 570).
Regeneron Pharmaceuticals, "An Exploratory Tumor Biopsy-driven Study to Understand the Relationship Between Biomarkers and Clinical Response in Melanoma Patients Receiving REGN2810 (Anti-PD-1)," ClinicalTrials.gov: NCT03002376, First Posted: Dec. 23, 2016, Last Update. Jan. 11, 2019, https://clinicaltrials.gov/ct2/show/study/NCT03002376. Date Accessed, Mar. 25, 2019 (6 pages).
Regeneron Pharmaceuticals, "PD-1 in Patients With Advanced Basal Cell Carcinoma Who Experienced Progression of Disease on Hedgehog Pathway Inhibitor Therapy, or Were Intolerant of Prior Hedgehog Pathway Inhibitor Therapy," ClinicalTrials.gov: NCT03132636, First Posted: Apr. 28, 2017, Last Update: Oct. 2, 2018, https://clinicaltrials.gov/ct2/show/study/NCT03132636. Date Accessed, Mar. 25, 2019 (6 pages).
Regeneron Pharmaceuticals, "Study of REGN 2810 Compared to Platinum-Based Chemotherapies in Participants With Metastatic

(56) References Cited

OTHER PUBLICATIONS

Non-Small Cell Lung Cancer (NSCLC)," ClinicalTrials.gov: NCT03088540, First Posted: Mar. 23, 2017, Last Update: Nov. 5, 2018, https://clinicaltrials.gov/ct2/show/study/NCT03088540. Date Accessed, Mar. 25, 2019 (9 pages).
Regeneron Pharmaceuticals, "Study of REGN2810 and REGN1979 in Patients With Lymphoma," ClinicalTrials.gov: NCT02651662, First Posted: Jan. 11, 2016, Last Update: Sep. 11, 2018, https://clinicaltrials.gov/ct2/show/study/NCT02651662. Date Accessed, Mar. 25, 2019 (7 pages).
Regeneron Pharmaceuticals, "Study of REGN2810 in Patients With Advanced Cutaneous Squamous Cell Carcinoma," ClinicalTrials. gov: NCT02760498, First Posted: May 3, 2016, Last Update. Jan. 14, 2019, hops://clinicaltrials.gov/ct2/show/study/NCT02760498. Date Accessed, Mar. 25, 2019 (6 pages).
Regeneron Pharmaceuticals, "Study of REGN3767 (Anti-LAG-3) With or Without REGN2810 (Anti-PD1) in Advanced Cancers," ClinicalTrials.gov: NCT03005782, First Posted: Dec. 29, 2016, Last Update: Jun. 18, 2018, https://clinicaltrials.gov/ct2/show/study/NCT03005782. Date Accessed, Mar. 25, 2019 (7 pages).
Righi E. et al., "CXCL12/CXCR4 Blockade Induces Multimodal Antitumor Effects That Prolong Survival in an Immunocompetent Mouse Model of Ovarian Cancer," Cancer Research, vol. 71, No. 16, Aug. 15, 2011 (pp. 5522-5534).
Rini et al., "Comparative effectiveness of axitinib versus sorafenib in advanced renal cell carcinoma (AXIS): a randomised phase 3 trial," Lancet, vol. 378, 2011 (pp. 1931-1939).
Robert Lowsky, "A Phase I/II Study of Intratumoral Injection of SD-101," ClinicalTrials.gov: NCT02254772, First Posted: Oct. 2, 2014, Last Update: Sep. 29, 2017, https://clinicaltrials.gov/ct2/show/study/NCT02254772. Date Accessed, Mar. 25, 2019 (9 pages).
Robert, et al., "Pembrolizumab versus Ipilimumab in Advanced Melanoma," New England Journal of Medicine, vol. 372, 2015 (pp. 2521-2532).
Salcedo et al., "Vascular endothelial growth factor and basic fibroblast growth factor induce expression of CXCR4 on human endothelial cells: In vivo neovascularization induced by stromal-derived factor-1alpha.Am," The American Journal of Pathology, vol. 154, No. 4, 1999 (pp. 1125-1135).
Saxena et al., "Efficacy and Mechanism of Action of CXCR4 Inhibition in B16 OVA Melanoma Model," The Society for Immunotherapy of Cancer Annual Meeting, National Harbor, Maryland, Nov. 8-12, 2017 (1 page).
Saxena et al., "Efficacy and Mechanism of Action of CXCR4 Inhibition in B16-OVA Melanoma Model," Journal for ImmunoTherapy of Cancer, Abstract, vol. 5, Suppl. 2, 2017 (p. 356).
Scala, et al., "Expression of CXCR4 predicts poor prognosis in patients with malignant melanoma," Clinical Cancer Research, vol. 11, Mar. 1, 2005 (pp. 1835-1841).
Scala et al., "Molecular Pathways: Targeting the CXCR4-CXCL12 Axis—Untapped Potential in the Tumor Microenvironment," Clinical Cancer Research, vol. 21, No. 19, Jul. 21, 2015 (pp. 4278-4285).
Schlabach et al., "Cancer proliferation gene discovery through functional genomics," Science, vol. 319, No. 5863, Feb. 1, 2008 (pp. 620-624).
Schols et al., "Bicyclams, a class of potent anti-HIV agents, are targeted at the Hiv coreceptor for Fusin/CXCR-4," Antiviral Research, vol. 35, 1997 (pp. 147-156).
Schols et al., "Inhibition of T-tropic HIV Strains by Selective Antagonization of the Chemokine Receptor CXCR4J," Journal of Experimental Medicine, vol. 186, No. 8, 1997 (pp. 1383-1388).
Schramm et al., "Cytopathicity of Human Immunodeficiency Virus Type 2 (HIV-2) in Human Lymphoid Tissue Is Coreceptor Dependent and Comparable to That of HIV-1," Journal of Virology, vol. 74., No. 20, 2000 (pp. 184-192).
Schuitemaker et al., "Biological phenotype of human immunodeficiency virus type 1 clones at different stages of infection: progression of disease is associated with a shift from monocytotropic to T-cell-tropic virus population," Journal of Virology, vol. 66, No. 3, 1992 (pp. 1354-1360).

Sharma, P. et al., "Primary, Adaptive, and Acquired Resistance to Cancer Immunotherapy," Cell, vol. 168, No. 4, Feb. 9, 2017 (pp. 707-723).
Shen et al., "CXCR4-mediated STAT3 activation is essential for CXCL12-induced invasion in bladder cancer," Tumour Biology, vol. 34, 2013 (pp. 1839-45).
Shojaei F. et al., "Tumor refractoriness to anti-VEGF treatment is mediated by CD11b+Gr1+ myeloid cells," Nature Biotechnology, vol. 25, No. 8, Aug. 2007 (pp. 911-920).
Sidney Kimmel Comprehensive Cancer Center at Johns Hopkins, "Anti-LAG-3 Alone & in Combination w/ Nivolumab Treating Patients w/ Recurrent GBM (Anti-CD137 Arm Closed Oct. 16, 2018)," ClinicalTrials.gov: NCT02658981, First Posted: Jan. 20, 2016, Last Update: Feb. 11, 2019, https://clinicaltrials.gov/ct2/show/study/NCT02658981. Date Accessed, Mar. 18, 2019 (13 pages).
Sidney Kimmel Comprehensive Cancer Center at Johns Hopkins, "Pilot Study With CY, Pembrolizumab, GVAX, and IMC-CS4 (LY3022855) in Patients With Borderline Resectable Adenocarcinoma of the Pancreas," ClinicalTrials.gov: NCT03153410, First Posted: May 15, 2017, Last Update: Mar. 19, 2019, https://clinicaltrials.gov/ct2/show/study/NCT03153410. Date Accessed, Mar. 18, 2019 (8 pages).
SillaJen, Inc., "Hepatocellular Carcinoma Study Comparing Vaccinia Virus Based Immunotherapy Plus Sorafenib vs Sorafenib Alone (PHOCUS)," ClinicalTrials.gov: NCT02562755, First Posted: Sep. 29, 2015, Last Update: Feb. 6, 2019, https://clinicaltrials.gov/ct2/show/study/NCT02562755. Date Accessed, Mar. 25, 2019 (7 pages).
Silva et al., "Profiling essential genes in human mammary cells by multiplex RNA1 screening," Science, vol. 319, Feb. 1, 2008 (pp. 617-620).
Simmons et al., "CXCR4 as a Functional Coreceptor for Human Immunodeficiency Virus Type 1 Infection of Primary Macrophages," Journal of Virology, vol. 72, No. 10, 1998 (pp. 8453-8457).
Simmons et al., "Primary, syncytium-inducing human immunodeficiency virus type 1 isolates are dual-tropic and most can use either Lestr or CCR5 as coreceptors for virus entry," Journal of Virology, vol. 70, No. 12, 1996 (pp. 8355-8360).
SK Chemicals Co., Ltd., "Study to Evaluate SID 530 Compared to Taxotere," ClinicalTrials.gov: NCT00931008, First Posted: Jul. 2, 2009, Last Update. Jan. 24, 2013, https://clinicaltrials.gov/ct2/show/study/NCT00931008. Date Accessed, Mar. 25, 2019 (6 pages).
Skerlj R. et al., "Discovery of Novel Small Molecule Orally Bioavailable C-X-C Chemokine Receptor 4 Antagonists That Are Potent Inhibitors of T-Tropic (X4) HIV-1 Replication," Journal of Medicinal Chemistry, vol. 53, No. 8, 2010 (pp. 3376-3388).
Stone, et al., "Multiple-Dose Escalation Study of the Safety, Pharmacokinetics, and Biologic Activity of Oral AMD070, a Selective CXCR4 Receptor Inhibitor, in Human Subjects.," Antimicrobial Agents and Chemotherapy, vol. 51, No. 7, Jul. 2007 (pp. 2351-2358).
Sullivan et al., "Pembrolizumab for Treatment of Patients with Advanced or Unresectable Melanoma," Clincal Cancer Research, vol. 12, No. 13, Apr. 30, 2015 (pp. 2892-2897).
Supplementary European Search Report issued by the European Patent Office for European Patent App. No. 02775823.4, dated Dec. 23, 2004 (3 pages).
Supplementary European Search Report issued by the European Patent Office for European Patent App. No. 02805977.2, dated Apr. 16, 2008 (3 pages).
Supplementary European Search Report issued by the European Patent Office for European Patent App. No. 04752905.2, dated Mar. 12, 2010 (6 pages).
Supplementary European Search Report issued by the European Patent Office for European Patent App. No. 04814091.7, dated Mar. 10, 2008 (4 pages).
Supplementary European Search Report issued by the European Patent Office for European Patent App. No. 04760161.2, dated Jun. 10, 2008 (3 pages).
Syndax Pharmaceuticals, "A Phase 2 Multi-Center Study of Entinostat (SNDX-275) in Patient With Relapsed or Refractory Hodgkin's Lymphoma," ClinicalTrials.gov: NCT00866333, First Posted: Mar.

(56) References Cited

OTHER PUBLICATIONS 20, 2009, Last Update: Jul. 1, 2016, https://clinicaltrials.gov/ct2/show/study/NCT00866333. Date Accessed, Mar. 20, 2019 (6 pages).
Targovax Oy, "A Pilot Study of Sequential Oncos-102, an Engineered Oncolytic Adenovirus Expressing GMCSF, and Pembrolizumab in Patients With Advanced or Unresectable Melanoma Progressing After Programmed Cell Death Protein 1 (PD1) Blockade," ClinicalTrials.gov: NCT03003676, First Posted: Dec. 28, 2016, Last Update: Oct. 25, 2018, https://clinicaltrials.gov/ct2/show/study/NCT03003676. Date Accessed, Mar. 25, 2019 (8 pages).
"Immune Monitoring of the Circulation and the Tumor, Microenvironment in Patients with Regionally Advanced Melanoma Receiving Neoadjuvant Ipilimumab," PLoS One, vol. 9, No. 2, Feb. 2014 (p. e87705).
Teasdale et al., "Risk Assessment of Genotoxic Impurities in New Chemical Entities: Strategies to Demonstrate Control," Organic Process Research and Development, vol. 17, 2013 (p. 221-230).
Tersmette et al., "Differential Syncytium-Inducing Capacity of Human Immunodeficiency Virus Isolates: Frequent Detection of Syncytium- Inducing Isolates in Patients with Aquired Immune Deficiency Syndrome (AIDS) and AIDS-Related Complex," Journal of Virology, vol. 62, No. 6. (pp. 2026-2032).
Tesaro, Inc., "A Phase 1 Study of TSR-022, an Anti-TIM-3 Monoclonal Antibody, in Patients With Advanced Solid Tumors (AMBER)," ClinicalTrials.gov: NCT02817633, First Posted: Jun. 29, 2016, Last Update: Mar. 19, 2019, https://clinicaltrials.gov/ct2/show/study/NCT02817633. Date Accessed, Mar. 25, 2019 (8 pages).
Therasse et al., "New Guidelines to Evaluate the Response to Treatment in Solid Tumors," Journal of the National Cancer Institute, vol. 92, No. 3, Feb. 2, 2000 (pp. 205-216).
Tortorici et al., "Influence of mild and moderate hepatic impairment on axitinib pharmacokinetics," Investigational New Drugs, vol. 29, 2011 (pp. 1370-1380).
Toyozawa, et al., "Chemokine receptor CXCR4 is a novel marker for the progression of cutaneous malignant melanoma," Japan Society of Histochemisty and Cytochemistry, vol. 45, No. 5, 2012 (pp. 293-299).
Trillium Therapeutics Inc., "A Trial of TTI-621 for Patients With Hematologic Malignancies and Selected Solid Tumors," ClinicalTrials.gov: NCT02663518, First Posted: Jan. 26, 2016, Last Update: Oct. 29, 2018, https://clinicaltrials.gov/ct2/show/study/NCT02663518. Date Accessed, Mar. 18, 2019 (9 pages).
Trillium Therapeutics Inc., "Trial of Intratumoral Injections of TTI-621 in Subjects With Relapsed and Refractory Solid Tumors and Mycosis Fungoides," ClinicalTrials.gov: NCT02890368, First Posted: Sep. 7, 2016, Last Update: Mar. 13, 2019, https://clinicaltrials.gov/ct2/show/study/NCT02890368. Date Accessed, Mar. 18, 2019 (9 pages).
Tu S.P. et al., "Curcumin induces the differentiation of myeloid-derived suppressor cells and inhibits their interaction with cancer cells and related tumor growth," Cancer Prevention Research, vol. 5, No. 2, Feb. 2012 (pp. 205-215).
Tumeh, et al., "PD-1 blockade induces responses by inhibiting adaptive immune resistance," Nature, vol. 515, No. 7528, Nov. 2014 (pp. 568-571).
U.S. Appl. No. 16/091,689, filed Oct. 5, 2018 (27 pages).
U.S. Appl. No. 16/215,963, filed Dec. 11, 2018 (132 pages).
U.S. Appl. No. 16/311,020, filed Dec. 18, 2018 (237 pages).
U.S. Appl. No. 16/311,055, filed Dec. 18, 2018 (186 pages).
U.S. Appl. No. 16/311,083, filed Dec. 18, 2018 (276 pages).
University of Southern California, "Axitinib With or Without Anti-OX40 Antibody PF-04518600 in Treating Patients With Metastatic Kidney Cancer," ClinicalTrials.gov: NCT03092856, First Posted: Mar. 28, 2017, Last Update: Aug. 13, 2018, https://clinicaltrials.gov/ct2/show/study/NCT03092856. Date Accessed, Mar. 18, 2019 (11 pages).
University of Texas Southwestern Medical Center, "Phase 2 Study of IDH305 in Low Grade Gliomas," ClinicalTrials.gov: NCT02987010, First Posted: Dec. 8, 2016, Last Update: Oct. 11, 2017, https://clinicaltrials.gov/ct2/show/study/NCT02987010. Date Accessed, Mar. 25, 2019 (7 pages).
Vanharanta et al., "Epigenetic expansion of VHL-HIF signal output drives multiorgan metastasis in renal cancer," Natural Medicine, vol. 19, No. 1., Jan. 2013 (pp. 50-56).
VentiRx Pharmaceuticals Inc., "A Phase Ib Study of Neoadjuvant of Cetuximab Plus Motolimod and Cetuximab Plus Motolimod Plus Nivolumab," ClinicalTrials.gov: NCT02124850, First Posted: Apr. 28, 2014, Last Update: Jul. 22, 2016, https://clinicaltrials.gov/ct2/show/study/NCT02124850. Date Accessed, Mar. 25, 2019 (6 pages).
Ward et al., "Genetic and molecular diagnosis of severe congenital neutropenia," Current Opinion in Hematology, vol. 16, No. 1, Jan. 2009 (pp. 9-13).
Wong, "Comparison of the potential multiple binding modes of bicyclam, monocylam, and noncyclam small molecule CXC chemokine receptor 4 inhibitors," Molecular Pharmacology, vol. 74, No. 6, 2008 (pp. 1485-1495).
Zea A.H. et al. "Arginase-producing myeloid suppressor cells in renal cell carcinoma patients: a mechanism of tumor evasion," Cancer Research, vol. 65, No. 8, 2005 (pp. 3044-3048).
Zhang et al. "Preferential involvement of CXCR4 and CXCL12 in T cell migration toward melanoma cells," Cancer Biology & Therapy, vol. 5, No. 10, Oct. 2006 (pp. 1034-1312).
Zhang et al., "Chemokine Coreceptor Usage by Diverse Primary Isolates of Human Immunodeficiency Virus Type 1," Journal of Virology, vol. 72, No. 11, 1998 (pp. 9307-9312).
Zhang et al., "Will Multiple Coreceptors Need to Be Targeted by Inhibitors of Human Immunodeficiency Virus Type 1 Entry?," Journal of Virology, vol. 73, No. 4., 1999 (pp. 3443-3448).
Zhao et al., "TNF signaling drives myeloid-derived suppressor cell accumulation," Journal of Clinical Investigation, vol. 122, No. 11, Nov. 2012 (pp. 4094-4104).
Zlotnik et al., "Chemokines: a new classification system and their role in immunity," Immunity, vol. 12, Feb. 2000 (pp. 121-127).
Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).
Zuelzer, "'Myelokathexis'—A New Form of Chronic Granulocytopenia. Report of a case," New England Journal of Medicine, vol. 270, No. 14, 1964 (pp. 699-704).

* cited by examiner

CXCR4 INHIBITORS AND USES THEREOF

CROSS-REFERENCE TO RELATED APPLICATIONS

This application claims the benefit under 35 U.S.C. § 119(e) of U.S. Provisional Application Nos. 62/352,820, filed Jun. 21, 2016, and 62/456,526, filed Feb. 8, 2017, the contents of all of which are incorporated herein in their entireties by reference.

TECHNICAL FIELD OF THE INVENTION

The present invention relates to compounds and methods useful for inhibition of C-X-C receptor type 4 (CXCR4). The invention also provides pharmaceutically acceptable compositions comprising compounds of the present invention and methods of using said compositions in the treatment of various disorders.

BACKGROUND OF THE INVENTION

C-X-C chemokine receptor type 4 (CXCR4), also known as fusin or cluster of differentiation 184 (CD184), is a seven transmembrane G-protein coupled receptor (GPCR) belonging to Class I GPCR or rhodopsin-like GPCR family. Under normal physiological conditions, CXCR4 carries out multiple roles and is principally expressed in the hematopoietic and immune systems. CXCR4 was initially discovered as one of the co-receptors involved in human immunodeficiency virus (HIV) cell entry. Subsequent studies showed that it is expressed in many tissues, including brain, thymus, lymphatic tissues, spleen, stomach, and small intestine, and also specific cell types such as hematopoietic stem cells (HSC), mature lymphocytes, and fibroblasts. CXCL12, previously designated SDF-la, is the only known ligand for CXCR4. CXCR4 mediates migration of stem cells during embryonic development as well as in response to injury and inflammation. Multiple roles have been demonstrated for CXCR4 in human diseases such as cellular proliferative disorders, Alzheimer's disease, HIV, rheumatoid arthritis, pulmonary fibrosis, and others. For example, expression of CXCR4 and CXCL12 have been noted in several tumor types. CXCL12 is expressed by cancer-associated fibroblast (CAFs) and is often present at high levels in the tumor microenvironment (TME). In clinical studies of a wide range of tumor types, including breast, ovarian, renal, lung, and melanoma, expression of CXCR4/CXCL12 has been associated with a poor prognosis and with an increased risk of metastasis to lymph nodes, lung, liver, and brain, which are sites of CXCL12 expression. CXCR4 is frequently expressed on melanoma cells, particularly the CD133+ population that is considered to represent melanoma stem cells; in vitro experiments and murine models have demonstrated that CXCL12 is chemotactic for such cells.

Furthermore, there is now evidence implicating the CXCL12/CXCR4 axis in contributing to the loss or lack of tumor responsiveness to angiogenesis inhibitors (also referred to as "angiogenic escape"). In animal cancer models, interference with CXCR4 function has been demonstrated to alter the TME and sensitize the tumor to immune attack by multiple mechanisms such as elimination of tumor re-vascularization and increasing the ratio of CD8+ T cells to Treg cells. These effects result in significantly decreased tumor burden and increased overall survival in xenograft, syngeneic, and transgenic cancer models. See Vanharanta et al. (2013) Nat Med 19: 50-56; Gale and McColl (1999) BioEssays 21: 17-28; Highfill et al. (2014) Sci Transl Med 6: ra67; Facciabene et al. (2011) Nature 475: 226-230.

These data underscore the significant, unmet need for CXCR4 inhibitors to treat the many diseases and conditions mediated by aberrant or undesired expression of the receptor, for example in cellular proliferative disorders.

SUMMARY OF THE INVENTION

It has now been found that compounds of the present invention, and pharmaceutically acceptable compositions thereof, are effective as CXCR4 inhibitors. In one aspect, the present invention provides a compound of Formula I:

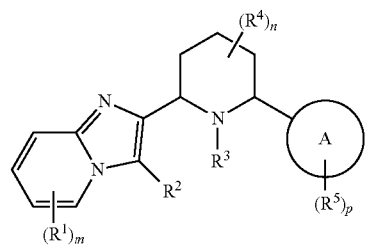

I or a pharmaceutically acceptable salt thereof, wherein each variable is as defined and described herein.

Compounds of the present invention, and pharmaceutically acceptable compositions thereof, are useful for treating a variety of diseases, disorders or conditions, associated with CXC receptor type 4 (CXCR4). Such diseases, disorders, or conditions include cellular proliferative disorders (e.g., cancer) such as those described herein.

DETAILED DESCRIPTION OF CERTAIN EMBODIMENTS

1. General Description of Certain Embodiments of the Invention

Compounds of the present invention, and pharmaceutical compositions thereof, are useful as inhibitors of CXCR4. Without wishing to be bound by any particular theory, it is believed that compounds of the present invention, and pharmaceutical compositions thereof, may inhibit the activity of CXCR4 and thus treat certain diseases, such as cancer.

It has now been found that compounds of this invention, and pharmaceutically acceptable compositions thereof, are effective as CXCR4 inhibitors. In one aspect, the present invention provides a compound of Formula I:

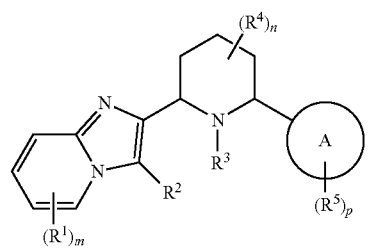

I or a pharmaceutically acceptable salt thereof, wherein:

Ring A is a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^1$ is independently —R, halogen, —CN, —OR, —N(R)$_2$, —NO$_2$, —N$_3$, —SR, or -L$^1$-R$^6$;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $L^1$ and $L^2$ is independently a covalent bond or a $C_{1-8}$ bivalent straight or branched hydrocarbon chain wherein 1, 2, or 3 methylene units of the chain are independently and optionally replaced with —O—, —C(O)—, —C(O)O—, —OC(O)—, —N(R)—, —(R)NC(O)—, —OC(O)N(R)—, —(R)NC(O)O—, —N(R)C(O)N(R)—, —S—, —SO—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur;

$R^2$ is hydrogen, halogen, —CN, —OR, —N(R)$_2$, —NO$_2$, —N$_3$, —SR, -L$^2$-R$^6$, or optionally substituted $C_{1-8}$ aliphatic;

$R^3$ is hydrogen, optionally substituted $C_{1-6}$ aliphatic, or -L$^3$-R$^6$;

$L^3$ is a $C_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —S—, —SO—, —SO$_2$—, —C(S)—, or -Cy-;

each $R^4$ is independently hydrogen, deuterium, halogen, —CN, —OR$^6$, or $C_{1-4}$ alkyl, or two $R^4$ groups on the same carbon are optionally taken together to form =NR$^6$, =NOR$^6$, =O, or =S;

each $R^5$ is independently R, halogen, —CN, —OR, —N(R)$_2$, —NO$_2$, —N$_3$, —SR, or -L$^2$-R$^6$, or two $R^5$ groups on the same saturated carbon atom are optionally taken together to form =NR, =NOR, =O, =S, or a spirocyclic 3-6 membered carbocyclic ring;

each $R^6$ is independently hydrogen or $C_{1-6}$ alkyl optionally substituted with 1, 2, 3, 4, 5, or 6 deuterium or halogen atoms;

m is 0, 1, 2, 3, or 4;

n is 0, 1, 2, 3, or 4; and p is 0, 1, 2, 3, or 4.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bicyclic ring" or "bicyclic ring system" refers to any bicyclic ring system, i.e. carbocyclic or heterocyclic, saturated or having one or more units of unsaturation, having one or more atoms in common between the two rings of the ring system. Thus, the term includes any permissible ring fusion, such as ortho-fused or spirocyclic. As used herein, the term "heterobicyclic" is a subset of "bicyclic" that requires that one or more heteroatoms are present in one or both rings of the bicycle. Such heteroatoms may be present at ring junctions and are optionally substituted, and may be selected from nitrogen (including N-oxides), oxygen, sulfur (including oxidized forms such as sulfones and sulfonates), phosphorus (including oxidized forms such as phosphates), boron, etc. In some embodiments, a bicyclic group has 7-12 ring members and 0-4 heteroatoms independently selected from nitrogen, oxygen, or sulfur. As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bicyclic rings include:

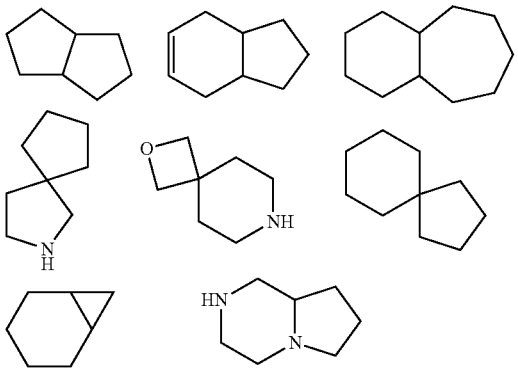

Exemplary bridged bicyclics include:

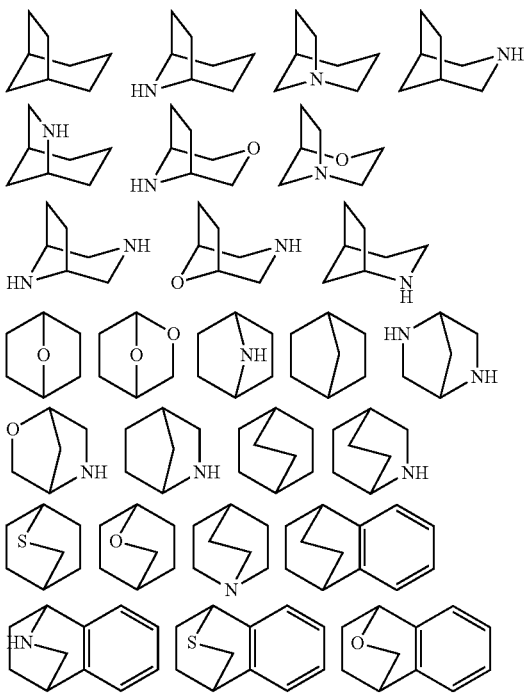

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated", as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —$(CH_2)_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

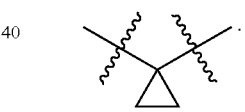

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl, pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "option-ally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Each optional substituent on a substitutable carbon is a monovalent substituent independently selected from halogen; $-(CH_2)_{0-4}R^\circ$; $-(CH_2)_{0-4}OR^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $(CH_2)_{0-4}O(CH_2)_{0-1}Ph$ which may be substituted with $R^\circ$; $-CH=CHPh$, which may be substituted with $R^\circ$; $-(CH_2)_{0-4}O(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)O\ SiR^\circ_3$; $-(CH_2)_{0-4}OC(O)R^\circ$; $-OC(O)(CH_2)_{0-4}SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-SC(S)SR^\circ$, $-(CH_2)_{0-4}OCC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-S(O)(NR^\circ)R^\circ$; $-S(O)_2N=C(NR^\circ_2)_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)$O-N(R^\circ)_2$; or $-(C_{1-4}$ straight or branched alkylene)$C(O)O-N(R^\circ)_2$.

Each $R^\circ$ is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted by a divalent substituent on a saturated carbon atom of $R^\circ$ selected from $=O$ and $=S$; or each $R^\circ$ is optionally substituted with a monovalent substituent independently selected from halogen, $-(CH_2)_{0-2}R^\bullet$, -(halo$R^\bullet$), $-(CH_2)_{0-2}OH$, $-(CH_2)_{0-2}OR^\bullet$, $-(CH_2)_{0-2}CH(OR^\bullet)_2$; $-O($halo$R^\bullet)$, $-CN$, $-N_3$, $-(CH_2)_{0-2}C(O)R^\bullet$, $-(CH_2)_{0-2}C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-C(O)SR^\bullet_3$, $-(C_{1-4}$ straight or branched alkylene)$C(O)OR^\bullet$, or $-SSR^\bullet$.

Each $R^\bullet$ is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur, and wherein each $R^\bullet$ is unsubstituted or where preceded by halo is substituted only with one or more halogens; or wherein an optional substituent on a saturated carbon is a divalent substituent independently selected from =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, or a divalent substituent bound to vicinal substitutable carbons of an "optionally substituted" group is —O(CR*$_2$)$_{2-3}$O—, wherein each independent occurrence of R* is selected from hydrogen, C$_{1-6}$ aliphatic or an unsubstituted 5-6-membered saturated, partially unsaturated, or aryl ring having 0-4 heteroatoms independently selected from nitrogen, oxygen, or sulfur.

When R* is C$_{1-6}$ aliphatic, R* is optionally substituted with halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R● is unsubstituted or where preceded by halo is substituted only with one or more halogens.

An optional substituent on a substitutable nitrogen is independently —R†, —NR†$_2$, —C(O)R†, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, C$_{1-6}$ aliphatic, unsubstituted —OPh, or an unsubstituted 5-6-membered saturated, partially unsaturated, or aryl ring having 0-4 heteroatoms independently selected from nitrogen, oxygen, or sulfur, or, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur; wherein when R† is C$_{1-6}$ aliphatic, R† is optionally substituted with halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur, and wherein each R● is unsubstituted or where preceded by halo is substituted only with one or more halogens.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and N$^+$(C$_{1-4}$ alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, R$^1$, of a provided compound comprises one or more deuterium atoms.

As used herein, the term "inhibitor" is defined as a compound that binds to and/or inhibits CXCR4 with measurable affinity. In certain embodiments, an inhibitor has an IC$_{50}$ and/or binding constant of less than about 100 μM, less than about 50 μM, less than about 1 μM, less than about 500 nM, less than about 100 nM, less than about 10 nM, or less than about 1 nM.

The terms "measurable affinity" and "measurably inhibit," as used herein, means a measurable change in CXCR4 activity between a sample comprising a compound of the present invention, or composition thereof, and CXCR4, and an equivalent sample comprising CXCR4, in the absence of said compound, or composition thereof.

3. Description of Exemplary Embodiments

In one aspect, the present invention provides a compound of Formula I:

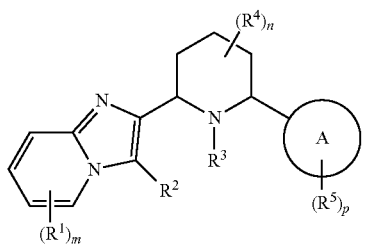

I or a pharmaceutically acceptable salt thereof, wherein:
Ring A is a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $R^1$ is independently —R, halogen, —CN, —OR, —N(R)$_2$, —NO$_2$, —N$_3$, —SR, or -L$^1$-R$^6$;

each R is independently hydrogen or an optionally substituted group selected from $C_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each $L^1$ and $L^2$ is independently a covalent bond or a $C_{1-8}$ bivalent straight or branched hydrocarbon chain wherein 1, 2, or 3 methylene units of the chain are independently and optionally replaced with —O—, —C(O)—, —C(O)O—, —OC(O)—, —N(R)—, —(R)NC(O)—, —OC(O)N(R)—, —(R)NC(O)O—, —N(R)C(O)N(R)—, —S—, —SO—, —SO$_2$N(R)—, —(R)NSO$_2$—, —C(S)—, —C(S)O—, —OC(S)—, —C(S)N(R)—, —(R)NC(S)—, —(R)NC(S)N(R)—, or -Cy-;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur;

$R^2$ is hydrogen, halogen, —CN, —OR, —N(R)$_2$, —NO$_2$, —N$_3$, —SR, -L$^2$-R$^6$, or optionally substituted $C_{1-8}$ aliphatic;

$R^3$ is hydrogen, optionally substituted $C_{1-6}$ aliphatic, or -L$^3$-R$^6$;

$L^3$ is a $C_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —S—, —SO—, —C(S)—, or -Cy-;

each $R^4$ is independently hydrogen, deuterium, halogen, —CN, —OR$^6$, or $C_{1-4}$ alkyl, or two $R^4$ groups on the same carbon are optionally taken together to form =NR$^6$, =NOR$^6$, =O, or =S;

each $R^5$ is independently R, halogen, —CN, —OR, —N(R)$_2$, —NO$_2$, —N$_3$, —SR, or -L$^2$-R$^6$, or two $R^5$ groups on the same saturated carbon atom are optionally taken together to form =NR, =NOR, =O, =S, or a spirocyclic 3-6 membered carbocyclic ring;

each $R^6$ is independently hydrogen or $C_{1-6}$ alkyl optionally substituted with 1, 2, 3, 4, 5, or 6 deuterium or halogen atoms;

m is 0, 1, 2, 3, or 4;
n is 0, 1, 2, 3, or 4; and
p is 0, 1, 2, 3, or 4.

As defined generally above, Ring A is a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.

In some embodiments, Ring A is a 3-8 membered saturated or partially unsaturated monocyclic carbocyclic ring. In some embodiments, Ring A is phenyl. In some embodiments, Ring A is an 8-10 membered bicyclic aromatic carbocyclic ring. In some embodiments, Ring A is a 4-8 membered saturated or partially unsaturated monocyclic heterocyclic ring having 1-2 heteroatoms independently selected from nitrogen, oxygen, or sulfur. In some embodiments, Ring A is a 5-6 membered monocyclic heteroaromatic ring having 1-4 heteroatoms independently selected from nitrogen, oxygen, or sulfur. In some embodiments, Ring A is an 8-10 membered bicyclic heteroaromatic ring having 1-5 heteroatoms independently selected from nitrogen, oxygen, or sulfur.

In some embodiments, Ring A is a 5-6 membered monocyclic heteroaromatic ring having 1-2 heteroatoms independently selected from nitrogen, oxygen, or sulfur.

In some embodiments, Ring A is selected from:

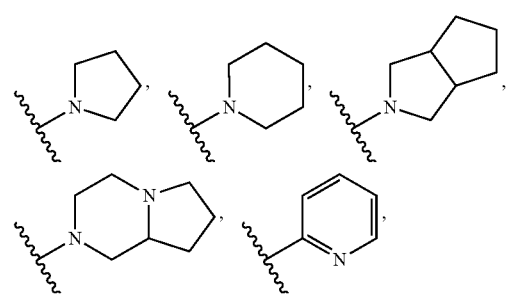

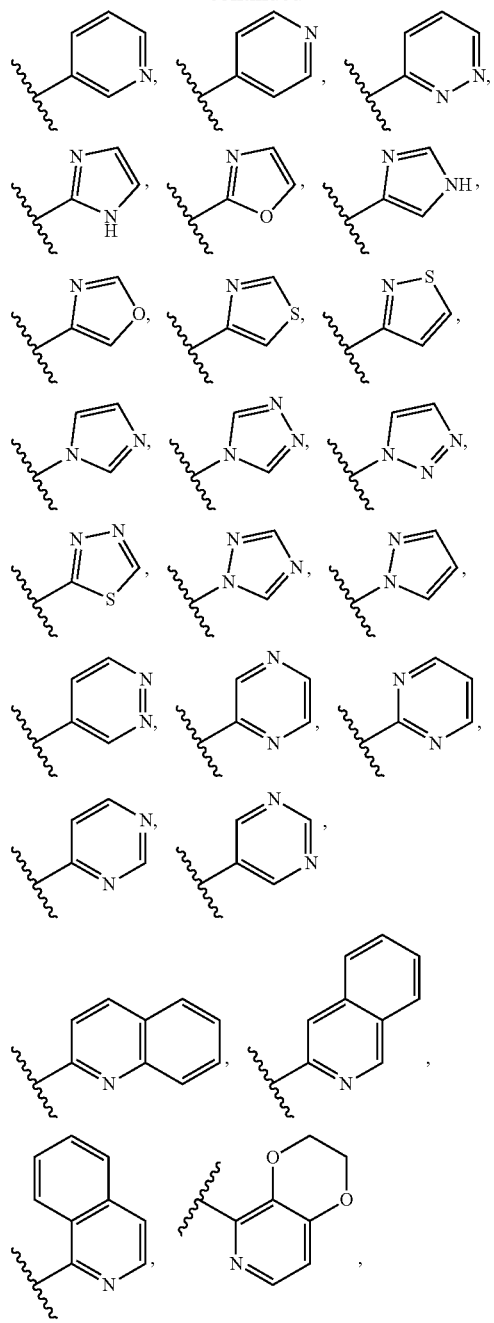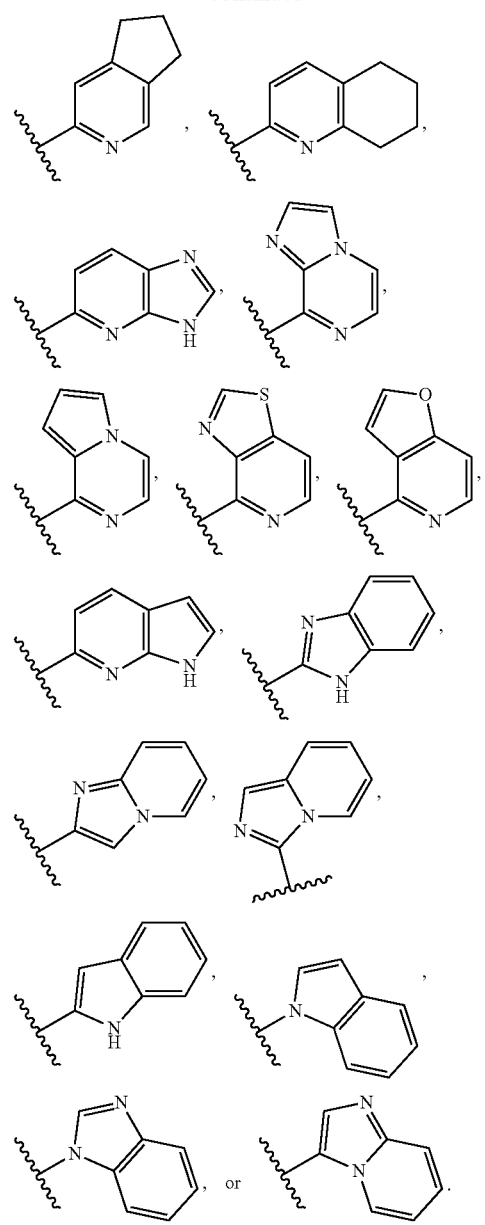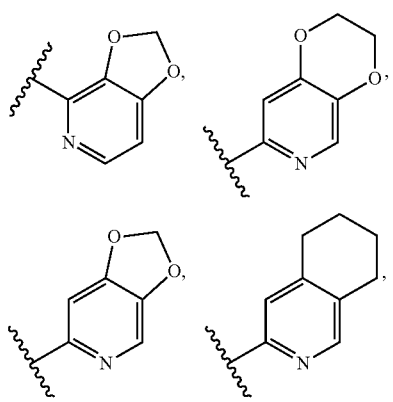
In some embodiments, Ring A is selected from
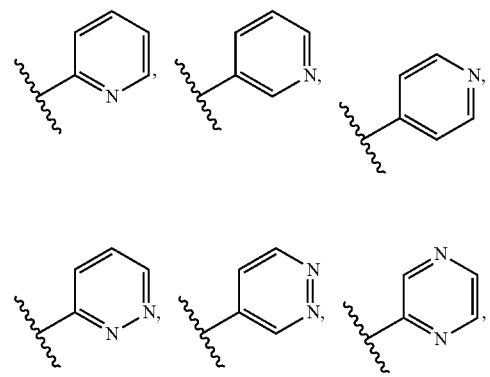

-continued

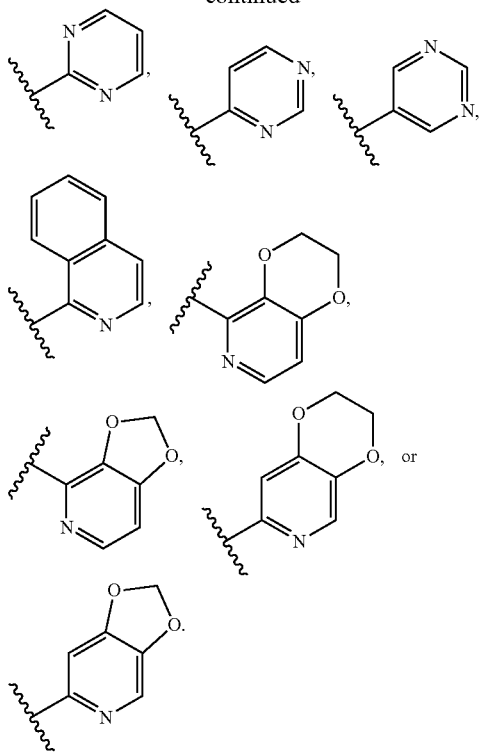

In some embodiments, Ring A is selected from

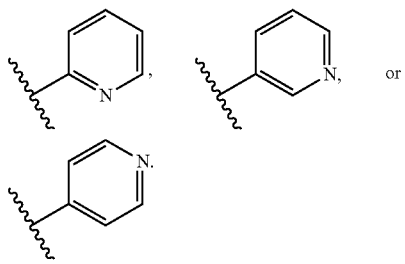

In some embodiments, Ring A is

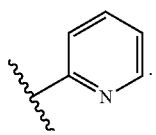

In some embodiments, Ring A is not

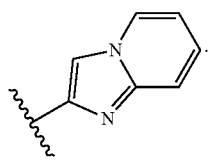 [SMILES: *c1cn2ccccc2n1]

In some embodiments, Ring A is not imidazo[1,2-a]pyridine.

In some embodiments, Ring A is selected from those depicted in Table 1, below.

As defined generally above, each $R^1$ is independently R, halogen, —CN, —OR, —N(R)$_2$, —NO$_2$, —N$_3$, —SR, or -L$^2$-R$^6$.

In some embodiments, $R^1$ is R. In some embodiments, $R^1$ is halogen. In some embodiments, $R^1$ is —CN. In some embodiments, $R^1$ is —OR. In some embodiments, $R^1$ is —N(R)$_2$. In some embodiments, $R^1$ is —NO$_2$. In some embodiments, $R^1$ is —N$_3$. In some embodiments, $R^1$ is —SR. In some embodiments, $R^1$ is -L$^1$-R$^6$.

In some embodiments, $R^1$ is hydrogen. In some embodiments, $R^1$ is an optionally substituted $C_{1-6}$ aliphatic group. In some embodiments, $R^1$ is an optionally substituted 3-8 membered saturated or partially unsaturated monocyclic carbocyclic ring. In some embodiments, $R^1$ is an optionally substituted phenyl. In some embodiments, $R^1$ is an optionally substituted 8-10 membered bicyclic aromatic carbocyclic ring. In some embodiments, $R^1$ is an optionally substituted 4-8 membered saturated or partially unsaturated monocyclic heterocyclic ring having 1-2 heteroatoms independently selected from nitrogen, oxygen, or sulfur. In some embodiments, $R^1$ is an optionally substituted 5-6 membered monocyclic heteroaromatic ring having 1-4 heteroatoms independently selected from nitrogen, oxygen, or sulfur. In some embodiments, $R^1$ is an optionally substituted 8-10 membered bicyclic heteroaromatic ring having 1-5 heteroatoms independently selected from nitrogen, oxygen, or sulfur.

In some embodiments, $R^1$ is selected from R, halogen, —CN, —OR, —N(R)$_2$, —SR, $C_{1-6}$ aliphatic, or -L$^1$-R$^6$, wherein L$^1$ is a $C_{1-6}$ bivalent straight or branched hydrocarbon chain wherein 1, 2, or 3 methylene units of the chain are independently and optionally replaced with —O—, —C(O)—, —N(R)—, —S—, —SO—, —SO$_2$—, —C(S)—, or -Cy-; wherein the $C_{1-6}$ aliphatic group is optionally substituted with 1, 2, or 3 groups independently selected from halogen, —CN, —N(R)$_2$, —NO$_2$, —N$_3$, =NR, =NOR, =O, =S, —OR, —SR, —SO$_2$R, —S(O)R, —R, -Cy-R, —C(O)R, —C(O)OR, —OC(O)R, —C(O)N(R)$_2$, —(R)NC(O)R, —OC(O)N(R)$_2$, —(R)NC(O)OR, —N(R)C(O)N(R)$_2$, —SO$_2$N(R)$_2$, —(R)NSO$_2$R, —C(S)R, or —C(S)OR; and each R is independently hydrogen, —CH$_2$-phenyl, phenyl, $C_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, $R^1$ is selected from hydrogen, halogen, $C_{1-6}$ alkyl (optionally substituted with 1, 2, or 3 halogens), —CN, —N(R)$_2$, —OR, —SR, —S(O)R$^6$, —SO$_2$R$^6$, —SO$_2$NHR$^6$,

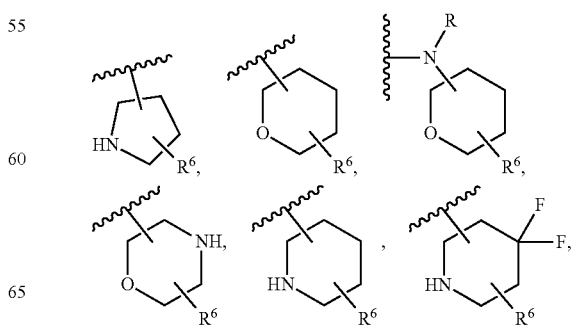

-continued

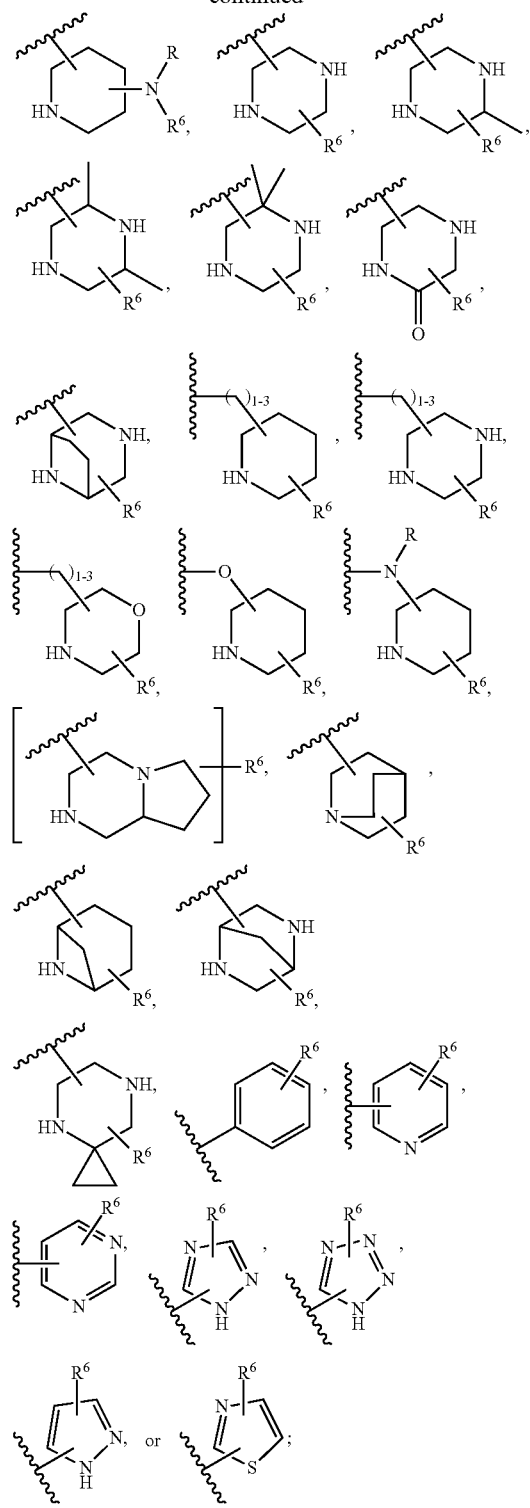
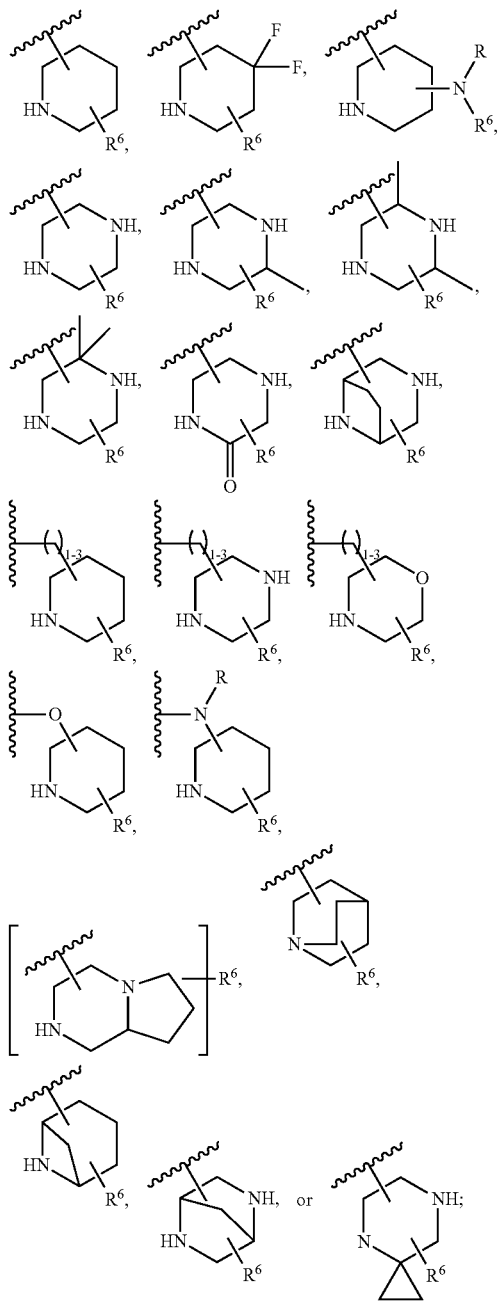

and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, R$^1$ is selected from hydrogen, halogen, C$_{1-6}$ alkyl, —CN, —N(R)$_2$, —OR, —SR, and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, R$^1$ is selected from those depicted in Table 1, below.

As defined generally above, each L$^1$ and L$^2$ is independently a covalent bond or a C$_{1-8}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —OC(O)N(R)—, —(R)NC(O)O—, —N(R)C(O)N(R)—, —S—, —SO—, —SO₂—, —SO₂N(R)—, —(R)NSO₂—, —C(S)—, —C(S)O—, —OC(S)—, —C(S)N(R)—, —(R)NC(S)—, —(R)NC(S)N(R)—, or -Cy-.

In some embodiments, L¹ is a covalent bond. In some embodiments, L¹ is a C₁₋₈ bivalent straight or branched hydrocarbon chain. In some embodiments, L¹ is a C₁₋₈ bivalent straight or branched hydrocarbon chain wherein 1, 2, or 3 methylene units of the chain are independently and optionally replaced with —O—, —C(O)—, —C(O)O—, —OC(O)—, —N(R)—, —(R)NC(O)—, —OC(O)N(R)—, —(R)NC(O)O—, —N(R)C(O)N(R)—, —S—, —SO—, —SO₂N(R)—, —(R)NSO₂—, —C(S)—, —C(S)O—, —OC(S)—, —C(S)N(R)—, —(R)NC(S)—, —(R)NC(S)N(R)—, or -Cy-.

In some embodiments, L¹ is a C₁₋₆ bivalent straight or branched hydrocarbon chain wherein 1, 2, or 3 methylene units of the chain are independently and optionally replaced with —O—, —C(O)—, —N(R)—, —S—, —SO—, —SO₂N(R)—, —(R)NSO₂—, —C(S)—, or -Cy-, and each R is independently hydrogen, —CH₂-phenyl, phenyl, C₁₋₆ alkyl, cyclopropyl, cyclobutyl, cyclopentyl, cyclohexyl, —CH₂F, —CHF₂, —CF₃, —CH₂CHF₂, or —CH₂CF₃; or each R is independently hydrogen or methyl; or R is hydrogen.

In some embodiments, L¹ is selected from those depicted in Table 1, below.

In some embodiments, L² is a covalent bond. In some embodiments, L² is a C₁₋₈ bivalent straight or branched hydrocarbon chain. In some embodiments, L² is a C₁₋₈ bivalent straight or branched hydrocarbon chain wherein 1, 2, or 3 methylene units of the chain are independently and optionally replaced with —O—, —C(O)—, —C(O)O—, —OC(O)—, —N(R)—, —(R)NC(O)—, —OC(O)N(R)—, —(R)NC(O)O—, —N(R)C(O)N(R)—, —S—, —SO—, —SO₂N(R)—, —(R)NSO₂—, —C(S)—, —C(S)O—, —OC(S)—, —C(S)N(R)—, —(R)NC(S)—, —(R)NC(S)N(R)—, or -Cy-.

In some embodiments, L² is a C₁₋₆ bivalent straight or branched hydrocarbon chain wherein 1, 2, or 3 methylene units of the chain are independently and optionally replaced with —O—, —C(O)—, —N(R)—, —S—, —SO—, —SO₂N(R)—, —(R)NSO₂—, —C(S)—, or -Cy-, and each R is independently hydrogen, —CH₂-phenyl, phenyl, C₁₋₆ alkyl, cyclopropyl, cyclobutyl, cyclopentyl, cyclohexyl, —CH₂F, —CHF₂, —CF₃, —CH₂CHF₂, or —CH₂CF₃; or each R is independently hydrogen or methyl; or R is hydrogen.

In some embodiments, L² is selected from those depicted in Table 1, below.

As defined generally above, each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur.

In some embodiments, -Cy- is a bivalent optionally substituted 3-8 membered saturated or partially unsaturated monocyclic carbocyclic ring. In some embodiments, -Cy- is an optionally substituted phenylene. In some embodiments, -Cy- is an optionally substituted 4-8 membered saturated or partially unsaturated monocyclic heterocyclic ring having 1-3 heteroatoms independently selected from nitrogen, oxygen, or sulfur. In some embodiments, -Cy- is an optionally substituted 5-6 membered monocyclic heteroaromatic ring having 1-4 heteroatoms independently selected from nitrogen, oxygen, or sulfur. In some embodiments, -Cy- is an optionally substituted 8-10 membered bicyclic or bridged bicyclic saturated or partially unsaturated heterocyclic ring having 1-5 heteroatoms independently selected from nitrogen, oxygen, or sulfur. In some embodiments, -Cy- is an optionally substituted 8-10 membered bicyclic or bridged bicyclic heteroaromatic ring having 1-5 heteroatoms independently selected from nitrogen, oxygen, or sulfur.

In some embodiments, -Cy- is

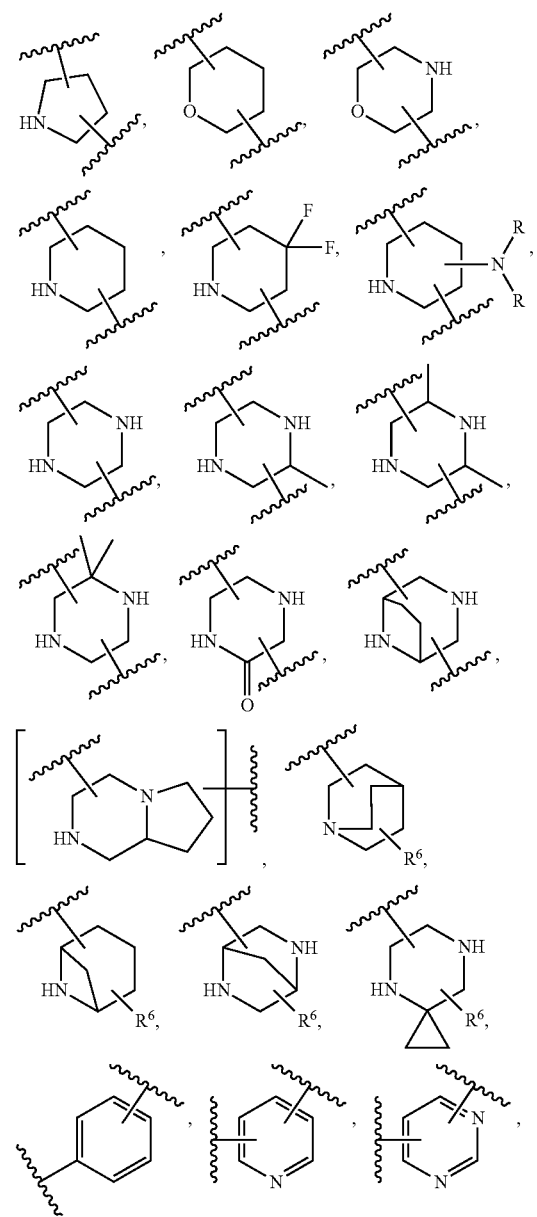

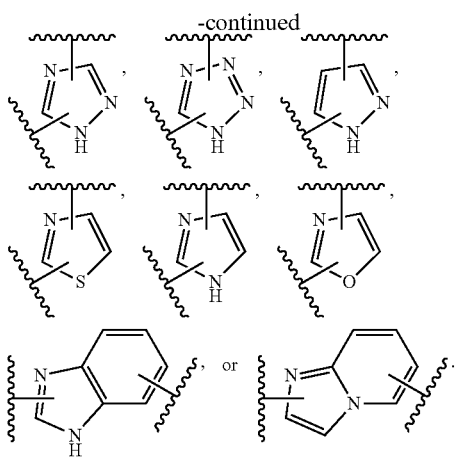

In some embodiments, -Cy- is selected from those depicted in Table 1, below.

As defined generally above, $R^2$ is hydrogen, halogen, —CN, —OR, —N(R)$_2$, —NO$_2$, —N$_3$, —SR, -L$^2$-R$^6$, or optionally substituted C$_{1-8}$ aliphatic.

In some embodiments, $R^2$ is hydrogen. In some embodiments, $R^2$ is halogen. In some embodiments, $R^2$ is —CN. In some embodiments, $R^2$ is —OR. In some embodiments, $R^2$ is —N(R)$_2$. In some embodiments, $R^2$ is —NO$_2$. In some embodiments, $R^2$ is —N$_3$. In some embodiments, $R^2$ is —SR. In some embodiments, $R^2$ is -L$^2$-R$^6$. In some embodiments, $R^2$ is optionally substituted C$_{1-8}$ aliphatic.

In some embodiments, $R^2$ is hydrogen, halogen, —CN, —OR, —N(R)$_2$, —SR, optionally substituted C$_{1-6}$ aliphatic, or -L$^2$-R$^6$, wherein L$^2$ is a C$_{1-6}$ bivalent straight or branched hydrocarbon chain wherein 1, 2, or 3 methylene units of the chain are independently and optionally replaced with —O—, —C(O)—, —N(R)—, —S—, —SO—, —SO$_2$—, —C(S)—, or -Cy-; wherein the C$_{1-6}$ aliphatic group is optionally substituted with 1, 2, or 3 groups independently selected from halogen, —CN, —N(R)$_2$, —NO$_2$, —N$_3$, =NR, =NOR, =O, =S, —OR, —SR, —SO$_2$R, —S(O)R, —R, -Cy-R, —C(O)R, —C(O)OR, —OC(O)R, —C(O)N(R)$_2$, —(R)NC(O)R, —OC(O)N(R)$_2$, —(R)NC(O)OR, —N(R)C(O)N(R)$_2$, —SO$_2$N(R)$_2$, —(R)NSO$_2$R, —C(S)R, or —C(S)OR; wherein each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, $R^2$ is selected from hydrogen, halogen, —CN, —OR, —N(R)$_2$, C$_{1-6}$ alkyl (optionally substituted with 1, 2, or 3 deuterium or halogen atoms), C$_{2-6}$ alkynyl, —S(O)R$^6$, —SO$_2$R$^6$, —SO$_2$NHR$^6$, —(CH$_2$)$_{1-6}$—N(R)R$^6$, —(CH$_2$)$_{1-6}$—OR$^6$, or —(CH$_2$)$_{0-6}$-Cy-R$^6$. In some embodiments, $R^2$ is selected from hydrogen, halogen, —OR, —N(R)$_2$, —S(O)R$^6$, —SO$_2$R$^6$, —SO$_2$NHR$^6$, —(CH$_2$)$_{1-6}$—N(R)R$^6$, —(CH$_2$)$_{1-6}$—OR$^6$,

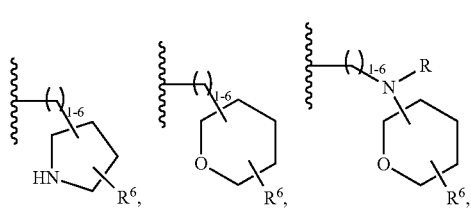

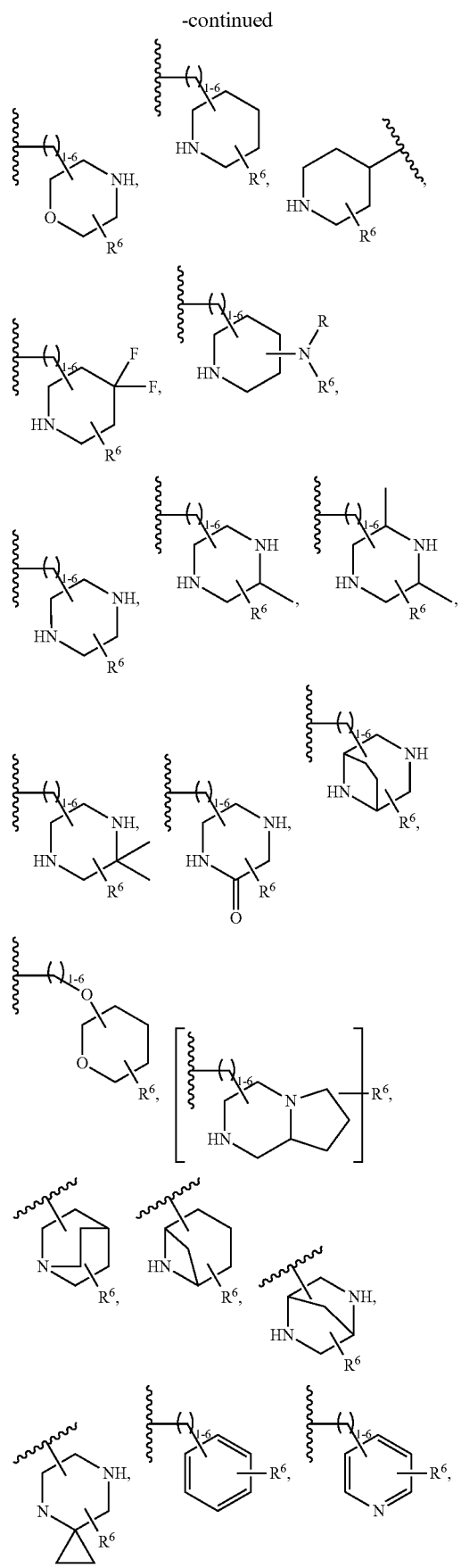

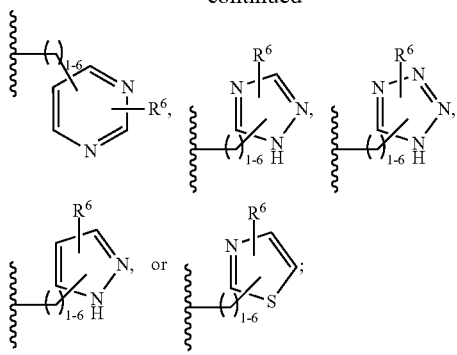

and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, R$^2$ is C$_{2-4}$ alkynyl, —NH$_2$, F, Cl, Br, or I. In some embodiments, R$^2$ is hydrogen, Cl, —NH$_2$, or ethynyl. In some embodiments, R$^2$ is Cl.

In some embodiments, R$^2$ is selected from those depicted in Table 1, below.

As defined generally above, R$^3$ is hydrogen, optionally substituted C$_{1-6}$ aliphatic, or -L$^3$-R$^6$.

In some embodiments, R$^3$ is hydrogen. In some embodiments, R$^3$ is optionally substituted C$_{1-6}$ aliphatic. In some embodiments, R$^3$ is -L$^3$-R$^6$.

In some embodiments, R$^3$ is selected from hydrogen or C$_{1-6}$ alkyl optionally substituted with 1, 2, or 3 groups independently selected from deuterium, halogen, —CN, —N(R)$_2$, —NO$_2$, —N$_3$, =NR, =NOR, =O, =S, —OR, —SR, —SO$_2$R, —S(O)R, —R, -Cy-R, —C(O)R, —C(O)OR, —OC(O)R, —C(O)N(R)$_2$, —(R)NC(O)R, —OC(O)N(R)$_2$, —(R)NC(O)OR, —N(R)C(O)N(R)$_2$, —SO$_2$N(R)$_2$, —(R)NSO$_2$R, —C(S)R, or —C(S)OR. In some embodiments, R$^3$ is selected from hydrogen or C$_{1-6}$ alkyl (optionally substituted with 1, 2, or 3 deuterium or halogen atoms), —(CH$_2$)$_{1-6}$—CN, —(CH$_2$)$_{1-6}$—N(R)(R$^6$), —(CH$_2$)$_{1-6}$—OR$^6$, or —(CH$_2$)$_{0-6}$-Cy-R$^6$. In some embodiments, R$^3$ is selected from hydrogen, C$_{1-6}$ alkyl (optionally substituted with 1, 2, or 3 deuterium or halogen atoms), —(CH$_2$)$_{1-6}$—CN, —(CH$_2$)$_{1-6}$—N(R)(R$^6$), —(CH$_2$)$_{1-6}$—OR$^6$,

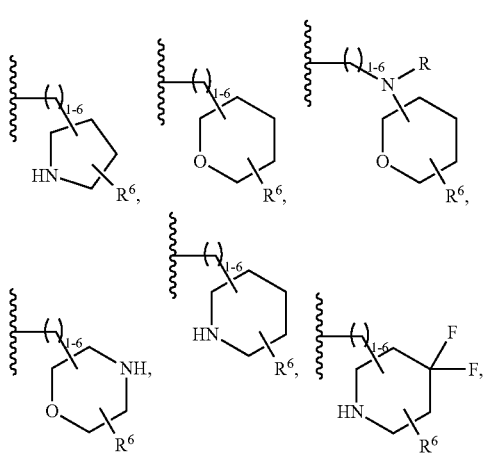

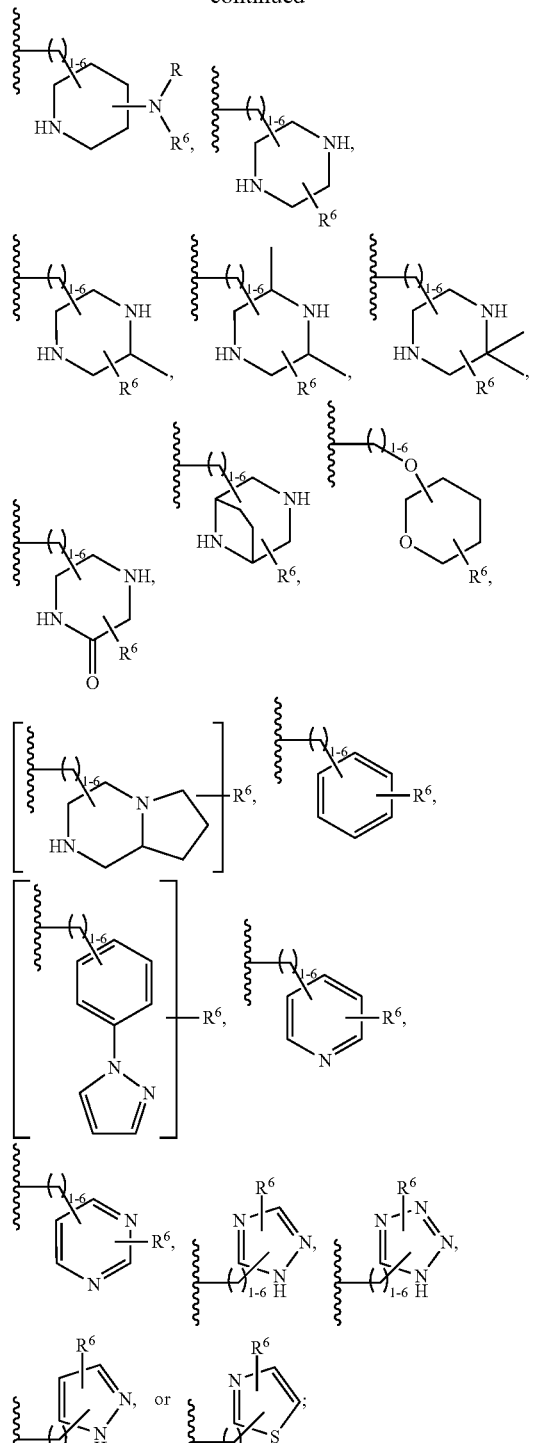

and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$; or each R is independently hydrogen or methyl; or R is hydrogen.

In some embodiments, R$^3$ is hydrogen or C$_{1-6}$ alkyl optionally substituted with 1, 2, or 3 deuterium or halogen atoms, phenyl, pyridyl, —CN, —N(R)$_2$, or —OR, wherein each R is independently hydrogen, —CH$_2$-phenyl, phenyl, $C_{1-6}$ alkyl, cyclopropyl, cyclobutyl, cyclopentyl, cyclohexyl, —$CH_2F$, —$CHF_2$, —$CF_3$, —$CH_2CHF_2$, or —$CH_2CF_3$; or each R is independently hydrogen or methyl; or R is hydrogen. In some embodiments, $R^3$ is $C_{1-4}$ alkyl optionally substituted with

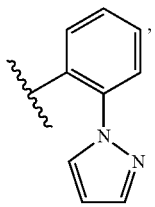

pyridyl, —$N(R)_2$, —CN, or 1, 2, or 3 deuterium or halogen atoms, wherein R is hydrogen or $C_{1-3}$ alkyl. In some embodiments, $R^3$ is methyl, ethyl, —$CD_3$, or —$CH_2CF_3$. In some embodiments, $R^3$ is methyl.

In some embodiments, $R^3$ is selected from those depicted in Table 1, below.

As defined generally above, $L^3$ is a $C_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —S—, —SO—, —$SO_2$—, —C(S)—, or -Cy-.

In some embodiments, $L^3$ is a $C_{1-6}$ bivalent straight or branched hydrocarbon chain. In some embodiments, $L^3$ is a $C_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)—, —(R)NC(O)—, —S—, —SO—, —$SO_2$—, —C(S)—, or -Cy-.

In some embodiments, $L^3$ is selected from those depicted in Table 1, below.

As defined generally above, each $R^4$ is independently hydrogen, deuterium, halogen, —CN, —$OR^6$, or $C_{1-4}$ alkyl, or two $R^4$ groups on the same carbon are optionally taken together to form =$NR^6$, =$NOR^6$, =O, or =S.

In some embodiments, $R^4$ is hydrogen. In some embodiments, $R^4$ is deuterium. In some embodiments, $R^4$ is halogen. In some embodiments, $R^4$ is —CN. In some embodiments, $R^4$ is —$OR^6$. In some embodiments, $R^4$ is $C_{1-4}$ alkyl. In some embodiments, two $R^4$ groups on the same carbon are optionally taken together to form =$NR^6$, =$NOR^6$, =O, or =S.

In some embodiments, $R^4$ is hydrogen, deuterium, halogen, —CN, $C_{1-2}$ alkyl, or two $R^4$ groups on the same carbon are taken together to form =O or =S.

In some embodiments, $R^4$ is selected from those depicted in Table 1, below.

As defined generally above, each $R^5$ is independently R, halogen, —CN, —OR, —$N(R)_2$, —$NO_2$, —$N_3$, —SR, or -$L^1$-$R^6$, or two $R^5$ groups on the same saturated carbon atom are optionally taken together to form =NR, =NOR, =O, =S, or a spirocyclic 3-6 membered carbocyclic ring.

In some embodiments, $R^5$ is R. In some embodiments, $R^5$ is halogen. In some embodiments, $R^5$ is —CN. In some embodiments, $R^5$ is —OR. In some embodiments, $R^5$ is —$N(R)_2$. In some embodiments, $R^5$ is —$NO_2$. In some embodiments, $R^5$ is —$N_3$. In some embodiments, $R^5$ is —SR. In some embodiments, $R^5$ is -$L^1$-$R^6$. In some embodiments, two $R^5$ groups on the same saturated carbon atom are taken together to form =NR, =NOR, =O, =S, or a spirocyclic 3-6 membered carbocyclic ring.

In some embodiments, $R^5$ is hydrogen. In some embodiments, $R^5$ is an optionally substituted $C_{1-6}$ aliphatic group. In some embodiments, $R^5$ is a $C_{1-6}$ alkyl group optionally substituted with 1, 2, 3, or 4 deuterium or halogen atoms. In some embodiments, $R^5$ is an optionally substituted 3-8 membered saturated or partially unsaturated monocyclic carbocyclic ring. In some embodiments, $R^5$ is an optionally substituted phenyl. In some embodiments, $R^5$ is an optionally substituted 8-10 membered bicyclic aromatic carbocyclic ring. In some embodiments, $R^5$ is an optionally substituted 4-8 membered saturated or partially unsaturated monocyclic heterocyclic ring having 1-2 heteroatoms independently selected from nitrogen, oxygen, or sulfur. In some embodiments, $R^5$ is an optionally substituted 5-6 membered monocyclic heteroaromatic ring having 1-4 heteroatoms independently selected from nitrogen, oxygen, or sulfur. In some embodiments, $R^5$ is an optionally substituted 8-10 membered bicyclic heteroaromatic ring having 1-5 heteroatoms independently selected from nitrogen, oxygen, or sulfur.

In some embodiments, $R^5$ is hydrogen, $C_{1-6}$ alkyl, halogen, —CN, —$CF_3$, —$CD_3$, cyclopropyl, ethynyl, —$OCH_3$, —$OCF_3$, or

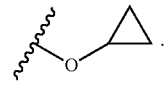 [SMILES: *OC1CC1]

In some embodiments, $R^5$ is methyl.

In some embodiments, $R^5$ is selected from those depicted in Table 1, below.

As defined generally above, each $R^6$ is independently hydrogen or $C_{1-6}$ alkyl optionally substituted with 1, 2, 3, 4, 5, or 6 deuterium or halogen atoms.

In some embodiments, $R^6$ is hydrogen. In some embodiments, $R^6$ is $C_{1-6}$ alkyl optionally substituted with 1, 2, 3, 4, 5, or 6 deuterium or halogen atoms.

In some embodiments, $R^6$ is $C_{1-3}$ alkyl optionally substituted with 1, 2, or 3 deuterium or halogen atoms.

In some embodiments, $R^6$ is selected from those depicted in Table 1, below.

As defined generally above, m is 0, 1, 2, 3, or 4. In some embodiments, m is 0. In some embodiments, m is 1. In some embodiments, m is 2. In some embodiments, m is 3. In some embodiments, m is 4. In some embodiments, m is 0, 1, 2, or 3. In some embodiments, m is 0, 1, or 2. In some embodiments, m is 1, 2, or 3.

As defined generally above, n is 0, 1, 2, 3, or 4. In some embodiments, n is 0. In some embodiments, n is 1. In some embodiments, n is 2. In some embodiments, n is 3. In some embodiments, n is 4. In some embodiments, n is 0, 1, 2, or 3. In some embodiments, n is 0, 1, or 2. In some embodiments, n is 1, 2, or 3.

As defined generally above, p is 0, 1, 2, 3, or 4. In some embodiments, p is 0. In some embodiments, p is 1. In some embodiments, p is 2. In some embodiments, p is 3. In some embodiments, p is 4. In some embodiments, p is 0, 1, 2, or 3. In some embodiments, p is 0, 1, or 2. In some embodiments, p is 1, 2, or 3.

In some embodiments, the present invention provides a compound of Formulae II-a or II-b:

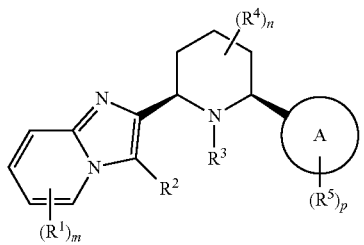
II-a

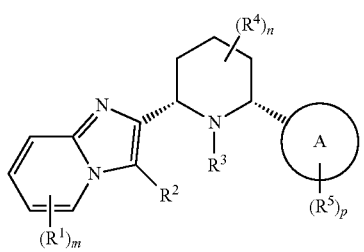
II-b or a pharmaceutically acceptable salt thereof, wherein each of Ring A, R, $R^1$, $R^2$, $R^3$, $R^4$, $R^5$, $R^6$, $L^1$, $L^2$, $L^3$, -Cy-, m, n, and p is as defined above and described in embodiments herein, both singly and in combination.

In some embodiments, the present invention provides a compound of Formula III:

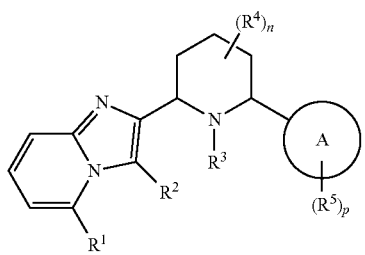
III or a pharmaceutically acceptable salt thereof, wherein each of Ring A, R, $R^1$, $R^2$, $R^3$, $R^4$, $R^5$, $R^6$, $L^1$, $L^2$, $L^3$, -Cy-, n, and p is as defined above and described in embodiments herein, both singly and in combination.

In some embodiments, the present invention provides a compound of Formula IV:

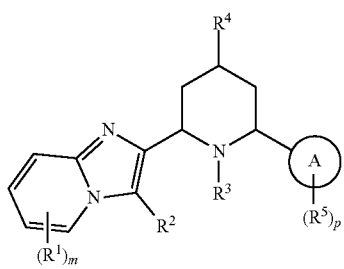
IV or a pharmaceutically acceptable salt thereof, wherein each of Ring A, R, $R^1$, $R^2$, $R^3$, $R^4$, $R^5$, $R^6$, $L^1$, $L^2$, $L^3$, -Cy-, m, and p is as defined above and described in embodiments herein, both singly and in combination.

In some embodiments, the present invention provides a compound of Formula V:

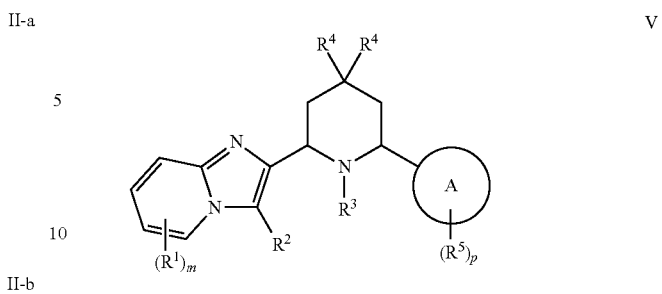
V or a pharmaceutically acceptable salt thereof, wherein each of Ring A, R, $R^1$, $R^2$, $R^3$, $R^4$, $R^5$, $R^6$, $L^1$, $L^2$, $L^3$, -Cy-, m, and p is as defined above and described in embodiments herein, both singly and in combination.

In some embodiments, the present invention provides a compound of Formula VI:

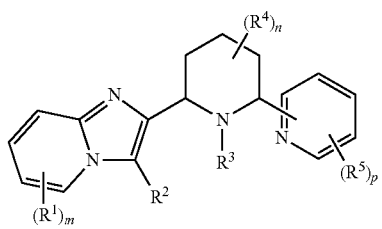
VI or a pharmaceutically acceptable salt thereof, wherein each of R, $R^1$, $R^2$, $R^3$, $R^4$, $R^5$, $R^6$, $L^1$, $L^2$, $L^3$, -Cy-, m, n, and p is as defined above and described in embodiments herein, both singly and in combination.

In some embodiments, the present invention provides a compound of Formula VII:

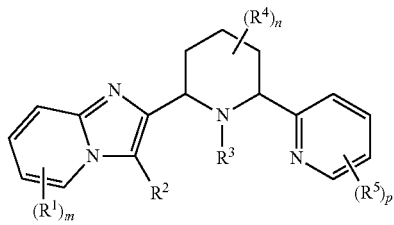
VII or a pharmaceutically acceptable salt thereof, wherein each of R, $R^1$, $R^2$, $R^3$, $R^4$, $R^5$, $R^6$, $L^1$, $L^2$, $L^3$, -Cy-, m, n, and p is as defined above and described in embodiments herein, both singly and in combination.

In some embodiments, the present invention provides a compound of Formulae VIII-a or VIII-b:

VIII-a

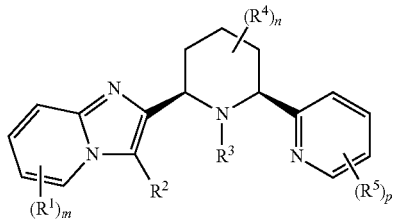

VIII-b

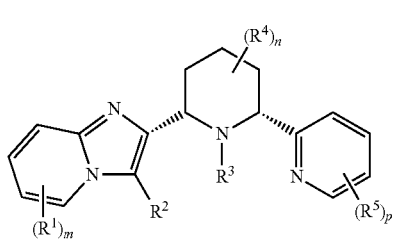

or a pharmaceutically acceptable salt thereof, wherein each of R, $R^1$, $R^2$, $R^3$, $R^4$, $R^5$, $R^6$, $L^1$, $L^2$, $L^3$, -Cy-, m, n, and p is as defined above and described in embodiments herein, both singly and in combination.

In some embodiments, the present invention provides a compound of Formula IX:

IX

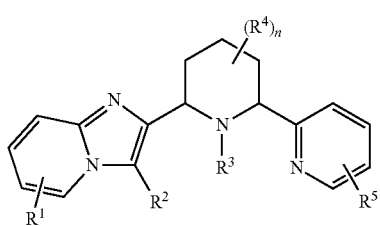

or a pharmaceutically acceptable salt thereof, wherein each of R, $R^1$, $R^2$, $R^3$, $R^4$, $R^5$, $R^6$, $L^1$, $L^2$, $L^3$, -Cy-, and n is as defined above and described in embodiments herein, both singly and in combination.

In some embodiments, the present invention provides a compound of Formulae X-a, X-b, X-c, X-d, or X-e:

X-a

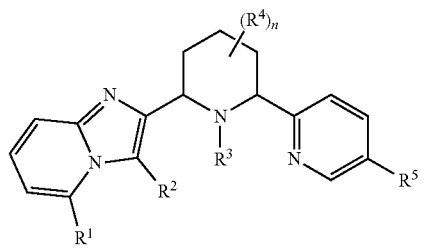

X-b

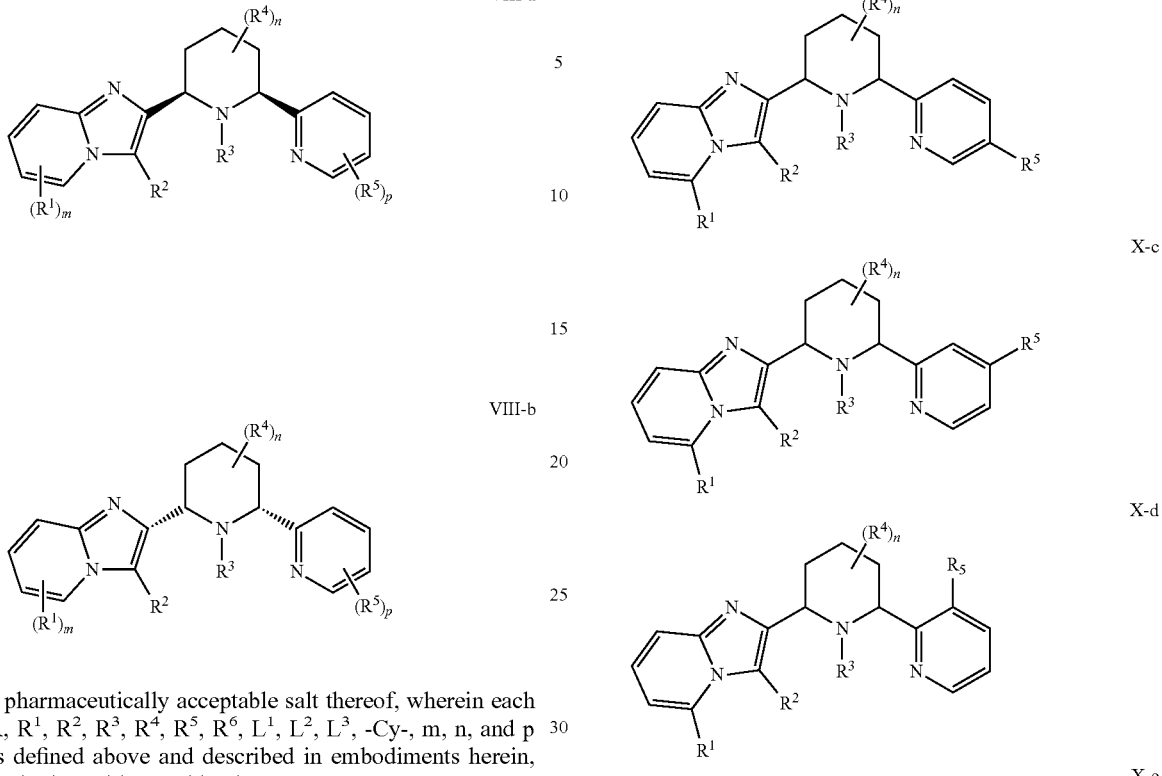

X-c

X-d

X-e or a pharmaceutically acceptable salt thereof, wherein each of R, $R^1$, $R^2$, $R^3$, $R^4$, $R^5$, $R^6$, $L^1$, $L^2$, $L^3$, -Cy-, and n is as defined above and described in embodiments herein, both singly and in combination.

In some embodiments, the present invention provides a compound of Formula XI:

XI

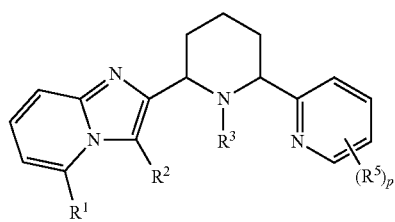

or a pharmaceutically acceptable salt thereof, wherein each of R, $R^1$, $R^2$, $R^3$, $R^5$, $R^6$, $L^1$, $L^2$, $L^3$, -Cy-, and p is as defined above and described in embodiments herein, both singly and in combination.

In some embodiments, the present invention provides a compound of Formulae XII-a or XII-b:

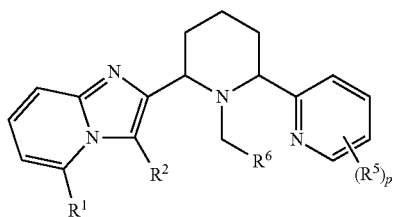

XII-a

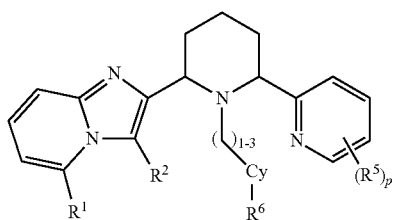

XII-b or a pharmaceutically acceptable salt thereof, wherein each of R, $R^1$, $R^2$, $R^3$, $R^5$, $R^6$, $L^1$, $L^2$, $L^3$, -Cy-, and p is as defined above and described in embodiments herein, both singly and in combination.

In some embodiments, the present invention provides a compound of Formulae XIII-a or XIII-b

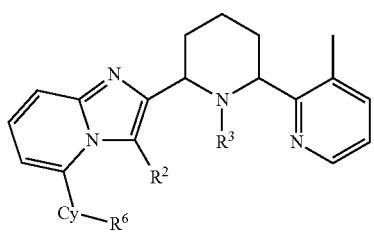

XIII-a

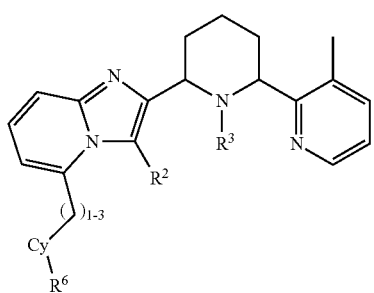

XIII-b or a pharmaceutically acceptable salt thereof, wherein each of R, $R^2$, $R^3$, $R^6$, $L^2$, $L^3$, and -Cy- is as defined above and described in embodiments herein, both singly and in combination. In some embodiments of Formulae XIII-a or XIII-b, -Cy- is an optionally substituted 4-8 membered saturated or partially unsaturated monocyclic heterocyclic ring having 1-3 heteroatoms independently selected from nitrogen, oxygen, or sulfur. In some embodiments, -Cy- is a 5- or 6-membered saturated or partially unsaturated monocyclic heterocyclic ring having 2 nitrogen atoms.

In some embodiments, the present invention provides a compound of Formulae XIV-a, XIV-b, or XIV-c:

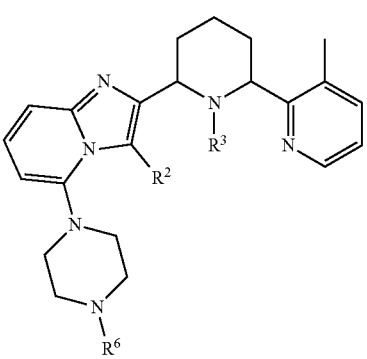

XIV-a

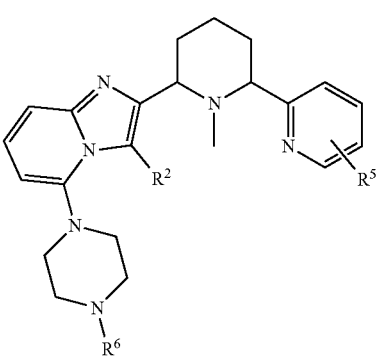

XIV-b

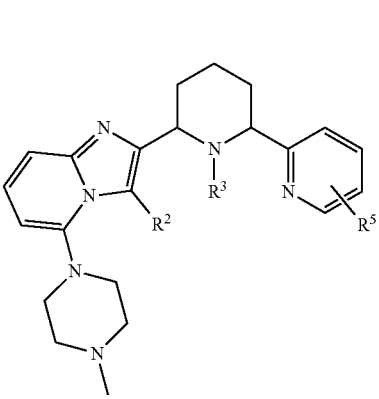

XIV-c or a pharmaceutically acceptable salt thereof, wherein each of R, $R^2$, $R^3$, $R^5$, $R^6$, $L^2$, $L^3$, and -Cy- is as defined above and described in embodiments herein, both singly and in combination. In some embodiments of Formulae XIV-a, XIV-b, and XIV-c, $R^2$ is selected from hydrogen or halogen. In some embodiments, $R^2$ is halogen. In some embodiments, $R^2$ is Cl or Br. In some embodiments, $R^2$ is Cl. In some embodiments, $R^2$ is $C_{2-4}$ alkynyl, —$NH_2$, F, Cl, Br, or I. In some embodiments, $R^2$ is hydrogen, Cl, —$NH_2$, or ethynyl.

Exemplary compounds of the invention are set forth in Table 1, below.

TABLE 1
Exemplary Compounds
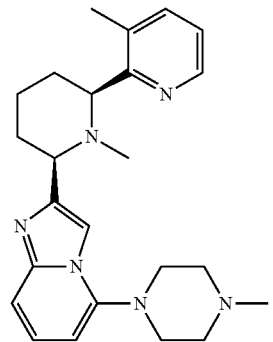 [SMILES: Cc1cccnc1[C@@H]1CCC[C@H](c2cn3c(N4CCN(C)CC4)cccc3n2)N1C]
I-1
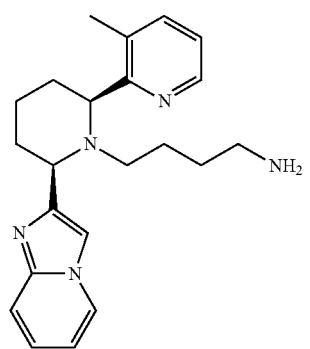 [SMILES: Cc1cccnc1[C@@H]1CCC[C@H](c2cn3ccccc3n2)N1CCCCN]
I-2
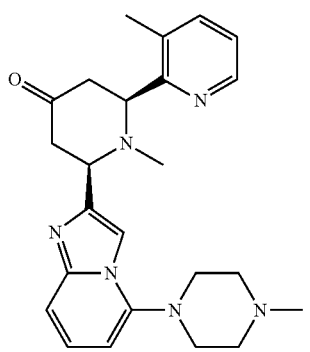 [SMILES: Cc1cccnc1[C@@H]1CC(=O)C[C@H](c2cn3c(N4CCN(C)CC4)cccc3n2)N1C]
I-3
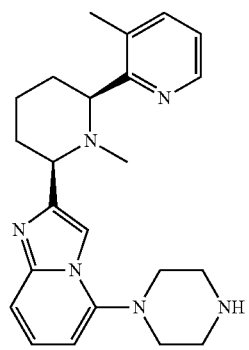 [SMILES: Cc1cccnc1[C@@H]1CCC[C@H](c2cn3c(N4CCNCC4)cccc3n2)N1C]
I-4
TABLE 1-continued
Exemplary Compounds
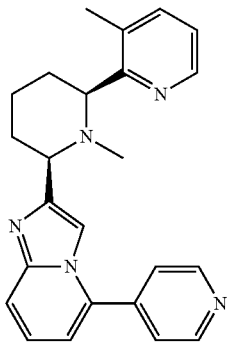 [SMILES: Cc1cccnc1[C@@H]1CCC[C@H](c2cn3c(-c4ccncc4)cccc3n2)N1C]
I-5
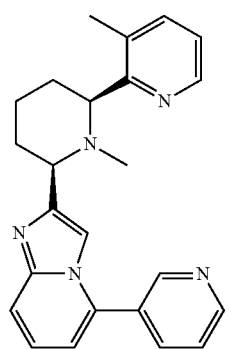 [SMILES: Cc1cccnc1[C@@H]1CCC[C@H](c2cn3c(-c4cccnc4)cccc3n2)N1C]
I-6
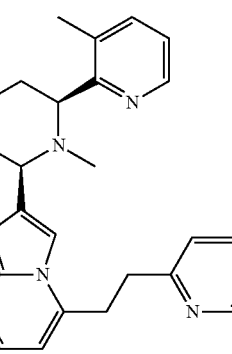
I-7
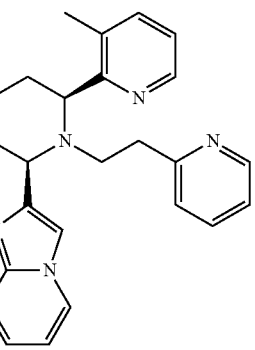
I-8

TABLE 1-continued
Exemplary Compounds
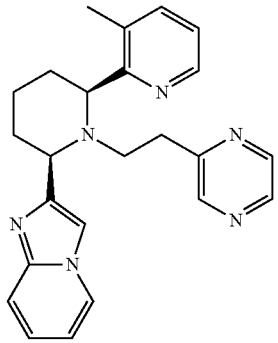 [SMILES: Cc1cccnc1[C@@H]1CCC[C@H](c2cn3ccccc3n2)N1CCc1cnccn1] I-9
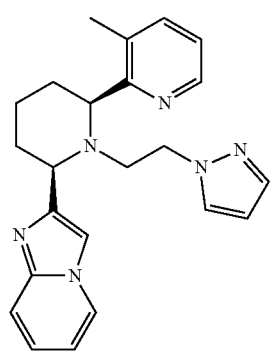 [SMILES: Cc1cccnc1[C@@H]1CCC[C@H](c2cn3ccccc3n2)N1CCn1cccn1] I-10
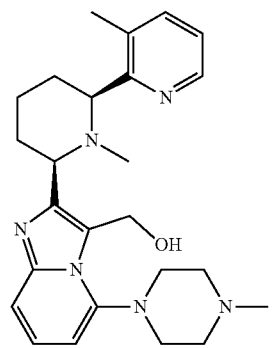 [SMILES: Cc1cccnc1[C@@H]1CCC[C@H](c2nc3cccc(N4CCN(C)CC4)n3c2CO)N1C] I-11
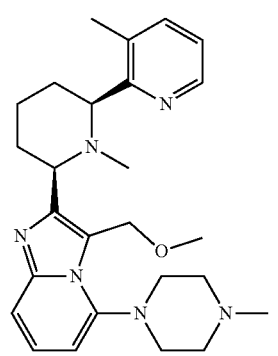 [SMILES: COCc1c([C@H]2CCC[C@@H](c3ncccc3C)N2C)nc2cccc(N3CCN(C)CC3)n12] I-12
TABLE 1-continued
Exemplary Compounds
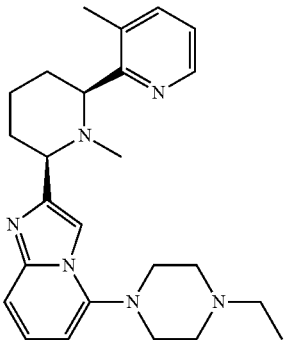 [SMILES: CCN1CCN(c2cccc3nc([C@H]4CCC[C@@H](c5ncccc5C)N4C)cn23)CC1] I-13
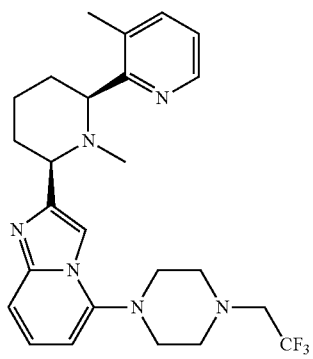 [SMILES: Cc1cccnc1[C@@H]1CCC[C@H](c2cn3c(N4CCN(CC(F)(F)F)CC4)cccc3n2)N1C] I-14
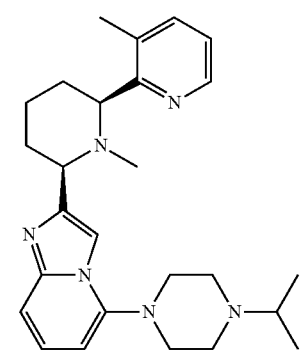 [SMILES: Cc1cccnc1[C@@H]1CCC[C@H](c2cn3c(N4CCN(C(C)C)CC4)cccc3n2)N1C] I-15
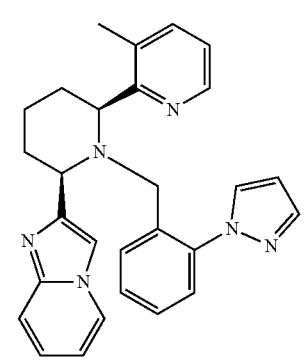 [SMILES: Cc1cccnc1[C@@H]1CCC[C@H](c2cn3ccccc3n2)N1Cc1ccccc1-n1cccn1] I-16

TABLE 1-continued
Exemplary Compounds
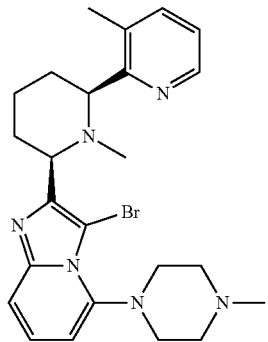 [SMILES: Cc1cccnc1[C@@H]1CCC[C@H](c2nc3cccc(N4CCN(C)CC4)n3c2Br)N1C] I-17
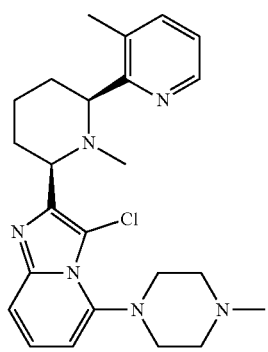 [SMILES: Cc1cccnc1[C@@H]1CCC[C@H](c2nc3cccc(N4CCN(C)CC4)n3c2Cl)N1C] I-18
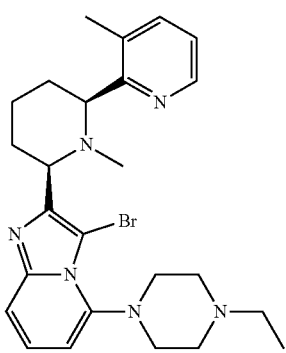 [SMILES: CCN1CCN(c2cccc3nc([C@H]4CCC[C@@H](c5ncccc5C)N4C)c(Br)n23)CC1] I-19
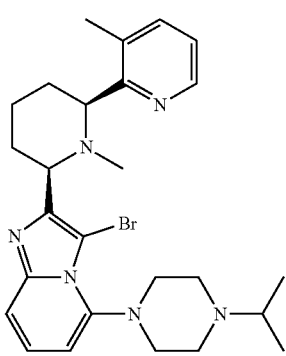 [SMILES: Cc1cccnc1[C@@H]1CCC[C@H](c2nc3cccc(N4CCN(C(C)C)CC4)n3c2Br)N1C] I-20
TABLE 1-continued
Exemplary Compounds
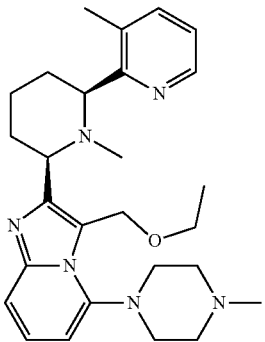 [SMILES: CCOCc1c([C@H]2CCC[C@@H](c3ncccc3C)N2C)nc2cccc(N3CCN(C)CC3)n12] I-21
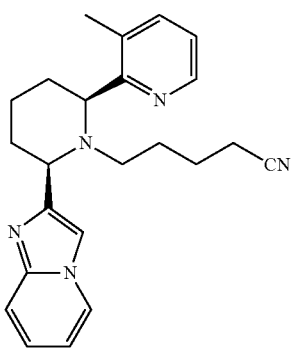 [SMILES: Cc1cccnc1[C@@H]1CCC[C@H](c2cn3ccccc3n2)N1CCCCC#N] I-22
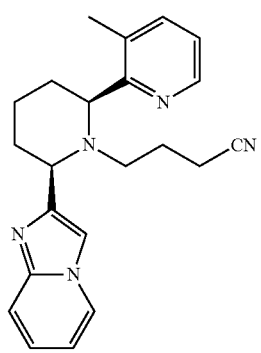 [SMILES: Cc1cccnc1[C@@H]1CCC[C@H](c2cn3ccccc3n2)N1CCCC#N] I-23
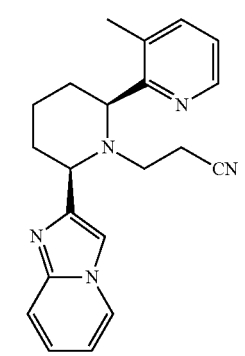 [SMILES: Cc1cccnc1[C@@H]1CCC[C@H](c2cn3ccccc3n2)N1CCC#N] I-24

TABLE 1-continued
Exemplary Compounds
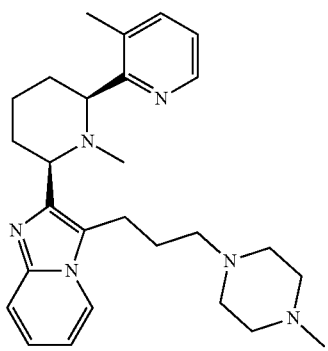 [SMILES: Cc1cccnc1[C@@H]1CCC[C@H](c2nc3ccccn3c2CCCN2CCN(C)CC2)N1C] I-25
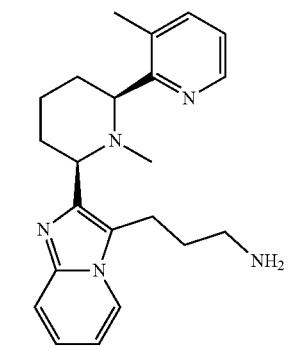 [SMILES: Cc1cccnc1[C@@H]1CCC[C@H](c2nc3ccccn3c2CCCN)N1C] I-26
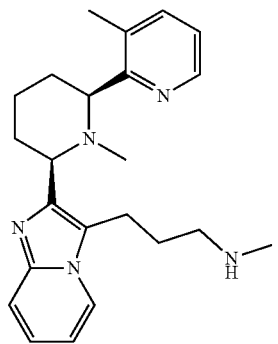 [SMILES: CNCCCc1c([C@H]2CCC[C@@H](c3ncccc3C)N2C)nc2ccccn12] I-27
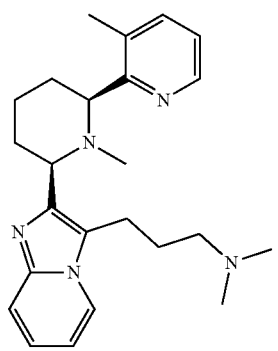 [SMILES: Cc1cccnc1[C@@H]1CCC[C@H](c2nc3ccccn3c2CCCN(C)C)N1C] I-28
TABLE 1-continued
Exemplary Compounds
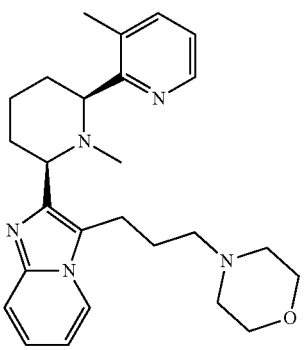 [SMILES: Cc1cccnc1[C@@H]1CCC[C@H](c2nc3ccccn3c2CCCN2CCOCC2)N1C] I-29
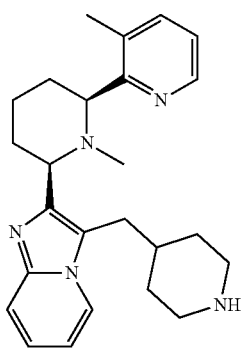 [SMILES: Cc1cccnc1[C@@H]1CCC[C@H](c2nc3ccccn3c2CC2CCNCC2)N1C] I-30
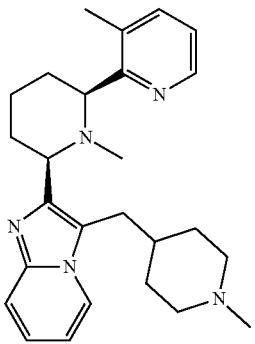 I-31
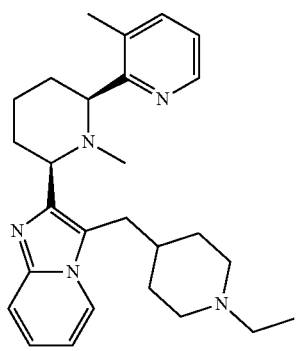 [SMILES: CCN1CCC(Cc2c([C@H]3CCC[C@@H](c4ncccc4C)N3C)nc3ccccn23)CC1] I-32

TABLE 1-continued
Exemplary Compounds
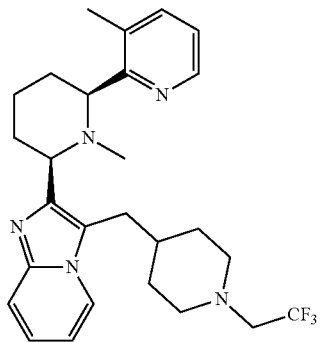 [SMILES: Cc1cccnc1[C@@H]1CCC[C@H](c2nc3ccccn3c2CC2CCN(CC(F)(F)F)CC2)N1C]
I-33
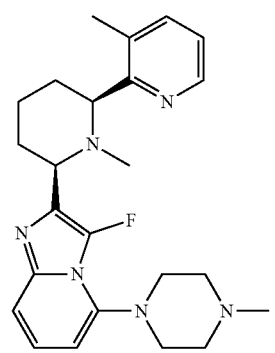 [SMILES: Cc1cccnc1[C@@H]1CCC[C@H](c2nc3cccc(N4CCN(C)CC4)n3c2F)N1C]
I-34
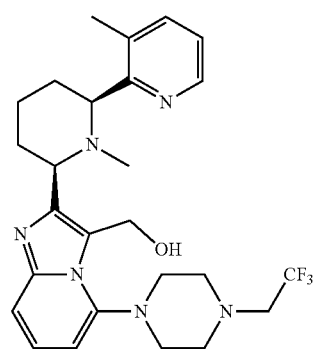 [SMILES: Cc1cccnc1[C@@H]1CCC[C@H](c2nc3cccc(N4CCN(CC(F)(F)F)CC4)n3c2CO)N1C]
I-35
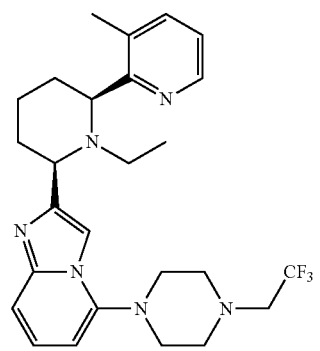 [SMILES: CCN1[C@@H](c2cn3c(N4CCN(CC(F)(F)F)CC4)cccc3n2)CCC[C@H]1c1ncccc1C]
I-36
TABLE 1-continued
Exemplary Compounds
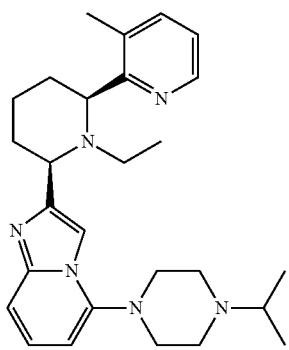 [SMILES: CCN1[C@@H](c2cn3c(N4CCN(C(C)C)CC4)cccc3n2)CCC[C@H]1c1ncccc1C]
I-37
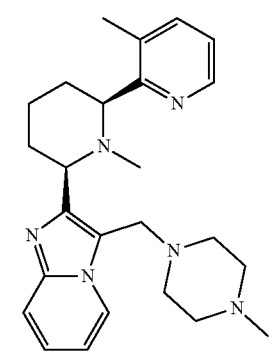
I-38
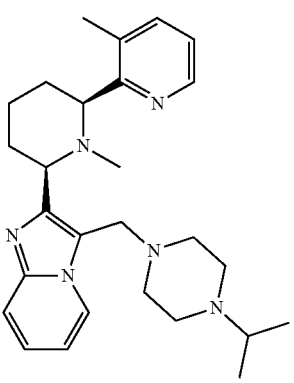 [SMILES: Cc1cccnc1[C@@H]1CCC[C@H](c2nc3ccccn3c2CN2CCN(C(C)C)CC2)N1C]
I-39
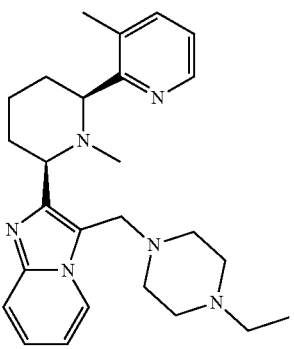 [SMILES: CCN1CCN(Cc2c([C@H]3CCC[C@@H](c4ncccc4C)N3C)nc3ccccn23)CC1]
I-40

TABLE 1-continued
Exemplary Compounds
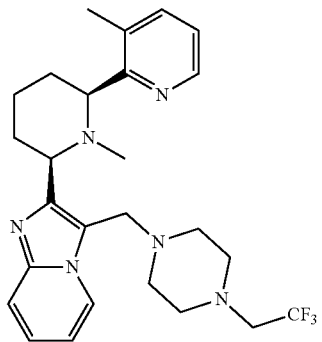 [SMILES: Cc1cccnc1[C@@H]1CCC[C@H](c2nc3ccccn3c2CN2CCN(CC(F)(F)F)CC2)N1C]
I-41
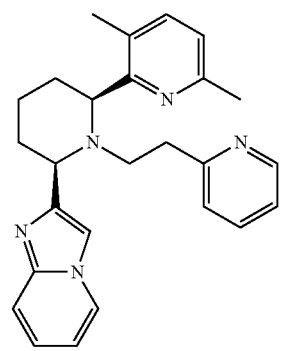 [SMILES: Cc1ccc(C)c([C@@H]2CCC[C@H](c3cn4ccccc4n3)N2CCc2ccccn2)n1]
I-42
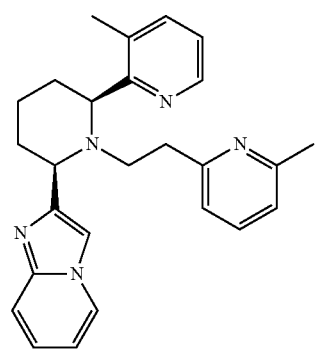 [SMILES: Cc1cccc(CCN2[C@@H](c3cn4ccccc4n3)CCC[C@H]2c2ncccc2C)n1]
I-43
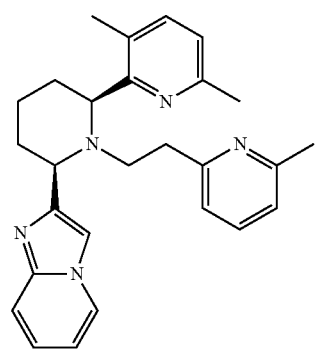 [SMILES: Cc1cccc(CCN2[C@@H](c3cn4ccccc4n3)CCC[C@H]2c2nc(C)ccc2C)n1]
I-44
TABLE 1-continued
Exemplary Compounds
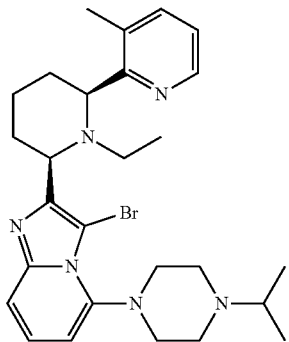 [SMILES: CCN1[C@@H](c2nc3cccc(N4CCN(C(C)C)CC4)n3c2Br)CCC[C@H]1c1ncccc1C]
I-45
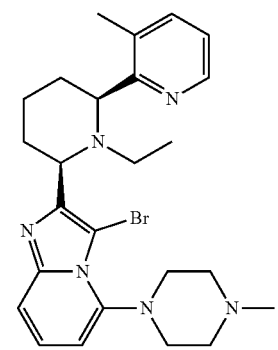 [SMILES: CCN1[C@@H](c2nc3cccc(N4CCN(C)CC4)n3c2Br)CCC[C@H]1c1ncccc1C]
I-46
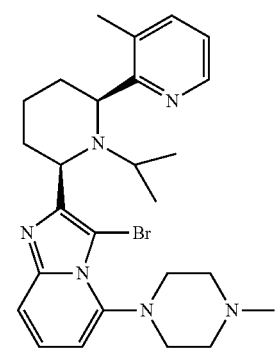 [SMILES: Cc1cccnc1[C@@H]1CCC[C@H](c2nc3cccc(N4CCN(C)CC4)n3c2Br)N1C(C)C]
I-47
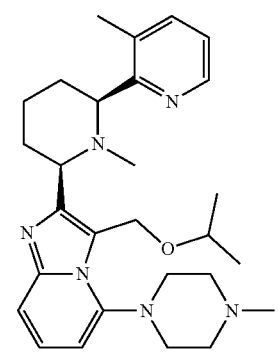 [SMILES: Cc1cccnc1[C@@H]1CCC[C@H](c2nc3cccc(N4CCN(C)CC4)n3c2COC(C)C)N1C]
I-48

TABLE 1-continued
Exemplary Compounds
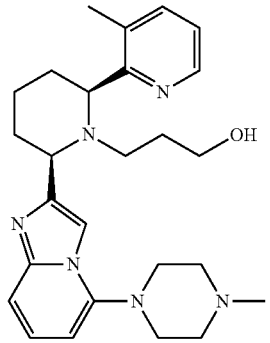 [SMILES: Cc1cccnc1[C@@H]1CCC[C@H](c2cn3c(N4CCN(C)CC4)cccc3n2)N1CCCO]
I-49
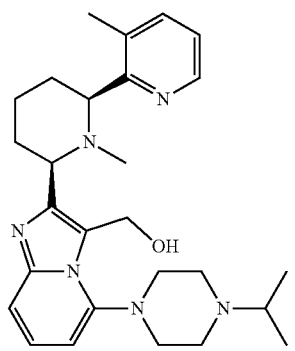 [SMILES: Cc1cccnc1[C@@H]1CCC[C@H](c2nc3cccc(N4CCN(C(C)C)CC4)n3c2CO)N1C]
I-50
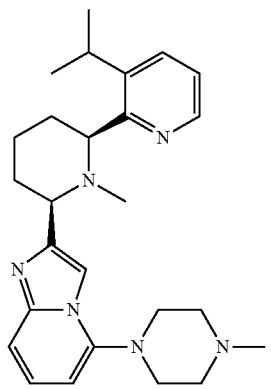 [SMILES: CC(C)c1cccnc1[C@@H]1CCC[C@H](c2cn3c(N4CCN(C)CC4)cccc3n2)N1C]
I-51
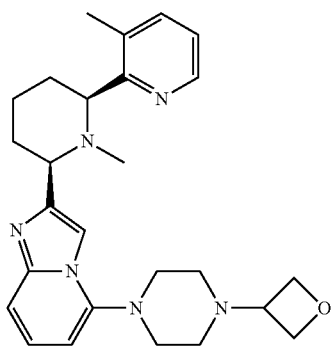 [SMILES: Cc1cccnc1[C@@H]1CCC[C@H](c2cn3c(N4CCN(C5COC5)CC4)cccc3n2)N1C]
I-52
TABLE 1-continued
Exemplary Compounds
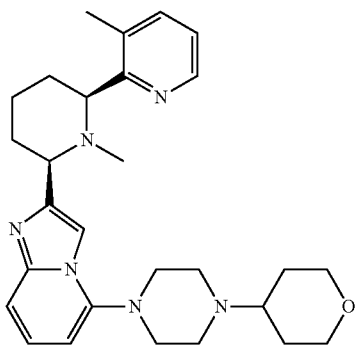 [SMILES: Cc1cccnc1[C@@H]1CCC[C@H](c2cn3c(N4CCN(C5CCOCC5)CC4)cccc3n2)N1C]
I-53
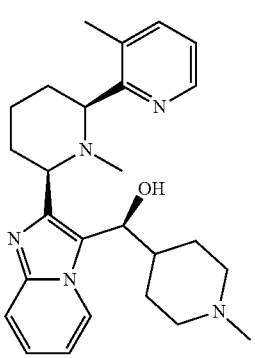 [SMILES: Cc1cccnc1[C@@H]1CCC[C@H](c2nc3ccccn3c2[C@@H](O)C2CCN(C)CC2)N1C]
I-54
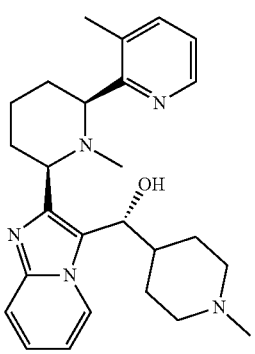 [SMILES: Cc1cccnc1[C@@H]1CCC[C@H](c2nc3ccccn3c2[C@H](O)C2CCN(C)CC2)N1C]
I-55
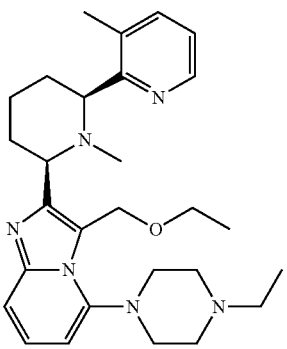
I-56

TABLE 1-continued
Exemplary Compounds
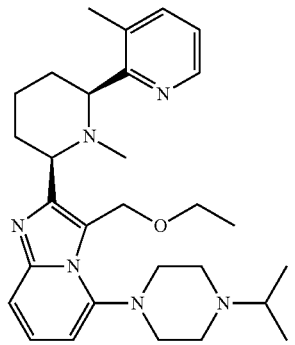 [SMILES: CCOCc1c([C@H]2CCC[C@@H](c3ncccc3C)N2C)nc2cccc(N3CCN(C(C)C)CC3)n12] I-57
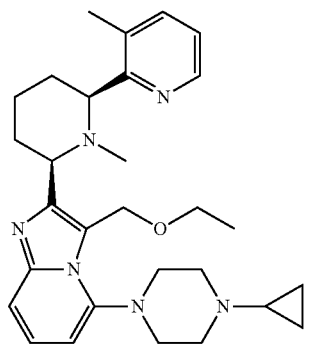 [SMILES: CCOCc1c([C@H]2CCC[C@@H](c3ncccc3C)N2C)nc2cccc(N3CCN(C4CC4)CC3)n12] I-58
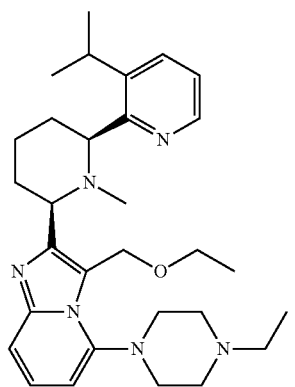 [SMILES: CCOCc1c([C@H]2CCC[C@@H](c3ncccc3C(C)C)N2C)nc2cccc(N3CCN(CC)CC3)n12] I-59
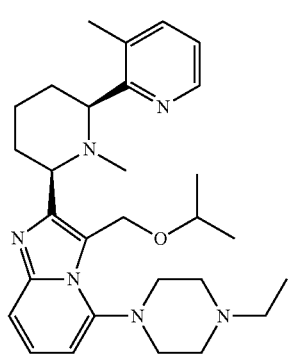 [SMILES: CCN1CCN(c2cccc3nc([C@H]4CCC[C@@H](c5ncccc5C)N4C)c(COC(C)C)n23)CC1] I-60
TABLE 1-continued
Exemplary Compounds
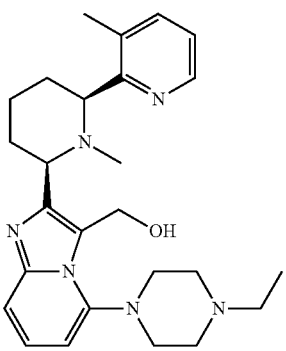 I-61
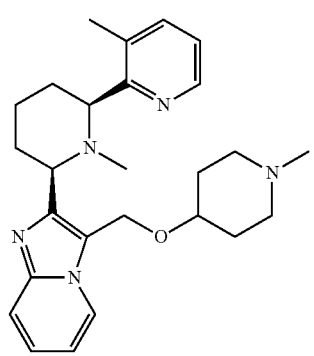 [SMILES: Cc1cccnc1[C@@H]1CCC[C@H](c2nc3ccccn3c2COC2CCN(C)CC2)N1C] I-62
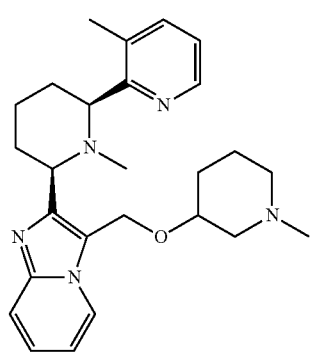 [SMILES: Cc1cccnc1[C@@H]1CCC[C@H](c2nc3ccccn3c2COC2CCCN(C)C2)N1C] I-63
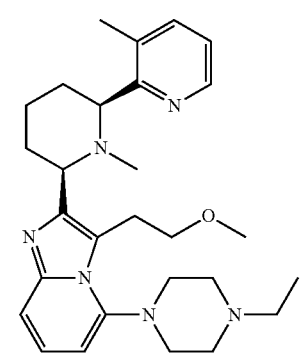 I-64

TABLE 1-continued
Exemplary Compounds
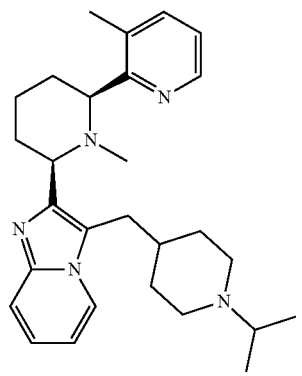 [SMILES: Cc1cccnc1[C@@H]1CCC[C@H](c2nc3ccccn3c2CC2CCN(C(C)C)CC2)N1C]
I-65
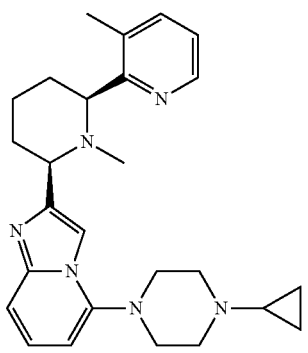 [SMILES: Cc1cccnc1[C@@H]1CCC[C@H](c2cn3c(N4CCN(C5CC5)CC4)cccc3n2)N1C]
I-66
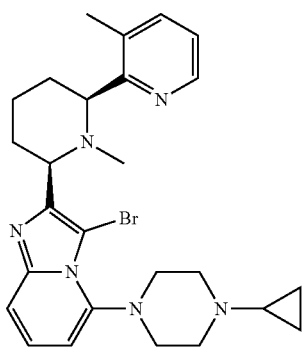 [SMILES: Cc1cccnc1[C@@H]1CCC[C@H](c2nc3cccc(N4CCN(C5CC5)CC4)n3c2Br)N1C]
I-67
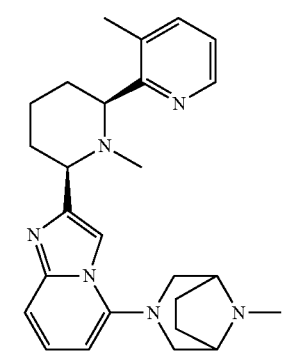 [SMILES: Cc1cccnc1[C@@H]1CCC[C@H](c2cn3c(N4CC5CCC(C4)N5C)cccc3n2)N1C]
I-68
TABLE 1-continued
Exemplary Compounds
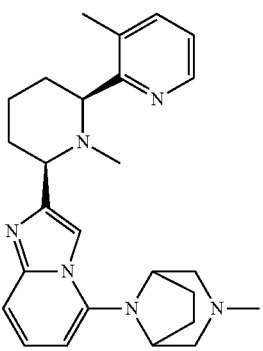 [SMILES: Cc1cccnc1[C@@H]1CCC[C@H](c2cn3c(N4C5CCC4CN(C)C5)cccc3n2)N1C]
I-69
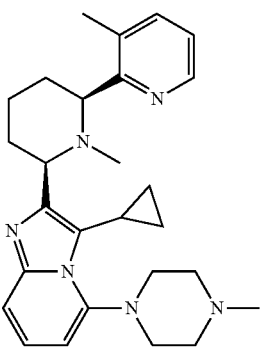 [SMILES: Cc1cccnc1[C@@H]1CCC[C@H](c2nc3cccc(N4CCN(C)CC4)n3c2C2CC2)N1C]
I-70
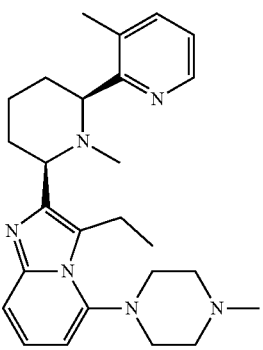 [SMILES: CCc1c([C@H]2CCC[C@@H](c3ncccc3C)N2C)nc2cccc(N3CCN(C)CC3)n12]
I-71
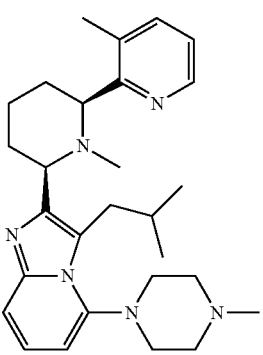 [SMILES: Cc1cccnc1[C@@H]1CCC[C@H](c2nc3cccc(N4CCN(C)CC4)n3c2CC(C)C)N1C]
I-72

TABLE 1-continued
Exemplary Compounds
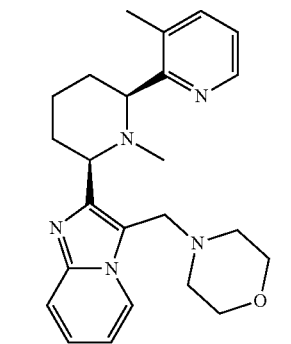 [SMILES: Cc1cccnc1[C@@H]1CCC[C@H](c2nc3ccccn3c2CN2CCOCC2)N1C]
I-73
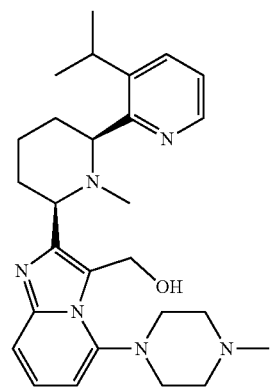 [SMILES: CC(C)c1cccnc1[C@@H]1CCC[C@H](c2nc3cccc(N4CCN(C)CC4)n3c2CO)N1C]
I-74
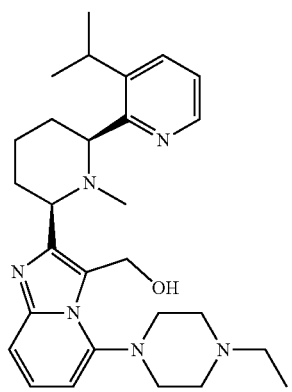 [SMILES: CCN1CCN(c2cccc3nc([C@H]4CCC[C@@H](c5ncccc5C(C)C)N4C)c(CO)n23)CC1]
I-75
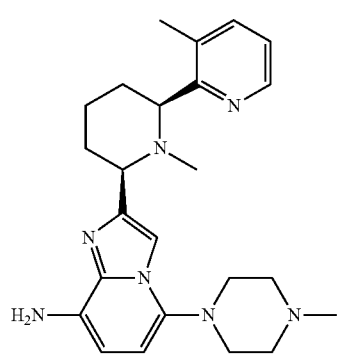
I-76
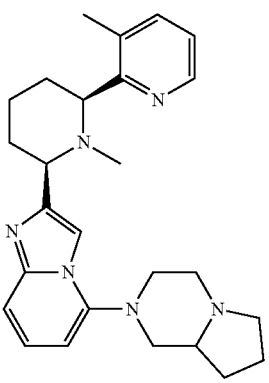 [SMILES: Cc1cccnc1[C@@H]1CCC[C@H](c2cn3c(N4CCN5CCCC5C4)cccc3n2)N1C]
I-77
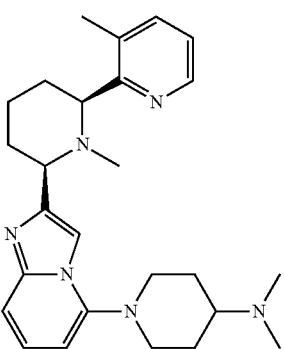
I-78
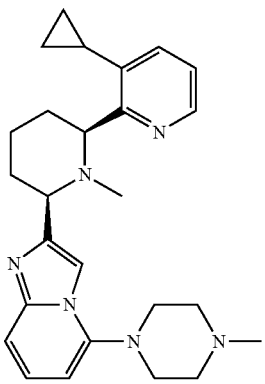 [SMILES: CN1CCN(c2cccc3nc([C@H]4CCC[C@@H](c5ncccc5C5CC5)N4C)cn23)CC1]
I-79
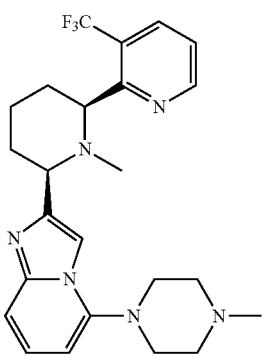 [SMILES: CN1CCN(c2cccc3nc([C@H]4CCC[C@@H](c5ncccc5C(F)(F)F)N4C)cn23)CC1]
I-80

TABLE 1-continued
Exemplary Compounds
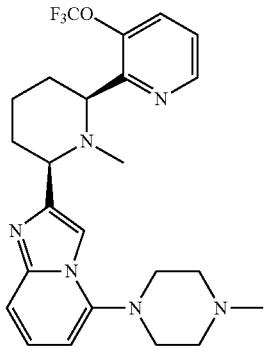 [SMILES: CN1CCN(c2cccc3nc([C@H]4CCC[C@@H](c5ncccc5OC(F)(F)F)N4C)cn23)CC1] I-81
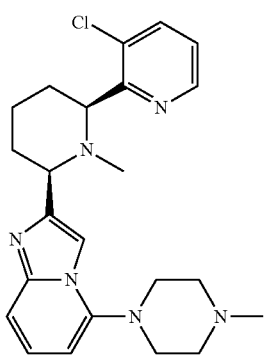 [SMILES: CN1CCN(c2cccc3nc([C@H]4CCC[C@@H](c5ncccc5Cl)N4C)cn23)CC1] I-82
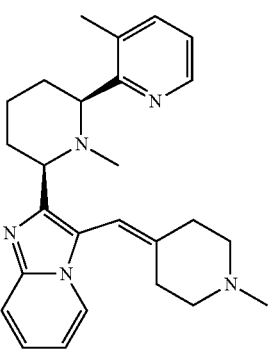 [SMILES: Cc1cccnc1[C@@H]1CCC[C@H](c2nc3ccccn3c2C=C2CCN(C)CC2)N1C] I-83
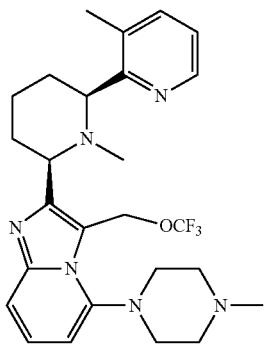 [SMILES: Cc1cccnc1[C@@H]1CCC[C@H](c2nc3cccc(N4CCN(C)CC4)n3c2COC(F)(F)F)N1C] I-84
TABLE 1-continued
Exemplary Compounds
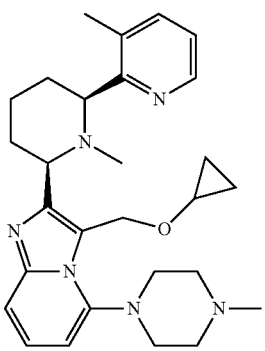 [SMILES: Cc1cccnc1[C@@H]1CCC[C@H](c2nc3cccc(N4CCN(C)CC4)n3c2COC2CC2)N1C] I-85
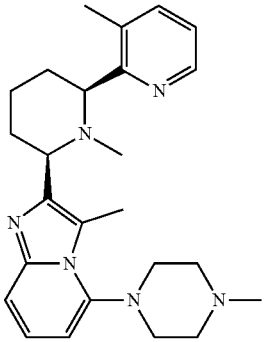 [SMILES: Cc1cccnc1[C@@H]1CCC[C@H](c2nc3cccc(N4CCN(C)CC4)n3c2C)N1C] I-86
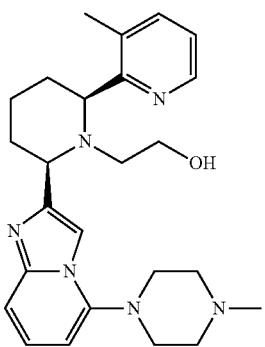 [SMILES: Cc1cccnc1[C@@H]1CCC[C@H](c2cn3c(N4CCN(C)CC4)cccc3n2)N1CCO] I-87
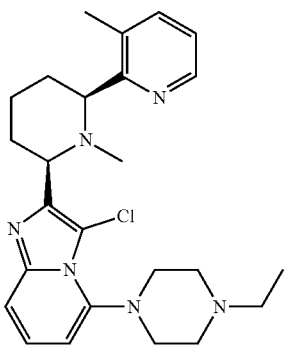 I-88

TABLE 1-continued
Exemplary Compounds
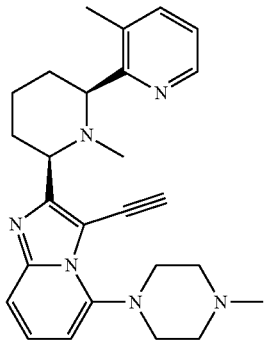 [SMILES: C#Cc1c([C@H]2CCC[C@@H](c3ncccc3C)N2C)nc2cccc(N3CCN(C)CC3)n12] I-89
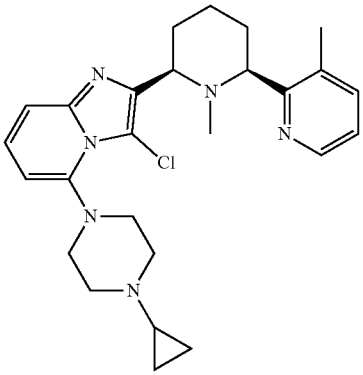 [SMILES: Cc1cccnc1[C@@H]1CCC[C@H](c2nc3cccc(N4CCN(C5CC5)CC4)n3c2Cl)N1C] I-93
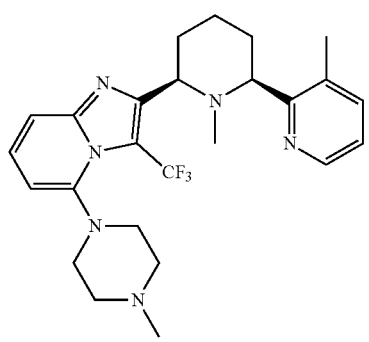 I-90
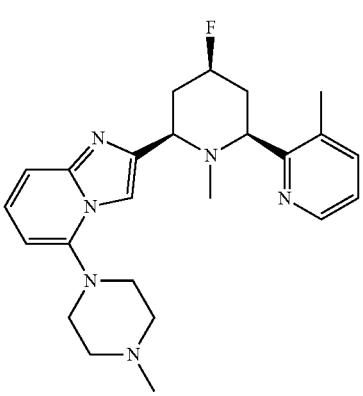 [SMILES: Cc1cccnc1[C@@H]1C[C@H](F)C[C@H](c2cn3c(N4CCN(C)CC4)cccc3n2)N1C] I-94
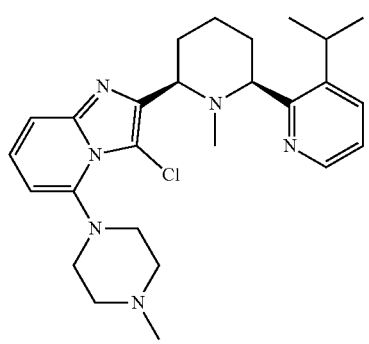 I-91
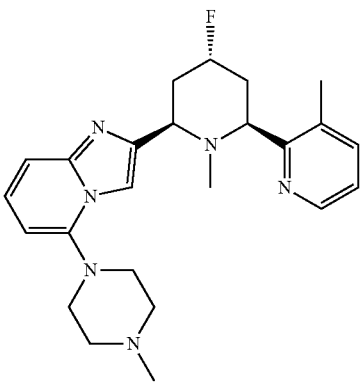 [SMILES: Cc1cccnc1[C@@H]1C[C@@H](F)C[C@H](c2cn3c(N4CCN(C)CC4)cccc3n2)N1C] I-95
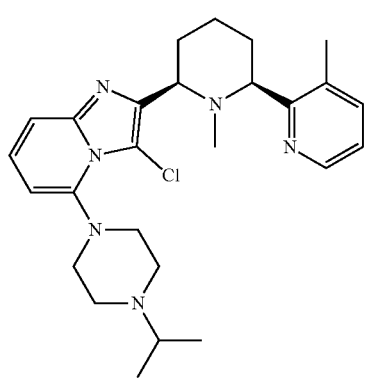 I-92
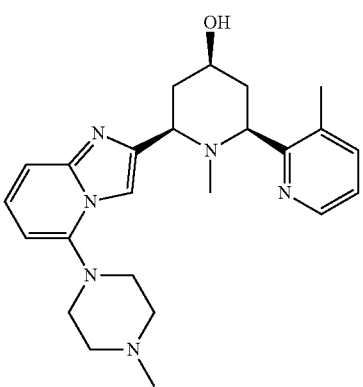 [SMILES: Cc1cccnc1[C@@H]1C[C@H](O)C[C@H](c2cn3c(N4CCN(C)CC4)cccc3n2)N1C] I-96

TABLE 1-continued
Exemplary Compounds
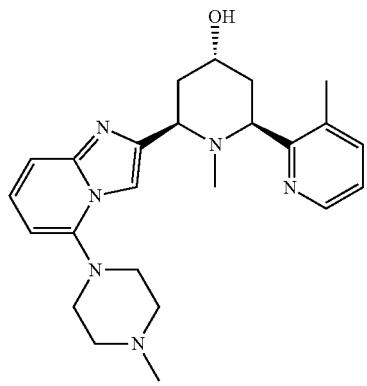 [SMILES: Cc1cccnc1[C@@H]1C[C@@H](O)C[C@H](c2cn3c(N4CCN(C)CC4)cccc3n2)N1C] I-97
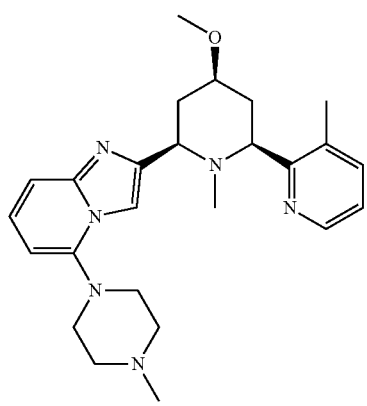 [SMILES: CO[C@@H]1C[C@H](c2cn3c(N4CCN(C)CC4)cccc3n2)N(C)[C@H](c2ncccc2C)C1] I-98
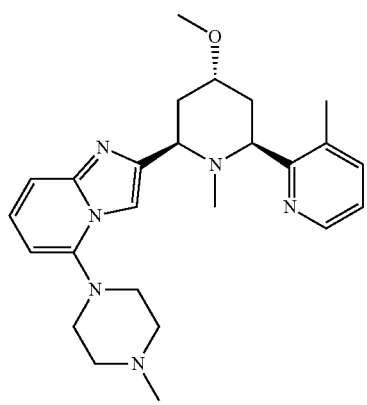 [SMILES: CO[C@H]1C[C@H](c2cn3c(N4CCN(C)CC4)cccc3n2)N(C)[C@H](c2ncccc2C)C1] I-99
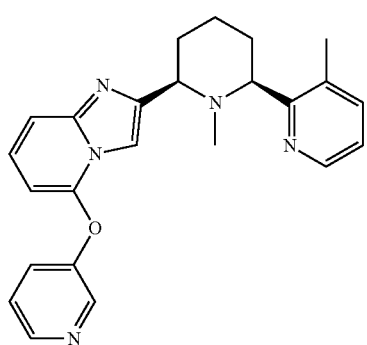 [SMILES: Cc1cccnc1[C@@H]1CCC[C@H](c2cn3c(Oc4cccnc4)cccc3n2)N1C] I-100
TABLE 1-continued
Exemplary Compounds
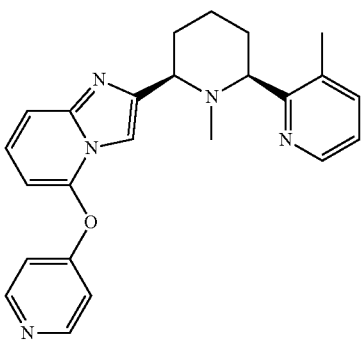 [SMILES: Cc1cccnc1[C@@H]1CCC[C@H](c2cn3c(Oc4ccncc4)cccc3n2)N1C] I-101
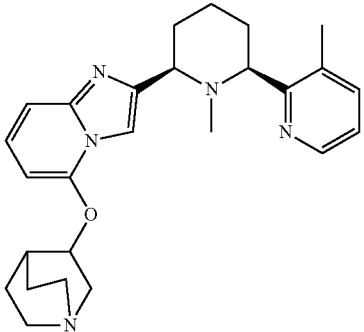 [SMILES: Cc1cccnc1[C@@H]1CCC[C@H](c2cn3c(OC4CN5CCC4CC5)cccc3n2)N1C] I-102
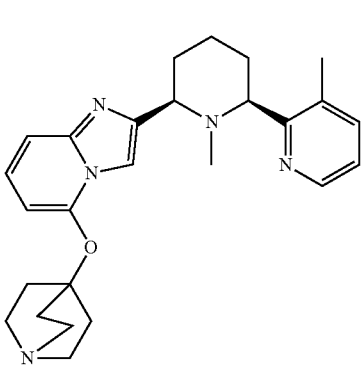 [SMILES: Cc1cccnc1[C@@H]1CCC[C@H](c2cn3c(OC45CCN(CC4)CC5)cccc3n2)N1C] I-103
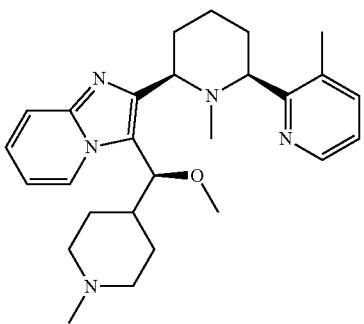 [SMILES: CO[C@H](c1c([C@H]2CCC[C@@H](c3ncccc3C)N2C)nc2ccccn12)C1CCN(C)CC1] I-104

TABLE 1-continued
Exemplary Compounds
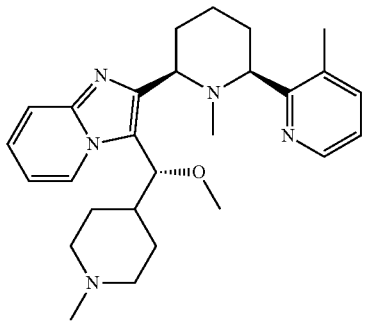 [SMILES: CO[C@@H](c1c([C@H]2CCC[C@@H](c3ncccc3C)N2C)nc2ccccn12)C1CCN(C)CC1]
I-105
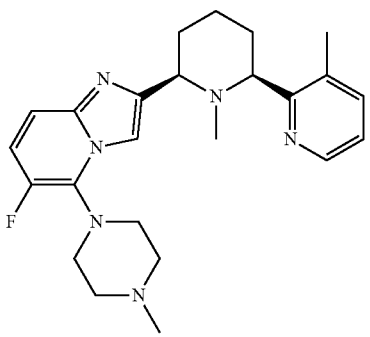 [SMILES: Cc1cccnc1[C@@H]1CCC[C@H](c2cn3c(N4CCN(C)CC4)c(F)ccc3n2)N1C]
I-106
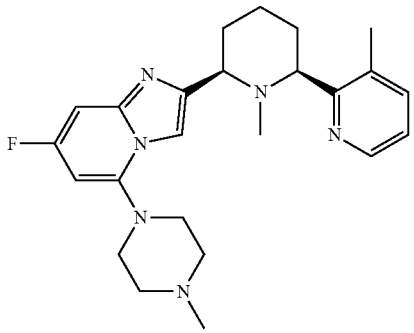 [SMILES: Cc1cccnc1[C@@H]1CCC[C@H](c2cn3c(N4CCN(C)CC4)cc(F)cc3n2)N1C]
I-107
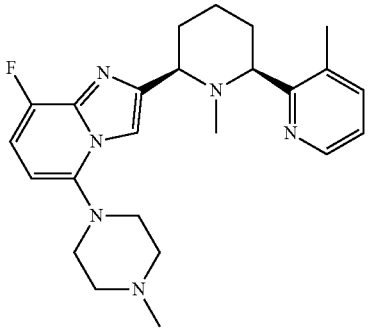 [SMILES: Cc1cccnc1[C@@H]1CCC[C@H](c2cn3c(N4CCN(C)CC4)ccc(F)c3n2)N1C]
I-108
TABLE 1-continued
Exemplary Compounds
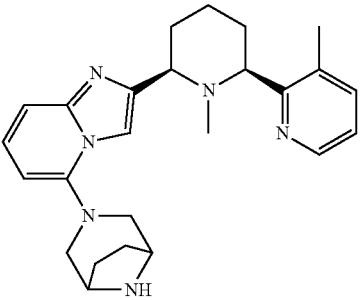 [SMILES: Cc1cccnc1[C@@H]1CCC[C@H](c2cn3c(N4CC5CCC(C4)N5)cccc3n2)N1C]
I-109
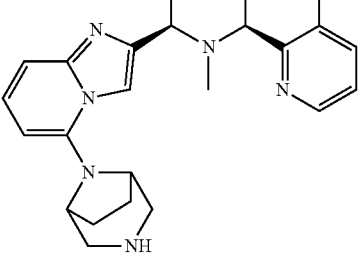
I-110
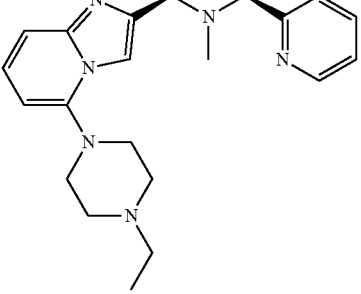
I-111
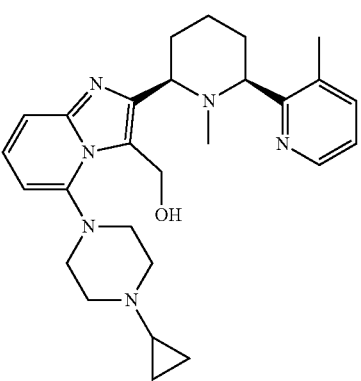 [SMILES: Cc1cccnc1[C@@H]1CCC[C@H](c2nc3cccc(N4CCN(C5CC5)CC4)n3c2CO)N1C]
I-112

TABLE 1-continued
Exemplary Compounds
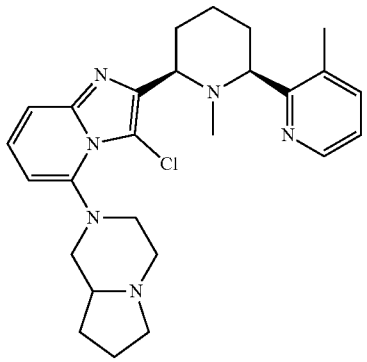 [SMILES: Cc1cccnc1[C@@H]1CCC[C@H](c2nc3cccc(N4CCN5CCCC5C4)n3c2Cl)N1C] I-113
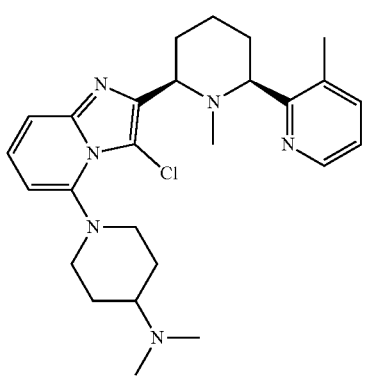 [SMILES: Cc1cccnc1[C@@H]1CCC[C@H](c2nc3cccc(N4CCC(N(C)C)CC4)n3c2Cl)N1C] I-114
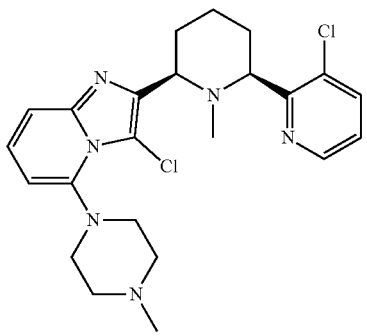 I-115
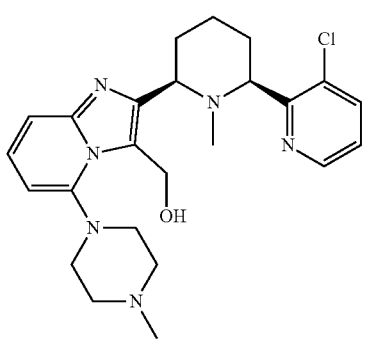 [SMILES: CN1CCN(c2cccc3nc([C@H]4CCC[C@@H](c5ncccc5Cl)N4C)c(CO)n23)CC1] I-116
TABLE 1-continued
Exemplary Compounds
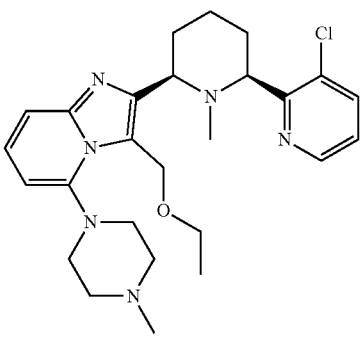 [SMILES: CCOCc1c([C@H]2CCC[C@@H](c3ncccc3Cl)N2C)nc2cccc(N3CCN(C)CC3)n12] I-117
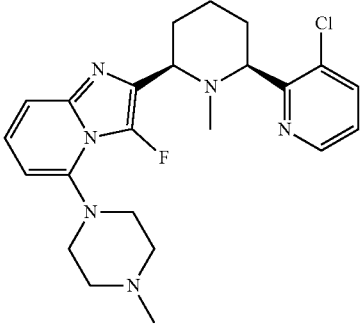 [SMILES: CN1CCN(c2cccc3nc([C@H]4CCC[C@@H](c5ncccc5Cl)N4C)c(F)n23)CC1] I-118
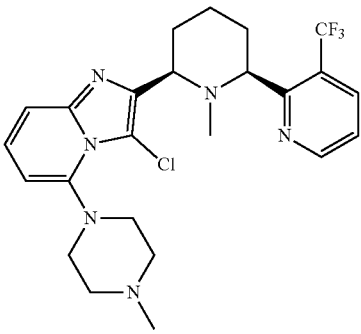 [SMILES: CN1CCN(c2cccc3nc([C@H]4CCC[C@@H](c5ncccc5C(F)(F)F)N4C)c(Cl)n23)CC1] I-119
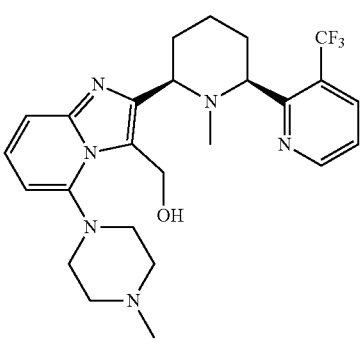 [SMILES: CN1CCN(c2cccc3nc([C@H]4CCC[C@@H](c5ncccc5C(F)(F)F)N4C)c(CO)n23)CC1] I-120

TABLE 1-continued
Exemplary Compounds
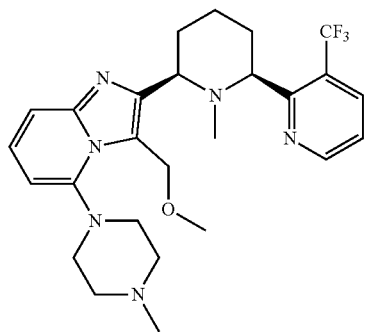 [SMILES: COCc1c([C@H]2CCC[C@@H](c3ncccc3C(F)(F)F)N2C)nc2cccc(N3CCN(C)CC3)n12] I-121
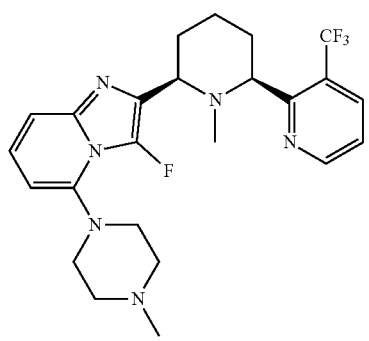 [SMILES: CN1CCN(c2cccc3nc([C@H]4CCC[C@@H](c5ncccc5C(F)(F)F)N4C)c(F)n23)CC1] I-122
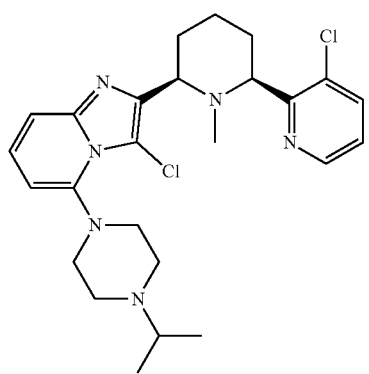 [SMILES: CC(C)N1CCN(c2cccc3nc([C@H]4CCC[C@@H](c5ncccc5Cl)N4C)c(F)n23)CC1] I-123
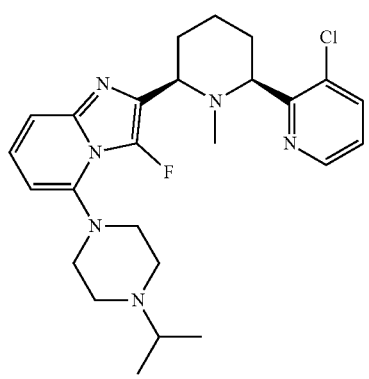 I-124
TABLE 1-continued
Exemplary Compounds
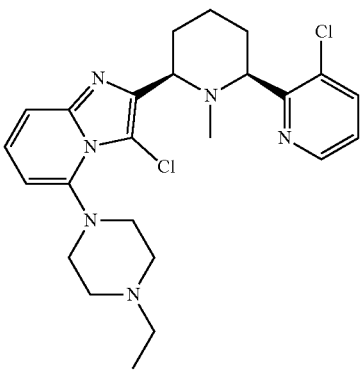 [SMILES: CCN1CCN(c2cccc3nc([C@H]4CCC[C@@H](c5ncccc5Cl)N4C)c(Cl)n23)CC1] I-125
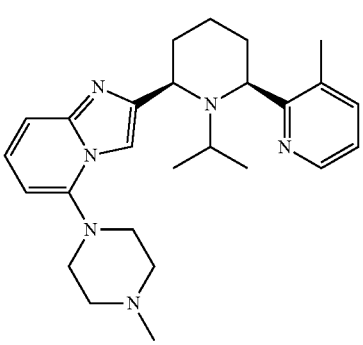 [SMILES: Cc1cccnc1[C@@H]1CCC[C@H](c2cn3c(N4CCN(C)CC4)cccc3n2)N1C(C)C] I-126
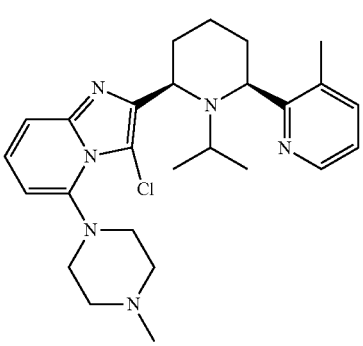 [SMILES: Cc1cccnc1[C@@H]1CCC[C@H](c2nc3cccc(N4CCN(C)CC4)n3c2Cl)N1C(C)C] I-127
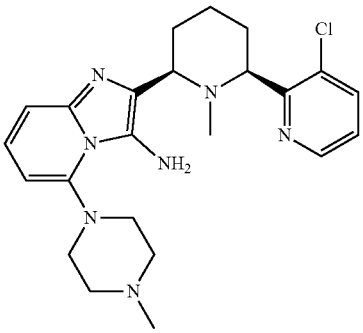 [SMILES: CN1CCN(c2cccc3nc([C@H]4CCC[C@@H](c5ncccc5Cl)N4C)c(N)n23)CC1] I-128

TABLE 1-continued
Exemplary Compounds
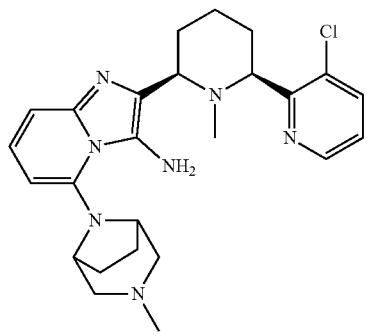 [SMILES: CN1CC2CCC(C1)N2c1cccc2nc([C@H]3CCC[C@@H](c4ncccc4Cl)N3C)c(N)n12]
I-129
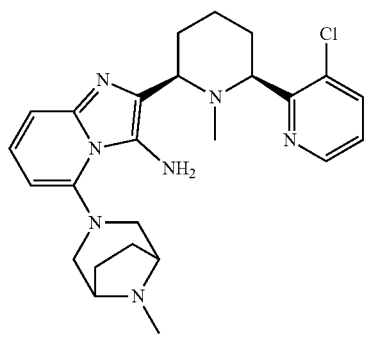 [SMILES: CN1C2CCC1CN(c1cccc3nc([C@H]4CCC[C@@H](c5ncccc5Cl)N4C)c(N)n13)C2]
I-130
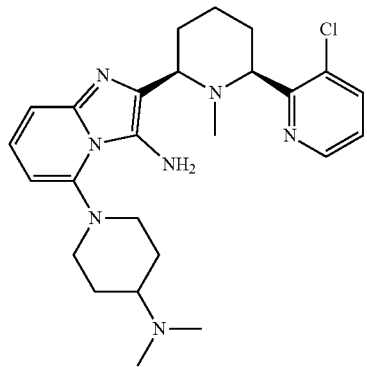 [SMILES: CN(C)C1CCN(c2cccc3nc([C@H]4CCC[C@@H](c5ncccc5Cl)N4C)c(N)n23)CC1]
I-131
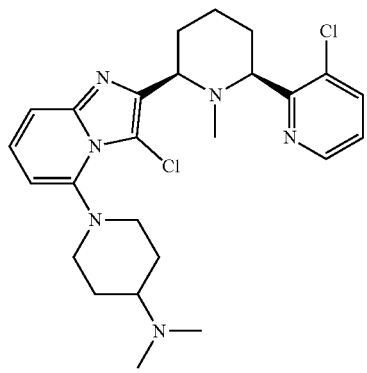 [SMILES: CN(C)C1CCN(c2cccc3nc([C@H]4CCC[C@@H](c5ncccc5Cl)N4C)c(Cl)n23)CC1]
I-132
TABLE 1-continued
Exemplary Compounds
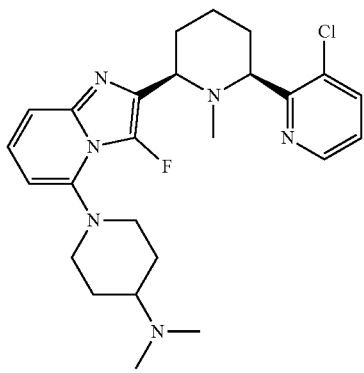 [SMILES: CN(C)C1CCN(c2cccc3nc([C@H]4CCC[C@@H](c5ncccc5Cl)N4C)c(F)n23)CC1]
I-133
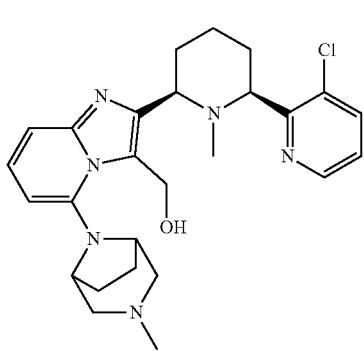 [SMILES: CN1CC2CCC(C1)N2c1cccc2nc([C@H]3CCC[C@@H](c4ncccc4Cl)N3C)c(CO)n12]
I-134
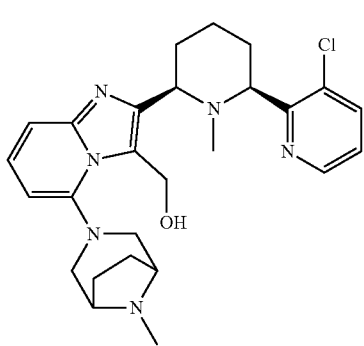 [SMILES: CN1C2CCC1CN(c1cccc3nc([C@H]4CCC[C@@H](c5ncccc5Cl)N4C)c(CO)n13)C2]
I-135
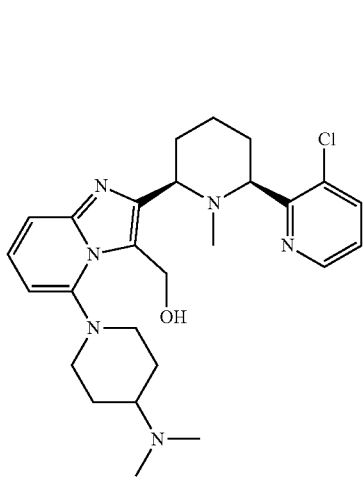 [SMILES: CN(C)C1CCN(c2cccc3nc([C@H]4CCC[C@@H](c5ncccc5Cl)N4C)c(CO)n23)CC1]
I-136

TABLE 1-continued
Exemplary Compounds
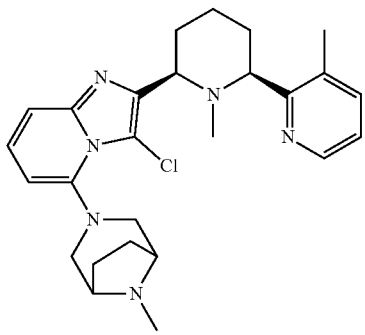 [SMILES: Cc1cccnc1[C@@H]1CCC[C@H](c2nc3cccc(N4CC5CCC(C4)N5C)n3c2Cl)N1C]
I-137
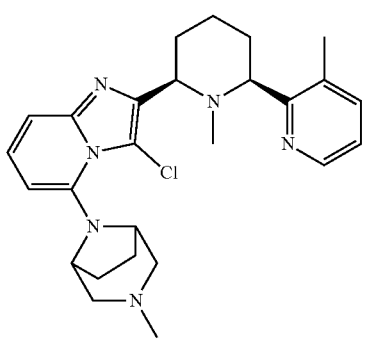 [SMILES: Cc1cccnc1[C@@H]1CCC[C@H](c2nc3cccc(N4C5CCC4CN(C)C5)n3c2Cl)N1C]
I-138
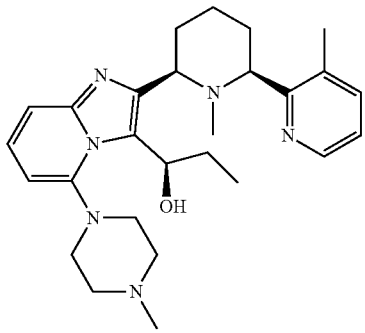 [SMILES: CC[C@@H](O)c1c([C@H]2CCC[C@@H](c3ncccc3C)N2C)nc2cccc(N3CCN(C)CC3)n12]
I-139
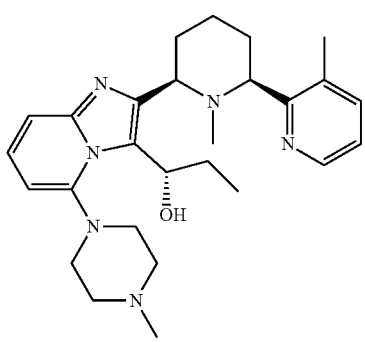 [SMILES: CC[C@H](O)c1c([C@H]2CCC[C@@H](c3ncccc3C)N2C)nc2cccc(N3CCN(C)CC3)n12]
I-140
TABLE 1-continued
Exemplary Compounds
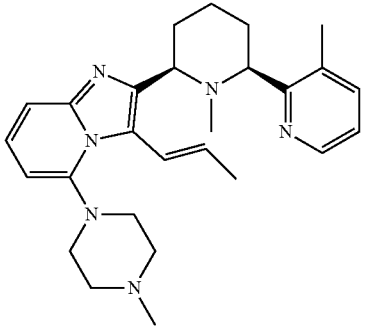 [SMILES: C/C=C/c1c([C@H]2CCC[C@@H](c3ncccc3C)N2C)nc2cccc(N3CCN(C)CC3)n12]
I-141
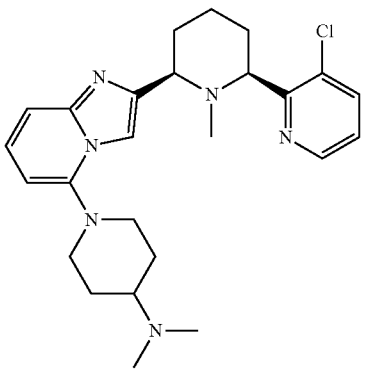 [SMILES: CN(C)C1CCN(c2cccc3nc([C@H]4CCC[C@@H](c5ncccc5Cl)N4C)cn23)CC1]
I-142
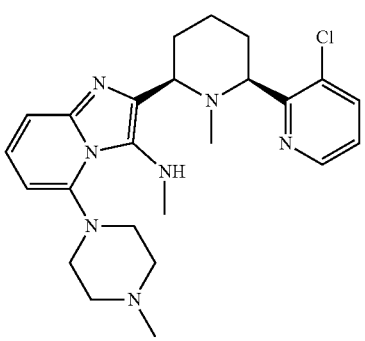 [SMILES: CNc1c([C@H]2CCC[C@@H](c3ncccc3Cl)N2C)nc2cccc(N3CCN(C)CC3)n12]
I-143
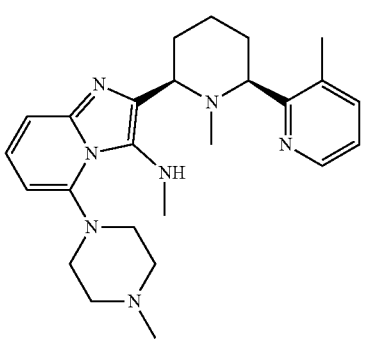 [SMILES: CNc1c([C@H]2CCC[C@@H](c3ncccc3C)N2C)nc2cccc(N3CCN(C)CC3)n12]
I-144

TABLE 1-continued
Exemplary Compounds
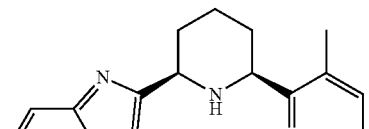
I-145
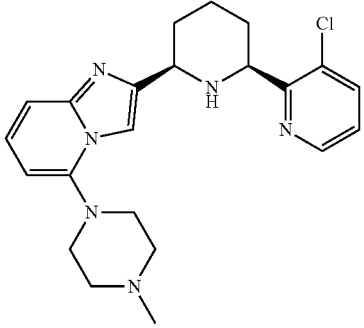 [SMILES: CN1CCN(c2cccc3nc([C@H]4CCC[C@@H](c5ncccc5Cl)N4)cn23)CC1]
I-149
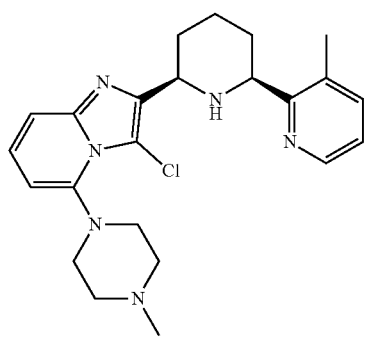
I-146
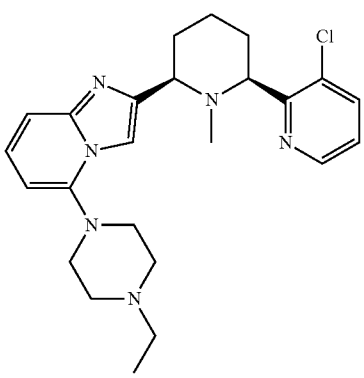 [SMILES: CCN1CCN(c2cccc3nc([C@H]4CCC[C@@H](c5ncccc5Cl)N4C)cn23)CC1]
I-150
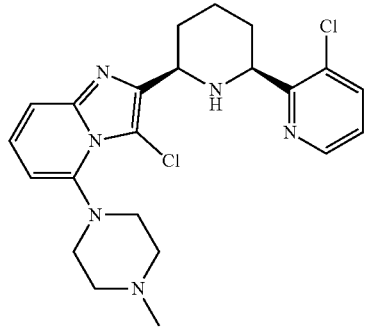
I-147
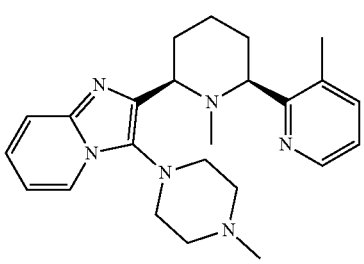 [SMILES: Cc1cccnc1[C@@H]1CCC[C@H](c2nc3ccccn3c2N2CCN(C)CC2)N1C]
I-151
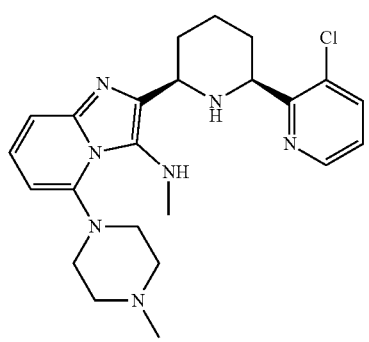
I-148
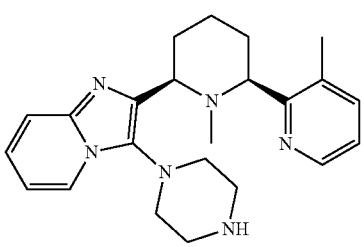 [SMILES: Cc1cccnc1[C@@H]1CCC[C@H](c2nc3ccccn3c2N2CCNCC2)N1C]
I-152
I-153

TABLE 1-continued
Exemplary Compounds
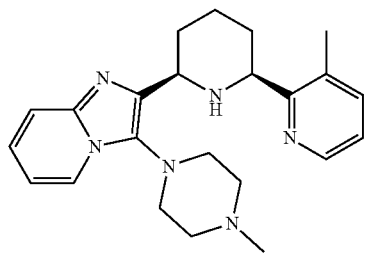 [SMILES: Cc1cccnc1[C@@H]1CCC[C@H](c2nc3ccccn3c2N2CCN(C)CC2)N1]
I-154
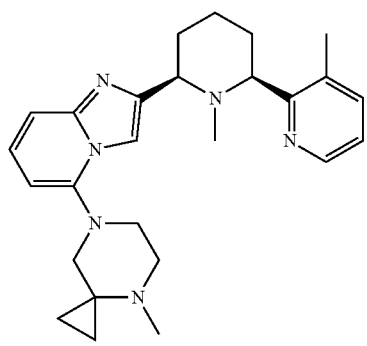 [SMILES: Cc1cccnc1[C@@H]1CCC[C@H](c2cn3c(N4CCN(C)C5(CC5)C4)cccc3n2)N1C]
I-155
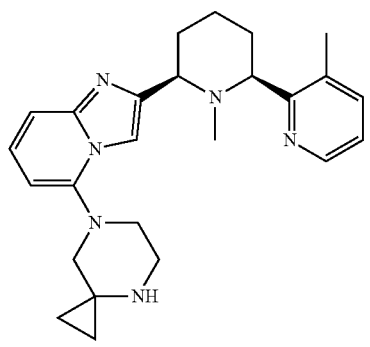 [SMILES: Cc1cccnc1[C@@H]1CCC[C@H](c2cn3c(N4CCNC5(CC5)C4)cccc3n2)N1C]
I-156
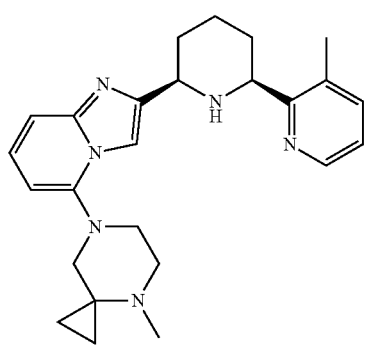 [SMILES: Cc1cccnc1[C@@H]1CCC[C@H](c2cn3c(N4CCN(C)C5(CC5)C4)cccc3n2)N1]
I-157
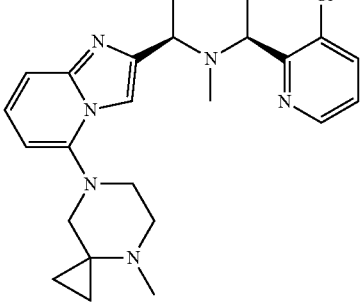
I-158
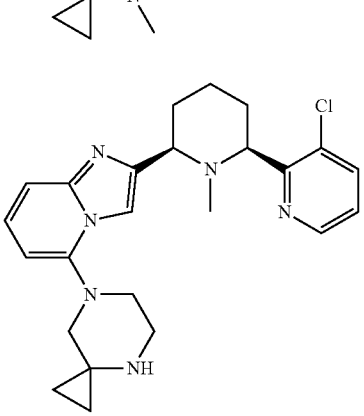
I-159
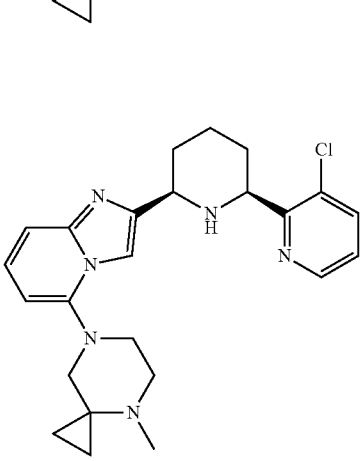
I-160
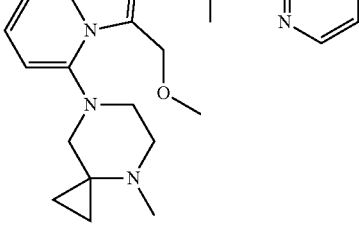
I-161

TABLE 1-continued
Exemplary Compounds
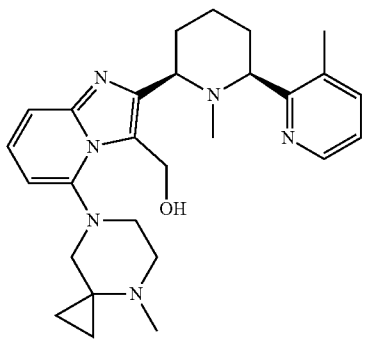 [SMILES: Cc1cccnc1[C@@H]1CCC[C@H](c2nc3cccc(N4CCN(C)C5(CC5)C4)n3c2CO)N1C]
I-162
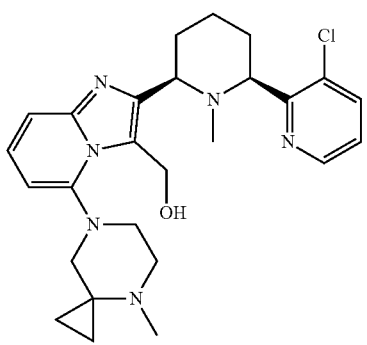 [SMILES: CN1[C@@H](c2nc3cccc(N4CCN(C)C5(CC5)C4)n3c2CO)CCC[C@H]1c1ncccc1Cl]
I-163
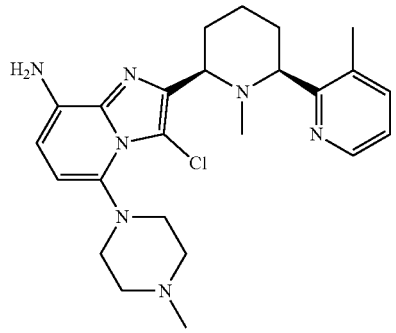 [SMILES: Cc1cccnc1[C@@H]1CCC[C@H](c2nc3c(N)ccc(N4CCN(C)CC4)n3c2Cl)N1C]
I-164
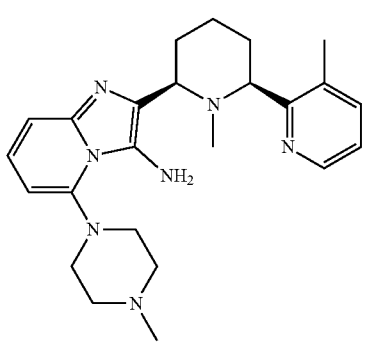 [SMILES: Cc1cccnc1[C@@H]1CCC[C@H](c2nc3cccc(N4CCN(C)CC4)n3c2N)N1C]
I-165
TABLE 1-continued
Exemplary Compounds
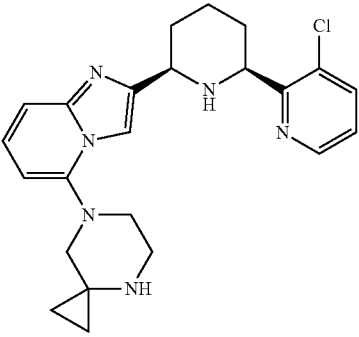
I-166
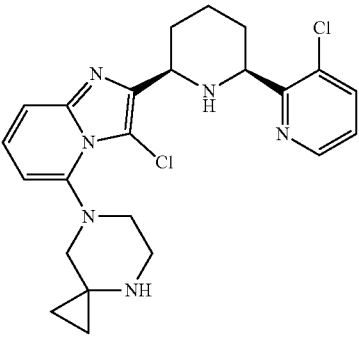 [SMILES: Clc1cccnc1[C@@H]1CCC[C@H](c2nc3cccc(N4CCNC5(CC5)C4)n3c2Cl)N1]
I-167
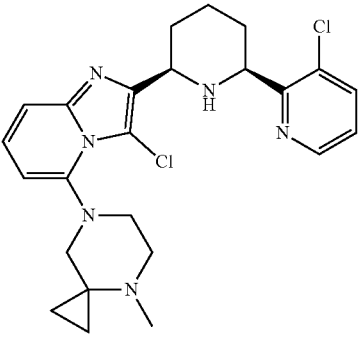 [SMILES: CN1CCN(c2cccc3nc([C@H]4CCC[C@@H](c5ncccc5Cl)N4)c(Cl)n23)CC12CC2]
I-168
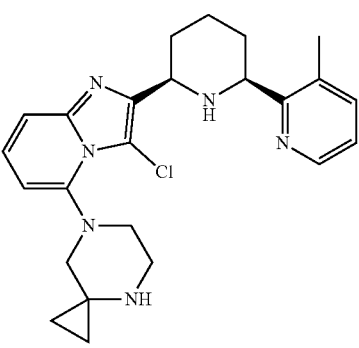 [SMILES: Cc1cccnc1[C@@H]1CCC[C@H](c2nc3cccc(N4CCNC5(CC5)C4)n3c2Cl)N1]
I-169

TABLE 1-continued
Exemplary Compounds
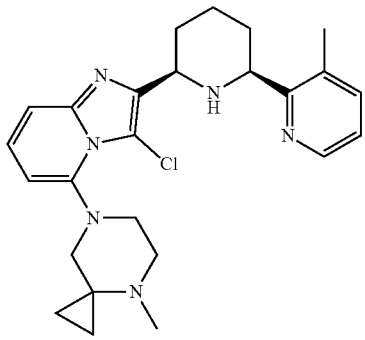 I-170
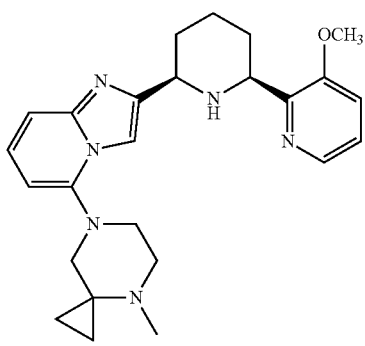 [SMILES: COc1cccnc1[C@@H]1CCC[C@H](c2cn3c(N4CCN(C)C5(CC5)C4)cccc3n2)N1] I-171
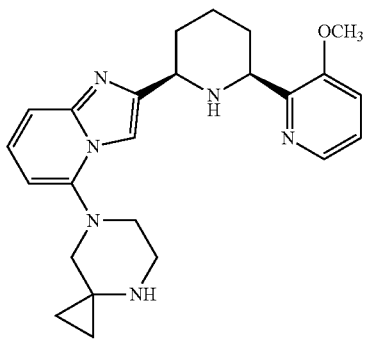 [SMILES: COc1cccnc1[C@@H]1CCC[C@H](c2cn3c(N4CCNC5(CC5)C4)cccc3n2)N1] I-172
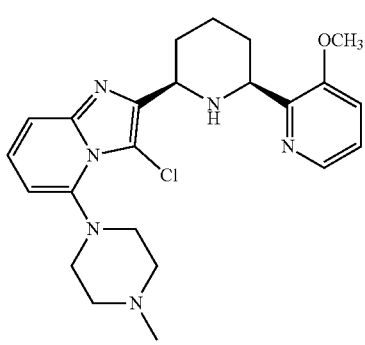 [SMILES: COc1cccnc1[C@@H]1CCC[C@H](c2nc3cccc(N4CCN(C)CC4)n3c2Cl)N1] I-173
TABLE 1-continued
Exemplary Compounds
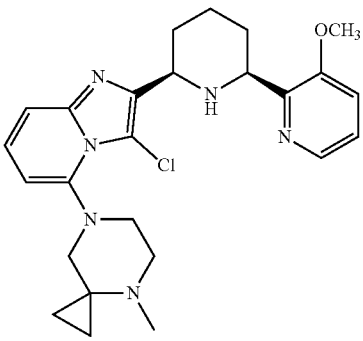 [SMILES: COc1cccnc1[C@@H]1CCC[C@H](c2nc3cccc(N4CCN(C)C5(CC5)C4)n3c2Cl)N1] I-174
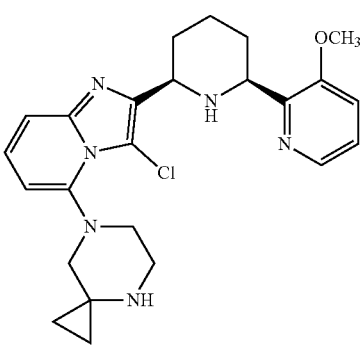 [SMILES: COc1cccnc1[C@@H]1CCC[C@H](c2nc3cccc(N4CCNC5(CC5)C4)n3c2Cl)N1] I-175
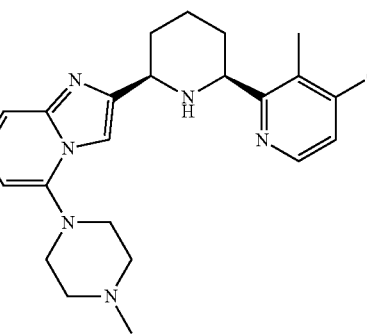 I-176
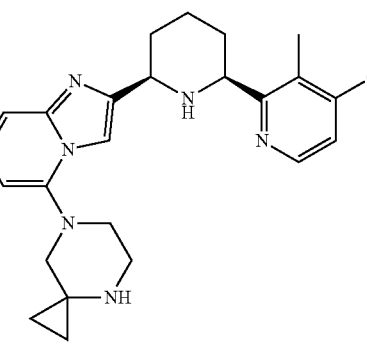 I-177

TABLE 1-continued
Exemplary Compounds
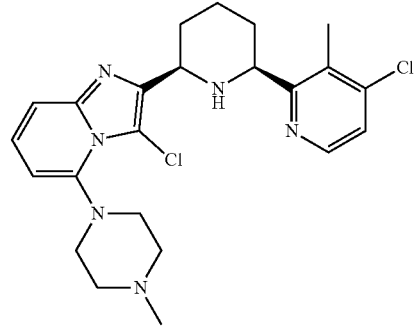 [SMILES: Cc1c(Cl)ccnc1[C@@H]1CCC[C@H](c2nc3cccc(N4CCN(C)CC4)n3c2Cl)N1]
I-178
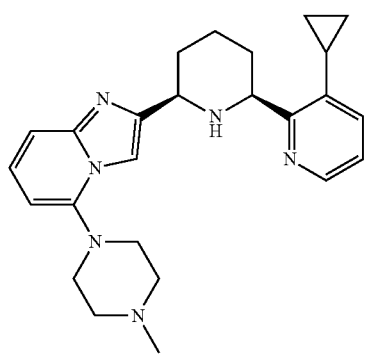 [SMILES: CN1CCN(c2cccc3nc([C@H]4CCC[C@@H](c5ncccc5C5CC5)N4)cn23)CC1]
I-179
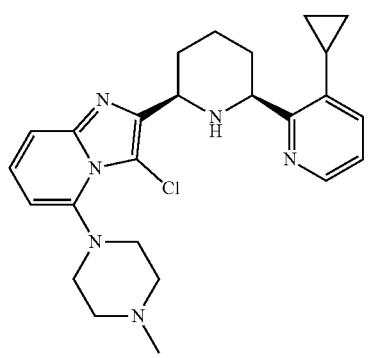 [SMILES: CN1CCN(c2cccc3nc([C@H]4CCC[C@@H](c5ncccc5C5CC5)N4)c(Cl)n23)CC1]
I-180
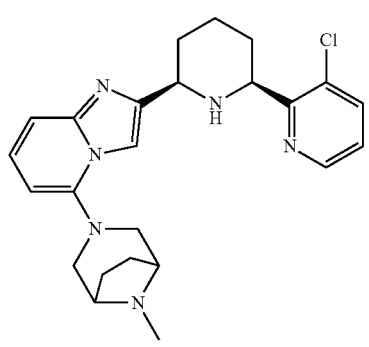 [SMILES: CN1C2CCC1CN(c1cccc3nc([C@H]4CCC[C@@H](c5ncccc5Cl)N4)cn13)C2]
I-181
TABLE 1-continued
Exemplary Compounds
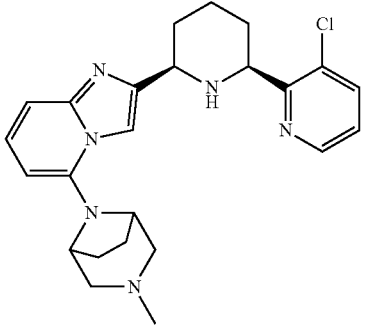 [SMILES: CN1CC2CCC(C1)N2c1cccc2nc([C@H]3CCC[C@@H](c4ncccc4Cl)N3)cn12]
I-182
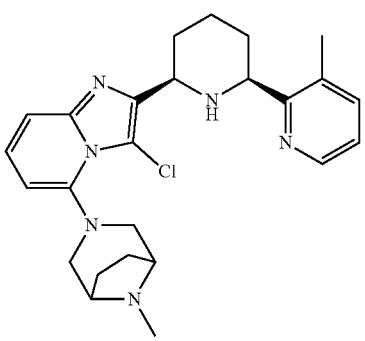 [SMILES: Cc1cccnc1[C@@H]1CCC[C@H](c2nc3cccc(N4CC5CCC(C4)N5C)n3c2Cl)N1]
I-183
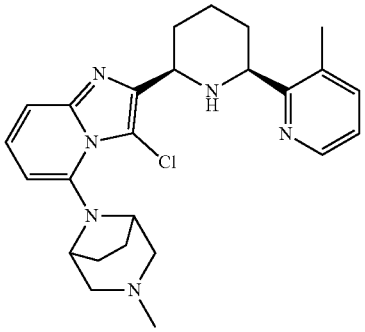 [SMILES: Cc1cccnc1[C@@H]1CCC[C@H](c2nc3cccc(N4C5CCC4CN(C)C5)n3c2Cl)N1]
I-184
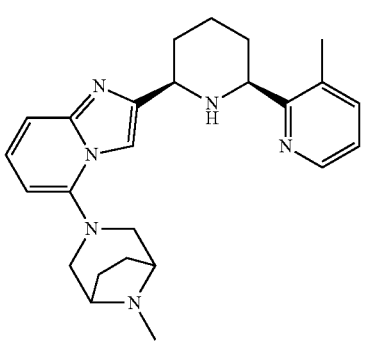 [SMILES: Cc1cccnc1[C@@H]1CCC[C@H](c2cn3c(N4CC5CCC(C4)N5C)cccc3n2)N1]
I-185

TABLE 1-continued
Exemplary Compounds
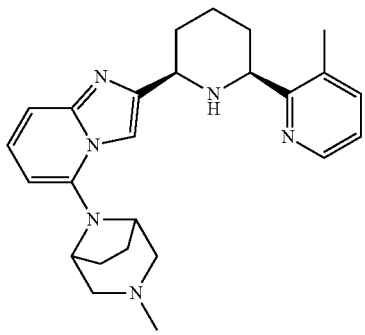 [SMILES: Cc1cccnc1[C@@H]1CCC[C@H](c2cn3c(N4C5CCC4CN(C)C5)cccc3n2)N1] I-186
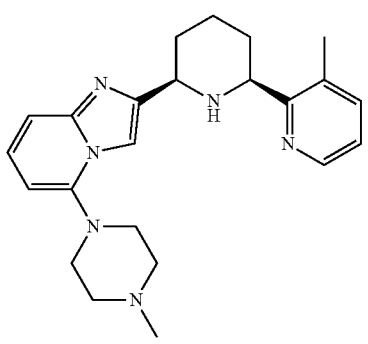 [SMILES: Cc1cccnc1[C@@H]1CCC[C@H](c2cn3c(N4CCN(C)CC4)cccc3n2)N1] I-187
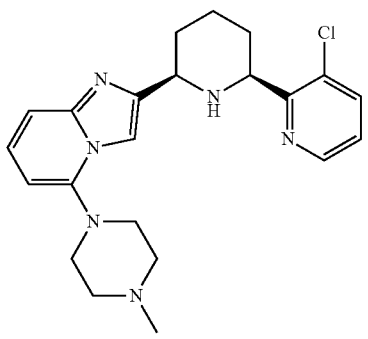 [SMILES: CN1CCN(c2cccc3nc([C@H]4CCC[C@@H](c5ncccc5Cl)N4)cn23)CC1] I-188
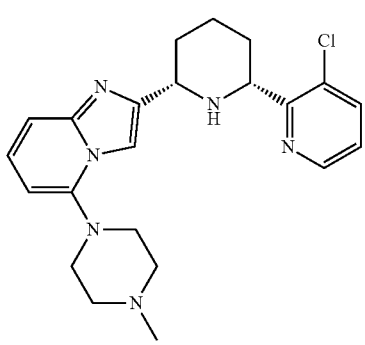 [SMILES: CN1CCN(c2cccc3nc([C@@H]4CCC[C@H](c5ncccc5Cl)N4)cn23)CC1] I-189
TABLE 1-continued
Exemplary Compounds
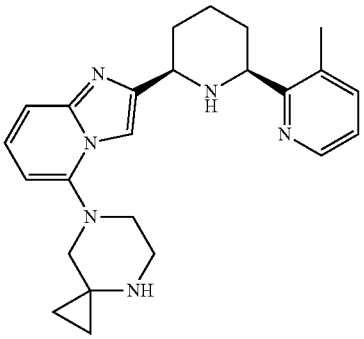 [SMILES: Cc1cccnc1[C@@H]1CCC[C@H](c2cn3c(N4CCNC5(CC5)C4)cccc3n2)N1] I-190
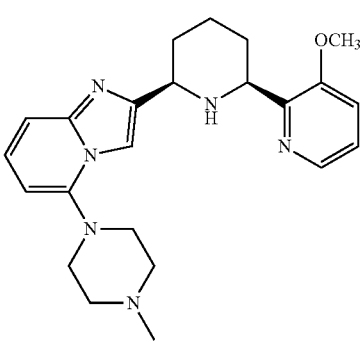 [SMILES: COc1cccnc1[C@@H]1CCC[C@H](c2cn3c(N4CCN(C)CC4)cccc3n2)N1] I-191
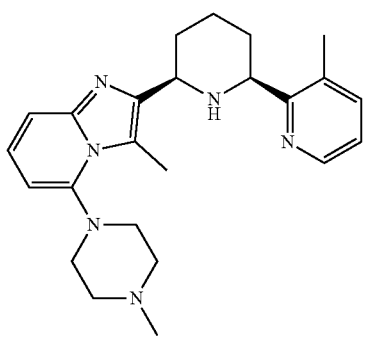 [SMILES: Cc1cccnc1[C@@H]1CCC[C@H](c2nc3cccc(N4CCN(C)CC4)n3c2C)N1] I-192
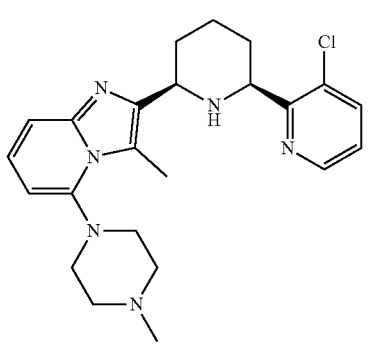 [SMILES: Cc1c([C@H]2CCC[C@@H](c3ncccc3Cl)N2)nc2cccc(N3CCN(C)CC3)n12] I-193

TABLE 1-continued
Exemplary Compounds
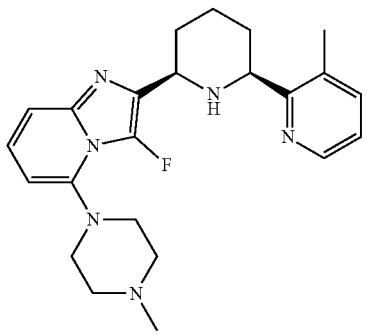 [SMILES: Cc1cccnc1[C@@H]1CCC[C@H](c2nc3cccc(N4CCN(C)CC4)n3c2F)N1]
I-194
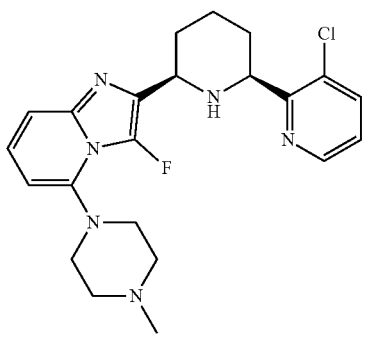 [SMILES: CN1CCN(c2cccc3nc([C@H]4CCC[C@@H](c5ncccc5Cl)N4)c(F)n23)CC1]
I-195
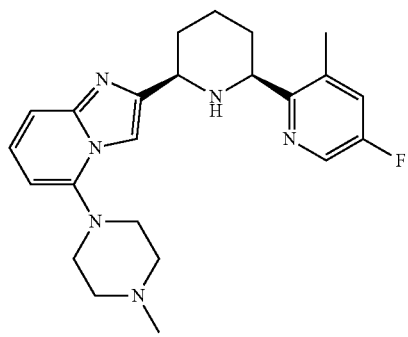 [SMILES: Cc1cc(F)cnc1[C@@H]1CCC[C@H](c2cn3c(N4CCN(C)CC4)cccc3n2)N1]
I-196
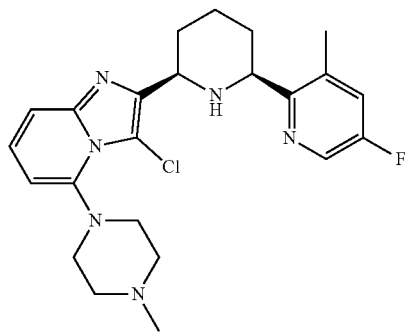 [SMILES: Cc1cc(F)cnc1[C@@H]1CCC[C@H](c2nc3cccc(N4CCN(C)CC4)n3c2Cl)N1]
I-197
TABLE 1-continued
Exemplary Compounds
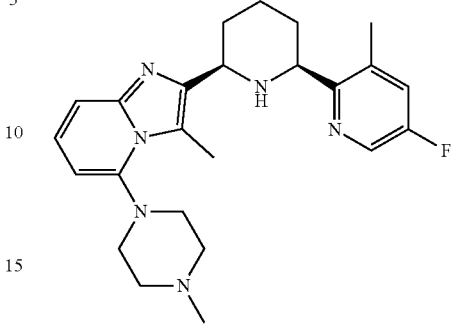
I-198
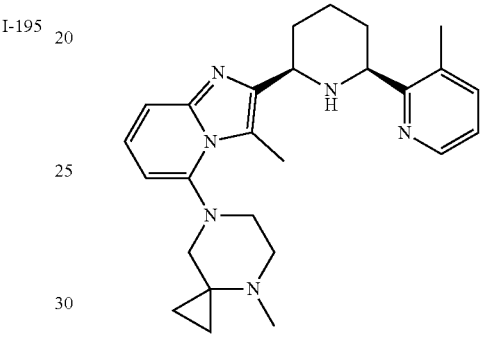
I-199
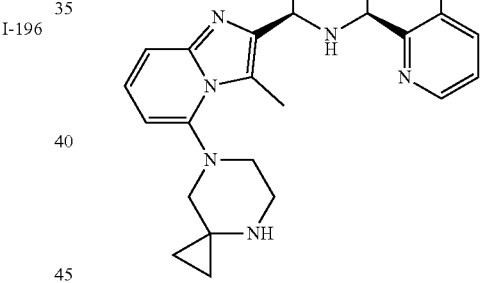
I-200
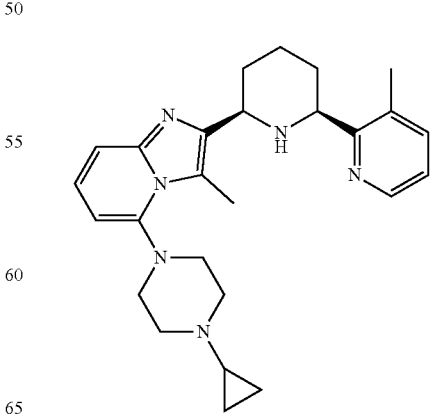
I-201

TABLE 1-continued
Exemplary Compounds
I-202 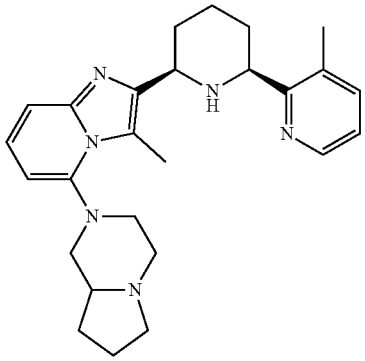 [SMILES: Cc1cccnc1[C@@H]1CCC[C@H](c2nc3cccc(N4CCN5CCCC5C4)n3c2C)N1]
I-203 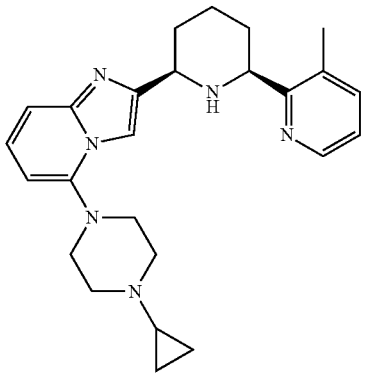 [SMILES: Cc1cccnc1[C@@H]1CCC[C@H](c2cn3c(N4CCN(C5CC5)CC4)cccc3n2)N1]
I-204 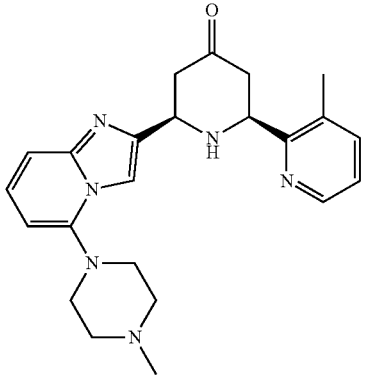 [SMILES: Cc1cccnc1[C@@H]1CC(=O)C[C@H](c2cn3c(N4CCN(C)CC4)cccc3n2)N1]
I-205 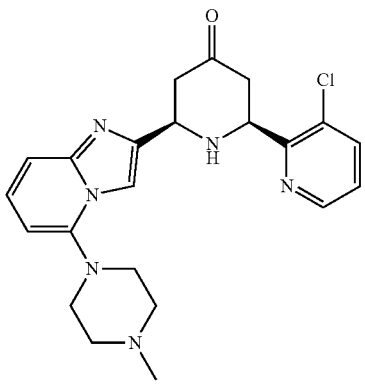 [SMILES: CN1CCN(c2cccc3nc([C@H]4CC(=O)C[C@@H](c5ncccc5Cl)N4)cn23)CC1]
I-206 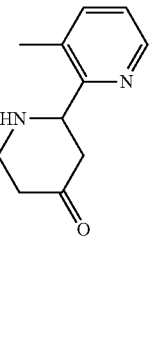
I-207 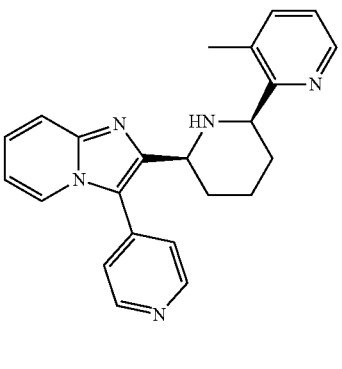 [SMILES: Cc1cccnc1[C@H]1CCC[C@@H](c2nc3ccccn3c2-c2ccncc2)N1]
I-208 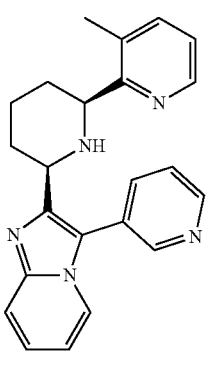 [SMILES: Cc1cccnc1[C@@H]1CCC[C@H](c2nc3ccccn3c2-c2cccnc2)N1]
I-209 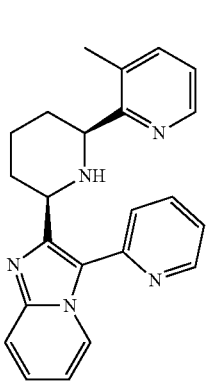 [SMILES: Cc1cccnc1[C@@H]1CCC[C@H](c2nc3ccccn3c2-c2ccccn2)N1]

TABLE 1-continued
Exemplary Compounds
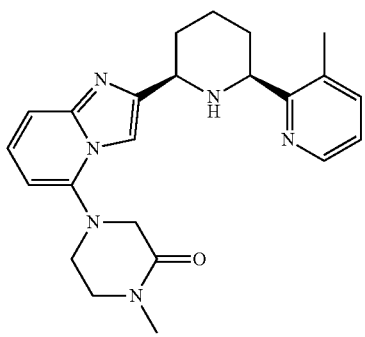 [SMILES: Cc1cccnc1[C@@H]1CCC[C@H](c2cn3c(N4CCN(C)C(=O)C4)cccc3n2)N1] I-210
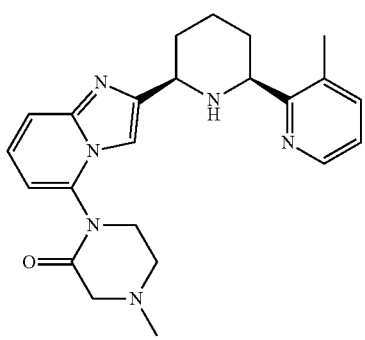 [SMILES: Cc1cccnc1[C@@H]1CCC[C@H](c2cn3c(N4CCN(C)CC4=O)cccc3n2)N1] I-211
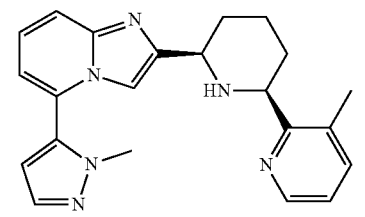 [SMILES: Cc1cccnc1[C@@H]1CCC[C@H](c2cn3c(-c4ccnn4C)cccc3n2)N1] I-212
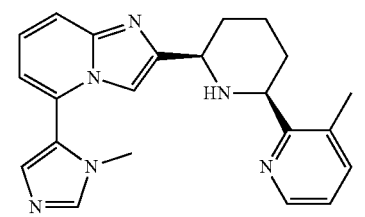 I-213
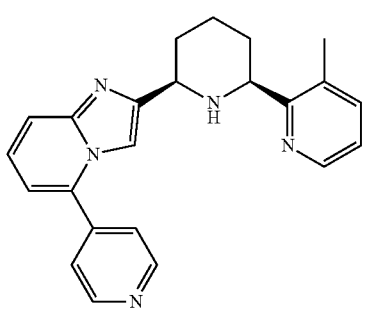 [SMILES: Cc1cccnc1[C@@H]1CCC[C@H](c2cn3c(-c4ccncc4)cccc3n2)N1] I-214
TABLE 1-continued
Exemplary Compounds
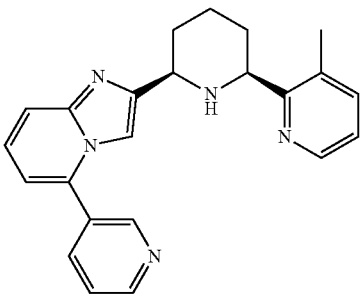 [SMILES: Cc1cccnc1[C@@H]1CCC[C@H](c2cn3c(-c4cccnc4)cccc3n2)N1] I-215
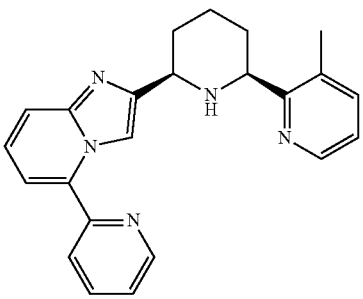 [SMILES: Cc1cccnc1[C@@H]1CCC[C@H](c2cn3c(-c4ccccn4)cccc3n2)N1] I-216
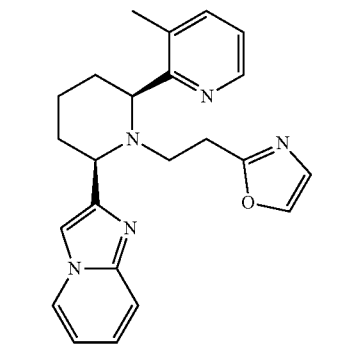 [SMILES: Cc1cccnc1[C@@H]1CCC[C@H](c2cn3ccccc3n2)N1CCc1ncco1] I-217
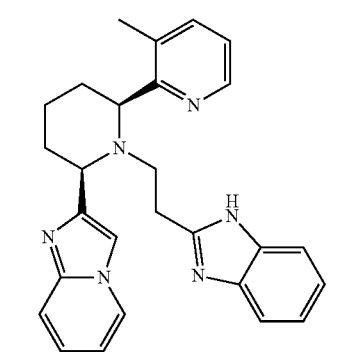 [SMILES: Cc1cccnc1[C@@H]1CCC[C@H](c2cn3ccccc3n2)N1CCc1nc2ccccc2[nH]1] I-218
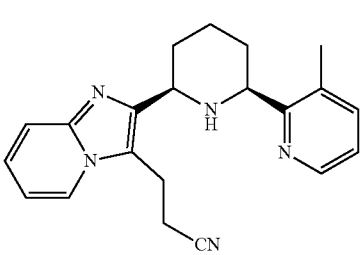 [SMILES: Cc1cccnc1[C@@H]1CCC[C@H](c2nc3ccccn3c2CCC#N)N1] I-219

TABLE 1-continued
Exemplary Compounds
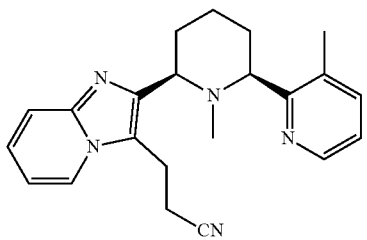 [SMILES: Cc1cccnc1[C@@H]1CCC[C@H](c2nc3ccccn3c2CCC#N)N1C]
I-220
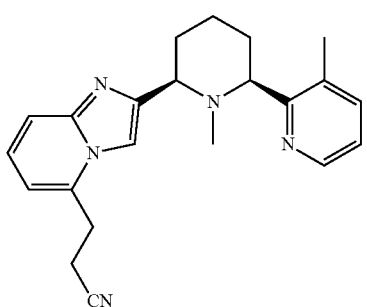 [SMILES: Cc1cccnc1[C@@H]1CCC[C@H](c2cn3c(CCC#N)cccc3n2)N1C]
I-221
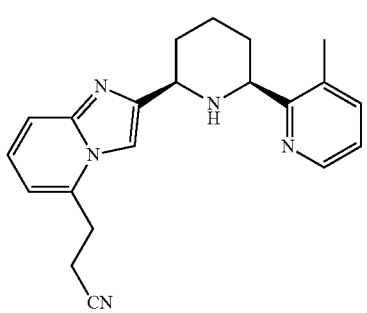 [SMILES: Cc1cccnc1[C@@H]1CCC[C@H](c2cn3c(CCC#N)cccc3n2)N1]
I-222
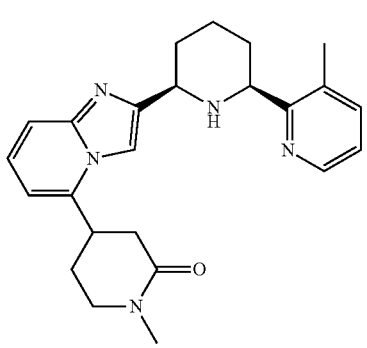 [SMILES: Cc1cccnc1[C@@H]1CCC[C@H](c2cn3c(C4CCN(C)C(=O)C4)cccc3n2)N1]
I-223
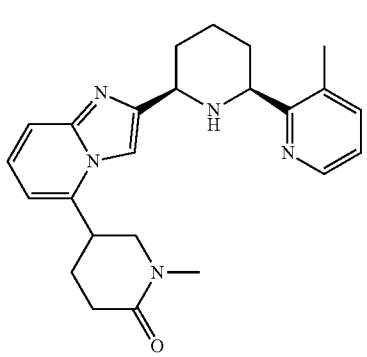 [SMILES: Cc1cccnc1[C@@H]1CCC[C@H](c2cn3c(C4CCC(=O)N(C)C4)cccc3n2)N1]
I-224
TABLE 1-continued
Exemplary Compounds
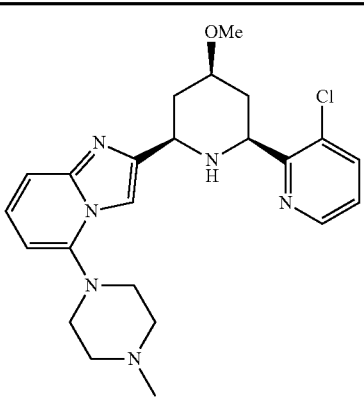
I-225
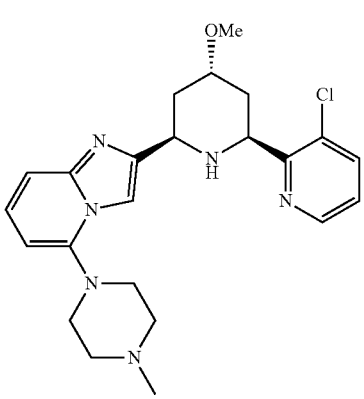 [SMILES: CO[C@@H]1C[C@@H](c2ncccc2Cl)N[C@@H](c2cn3c(N4CCN(C)CC4)cccc3n2)C1]
I-226
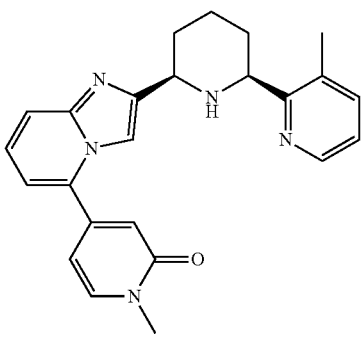 [SMILES: Cc1cccnc1[C@@H]1CCC[C@H](c2cn3c(-c4ccn(C)c(=O)c4)cccc3n2)N1]
I-227
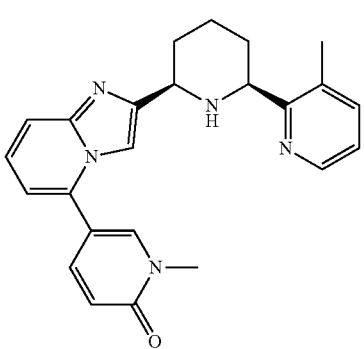 [SMILES: Cc1cccnc1[C@@H]1CCC[C@H](c2cn3c(-c4ccc(=O)n(C)c4)cccc3n2)N1]
I-228

TABLE 1-continued

Exemplary Compounds

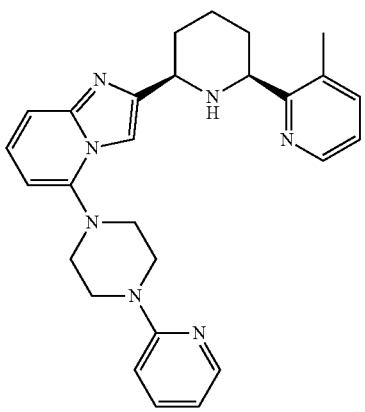 [SMILES: Cc1cccnc1[C@@H]1CCC[C@H](c2cn3c(N4CCN(c5ccccn5)CC4)cccc3n2)N1]

I-229

Note:
Stereochemistry arbitrarily assigned for I-188 and I-189; each compound was isolated in stereochemically enriched form; compound I-149 corresponds to their racemate.

In some embodiments, the present invention provides a compound set forth in Table 1, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group ("PG"), leaving group ("LG"), or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "leaving group" (LG) includes, but is not limited to, halogens (e.g. fluoride, chloride, bromide, iodide), sulfonates (e.g. mesylate, tosylate, benzenesulfonate, brosylate, nosylate, triflate), diazonium, and the like.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, New York, 1994, the entireties of which is incorporated herein by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetyl), crotonate, 4-methoxy-crotonate, benzoate, p-benzylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, and Philip Kocienski, in "Protecting Groups", Georg Thieme Verlag Stuttgart, New York, 1994, the entireties of which is incorporated herein by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See, for example, "March's Advanced Organic Chemistry", 5$^{th}$ Ed., Ed.: Smith, M. B. and March, J., John Wiley & Sons, New York: 2001, the entirety of which is incorporated herein by reference. Such interconversions may require one or more of the aforementioned techniques, and certain methods for synthesizing compounds of the invention are described below.

In one aspect, certain compounds of the present invention of Formula I, or subformulae thereof, are generally prepared according to Scheme 1 set forth below:

Scheme 1

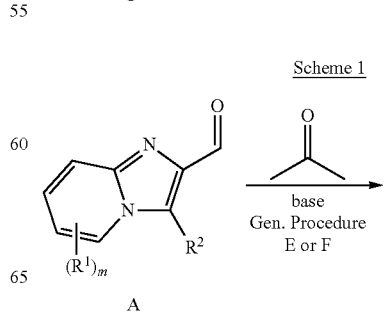

A

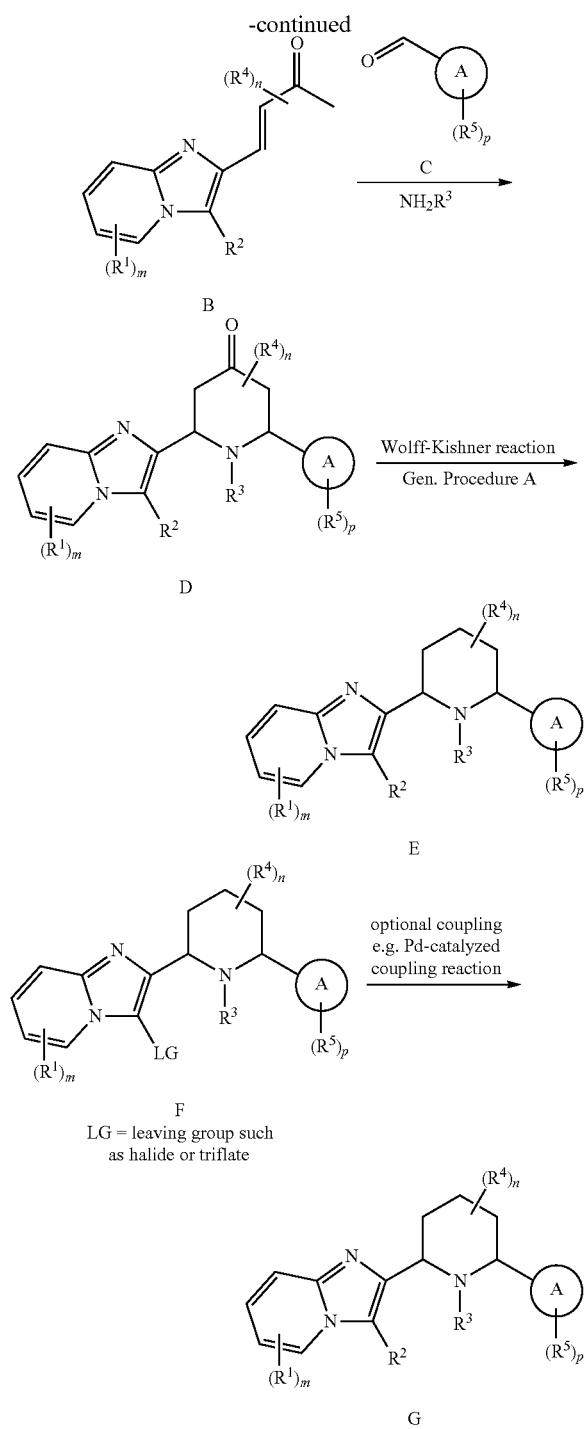

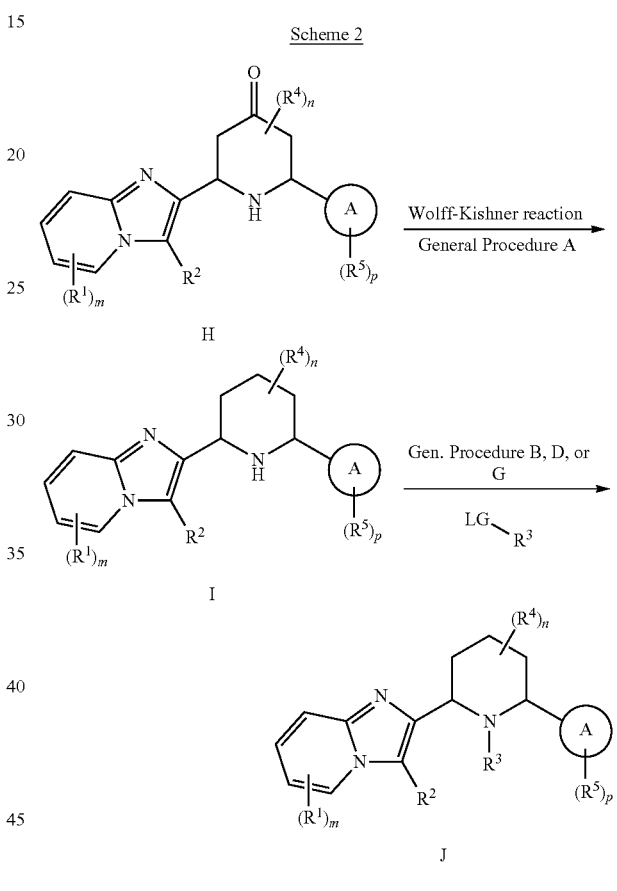

In Scheme 1 above, PG is a nitrogen protecting group, and each of $R^1$, $R^2$, $R^3$, $R^4$, $R^5$, Ring A, m, n, and p is as defined above and described in embodiments herein, both singly and in combination.

As shown generally in Scheme 1, an aldehyde according to structure A may be condensed with a ketone such as acetone in the presence of a base to yield intermediate B, for example by following General Procedures E or F. The General Procedures are described in more detail in the Exemplification, below. Condensation with an amine such as $NH_2R^3$, e.g. methylamine, and an aldehyde of structure C, provides compounds of structure D. In some embodiments, such compounds are CXCR4 inhibitors according to the present invention. In other embodiments, compounds of structure D are reduced according to General Procedure A to provide compounds of structure E. In compounds of structure F where $R^2$ is an appropriate leaving group (LG), cross-coupling (such as Pd-catalyzed coupling) may be performed to provide compounds of structure G. If $R^2$ is hydrogen in structure F, halogenation or formation of a leaving group such as triflate precedes the coupling reaction. Alternatively, if $R^2$ is hydrogen in structure F, alkylation such as a formylation with paraformaldehyde or DMF may be used to provide certain compounds of structure G.

Alternatively, as shown in Scheme 2, piperidone compounds of structure H may be reduced according to General Procedure A to afford compounds of structure I and subsequently reacted with an appropriate electrophile of formula LG-$R^3$, wherein LG refers to an appropriate leaving group such as halide or mesylate, affording compounds of structure J.

5. Uses, Formulation and Administration, and Co-Administered Additional Therapeutic Agents Pharmaceutically Acceptable Compositions According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit CXCR4, or a mutant thereof, in a biological sample or in a patient. In certain embodiments, the amount of compound in compositions of this invention is such that is effective to measurably inhibit CXCR4, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of CXCR4, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the inhibition of CXCR4 or a mutant thereof.

The activity of a compound utilized in this invention as an inhibitor of CXCR4, or a mutant thereof, may be assayed in vitro, in vivo or in a cell line. In vitro assays include assays that determine inhibition of CXCR4, or a mutant thereof. Alternate in vitro assays quantitate the ability of the inhibitor to bind to CXCR4. Detailed conditions for assaying a compound utilized in this invention as an inhibitor of CXCR4, or a mutant thereof, are set forth in the Examples below.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are inhibitors of CXCR4 and are therefore useful for treating one or more disorders associated with activity of CXCR4. Thus, in certain embodiments, the present invention provides a method for treating a CXCR4-mediated disorder comprising the step of administering to a patient in need thereof a compound of the present invention, or pharmaceutically acceptable composition thereof.

As used herein, the terms "CXCR4-mediated" disorders, diseases, and/or conditions as used herein means any disease or other deleterious condition in which CXCR4, or a mutant thereof, is known to play a role. Accordingly, another embodiment of the present invention relates to treating or lessening the severity of one or more diseases in which CXCR4, or a mutant thereof, are known to play a role.

In some embodiments, the present invention provides a method for treating one or more disorders, diseases, and/or conditions wherein the disorder, disease, or condition includes, but is not limited to, a cellular proliferative disorder.

Cellular Proliferative Disorders

The present invention features methods and compositions for the diagnosis and prognosis of cellular proliferative disorders (e.g., cancer) and the treatment of these disorders by targeting CXCR4. Cellular proliferative disorders described herein include, e.g., cancer, obesity, and proliferation-dependent diseases. Such disorders may be diagnosed using methods known in the art.

Cancer

Cancer includes, in one embodiment, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I—Pilocytic Astrocytoma, Grade II—Low-grade Astrocytoma, Grade III—Anaplastic Astrocytoma, or Grade IV—Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the present invention provides a method for treating a cancer that presents as a solid tumor, such as a sarcoma, carcinoma, or lymphoma, comprising the step of administering a disclosed compound, or a pharmaceutically acceptable salt thereof, to a patient in need thereof. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a tumor in a patient in need thereof, comprising administering to the patient any of the compounds, salts or pharmaceutical compositions described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the the tumor comprises small cell lung cancer (SCLC). In some embodiments the the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Primary Immune Deficiencies

In some embodiments, the present invention provides a method for treating one or more disorders, diseases, and/or conditions wherein the disorder, disease, or condition includes, but is not limited to, a primary immunodeficiency disease or disorder, comprising administering to a patient in need thereof an effective amount of a disclosed compound. Primary immune deficiencies treatable by the methods of the present invention include: warts, hypogammaglobulinemia, infections, myelokathexis (WHIMs) syndrome; severe congenital neutropenia (SCN), especially those arising from G6PC3 deficiency (McDermott et al. (2010) Blood 116: 2793-2802); GATA2 deficiency (Mono MAC syndrome) (Maciejweski-Duval et al. (2015) J. Leukoc. Biol. 5MA0815-288R (Epub. ahead of printing); idiopathic CD4+ T lymphocytopenia (ICL); and Wiskott-Aldrich Syndrome.

The compounds and compositions, according to the method of the present invention, may be administered using any amount and any route of administration effective for treating or lessening the severity of a cancer, an autoimmune disorder, a primary immune deficiency, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the disease or disorder, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting CXCR4 activity in a biological sample comprising the step of contacting said biological sample with a compound of this invention, or a composition comprising said compound.

According to another embodiment, the invention relates to a method of inhibiting CXCR4, or a mutant thereof, activity in a biological sample comprising the step of contacting said biological sample with a compound of this invention, or a composition comprising said compound. In certain embodiments, the invention relates to a method of irreversibly inhibiting CXCR4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of inhibiting CXCR4 in a patient comprising the step of administering to said patient a compound of the present invention, or a composition comprising said compound.

According to another embodiment, the invention relates to a method of inhibiting CXCR4, or a mutant thereof, activity in a patient comprising the step of administering to said patient a compound of the present invention, or a composition comprising said compound. According to certain embodiments, the invention relates to a method of irreversibly inhibiting CXCR4, or a mutant thereof, activity in a patient comprising the step of administering to said patient a compound of the present invention, or a composition comprising said compound. In other embodiments, the present invention provides a method for treating a disorder mediated by CXCR4, or a mutant thereof, in a patient in need thereof, comprising the step of administering to said patient a compound according to the present invention or pharmaceutically acceptable composition thereof. Such disorders are described in detail herein.

Co Administration of Additional Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

In some embodiments, the additional therapeutic agent is selected from an immunostimulatory therapeutic compound. In some embodiments, the immunostimulatory therapeutic compound is selected from elotuzumab, mifamurtide, an agonist or activator of a toll-like receptor, or an activator of RORγt.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, an immunostimulatory therapeutic compound, and an immune checkpoint inhibitor.

Other checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Other checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Other checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Other checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Other checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Other checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Other checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Other checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Other checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Other checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-054 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Other checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor.

In some embodiments, the IDO inhibitor is selected from epacadostat, indoximod, capmanitib, GDC-0919, PF-06840003, BMS:F001287, Phy906/KD108, or an enzyme that breaks down kynurenine.

In some embodiments, the PARP inhibitor is selected from olaparib, rucaparib, or niraparib.

In some embodiments, the HDAC inhibitor is selected from vorinostat, romidepsin, panobinostat, belinostat, entinostat, or chidamide.

In some embodiments, the CDK 4/6 inhibitor is selected from palbociclib, ribociclib, abemaciclib or trilaciclib.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from an indoleamine (2,3)-dioxygenase (IDO) inhibitor, a Poly ADP ribose polymerase (PARP) inhibitor, a histone deacetylase (HDAC) inhibitor, a CDK4/CDK6 inhibitor, or a phosphatidylinositol 3 kinase (PI3K) inhibitor, and a third therapeutic agent selected from an immune checkpoint inhibitor. In some embodiments, the immune checkpoint inhibitor is selected from nivolumab, pembrolizumab, ipilimumab, avelumab, durvalumab, atezolizumab, or pidilizumab.

Another immunostimulatory therapeutic that may be used in the present invention is recombinant human interleukin 15 (rhIL-15). rhIL-15 has been tested in the clinic as a therapy for melanoma and renal cell carcinoma (NCT01021059 and NCT01369888) and leukemias (NCT02689453). Another immunostimulatory therapeutic that may be used in the present invention is recombinant human interleukin 12 (rhIL-12). Another suitable IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). Recombinant human interleukin 12 (rhIL-12) has been tested in the clinic for many oncological indications, for example, as a therapy for lymphoma (NM-IL-12, Neumedicines, Inc.), (NCT02544724 and NCT02542124).

In some embodiments, the PI3K inhibitor is selected from idelalisib, alpelisib, taselisib, pictilisib, copanlisib, duvelisib, PQR309, or TGR1202.

In another aspect, the present invention provides a method of treating cancer in a patient in need thereof, wherein said method comprises administering to said patient a compound disclosed herein or a pharmaceutically acceptable salt thereof in combination with one or more additional therapeutic agents selected from a platinum-based therapeutic, a taxane, a nucleoside inhibitor, or a therapeutic agent that interferes with normal DNA synthesis, protein synthesis, cell replication, or will otherwise inhibit rapidly proliferating cells.

In some embodiments, the platinum-based therapeutic is selected from cisplatin, carboplatin, oxaliplatin, nedaplatin, picoplatin, or satraplatin.

In some embodiments, the taxane is selected from paclitaxel, docetaxel, albumin-bound paclitaxel, cabazitaxel, or SID530.

In some embodiments, the therapeutic agent that interferes with normal DNA synthesis, protein synthesis, cell replication, or will otherwise interfere with the replication of rapidly proliferating cells is selected from trabectedin, mechlorethamine, vincristine, temozolomide, cytarabine, lomustine, azacitidine, omacetaxine mepesuccinate, asparaginase *Erwinia chrysanthemi*, eribulin mesylate, capacetrine, bendamustine, ixabepilone, nelarabine, clorafabine, trifluridine, or tipiracil.

In some embodiments, the method further comprises administering to said patient a third therapeutic agent, such as an immune checkpoint inhibitor. In some embodiments, the method comprises administering to the patient in need thereof three therapeutic agents selected from a compound disclosed herein or a pharmaceutically acceptable salt thereof, a second therapeutic agent selected from a platinum-based therapeutic, a taxane, a nucleoside inhibitor, or a therapeutic agent that interferes with normal DNA synthesis, protein synthesis, cell replication, or will otherwise inhibit rapidly proliferating cells, and a third therapeutic agent selected from an immune checkpoint inhibitor.

In some embodiments, the immune checkpoint inhibitor is selected from nivolumab, pembrolizumab, ipilimumab, avelumab, durvalumab, atezolizumab, or pidilizumab.

In some embodiments, any one of the foregoing methods further comprises the step of obtaining a biological sample from the patient and measuring the amount of a disease-related biomarker.

In some embodiments, the biological sample is a blood sample.

In some embodiments, the disease-related biomarker is selected from circulating CD8+ T cells or the ratio of CD8+ T cells:Treg cells.

In one aspect, the present invention provides a method of treating an advanced cancer, comprising administering a compound disclosed herein or a pharmaceutically acceptable salt thereof or pharmaceutical composition thereof, either as a single agent (monotherapy), or in combination with a chemotherapeutic, a targeted therapeutic, such as a kinase inhibitor, and/or an immunomodulatory therapy, such as an immune checkpoint inhibitor. In some embodiments, the immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the additional therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, the additional therapeutic agent is an mTOR inhibitor, which inhibits cell proliferation, angiogenesis and glucose uptake. Approved mTOR inhibitors useful in the present invention include everolimus (Afinitor®, Novartis); temsirolimus (Torisel®, Pfizer); and sirolimus (Rapamune®, Pfizer).

In some embodiments, the additional therapeutic agent is a Poly ADP ribose polymerase (PARP) inhibitor. Approved PARP inhibitors useful in the present invention include olaparib (Lynparza®, AstraZeneca); rucaparib (Rubraca®, Clovis Oncology); and niraparib (Zejula®, Tesaro). Other PARP inhibitors being studied which may be used in the present invention include talazoparib (MDV3800/BMN 673/LT00673, Medivation/Pfizer/Biomarin); veliparib (ABT-888, AbbVie); and BGB-290 (BeiGene, Inc.).

In some embodiments, the additional therapeutic agent is a phosphatidylinositol 3 kinase (PI3K) inhibitor. Approved PI3K inhibitors useful in the present invention include idelalisib (Zydelig®, Gilead). Other PI3K inhibitors being studied which may be used in the present invention include alpelisib (BYL719, Novartis); taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the additional therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, the additional therapeutic agent is a histone deacetylase (HDAC) inhibitor. Approved HDAC inhibitors useful in the present invention include vorinostat (Zolinza®, Merck); romidepsin (Istodax®, Celgene); panobinostat (Farydak®, Novartis); and belinostat (Beleodaq®, Spectrum Pharmaceuticals). Other HDAC inhibitors being studied which may be used in the present invention include entinostat (SNDX-275, Syndax Pharmaceuticals) (NCT00866333); and chidamide (Epidaza®, HBI-8000, Chipscreen Biosciences, China).

In some embodiments, the additional therapeutic agent is a CDK inhibitor, such as a CDK 4/6 inhibitor. Approved CDK 4/6 inhibitors useful in the present invention include palbociclib (Ibrance®, Pfizer); and ribociclib (Kisqali®, Novartis). Other CDK 4/6 inhibitors being studied which may be used in the present invention include abemaciclib (Ly2835219, Eli Lilly); and trilaciclib (G1T28, G1 Therapeutics).

In some embodiments, the additional therapeutic agent is an indoleamine (2,3)-dioxygenase (IDO) inhibitor. IDO inhibitors being studied which may be used in the present invention include epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); and an enzyme that breaks down kynurenine (Kynase, Kyn Therapeutics).

In some embodiments, the additional therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, the additional therapeutic agent is an aromatase inhibitor. Approved aromatase inhibitors which may be used in the present invention include exemestane (Aromasin®, Pfizer); anastazole (Arimidex®, AstraZeneca) and letrozole (Femora®, Novartis).

In some embodiments, the additional therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, the additional therapeutic agent is a folic acid inhibitor. Approved folic acid inhibitors useful in the present invention include pemetrexed (Alimta®, Eli Lilly).

In some embodiments, the additional therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, the additional therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, the additional therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, the additional therapeutic agent is a glutaminase inhibitor. Glutaminase inhibitors being studied which may be used in the present invention include CB-839 (Calithera Biosciences).

In some embodiments, the additional therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, the additional therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, the additional therapeutic agent is a nucleoside inhibitor, or other therapeutic that interfere with normal DNA synthesis, protein synthesis, cell replication, or will otherwise inhibit rapidly proliferating cells. Such nucleoside inhibitors or other therapeutics include trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, the additional therapeutic agent is a platinum-based therapeutic, also referred to as platins. Platins cause cross-linking of DNA, such that they inhibit DNA repair and/or DNA synthesis, mostly in rapidly reproducing cells, such as cancer cells. Approved platinum-based therapeutics which may be used in the present invention include cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); and nedaplatin (Aqupla®, Shionogi). Other platinum-based therapeutics which have undergone clinical testing and may be used in the present invention include picoplatin (Poniard Pharmaceuticals); and satraplatin (JM-216, Agennix).

In some embodiments, the additional therapeutic agent is a taxane compound, which causes disruption of microtubules, which are essential for cell division. Approved taxane compounds which may be used in the present invention include paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), and cabazitaxel (Jevtana®, Sanofi-Aventis). Other taxane compounds which have undergone clinical testing and may be used in the present invention include SID530 (SK Chemicals, Co.) (NCT00931008).

In some embodiments, the additional therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, the present invention provides a method of treating prostate cancer comprising administering to a patient in need thereof an effective amount of a compound disclosed herein or a pharmaceutically acceptable salt thereof or pharmaceutical composition thereof in combination with an additional therapeutic agent that interferes with the synthesis or activity of androgens. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, the additional therapeutic agent is a selective estrogen receptor modulator (SERM), which interferes with the synthesis or activity of estrogens. Approved SERMs useful in the present invention include raloxifene (Evista®, Eli Lilly).

In some embodiments, the additional therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, the additional therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, the additional therapeutic agent is an inhibitor of transforming growth factor-beta (TGF-beta or TGFß). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGFß trap compound (NCT02699515); and (NCT02517398). M7824 is comprised of a fully human IgG1 antibody against PD-L1 fused to the extracellular domain of human TGF-beta receptor II, which functions as a TGFß "trap."

Additional Co Administered Therapeutic Agents—Targeted Therapeutics and Immunomodulatory Drugs In some embodiments, the additional therapeutic agent is selected from a targeted therapeutic or immunomodulatory drug. Adjuvant therapies with targeted therapeutics or immunomodulatory drugs have shown promising effectiveness when administered alone but are limited by the development of tumor immunity over time or evasion of the immune response.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a targeted therapeutic or an immunomodulatory drug. In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In other embodiments, the immunomodulatory therapeutic is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, the additional therapeutic agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, the additional therapeutic agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-

E2F-delta24-hTNFa-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, the present invention comprises administering to said patient a compound disclosed herein or a pharmaceutically acceptable salt thereof in combination with a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

Additional Co-Administered Therapeutic Agents—Immunostimulatory Drugs

In some embodiments, the additional therapeutic agent is an immunostimulatory drug. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the present invention provides a method of treating cancer, such as a cancer described herein, comprising administering to a patient in need thereof an effective amount of a compound disclosed herein or a pharmaceutically acceptable salt thereof or pharmaceutical composition thereof in combination with an additional therapeutic agent such as a immunostimulatory drug, such as an immune checkpoint inhibitor. In some embodiments, the compound and the checkpoint inhibitor are administered simultaneously or sequentially. In some embodiments, a compound disclosed herein is administered prior to the initial dosing with the immune checkpoint inhibitor. In certain embodiments, the immune checkpoint inhibitor is administered prior to the initial dosing with the compound disclosed herein.

In certain embodiments, the immune checkpoint inhibitor is selected from a PD-1 antagonist, a PD-L1 antagonist, or a CTLA-4 antagonist. In some embodiments, a CXCR4 antagonist such as a compound disclosed herein or a pharmaceutically acceptable salt thereof is administered in combination with nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); or atezolizumab (anti-PD-L1 antibody, Tecentriq®, Genentech).

Other immune checkpoint inhibitors suitable for use in the present invention include REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; and PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

Another paradigm for immune-stimulation is the use of oncolytic viruses. In some embodiments, the present invention provides a method for treating a patient by administering a CXCR4 antagonist such as a compound disclosed herein or a pharmaceutically acceptable salt thereof or pharmaceutical composition thereof in combination with an immunostimulatory therapy such as oncolytic viruses. Approved immunostimulatory oncolytic viruses which may be used in the present invention include talimogene laherparepvec (live, attenuated herpes simplex virus, Imlygic®, Amgen).

In some embodiments, the additional therapeutic agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. An activator of RORγt, that is being studied which may be used in the present invention is LYC-55716 (Lycera), which is currently being evaluated in clinical trials for the treatment of solid tumors (NCT02929862).

In some embodiments, the additional therapeutic agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other checkpoint inhibitors that may be used in the present invention include inhibitors of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

Other checkpoint inhibitors that may be used in the present invention include inhibitors of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

Checkpoint inhibitors that may be used in the present invention also include inhibitors of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Other immune-oncology agents that may be used in the present invention in combination with CXCR4 inhibitors such as a compound disclosed herein include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

Other additional therapeutic agents that may be used in the present invention include glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

A compound of the current invention may also be used to advantage in combination with other antiproliferative compounds. Such antiproliferative compounds include, but are not limited to checkpoint inhibitors; aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd$_6$244 from AstraZeneca, PD181461 from Pfizer and leucovorin.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signalling processes should proceed.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™ Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™.

Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™ Pamidronic acid is marketed under the trade name Aredia™. Alendronic acid is marketed under the trade name Fosamax™. Ibandronic acid is marketed under the trade name Bondranat™ Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88.

The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; Zd$_6$474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 μg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

General Synthetic Methods

The following examples are intended to illustrate the invention and are not to be construed as being limitations thereon. Unless otherwise stated, one or more tautomeric forms of compounds of the examples described hereinafter may be prepared in situ and/or isolated. All tautomeric forms of compounds of the examples described hereafter should be considered to be disclosed. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Abbreviations equiv or eq: molar equivalents
o/n: overnight
rt: room temperature
UV: ultra violet
HPLC: high pressure liquid chromatography
Rt: retention time
LCMS or LC-MS: liquid chromatography-mass spectrometry
NMR: nuclear magnetic resonance
CC: column chromatography
TLC: thin layer chromatography
sat: saturated
aq: aqueous
Ac: acetyl
DCM: dichloromethane
DCE: dichloroethane
DEA: diethylamine
DMF: dimethylformamide
DMSO: dimethylsulfoxide
ACN or MeCN: acetonitrile
DIPEA: diisopropylethylamine
EA or EtOAc: ethyl acetate
BINAP: (±)-2,2'-Bis(diphenylphosphino)-1,1'-binaphthalene
TEA: triethylamine
THF: tetrahydrofuran
TBS: tert-butyldimethylsilyl
KHMDS: potassium hexamethyl disilylazide
Tf: trifluoromethanesulfonate
Ms: methanesulfonyl
NBS: N-bromosuccinimide
PE: petroleum ether
TFA: trifluoroacetic acid
MMPP: magnesium monoperoxyphthalate
HATU: 1-[Bis(dimethylamino)methylene]-1H-1,2,3-triazolo[4,5-b]pyridinium 3-oxid Hexafluorophosphate
NCS: N-chlorosuccinimide
Cy: cyclohexyl
Tol: toluene
DMP: Dess-Martin periodinane
IBX: 2-iodoxybenzoic acid
PMB: p-methoxybenzyl
SEM: [2-(Trimethylsilyl)ethoxy]methyl
XPhos or X-Phos: 2-Dicyclohexylphosphino-2',4',6'-triisopropylbiphenyl General Information:

All evaporations were carried out in vacuo with a rotary evaporator. Analytical samples were dried in vacuo (1-5 mmHg) at rt. Thin layer chromatography (TLC) was performed on silica gel plates, spots were visualized by UV light (214 and 254 nm). Purification by column and flash chromatography was carried out using silica gel (200-300 mesh). Solvent systems are reported as mixtures by volume. All $^1$H NMR spectra were recorded on a Bruker 400 (400 MHz) spectrometer. $^1$H chemical shifts are reported in δ values in parts per million (ppm) with the deuterated solvent as the internal standard. Data are reported as follows: chemical shift, multiplicity (s=singlet, d=doublet, t=triplet, q=quartet, br=broad, m=multiplet), coupling constant (Hz), integration (i.e. number of protons). LCMS spectra were obtained on an Agilent 1200 series 6110 or 6120 mass spectrometer with electrospray ionization and except as otherwise indicated, the general LCMS conditions were as follows: Waters X Bridge C18 column (50 mm*4.6 mm*3.5 μm), Flow Rate: 2.0 mL/min, the column temperature: 40° C.

General Procedure A (Wolff-Kishner Reduction):

A mixture of 2,6-diaryl piperidin-4-one (concentration 0.1-1 M), KOH (20 eq.) and $N_2H_4 \cdot H_2O$ (40 eq.) in diethylene glycol was stirred for about 2 hours at 80° C. and then at approx. 150-200° C. until the reaction completed. After cooled down to room temperature, the reaction mixture was diluted with water and extracted with DCM. The organic layer was washed with water and brine, dried over $Na_2SO_4$, filtered and concentrated in vacuum. The residue was purified by column chromatography to give 2,6-diaryl piperidine.

General Procedure B (N-Alkylation of 2,6-Diaryl Piperidine):

To a solution of 2,6-diaryl piperidine (concentration 0.1-1 M) in DMF or ACN was added corresponding halide or mesylate (2 eq.) and $K_2CO_3$ (2 eq.) under Ar atmosphere. The mixture was stirred at 80° C. overnight, then it was diluted with $H_2O$ and extracted with DCM. The combined organic layers were washed with water, dried over $Na_2SO_4$, filtered and concentrated in vacuo to give desired N-alkylated target.

General Procedure C (Reaction of Alcohols with Methanesulfonyl Chloride):

To a solution of alcohol (concentration 0.1-1 M) and Et3N (approx. 2.5 eq.) in DCM was added MsCl (1.2-1.4 eq.) drop wise at −70° C., and the reaction mixture was stirred at room temperature for 30 mins, then the resulting mixture was quenched with $NaHCO_3$ aq. and extracted with DCM. The combined organic layers were washed with water and brine, dried over $Na_2SO_4$ and filtered. The filtrate was concentrated in vacuum to give the corresponding mesylate.

General Procedure D (Reaction of Mesylates or Halides with 2,6-Diaryl Piperidine):

A mixture of 2,6-diaryl piperidine (concentration 0.1-1 M), corresponding mesylate or halide (approx. 2-3 eq.), KI (0.2-0.3 eq.), DIPEA (2-3 eq.) in DMF or ACN was stirred overnight at 60-80° C. and filtered. The filtrate was purified by prep-HPLC to get the alkylated 2,6-diaryl piperidine.

General Procedure E (Reaction of Aryl Aldehyde with Acetone to Give 4-(Heteroaryl or Aryl)but-3-En-2-One):

A mixture of corresponding aryl aldehyde (concentration 0.1-1 M), acetone (20 eq.) and $K_2CO_3$ (1.5-2 eq.) in toluene/ EtOH/$H_2O$ (5:2:1) was stirred at 80° C. for approx. 13 hours and cooled down to room temperature. After diluted with EA, The reaction mixture was filtered through basic silica gel column and washed with DCM/MeOH (100/1). The filtrate was concentrated in vacuum to give 4-(heteroaryl or aryl)but-3-en-2-one which was used in the next step without further purification.

General Procedure F (Reaction of Aryl Aldehyde with Acetone to Give 4-(Heteroaryl or Aryl)but-3-En-2-One):

To a mixture of aryl aldehyde (concentration 0.1-1 M) in acetone were added a solution of NaOH (approx. 8 M, 1.5 eq.) in $H_2O$ at 0° C. The mixture was stirred at 0° C. for 1 hour. Then it was warmed to room temperature and stirred another 2 hours. The solution was adjusted pH to 8 with 35% HCl aq., dried over anhydrous $Na_2SO_4$, filtered and concentrated in vacuo. The residue was purified by column chromatography to give 4-(heteroaryl or aryl)but-3-en-2-one.

General Procedure G (Buchwald Coupling of Aryl Bromide with Alkyl Amine):

A mixture of aryl bromide (concentration 0.1-1 M), alkyl amine (2 eq, 0.2-2 M), $Pd(OAc)_2$ (0.1-0.15 eq), BINAP (0.2-0.3 eq), and $Cs_2CO_3$ (2-4 eq) in toluene was stirred at 75-120° C. overnight. After completed, the reaction mixture was concentrated in vacuum and purified by column chromatography to afford the desired product.

General Procedure H (Suzuki Coupling of Aryl Bromide with Aryl Boronic Acid):

aryl bromide (concentration 0.1-1 M), aryl boronic acid (1.1-1.5 eq), $PdCl_2(dppf)$ (0.05-0.08 eq), and $Na_2CO_3$ aq. (1 M, 2.5 eq) in 1,4-dioxane was stirred at 80-100° C. for 10 mins under microwave irradiation. After the reaction was completed, the mixture was diluted with water and the aqueous layer was extracted with DCM 3 times. The combined organic layers were washed with brine, dried over $Na_2SO_4$ and filtered. The filtrate was concentrated in vacuum and the residue was purified by silica gel column.

General Procedure I (Reductive Amination of Secondary Amine to Tertiary Amine):

To a mixture of secondary amine (concentration 0.1-1 M), corresponding aldehyde or ketone (1-2 eq) and NaBH $(OAc)_3$ (3-6 eq) in DCM was added several drops of acetic acid, and then the mixture was stirred at room temperature for 2-18 h. The mixture was neutralized with saturated $NaHCO_3$ aqueous solution to pH=8-9 and extracted with DCM. The organic layers were washed with brine, dried over $Na_2SO_4$, filtered and concentrated in vacuum to give the desired tertiary amine.

General Procedure J (Boc Cleavage of N-Boc Protected Amines):

To a solution of N-Boc protected amine (concentration 0.1-1 M) in DCM was added TFA (1/15 volume of DCM) at room temperature. The reaction mixture was stirred for 2 h, then concentrated and saturated $NaHCO_3$ aqueous solution was added and the mixture was extracted with DCM. The organic extracts were dried over $Na_2SO_4$, filtered and concentrated to give the free amine as the desired product.

General Procedure K (Halogenation of Imidazo[1,2-a] Pyridine to Give 3-Halogenated Imidazo[1,2-a]Pyridine):

A mixture of imidazo[1,2-a]pyridine derivatives (concentration 0.1-1 M) and NBS or NCS (0.8-0.9 eq) in DCM (10 mL) was stirred at room temperature for 1 hour. After the reaction was completed, the suspension was diluted with water and DCM, the separated organic layer was concentrated by vacuum and the residue was purified by prep-HPLC to give the desired product.

Example 1: Synthesis of I-1 and I-3

Synthetic Scheme for I-1 and I-3

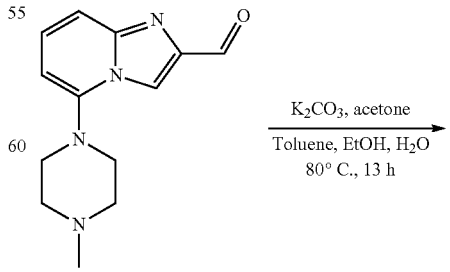

X4-019-6

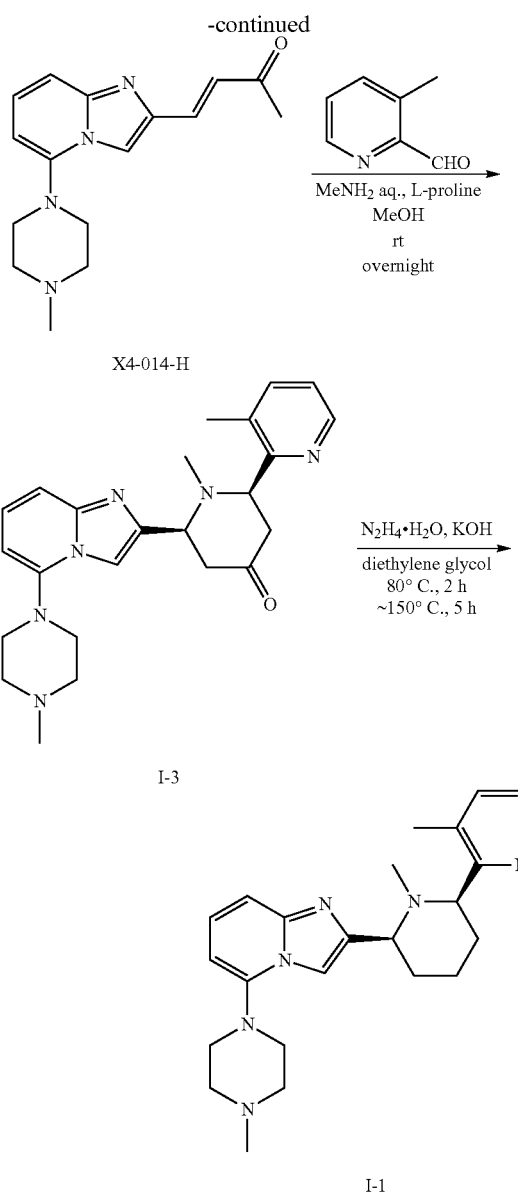

The Synthesis of X4-014-H:

Following general procedure E, X4-014-H (1.9 g, 41%) was obtained as yellow foam, which was used in the next step without further purification. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 69.13%; Rt=1.38 min; MS Calcd.: 284.4; MS Found: 285.4[M+H]$^+$.

The Synthesis of I-3:

To a solution of X4-014-H (1.4 g, 4.9 mmol) in MeOH (20 mL) was added L-proline (227 mg, 1.97 mmol), 3-methylpicolinaldehyde (656 mg, 5.4 mmol) and aq. MeNH$_2$ (1.5 g, 40% wt, 19.72 mmol) sequentially. The reaction mixture was stirred overnight at room temperature and concentrated in vacuum. The residue was purified by column chromatography to give cis/trans mixture of I-3 (mg, 50%) as a yellow foam, which was used in the next step without further purification. Cis/trans mixture of I-3 (270 mg, 0.65 mmol) was purified by prep-TLC to give I-3 (30 mg, 11%) as a white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). I-3: Purity: 92.86%. Rt=1.49 min (trans), 1.52 min (cis); MS Calcd.: 418.3; MS Found: 419.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min.); Purity: 97.88%. Rt=4.90 min. $^1$H NMR (400 MHz, CDCl$_3$) δ: 8.58-8.56 (m, 1H), 7.62 (s, 1H), 7.48 (dd, J=1.2 Hz, J=7.6 Hz, 1H), 7.36 (d, J=8.8 Hz 1H), 7.19 (dd, J=7.2 Hz, J=8.8 Hz, 1H), 7.13 (dd, J=4.8 Hz, J=7.6 Hz, 1H), 6.34 (d, J=6.4 Hz, 1H), 4.03 (dd, J=3.2 Hz, J=12.0 Hz, 1H), 3.93 (dd, J=7.2 Hz, J=8.8 Hz, 1H), 3.49 (s, 1H), 3.33-3.18 (m, 6H), 2.78-2.68 (m, 5H), 2.50 (s, 3H), 2.42 (s, 3H), 1.94 (s, 3H).

Synthesis of I-1:

Following general procedure A, a mixture of cis/trans mixture of I-3 (770 mg, 1.84 mmol), KOH (2.1 g, 36.8 mmol) and N$_2$H$_4$.H$_2$O (4.6 g, 80% wt, 73.6 mmol) in diethylene glycol was stirred for 2 hours at 80° C. and then 5 hours at 150° C. After cooled down to room temperature, the reaction mixture was diluted with water and extracted with DCM. The organic layer was washed with water and brine, dried over Na$_2$SO$_4$, filtered and concentrated in vacuum. The residue was purified by column chromatography to give 276 mg of crude I-1, which was purified by prep-HPLC to give 80 mg of I-1 as a white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.44%. Rt=1.66 min; MS Calcd.: 404.3; MS Found: 405.4 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 94.20%. Rt=4.44 min. $^1$H NMR (400 MHz, CD$_3$OD) δ: 8.46 (s, 1H), 7.96 (s, 1H), 7.62 (d, J=8.0 Hz, 1H), 7.34-7.25 (m, 2H), 7.22-7.19 (m, 1H), 6.51 (d, J=6.8 Hz, 1H), 3.65 (d, J=10.0 Hz, 1H), 3.46 (d, J=8.4 Hz, 1H), 3.17 (s, 4H), 2.81 (s, 4H), 2.51 (s, 3H), 2.47 (s, 3H), 2.05-1.94 (m, 4H), 1.89 (s, 3H), 1.79-1.68 (m, 2H).

Example 2: Synthesis of I-2

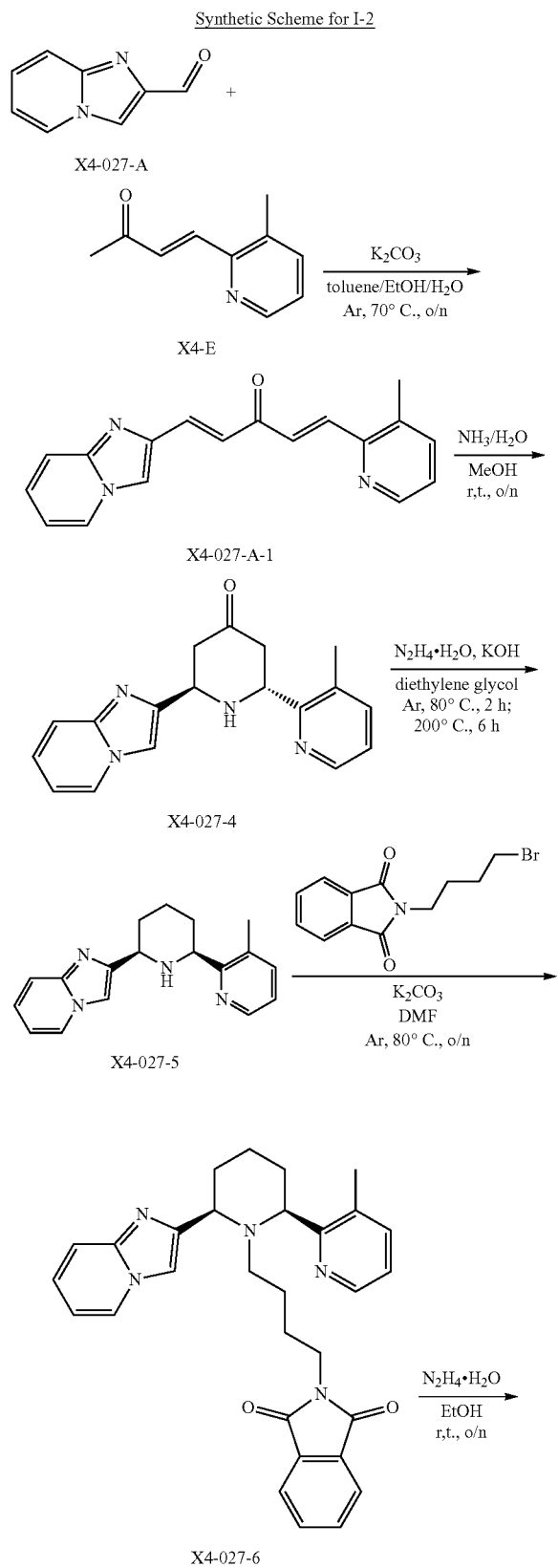

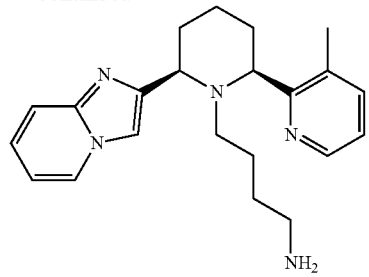

I-2

The Synthesis of X4-027-A-1:

To a solution of X4-027-A (731 mg, 5.0 mmol) and X4-E (806 mg, 5.0 mmol) in toluene (25 mL), EtOH (10 mL) and H$_2$O (5 mL) was added K$_2$CO$_3$ (1.037 g, 7.5 mmol). The mixture was stirred overnight at 70° C. under Ar atmosphere. Then it was diluted with H$_2$O and extracted with DCM three times. The combined organic layers were dried over Na$_2$SO$_4$, filtered and concentrated in vacuo. The residue was purified by chromatography of silica gel with DCM/MeOH/NH$_3$—H$_2$O (40/1/0.68) as eluent to provide product X4-027A-1 (952 mg, 66% yield) as yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 68.23%; Rt=1.55 min; MS Calcd.: 298.1; MS Found: 290.1 [M+H]$^+$.

The Synthesis of X4-027-4:

To a solution of X4-027-A-1 (676 mg, 2.34 mmol) in MeOH (20 mL) was added NH$_3$/H$_2$O (5 mL). The mixture was stirred at room temperature overnight. The solvent was evaporated in vacuo and the residue was purified by prep-TLC to give X4-027-4 (170 mg, 23% yield) as brown-red solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.20%. Rt=1.41 min; MS Calcd.: 306.1; MS Found: 307.4 [M+H]$^+$.

The Synthesis of X4-027-5:

Following general procedure A, X4-027-5 (77 mg, 47% yield) was obtained as brown-red solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 88.42%. Rt=1.47 min; MS Calcd.: 292.2; MS Found: 293.1 [M+H]$^+$.

The Synthesis of X4-027-6:

Following general procedure B, X4-027-6 (180 mg, >100% yield) was obtained as white solid, which was used to next step without further purification. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.); Purity: 48.71%. Rt=1.79 min; MS Calcd.: 493.6; MS Found: 494.4 [M+H]⁺.

The Synthesis of I-2:

To a solution of crude X4-027-5 (170 mg, 0.25 mmol) in EtOH (3 mL) was N₂H₄.H₂O (0.6 mL). The mixture was stirred at room temperature overnight. The solvent was evaporated in vacuo and the residue was purified by prep-HPLC to give I-2 (12 mg, 13% yield) as white solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 90% [(total 10 mM AcONH₄) H₂O/ACN=9/1 (v/v)] and 10% [(total 10 mM AcONH₄) H₂O/ACN=1/9 (v/v)] to 10% [(total 10 mM AcONH₄) H₂O/ACN=9/1 (v/v)] and 90% [(total 10 mM AcONH₄) H₂O/ACN=1/9 (v/v)] in 1.6 min, then under this condition for 2.4 min, finally changed to 90% [(total 10 mM AcONH₄) H₂O/ACN=9/1 (v/v)] and 10% [(total 10 mM AcONH₄) H₂O/ACN=1/9 (v/v)] in 0.1 min and under this condition for 0.7 min.); Purity: 98.47%; Rt=1.26 min; MS Calcd.: 363.5; MS Found: 364.3 [M+H]⁺. HPLC (Agilent HPLC 1200, Column: L-column2 ODS (150 mm*4.6 mm*5.0 µm); Column Temperature: 40° C.; Flow Rate: 1.5 mL/min; Mobile Phase: from 90% [(total 10 mM AcONH₄) H₂O/ACN=9/1 (v/v)] and 10% [total 10 mM AcONH₄) H₂O/ACN=1/9 (v/v)] to 15% [total 10 mM AcONH₄) H₂O/ACN=9/1 (v/v)] and 85% [total 10 mM AcONH₄) H₂O/ACN=1/9 (v/v)] in 5 min, then under this condition for 10 min, finally changed to 90% [(total 10 mM AcONH₄) H₂O/ACN=9/1 (v/v)] and 10% [total 10 mM AcONH₄) H₂O/ACN=1/9 (v/v)] in 0.1 min and under this condition for 5 min.); Purity: 98.11%. Rt=4.22 min. ¹H NMR (CDCl₃, 400 MHz) δ 8.47 (d, J=4.4 Hz, 1H), 8.08 (d, J=6.8 Hz, 1H), 7.64 (s, 1H), 7.56 (d, J=8.8 Hz, 1H), 7.42 (d, J=7.2 Hz, 1H), 7.14-7.10 (m, 1H), 7.06 (dd, J=4.8 Hz, 7.6 Hz, 1H), 6.77-6.73 (m, 1H), 4.02-3.99 (m, 1H), 3.90-3.87 (m, 1H), 2.52 (s, 3H), 2.38-2.20 (m, 4H), 2.02-1.86 (m, 4H), 1.37-1.29 (m, 2H), 1.13-1.01 (m, 1H), 0.87-0.79 (m, 3H).

Example 3: Synthesis of I-4

Synthetic Scheme for I-4

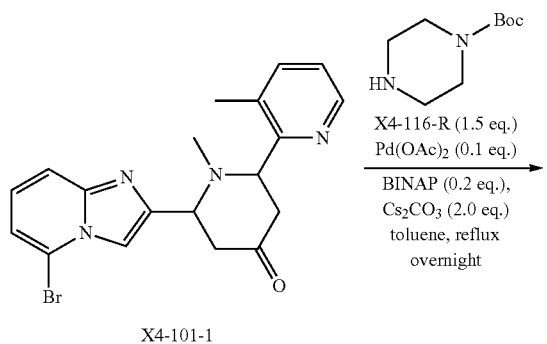

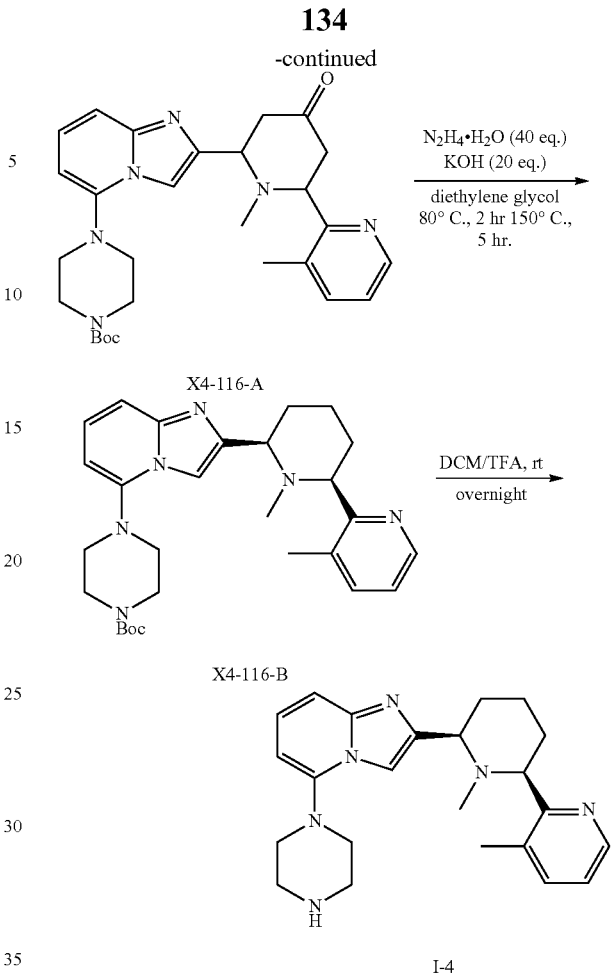

The Synthesis of X4-116-A:

Following general procedure G, X4-116-A (0.92 g, 24% yield) was obtained as a yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.); Purity: 92.35%; Rt=1.81 min; MS Calcd.: 504.7, MS Found: 505.7 [M+1]⁺.

The Synthesis of X4-116-B:

Following general procedure A, X4-116-B (140 mg, 16% yield) was obtained as a light-yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.); Purity: 93.71%; Rt=1.99 min; MS Calcd.: 490.7, MS Found: 491.7 [M+1]⁺.

The Synthesis of I-4:

Following general procedure J, I-4 (110 mg, 99% yield) was obtained as a light-yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 99.8%; Rt=1.48 min; MS Calcd.: 390.7; MS Found: 391.7 [M+H]⁺. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 0% [water+0.05% TFA] and 100% [CH₃CN+0.05% TFA] in 10 min, then under this condition for 5 min, finally changed to 95% [water+0.05% TFA] and 5% [CH₃CN+0.05% TFA] in 0.1 min and under this condition for 5 min.); Purity: 98.8%; Rt=4.362 min; MS Calcd.: 390.7; MS Found: 391.7 [M+H]⁺. ¹H NMR (400 MHz, CDCl₃) δ 8.51 (d, J=3.6 Hz, 1H), 7.63 (s, 1H), 7.43 (d, J=7.2 Hz, 1H), 7.33 (d, J=8.8 Hz, 1H), 7.12-7.16 (m, 1H), 7.04-7.07 (m, 1H), 6.27 (d, J=7.2 Hz, 1H), 3.57 (dd, J=11.2 Hz, J=2.4 Hz, 1H), 3.47 (dd, J=10.0 Hz, J=3.6 Hz, 1H), 3.11-3.15 (m, 8H), 2.47 (s, 3H), 2.22 (s, 3H), 1.97-2.06 (m, 4H), 1.61-1.75 (m, 2H).

Example 4: Synthesis of I-5, I-6, and I-7

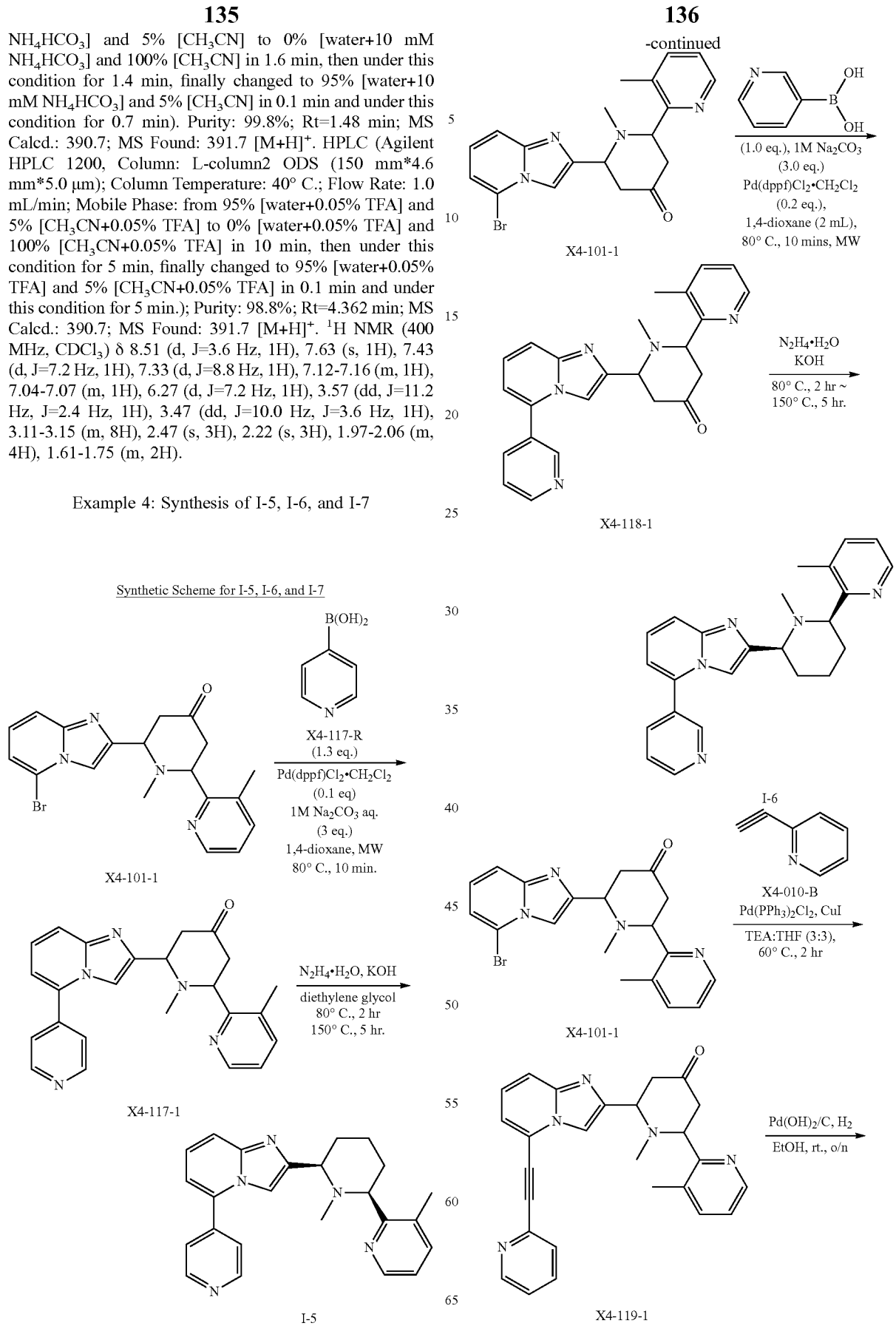

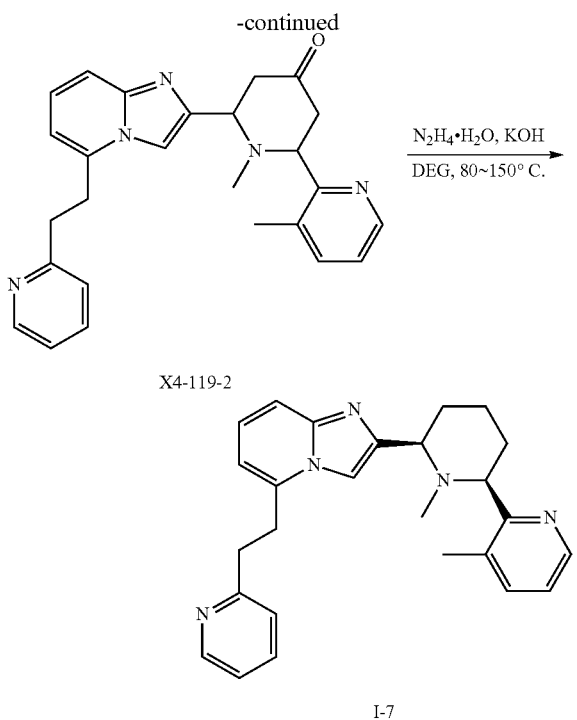

X4-119-2

I-7

The Synthesis of X4-117-1

Following general procedure H, X4-117-1 (63 mg, 32% yield) was obtained as yellow oil. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/ACN=9/1 (v/v)] and 10% [(total 10 mM AcONH$_4$) H$_2$O/ACN=1/9 (v/v)] to 10% [(total 10 mM AcONH$_4$) H$_2$O/ACN=9/1 (v/v)] and 90% [(total 10 mM AcONH$_4$) H$_2$O/ACN=1/9 (v/v)] in 1.6 min, then under this condition for 2.4 min, finally changed to 90% [(total 10 mM AcONH$_4$) H$_2$O/ACN=900/100 (v/v)] and 10% [(total 10 mM AcONH$_4$) H$_2$O/ACN=1/9 (v/v)] in 0.1 min and under this condition for 0.7 min.); Purity: 54.67%; Rt=1.49 min (trans) & 1.53 min (cis); MS Calcd.: 397.2; MS Found: 398.7[M+H]$^+$.

The Preparation of I-5

Following general procedure A, I-5 (13 mg, 21% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 100.00%; Rt=1.62 min; MS Calcd.: 383.2; MS Found: 384.7[M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 100.00%; Rt=4.70 min; MS Calcd.: 383.2; MS Found: 384.7[M+H]$^+$. $^1$H NMR (400 MHz, CDCl$_3$) δ 1.53-1.65 (m, 2H), 1.81 (s, 3H), 1.83-1.95 (m, 4H), 2.37 (s, 3H), 3.37-3.40 (m, 1H), 3.45-3.48 (m, 1H), 6.72 (d, J=6.8 Hz, 1H), 6.96-6.99 (m, 1H), 7.15-7.18 (m, 1H), 7.34 (d, J=7.6 Hz, 1H), 7.52 (d, J=6.0 Hz, 2H), 7.56 (d, J=9.2 Hz, 1H), 7.71 (s, 1H), 8.42 (d, J=2.4 Hz, 1H), 8.77 (d, J=6.0 Hz, 2H).

The Preparation of X4-118-1

Following general procedure H, X4-118-1 (116 mg, 80% yield) was obtained as yellow solid from X4-101-1 (150 mg, 0.38 mmol). LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/ACN=9/1 (v/v)] and 10% [(total 10 mM AcONH$_4$) H$_2$O/ACN=1/9 (v/v)] to 10% [(total 10 mM AcONH$_4$) H$_2$O/ACN=9/1 (v/v)] and 90% [(total 10 mM AcONH$_4$) H$_2$O/ACN=1/9 (v/v)] in 1.6 min, then under this condition for 2.4 min, finally changed to 90% [(total 10 mM AcONH$_4$) H$_2$O/ACN=900/100 (v/v)] and 10% [(total 10 mM AcONH$_4$) H$_2$O/ACN=1/9 (v/v)] in 0.1 min and under this condition for 0.7 min.); Purity: 82.37%; Rt=1.63 min (trans) & 1.67 min (cis); MS Calcd.: 397.7; MS Found: 398.7 [M+H]$^+$.

The Synthesis of I-6

Following general procedure A, I-6 (50 mg, 52% yield) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 95.04%; Rt=1.64 min; MS Calcd.: 383.7; MS Found: 384.7[M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 100%; Rt=4.79 min; MS Calcd.: 383.7; MS Found: 384.7 [M+H]$^+$. $^1$H NMR (400 MHz, CDCl$_3$) δ 1.53-1.81 (m, 2H), 1.86 (s, 3H), 1.89-2.01 (m, 4H), 2.43 (s, 3H), 3.41-3.45 (m, 1H), 3.51-3.55 (m, 1H), 6.76 (d, J=6.8 Hz, 1H), 7.04 (dd, $J_1$=4.4 Hz, $J_2$=7.2 Hz, 1H), 7.22-7.25 (m, 1H), 7.40 (d, J=7.6 Hz, 1H), 7.53 (dd, $J_1$=4.8 Hz, $J_2$=7.6 Hz, 1H), 7.62 (d, J=9.2 Hz, 1H), 7.68 (s, 1H), 8.01-8.03 (m, 1H), 8.48 (d, J=3.2 Hz, 1H), 8.79 (dd, $J_1$=1.2 Hz, $J_2$=5.2 Hz, 1H), 8.86 (d, J=1.6 Hz, 1H).

The Synthesis of X4-119-1

To the solution of X4-101-1 (500 mg, 1.3 mmol) in TEA and THF (20 mL, 1:1) were added CuI (12 mg, 0.07 mmol) and PdCl$_2$(PPh3)$_2$ (92 mg, 0.13 mmol). The resulting mixture was heated to 60° C. and stirred for 2 hours. After cooled to room temperature, the solid suspension was filtered through Celite; the filtrate was concentrated in vacuum and the residue was purified by flash chromatography to give X4-119-1 (350 mg, 66% yield) as off-white solid. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.7 min.); Purity: 90.26%; Rt=0.98 min; MS Calcd.: 421.2; MS Found: 422.2[M+H]$^+$.

The Synthesis of X4-119-2

To a solution of X4-119-1 (350 mg, 0.83 mmol) in EtOH (20 mL) was added Pd(OH)$_2$ (20% on carbon) (84 mg, 0.12 mmol) and the mixture was stirred at room temperature for 12 hours under hydrogen atmosphere. The resulting mixture was filtered through celite and the filtrate was concentrated in vacuum, which was purified by column chromatography to give X4-119-2 (130 mg, 37% yield) as off-white syrup. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.78%; Rt=1.60 min; MS Calcd.: 425.2; MS Found: 426.2 [M+H]$^+$.

The Synthesis of I-7

Following general procedure A, I-7 (20 mg, 16% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 100.00%; Rt=1.73 min; MS Calcd.: 411.2; MS Found: 412.4[M+H]$^+$. HPLC (Agilent LCMS 1200, Column: Waters X-Bridge C18 (150 mm*4.6 mm*3.5 μm); Column Temperature: 40° C.; Flow Rate: 1.0 mL/min; Mobile Phase: from 95% [water+5% TFA] and 5% [CH$_3$CN] to 0% [water+5% TFA] and 100% [CH$_3$CN+5% TFA] in 10 min, then under this condition for 5 min, finally changed to 95% [water+5% TFA] and 5% [CH$_3$CN] in 0.1 min and under this condition for 5 min.); Purity: 90.39%. Rt=4.54 min. $^1$HNMR (400 MHz, CDCl$_3$) δ: 8.60 (1H, dd, J$_1$=4.8 Hz, J$_2$=0.8 Hz), 8.50 (1H, br s), 7.74 (1H, s), 7.61 (1H, tt, J$_1$=7.6 Hz, J$_2$=1.6 Hz), 7.47 (1H, d, J=8.8 Hz), 7.42 (1H, d, J=7.2 Hz), 7.19-7.04 (4H, m), 6.58 (1H, d, J=6.8 Hz), 3.57 (1H, dd, J$_1$=11.2 Hz, J$_2$=2.4 Hz), 3.50-3.45 (1H, m), 3.38-3.27 (4H, m), 2.48 (3H, s), 2.07-1.94 (4H, m), 1.90 (3H, s), 1.74-1.61 (2H, m).

Example 5: Synthesis of I-8

Synthetic Scheme for I-8

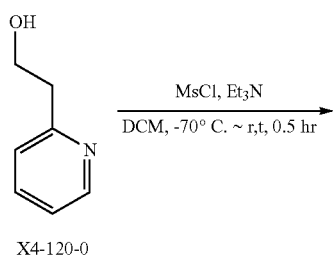

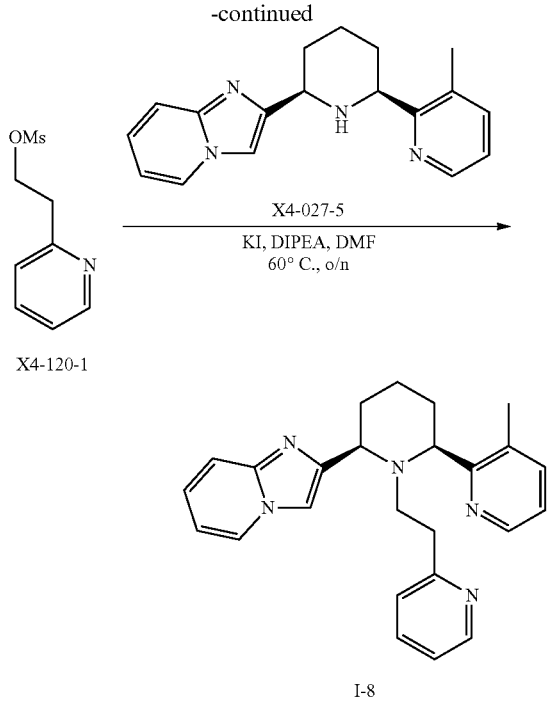

The Synthesis of X4-120-1 Following general procedure C, X4-120-1 (351 mg, 43% yield) was obtained as a brown solid, which was used in the next step without further purification. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 88.46%; Rt=1.30 min; MS Calcd.: 201.0; MS Found: 202.7 [M+H]$^+$.

The Synthesis of I-8

Following general procedure D, I-8 (18 mg, 22% yield) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 99.17%; Rt=1.65 min; MS Calcd.: 397.2; MS Found: 398.7 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 93.21%; Rt=4.19 min. $^1$H NMR (400 MHz, CDCl$_3$) δ 1.60-1.71 (m, 2H), 1.90-2.02 (m, 4H), 2.56 (s, 3H), 2.68-2.81 (m, 4H), 3.99 (t, J=6.8 Hz, 1H), 4.10-4.13 (m, 1H), 6.56 (d, J=8.0 Hz, 1H), 6.73 (t, J=6.8 Hz, 1H), 6.84-6.87 (m, 1H), 7.05-7.12 (m, 2H), 7.28-7.29 (m, 1H), 7.43 (d, J=8.0 Hz, 1H), 7.56 (d, J=9.2 Hz, 1H), 7.61 (s, 1H), 8.04 (d, J=6.8 Hz, 1H), 8.19 (d, J=4.0 Hz, 1H), 8.48 (d, J=4.0 Hz, 1H).

Example 6: Synthesis of I-9

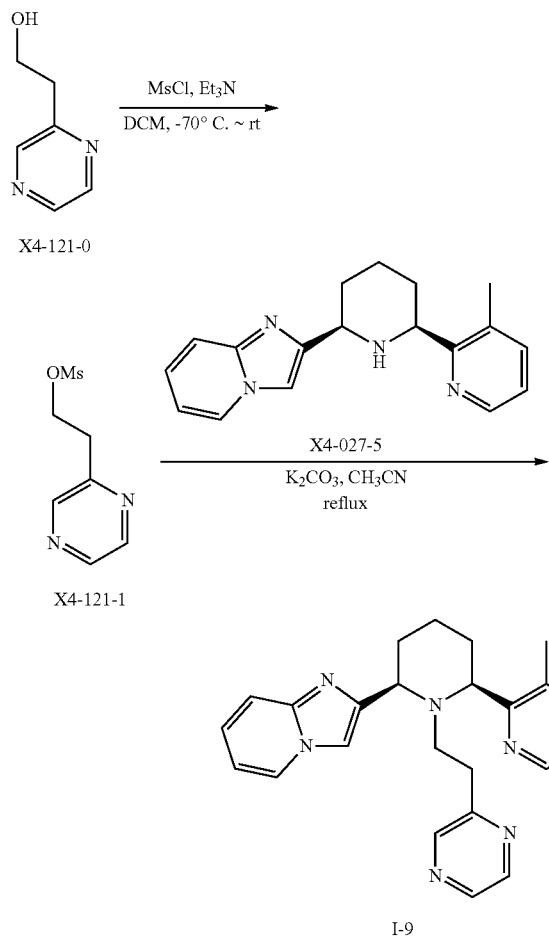

The Synthesis of X4-121-1

Following general procedure C, X4-121-1 (115 mg, 71% yield) was obtained as brown oil, which was used in the next step without further purification. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.); Purity: 44.91%; Rt=1.11 min; MS Calcd.: 202.0; MS Found: 203.7 [M+H]$^+$.

The Synthesis of I-9

Following general procedure B, I-9 (12 mg, 15% yield) was obtained as off-white solid. LCMS (Agilent LCMS 1200-6120, Column: WatersX-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.); Purity: 98.46%; Rt=1.57 min; MS Calcd.: 398.2; MS Found: 399.7 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [$CH_3CN$+0.05% TFA] to 0% [water+0.05% TFA] and 100% [$CH_3CN$+0.05% TFA] in 10 min, then under this condition for 5 min, finally changed to 95% [water+0.05% TFA] and 5% [$CH_3CN$+0.05% TFA] in 0.1 min and under this condition for 5 min.); Purity: 96.51%; Rt=4.50 min. $^1$H NMR (400 MHz, $CDCl_3$) δ 1.61-1.70 (m, 2H), 1.94-2.06 (m, 4H), 2.51 (br, 1H), 2.56 (s, 3H), 2.70-2.75 (m, 2H), 2.79-2.83 (m, 1H), 3.97-4.01 (m, 1H), 4.12 (dd, $J_1$=2.8 Hz, $J_2$=11.2 Hz, 1H), 6.73-6.77 (m, 1H), 7.07-7.15 (m, 2H), 7.44 (d, J=7.6 Hz, 1H), 7.58 (d, J=8.8 Hz, 1H), 7.62 (s, 1H), 7.92 (d, J=1.2 Hz, 1H), 8.06 (d, J=6.4 Hz, 1H), 8.12-8.14 (m, 2H), 8.49 (d, J=4.0 Hz, 1H).

Example 7: Synthesis of I-10

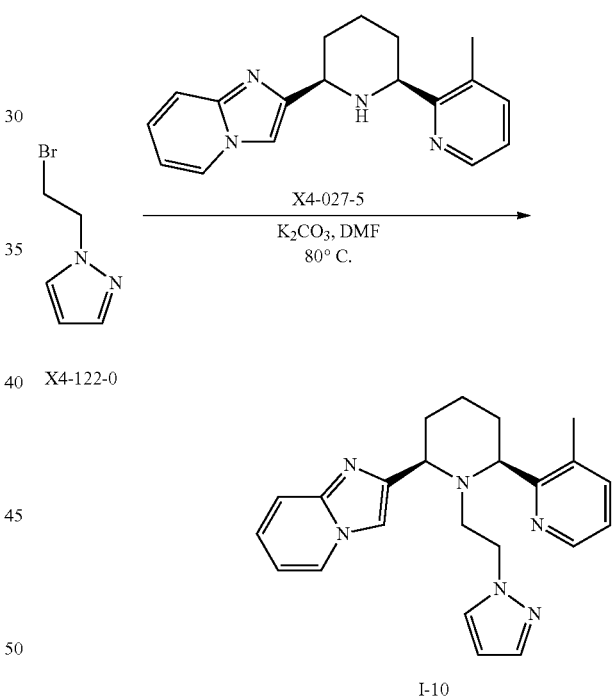

The Synthesis of I-10

Following general procedure B, I-10 (18 mg, 23% yield) was obtained as a white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min.); Purity: 93.04%; Rt=1.63 min; MS Calcd.: 386.2; MS Found: 387.7[M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 0% [water+0.05% TFA] and 100% [CH₃CN+0.05% TFA] in 10 min, then under this condition for 5 min, finally changed to 95% [water+0.05% TFA] and 5% [CH₃CN+0.05% TFA] in 0.1 min and under this condition for 5 min.); Purity: 95.05%; Rt=4.95 min. $^1$H NMR (400 MHz, CDCl₃) δ 1.59-1.66 (m, 2H), 1.93-2.08 (m, 4H), 2.51 (s, 3H), 2.63-2.69 (m, 1H), 2.87-2.94 (m, 1H), 3.40 (br, 1H), 3.71-3.75 (m, 1H), 3.88 (dd, $J_1$=2.8 Hz, $J_2$=11.2 Hz, 1H), 4.04 (dd, $J_1$=2.4 Hz, $J_2$=11.2 Hz, 1H), 5.96 (t, J=2.0 Hz, 1H), 6.73-6.78 (m, 2H), 7.09-7.16 (m, 3H), 7.45-7.46 (m, 2H), 7.56 (d, J=8.8 Hz, 1H), 8.03 (d, J=6.8 Hz, 1H), 8.52 (d, J=3.6 Hz, 1H).

Example 8: Synthesis of I-11

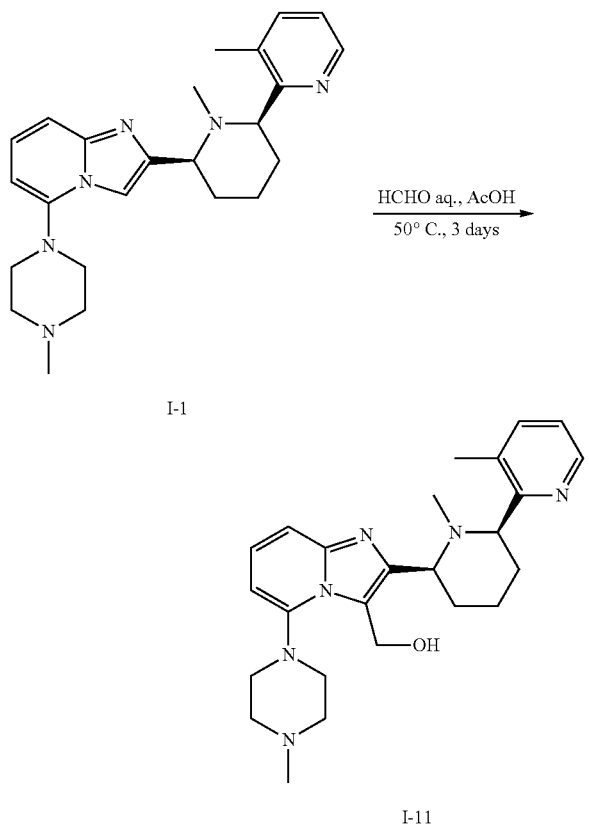

The Synthesis of I-11

A mixture of I-1 (120 mg, 0.3 mmol) and acetic acid (0.5 mL) in 37% formaldehyde aq. (10 mL) was stirred at 50° C. for 24 hours, then 37% formaldehyde aq. (5 mL) was added, and the mixture was stirred at 50° C. for another 48 hours. After reaction was completed, the suspension was adjust to pH 8 with sat. sodium carbonate aq. and extracted with DCM (20 mL). The organics layer was concentrated by vacuum and the residue was purified by prep-HPLC to give I-11 (90 mg, 70% yield) as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min.); Purity: 99.25%; Rt=1.54 min; MS Calcd.: 434.3; MS Found: 435.3 [M+H]⁺. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH₃CN+0.05% TFA] to 0% [water+0.05% TFA] and 100% [CH₃CN+0.05% TFA] in 10 min, then under this condition for 5 min, finally changed to 95% [water+0.05% TFA] and 5% [CH₃CN+0.05% TFA] in 0.1 min and under this condition for 5 min.); Purity: 95.82%; Rt=4.28 min. $^1$H NMR (400 MHz, CD₃OD) 1.81-1.60 (m, 2H), 1.85 (s, 3H), 1.97-2.01 (m, 2H), 2.10-2.22 (m, 2H), 2.45 (s, 6H), 2.48-2.62 (m, 4H), 2.95-3.11 (m, 4H), 3.45-3.50 (m, 1H), 3.62-3.70 (m, 2H), 5.32 (d, J=13.6 Hz, 1H), 5.71 (br, 1H), 6.70-6.72 (m, 1H), 7.19 (dd, $J_1$=4.4 Hz, $J_2$=4.8 Hz, 1H), 7.28-7.35 (m, 1H), 7.60 (d, J=7.6 Hz, 1H), 8.39-8.46 (m, 1H).

Example 9: Synthesis of I-12

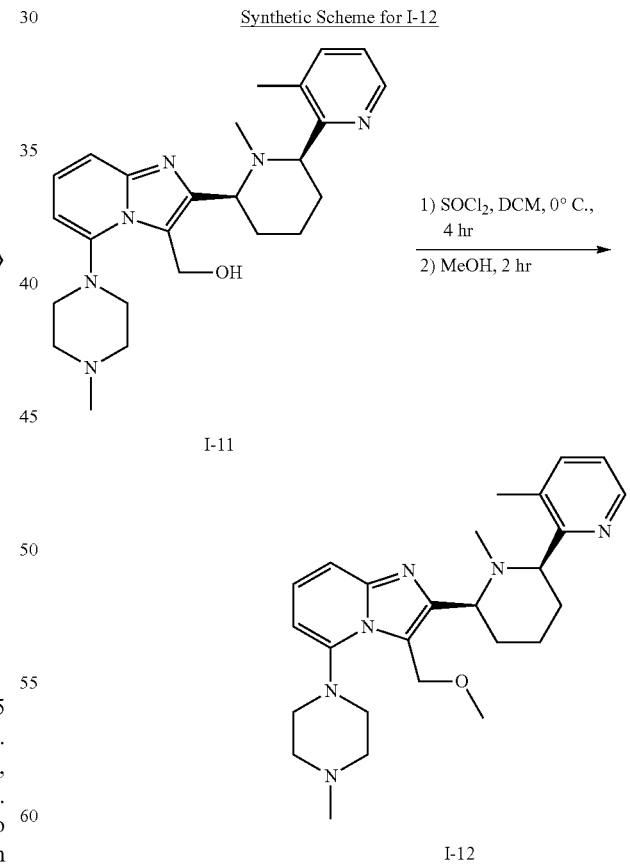

The Synthesis of I-12

To the solution of I-11 (50 mg, 0.11 mmol) in DCM (5 mL) was added thionyl chloride (20 mg, 0.17 mmol) at 0° C. under argon atmosphere, then the mixture was stirred at 0°

C. for 4 hours. After I-11 has been converted completely, the excess of thionyl chloride was removed in vacuum; the residue was dissolved in MeOH (2 mL) and stirred at 0° C. for another 2 hours. The mixture was neutralized with NH$_3$/MeOH and concentrated in vacuum. The residue was purified by column chromatography to give I-12 (10 mg, 20% yield) as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/ACN=9/1 (v/v)] and 10% [(total 10 mM AcONH$_4$) H$_2$O/ACN=1/9 (v/v)] to 10% [(total 10 mM AcONH$_4$) H$_2$O/ACN=9/1 (v/v)] and 90% [(total 10 mM AcONH$_4$) H$_2$O/ACN=1/9 (v/v)] in 1.6 min, then under this condition for 2.4 min, finally changed to 90% [(total 10 mM AcONH$_4$) H$_2$O/ACN=9/1 (v/v)] and 10% [(total 10 mM AcONH$_4$) H$_2$O/ACN=1/9 (v/v)] in 0.1 min and under this condition for 0.7 min.); Purity: 96.30%; Rt=2.00 min; MS Calcd.: 448.3; MS Found: 449.3[M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 89.34%; Rt=4.56 min. $^1$H NMR (400 MHz, CD$_3$OD) 1.20 (s, 3H), 1.55-1.65 (m, 2H), 1.70 (s, 3H), 1.84-1.92 (m, 2H), 1.93-2.05 (m, 2H), 2.32 (s, 3H), 2.38-2.57 (m, 4H), 2.83-2.94 (m, 4H), 3.11-3.16 (m, 2H), 3.41 (s, 3H), 5.13 (dd, J$_1$=9.2 Hz, J$_2$=61.2 Hz, 1H), 6.68 (d, J=6.8 Hz, 1H), 7.12 (d, J=5.6 Hz, 1H), 7.21-7.25 (m, 2H), 7.52 (d, J=7.2 Hz, 1H), 8.23 (d, J=2.0 Hz, 1H).

Example 10: Synthesis of I-13, I-14, and I-15

Synthetic Scheme for I-13, I-14, and I-15

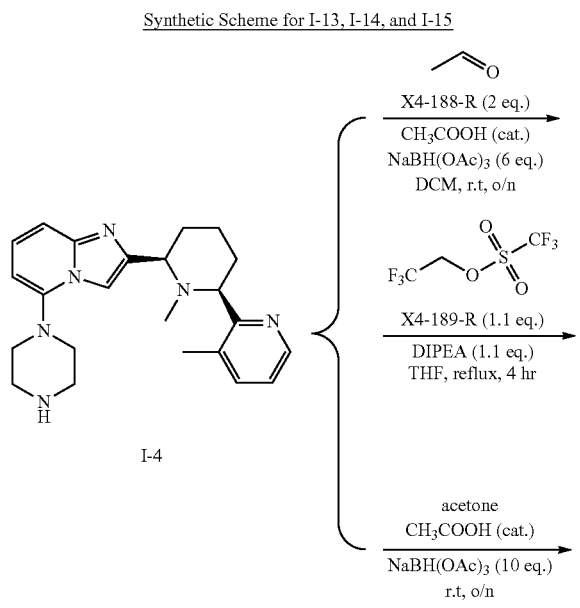

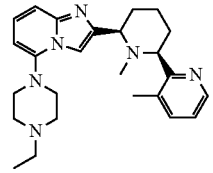

I-13

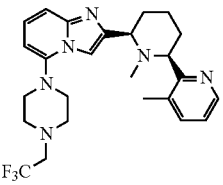

I-14

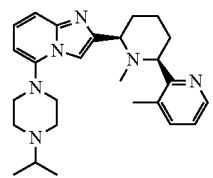

I-15

The Synthesis of I-13

Following general procedure I, I-13 (9 mg, 26% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 98.70%; Rt=1.77 min; MS Calcd.: 418.3; MS Found: 419.4 [M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 90.08%; Rt=4.50 min; MS Calcd.: 418.3; MS Found: 419.4 [M+H]$^+$. $^1$H NMR (400 MHz, CDCl$_3$) δ 8.51 (d, J=3.6 Hz, 1H), 7.62 (s, 1H), 7.42 (d, J=6.8 Hz, 1H), 7.32 (d, J=10.0 Hz, 1H), 7.11-7.15 (m, 1H), 7.05 (dd, J=7.6 Hz, J=4.8 Hz, 1H), 6.28 (d, J=7.2 Hz, 1H), 3.57 (d, J=9.2 Hz, 1H), 3.45-3.49 (m, 1H), 3.18 (s, 4H), 2.73 (s, 4H), 2.55-2.61 (m, 2H), 2.48 (s, 3H), 1.92-2.05 (m, 4H), 1.90 (s, 3H), 1.62-1.68 (m, 2H), 1.78 (t, 3H).

The Synthesis of I-14

A mixture of I-4 (33.0 mg, 0.085 mmol), X4-189-R (21.7 mg, 0.093 mmol) and DIPEA (12.1 mg, 0.094 mmol) in THF (4 mL) was stirred at 70° C. for 4 hours. The mixture was cooled to room temperature, concentrated and diluted with sat. NaHCO$_3$aq. (4 mL). The aqueous layer was extracted with DCM three times. The combined organic layers were washed with brine, dried over Na$_2$SO$_4$ and filtered. The filtrate was concentrated in vacuum and the residue was purified by prep-HPLC to give I-14 (8 mg, 20% yield) as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase:

from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 91.57%; Rt=1.96 min; MS Calcd.: 472.3; MS Found: 473.4 [M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 89.82%; Rt=6.11 min; MS Calcd.: 472.7; MS Found: 473.4 [M+H]$^+$. $^1$H NMR (400 MHz, CDCl$_3$) δ 8.50-8.52 (m, 1H), 7.61 (s, 1H), 7.43 (d, J=6.8 Hz, 1H), 7.33 (d, J=8.8 Hz, 1H), 7.14 (dd, J=8.4 Hz, J=7.2 Hz, 1H), 7.04-7.07 (m, 1H), 6.27 (d, J=6.4 Hz, 1H), 3.55-3.58 (m, 1H), 3.45-3.49 (m, 1H), 3.09-3.17 (m, 6H), 2.96-2.98 (m, 4H), 2.47 (s, 3H), 1.92-2.05 (m, 4H), 1.90 (s, 3H), 1.69-1.75 (m, 2H).

The Synthesis of I-15

Following general procedure I, I-15 (9 mg, 25% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 100.00%; Rt=1.88 min; MS Calcd.: 432.3; MS Found: 433.3 [M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 90.73%; Rt=4.52 min; MS Calcd.: 432.7; MS Found: 433.3 [M+H]$^+$. $^1$H NMR (400 MHz, CDCl$_3$) δ 8.51 (d, J=4.0 Hz, 1H), 7.63 (s, 1H), 7.42 (d, J=6.8 Hz, 1H), 7.31 (d, J=8.8 Hz, 1H), 7.11-7.15 (m, 1H), 7.05 (dd, J=7.6 Hz, J=4.8 Hz, 1H), 6.27 (d, J=6.8 Hz, 1H), 3.57 (d, J=10.0 Hz, 1H), 3.45-3.50 (m, 1H), 3.16 (m, 4H), 2.80-2.84 (s, 5H), 2.48 (s, 3H), 1.92-2.09 (m, 4H), 1.91 (s, 3H), 1.59-1.67 (m, 2H), 1.15 (d, J=6.4 Hz, 6H).

Example 11: Synthesis of I-16

Synthetic Scheme for I-16

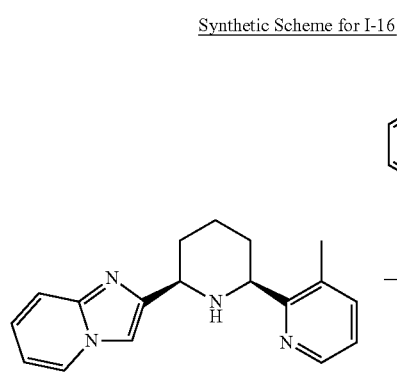

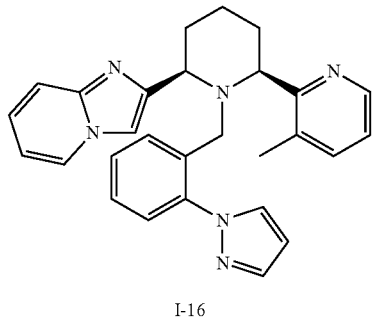

I-16

The Synthesis of I-16

Following general procedure D, I-16 (23 mg, 17% yield) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 98.43%; Rt=1.77 min; MS Calcd.: 448.2; MS Found: 449.2 [M+H]$^+$. HPLC (Agilent HPLC 1200; Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 94.25%; Rt=5.10 min. $^1$H NMR (400 MHz, CDCl$_3$) δ 1.57-1.68 (m, 2H), 1.92-1.96 (m, 2H), 2.12-2.19 (m, 2H), 2.26 (s, 3H), 3.40-3.44 (m, 1H), 3.58-3.62 (m, 1H), 3.74-3.77 (m, 1H), 3.85-3.89 (m, 1H), 6.33-6.34 (m, 1H), 6.63-6.69 (m, 2H), 6.79-6.87 (m, 2H), 7.03-7.09 (m, 2H), 7.17-7.18 (m, 1H), 7.24 (d, J=7.6 Hz, 1H), 7.36 (m, 1H), 7.43 (d, J=8.8 Hz, 1H), 7.60 (m, 1H), 7.88-7.92 (m, 2H), 8.25-8.26 (m, 1H).

Example 12: Synthesis of I-17

Synthetic Scheme for I-17

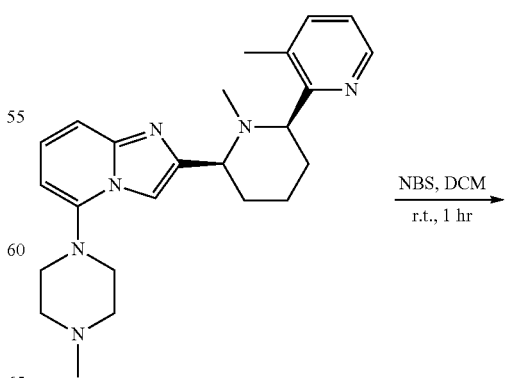

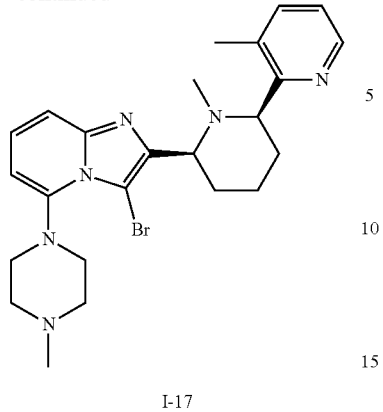

I-17

The Synthesis of I-17

Following general procedure K, I-17 (180 mg, 84% yield) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.10%; Rt=1.89 min; MS Calcd.: 482.2; MS Found: 483.3[M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 95.40%; Rt=5.00 min. $^1$H NMR (400 MHz, MeOD) 1.19-1.52 (m, 2H), 1.54-1.66 (m, 3H), 1.70 (s, 3H), 1.85-2.01 (m, 2H), 2.03-2.18 (m, 2H), 2.31 (s, 3H), 2.55-2.63 (m, 4H), 2.77-2.86 (m, 4H), 3.50 (br, 2H), 6.55 (dd, J$_1$=1.6 Hz, J$_2$=1.6 Hz, 1H), 7.10 (dd, J$_1$=4.8 Hz, J$_2$=5.2 Hz, 1H), 7.18-7.25 (m, 2H), 7.49 (d, J=8.0 Hz, 1H), 8.18 (d, J=4.8 Hz, 1H).

Example 13: Synthesis of I-18

Synthetic Scheme for I-18

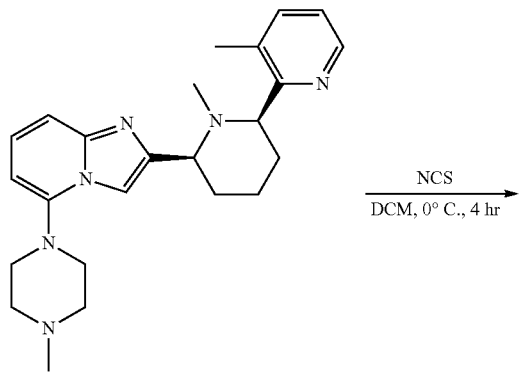

I-1

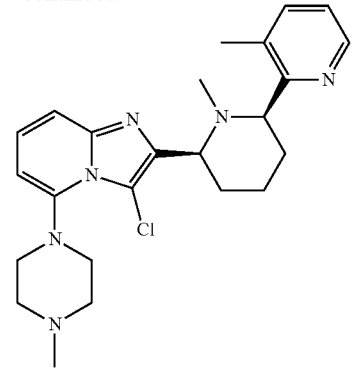

I-18

The Synthesis of I-18

Following general procedure K, I-18 (15 mg, 23% yield) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 90% [(total 10 mM AcONH$_4$) H$_2$O/ACN=9/1 (v/v)] and 10% [(total 10 mM AcONH$_4$) H$_2$O/ACN=1/9 (v/v)] to 10% [(total 10 mM AcONH$_4$) H$_2$O/ACN=9/1 (v/v)] and 90% [(total 10 mM AcONH$_4$) H$_2$O/ACN=1/9 (v/v)] in 1.6 min, then under this condition for 2.4 min, finally changed to 90% [(total 10 mM AcONH$_4$) H$_2$O/ACN=9/1 (v/v)] and 10% [(total 10 mM AcONH$_4$) H$_2$O/ACN=1/9 (v/v)] in 0.1 min and under this condition for 0.7 min.); Purity: 94.68%; Rt=2.02 min; MS Calcd.: 438.2; MS Found: 439.2[M+H]$^+$. HPLC (Agilent HPLC 1200, Column: L-column2 ODS (150 mm*4.6 mm*5.0 μm); Column Temperature: 40° C.; Flow Rate: 1.0 ml/min; Mobile Phase: from 90% [(total 10 mM AcONH$_4$) H$_2$O/ACN=9/1 (v/v)] and 10% [total 10 mM AcONH$_4$) H$_2$O/ACN=1/9 (v/v)] to 15% [total 10 mM AcONH$_4$) H$_2$O/ACN=9/1 (v/v)] and 85% [total 10 mM AcONH$_4$) H$_2$O/ACN=1/9 (v/v)] in 5 min, then under this condition for 10 min, finally changed to 90% [(total 10 mM AcONH$_4$) H$_2$O/ACN=9/1 (v/v)] and 10% [total 10 mM AcONH$_4$) H$_2$O/ACN=1/9 (v/v)] in 0.1 min and under this condition for 5 min.); Purity: 100%; Rt=6.60 min. $^1$H NMR (400 MHz, CD$_3$OD) 1.18-1.55 (m, 2H), 1.58-1.66 (m, 3H), 1.70 (s, 3H), 1.83-2.01 (m, 2H), 2.05-2.18 (m, 2H), 2.30 (s, 3H), 2.44-2.65 (m, 4H), 2.79-2.87 (m, 4H), 3.37-3.58 (m, 2H), 6.50 (dd, J$_1$=2.8 Hz, J$_2$=5.6 Hz, 1H), 7.10 (dd, J$_1$=4.8 Hz, J$_2$=7.6 Hz, 1H), 7.16-7.22 (m, 2H), 7.49 (d, J$_1$=7.2 Hz, 1H), 8.18 (d, J$_1$=4.0 Hz, 1H).

Example 14: Synthesis of I-19

Synthetic Scheme for I-19

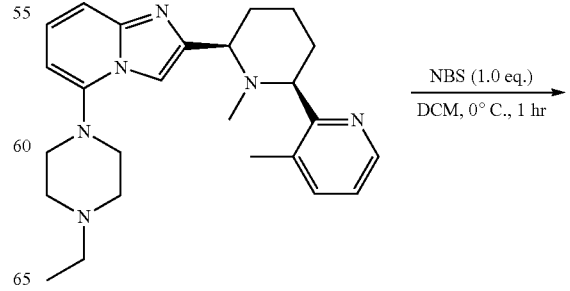

I-13

151

-continued

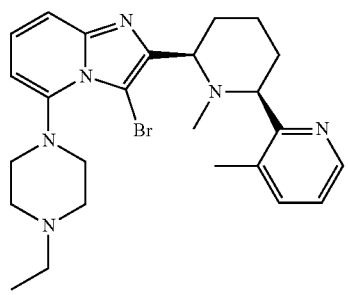

I-19

The Synthesis of I-19

Following general procedure K, I-19 (11 mg, 31% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.94%; Rt=2.025 min; MS Calcd.: 496.7; MS Found: 497.7 [M+H]$^+$. HPLC (Agilent HPLC 1200, Column: L-column2 ODS (150 mm*4.6 mm*5.0 μm); Column Temperature: 40° C.; Flow Rate: 1.0 ml/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 93.41%; Rt=5.15 min; MS Calcd.: 496.7; MS Found: 497.7 [M+H]$^+$. $^1$H NMR (400 MHz, CDCl$_3$) δ 8.48 (s, 1H), 7.42-7.37 (m, 2H), 7.12 (dd, J=8.8 Hz, 7.2 Hz, 1H), 7.05 (dd, J=7.6 Hz, 4.8 Hz, 1H), 6.41 (dd, J=7.2 Hz, 0.8 Hz, 1H), 3.61 (dd, J=11.2 Hz, 2.4 Hz, 2H), 3.33-3.27 (m, 2H), 2.97-2.85 (m, 4H), 2.60-2.51 (m, 4H), 2.46 (s, 3H), 2.19-1.92 (m, 4H), 1.78 (s, 3H), 1.74-1.54 (m, 2H), 1.15 (t, 3H).

Example 15: Synthesis of I-20

Synthetic Scheme for I-20

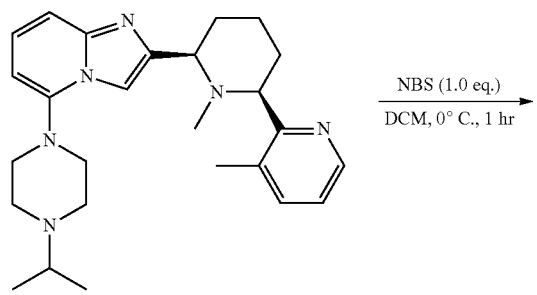

I-15

152

-continued

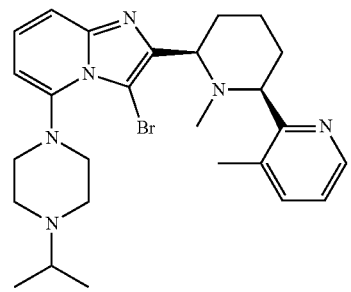

I-20

The Preparation of I-20

Following general procedure K, I-20 (12 mg, 29% yield) was obtained as off-white solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.); Purity: 96.27%; Rt=2.140 min; MS Calcd.: 510.7; MS Found: 511.7 [M+H]$^+$. HPLC (Agilent HPLC 1200, Column: L-column2 ODS (150 mm*4.6 mm*5.0 μm); Column Temperature: 40° C.; Flow Rate: 1.0 ml/min; Mobile Phase: from 95% [water+0.05% TFA] and 5% [CH$_3$CN+0.05% TFA] to 0% [water+0.05% TFA] and 100% [CH$_3$CN+0.05% TFA] in 10 min, then under this condition for 5 min, finally changed to 95% [water+0.05% TFA] and 5% [CH$_3$CN+0.05% TFA] in 0.1 min and under this condition for 5 min.); Purity: 96.35%; Rt=5.268 min; MS Calcd.: 510.7; MS Found: 511.7 [M+H]$^+$. $^1$H NMR (400 MHz, CDCl$_3$) δ 8.47 (s, 1H), 7.42-7.37 (m, 2H), 7.14-7.10 (m, 1H), 7.05 (dd, J=7.6 Hz, 4.8 Hz, 1H), 6.40 (dd, J=7.2 Hz, 0.8 Hz, 1H), 3.61 (d, J=9.6 Hz, 2H), 3.34-3.28 (m, 2H), 2.93-2.83 (m, 4H), 2.79-2.69 (m, 3H), 2.47 (s, 3H), 2.23-1.92 (m, 4H), 1.79 (s, 3H), 1.74-1.55 (m, 2H), 1.13 (d, J=6.4 Hz, 6H).

Example 16: Synthesis of I-21

Synthetic Scheme for I-21

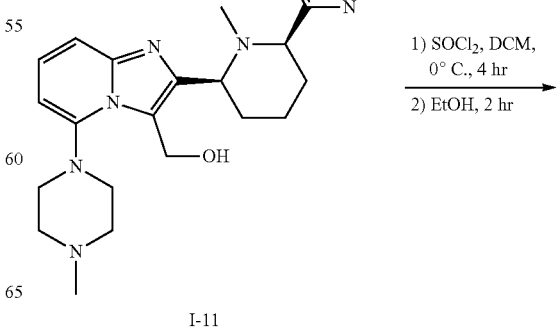

I-11

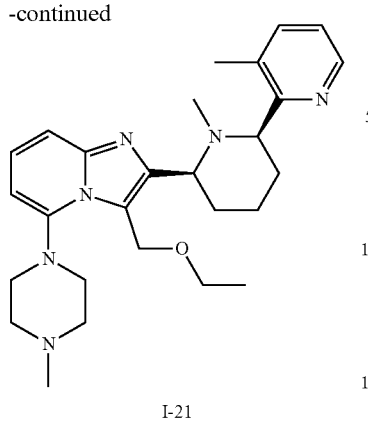

I-21

The Synthesis of I-21:

To the solution of I-11 (50 mg, 0.12 mmol) in DCM (5 ml) was added thionyl chloride (20 mg, 0.17 mmol) at 0° C. under argon atmosphere, then the mixture was stirred at 0° C. for 4 hours. After I-11 was consumed completed, the excess thionyl chloride was concentrated by vacuum, the residue was dissolved in ethanol (2 mL) and stirred at 0° C. for another 2 hours. The suspension was diluted with DCM (20 ml) and saturated sodium bicarbonate (6 ml), the separated organics was concentrated by vacuum and purified by prep-HPLC to give I-21 (15 mg, 28% yield) as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/ACN=900/100 (v/v)] and 10% [(total 10 mM AcONH$_4$) H$_2$O/ACN=100/900 (v/v)] to 10% [(total 10 mM AcONH$_4$) H$_2$O/ACN=9/1 (v/v)] and 90% [(total 10 mM AcONH$_4$) H$_2$O/ACN=1/9 (v/v)] in 1.6 min, then under this condition for 2.4 min, finally changed to 90% [(total 10 mM AcONH$_4$) H$_2$O/ACN=9/1 (v/v)] and 10% [(total 10 mM AcONH$_4$) H$_2$O/ACN=1/9 (v/v)] in 0.1 min and under this condition for 0.7 min.); Purity: 95.10%; Rt=2.08 min; MS Calcd.: 462.3; MS Found: 463.3[M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 90% [(total 10 mM AcONH$_4$) H$_2$O/ACN=9/1 (v/v)] and 10% [total 10 mM AcONH$_4$) H$_2$O/ACN=1/9 (v/v)] to 15% [total 10 mM AcONH$_4$) H$_2$O/ACN=9/1 (v/v)] and 85% [total 10 mM AcONH$_4$) H$_2$O/ACN=1/9 (v/v)] in 5 min, then under this condition for 10 min, finally changed to 90% [(total 10 mM AcONH$_4$) H$_2$O/ACN=9/1 (v/v)] and 10% [total 10 mM AcONH$_4$) H$_2$O/ACN=1/9 (v/v)] in 0.1 min and under this condition for 5 min.); Purity: 100%; Rt=6.50 min. $^1$H NMR (400 MHz, MeOD) 1.21-1.24 (m, 3H), 1.63-1.90 (m, 6H), 1.98-2.19 (m, 4H), 2.43 (s, 3H), 2.46-2.56 (m, 2H), 2.60-2.74 (m, 2H), 2.94-3.05 (m, 4H), 3.21-3.28 (m, 2H), 3.50-3.64 (m, 2H), 3.73-3.79 (m, 2H), 5.16-5.27 (m, 1H), 5.37-5.42 (m, 1H), 5.37-5.42 (m, 1H), 6.79 (d, J=7.6 Hz, 1H), 7.23 (dd, J$_1$=4.8 Hz, J$_2$=7.6 Hz, 1H), 7.31-7.38 (m, 2H), 7.62 (d, J$_1$=7.6 Hz, 1H), 8.34 (s, 1H).

Example 17: Synthesis of I-34

Synthetic Scheme for I-34

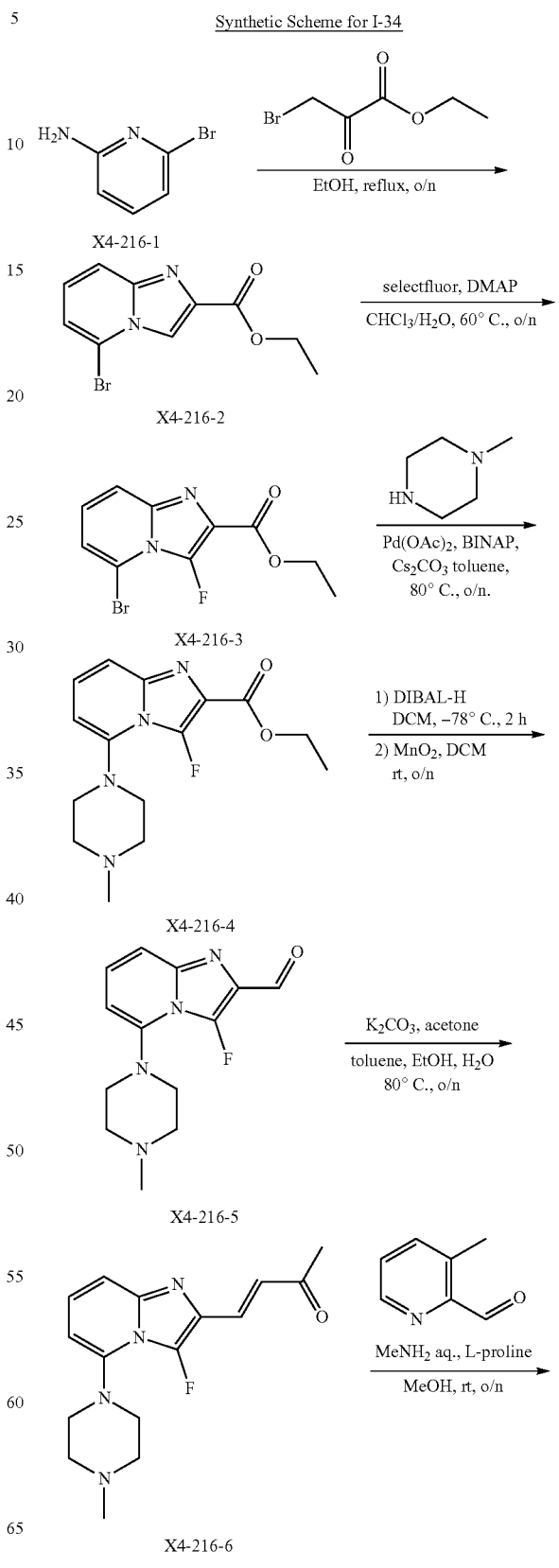

155
-continued

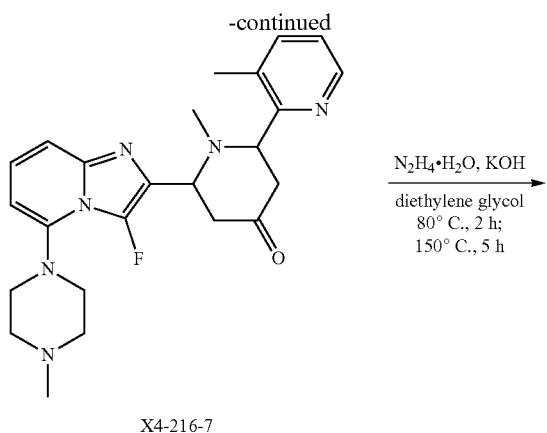

X4-216-7

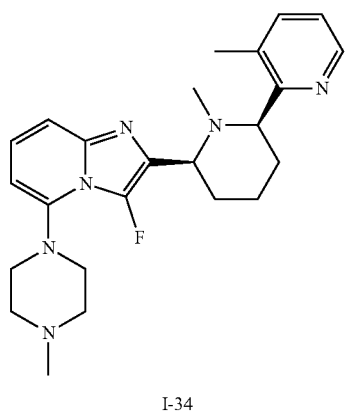

I-34

The Synthesis of rac-X4-216-2

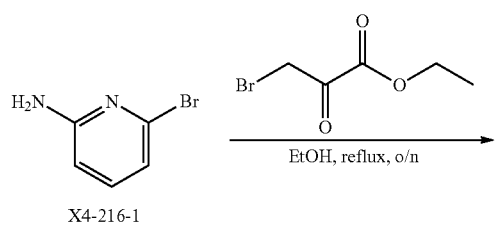

X4-216-2

A mixture of X4-216-1 (10.0 g, 58.0 mmol) and ethyl bromopyruvate (63.9 g, 12.9 mmol) in EtOH (60 mL) was stirred at reflux overnight. Then the mixture was returned to room temperature, and the solids were collected by filtration to give X4-216-2 (10.0 g, yield: 64%) as a yellow solid. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min). Purity: 89%, Rt=0.97 min; MS Calcd.: 267.9; MS Found: 268.9 [M+H]$^+$.

156
The Synthesis of X4-216-3

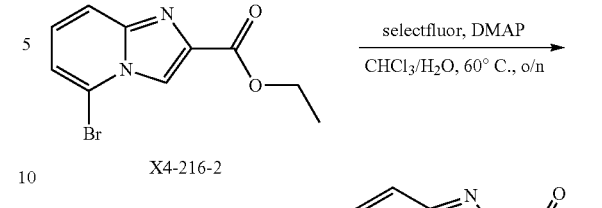

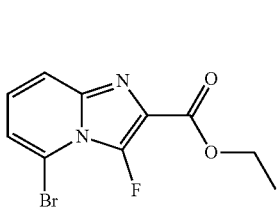

A mixture of X4-216-2 (10.0 g, 37.3 mmol), Selectfluor (1-Chloromethyl-4-fluoro-1,4-diazoniabicyclo[2.2.2]octane bis(tetrafluoroborate)) (26.4 g, 74.6 mmol) and DMAP (4.55 g, 37.3 mmol) in CH$_2$Cl$_2$/H$_2$O (3/1, 40 mL) was stirred at 60° C. overnight. The mixture was concentrated in vacuum. Water was added to the residue, and extracted with DCM (150 mL×3). The combined organic layers were washed with brine (50 mL×2), dried over anhydrous Na$_2$SO$_4$, filtered and concentrated in vacuum. The residue was purified by reverse phase column chromatography to give X4-216-3 (3.00 g, yield: 28%) as a white solid. LCMS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min). Purity: 99%, Rt=1.64 min; MS Calcd.: 286.0; MS Found: 287.1 [M+H]$^+$.

The Synthesis of X4-216-4

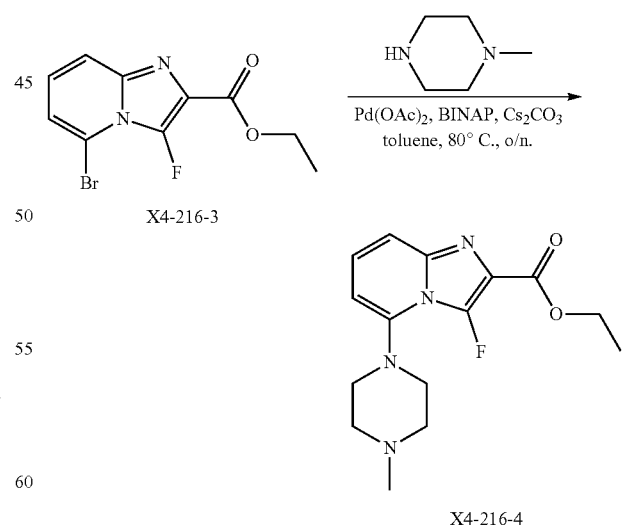

X4-216-4

Following general procedure G, X4-216-4 (1.00 g, yield: 62%) was obtained as a white solid. LCMS (Agilent LCMS 1200-6110, Column: Waters X-Bridge C18 (50 mm*4.6 mm*3.5 μm); Column Temperature: 40° C.; Flow Rate: 2.0 mL/min; Mobile Phase: from 95% [water+0.05% TFA] and 5% [CH₃CN+0.05% TFA] to 0% [water+0.05% TFA] and 100% [CH₃CN+0.05 TFA] in 1.6 min, then under this condition for 1.4 min, finally changed to 95% [water+0.05% TFA] and 5% [CH₃CN+0.05% TFA] in 0.05 min and under this condition for 0.7 min). Purity: 96%, Rt=0.58 min; MS Calcd.: 306.1; MS Found: 307.2 [M+H]⁺.

The Synthesis of X4-216-5

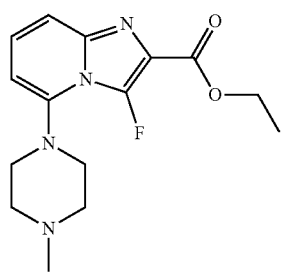

X4-216-4

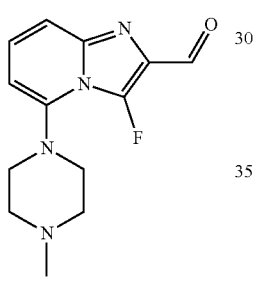

X4-216-5

To a solution of X4-216-4 (1.00 g, 3.27 mmol) in DCM (20 mL) at −78° C. was added DIBAL-H (6.54 mL, 6.54 mmol) dropwise, and the mixture was slowly returned to room temperature and stirred for another 2 h. Water was added to the residue and the mixture was extracted with DCM (150 mL×3). The combined organic layers were washed with brine (50 mL×2), dried over anhydrous Na₂SO₄, filtered and concentrated in vacuum. The residue was re-dissolved in DCM (20 mL) and added MnO2 (2.84 g, 32.7 mmol). The mixture was stirred at room temperature overnight and filtered through Celite. The filtrate was concentrated in vacuum to give X4-013-5 (700 mg, yield: 82%) as a yellow solid. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH₄HCO₃] and 10% [CH₃CN] to 5% [water+10 mM NH₄HCO₃] and 95% [CH₃CN] in 0.5 min, then under this condition for 1.5 min, finally changed to 90% [water+10 mM NH₄HCO₃] and 10% [CH₃CN] in 0.1 min and under this condition for 0.5 min). Purity: 77%, Rt=0.99 min; MS Calcd.: 262.1; MS Found: 263.0 [M+H]⁺.

The Synthesis of X4-216-6

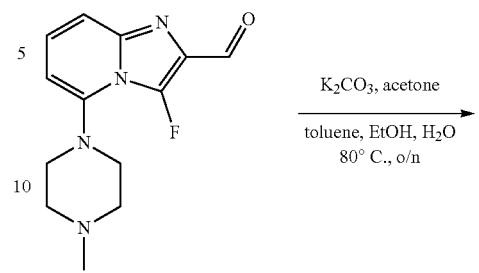

X4-216-5

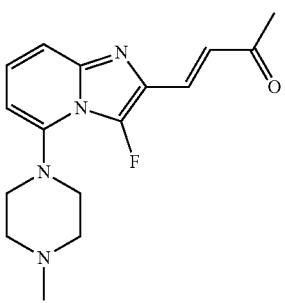

X4-216-6

Following general procedure E, X4-216-6 (500 mg, crude, 72%) was obtained as a yellow foam, which was used in the next step without further purification. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH₄HCO₃] and 10% [CH₃CN] to 5% [water+10 mM NH₄HCO₃] and 95% [CH₃CN] in 0.5 min, then under this condition for 1.5 min, finally changed to 90% [water+10 mM NH₄HCO₃] and 10% [CH₃CN] in 0.1 min and under this condition for 0.5 min.). Purity: 71.5%; Rt=1.07 min; MS Calcd.: 302.1; MS Found: 303.1 [M+H]⁺.

The Synthesis of X4-216-7

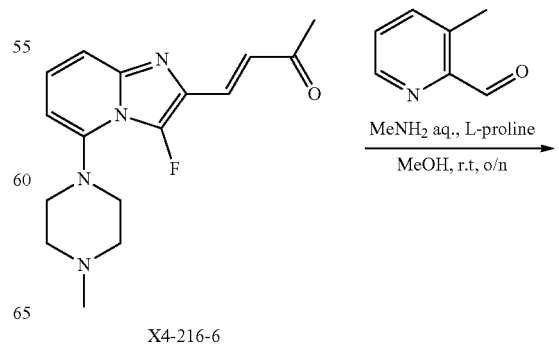

X4-216-6

-continued

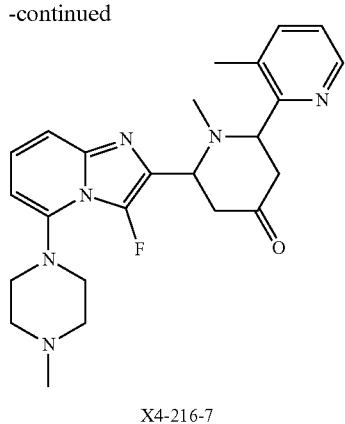

X4-216-7

To a solution of X4-216-6 (500 mg, 1.66 mmol) in MeOH (20 ml) was added L-proline (76.4 mg, 0.664 mmol), 3-methylpicolinaldehyde (223 mg, 1.83 mmol) and MeNH$_2$ aq. (206 mg, 40% w/w, 6.64 mmol). The reaction mixture was stirred overnight at room temperature and concentrated in vacuum. The residue was purified by prep-TLC (DCM/MeOH=20:1) to give X4-216-7 (200 mg, 28%) as a yellow solid. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min.). Purity: 59.4%. Rt=1.13 min; MS Calcd.: 436.2; MS Found: 437.0 [M+H]$^+$.

Synthesis of I-34

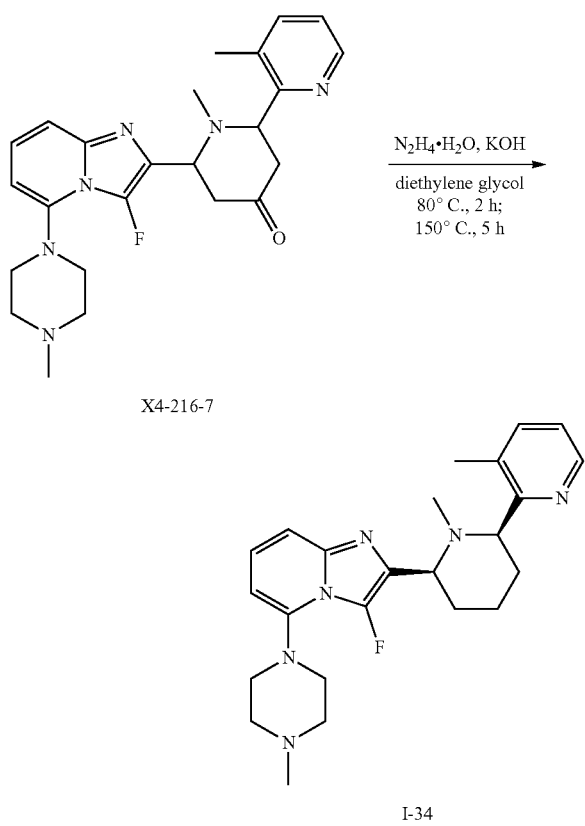

Following general procedure A, I-34 (7.70 mg, 7%) was obtained as a brown solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 0.7 min) Purity: 91.15%. Rt=1.96 min; MS Calcd.: 422.3; MS Found: 423.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 92.8%. Rt=8.85 min. $^1$H NMR (400 MHz, CDCl$_3$) δ 8.47-8.49 (m, 1H), 7.42-7.40 (m, 1H), 7.19-7.16 (m, 1H), 7.07-6.99 (m, 2H), 6.18 (d, J=7.2 Hz, 1H), 3.58-3.54 (m, 1H), 3.49-3.44 (m, 1H), 3.29-3.24 (m, 2H), 2.98-2.79 (m, 4H), 2.47 (s, 3H), 2.39 (s, 3H), 2.25-2.17 (m, 2H), 2.03-1.90 (m, 2H), 1.85 (s, 3H), 1.66-1.53 (m, 2H), 1.42-1.22 (m, 2H).

Example 18: Synthesis of I-66

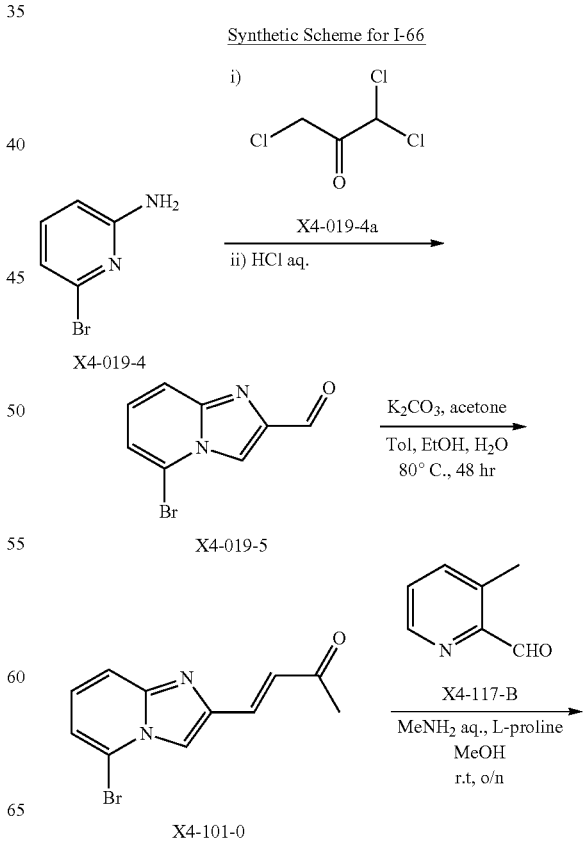

The Synthesis of X4-019-5

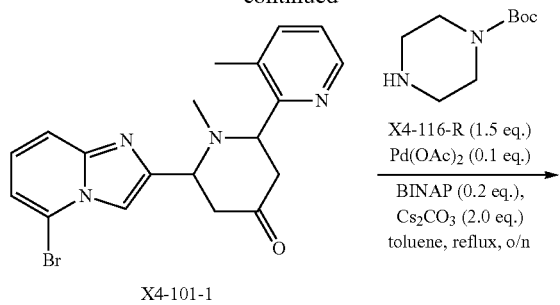

X4-101-1

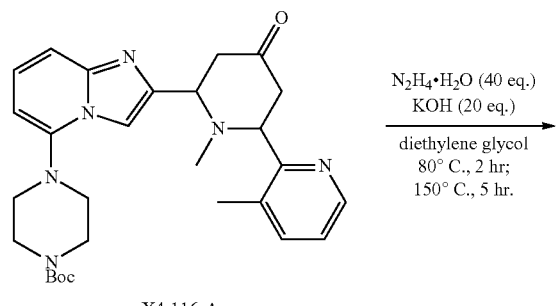

X4-116-A

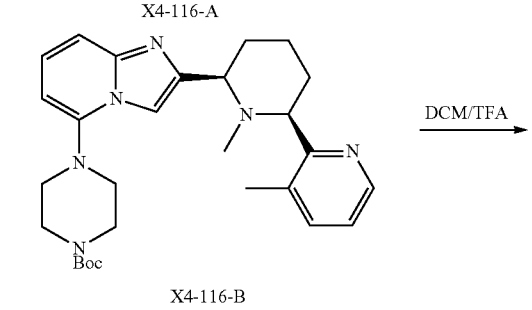

X4-116-B

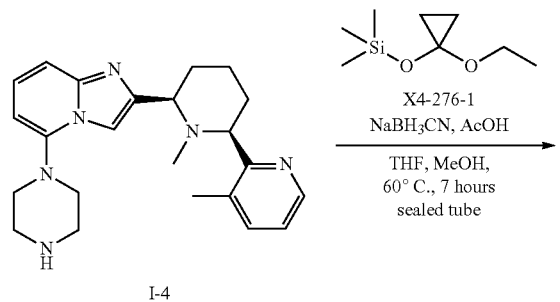

I-4

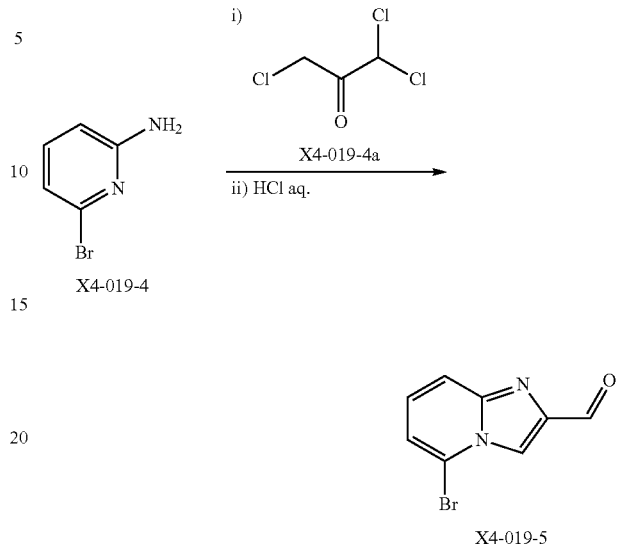

To a solution of X4-019-4 (3.0 g, 1.73 mol) and DME (120 ml) was added X4-019-4a (5.6 g, 3.03 mol) in one portion at room temperature, the reaction mixture was stirred at 65° C. for 4 hours. After being cooled down to 10° C., the mixture was stirred for 1 hour and filtered. After washing with DME, The filtered solid was suspended in DME (120 ml) and 2 M HCl aq. (120 ml), and stirred overnight at 75° C. After being cooled down to 10° C., the mixture was neutralized with 3 M NaOH aq. to pH=8 and filtered. The filtered cake was washed with water and dried in vacuum at 50° C. to give X4-019-5 as an off-white solid (2.81 g, 72% yield). LC-MS (Agilent LCMS 1200-6110, Mobile Phase: from 95% [water+0.05% TFA] and 5% [CH$_3$CN+0.05% TFA] to 0% [water+0.05% TFA] and 100% [CH$_3$CN+0.05% TFA] in 1.6 min, then under this condition for 1.4 min, finally changed to 95% [water+0.05% TFA] and 5% [CH$_3$CN+0.05% TFA] in 0.05 min and under this condition for 0.7 min). Purity: 94.5%, Rt=1.26 min; MS Calcd.: 223.96; MS Found: 225.1 [M+H]$^+$.

Using X4-019-5 and X4-117-B, X4-101-1 was prepared according to General Procedures E and F and methods described herein elsewhere via intermediate X4-101-0.

The Synthesis of X4-116-A

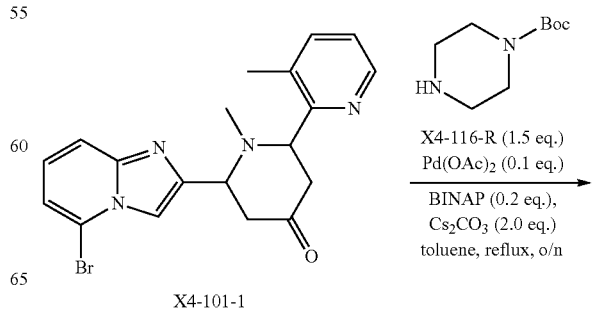

The Synthesis of I-4

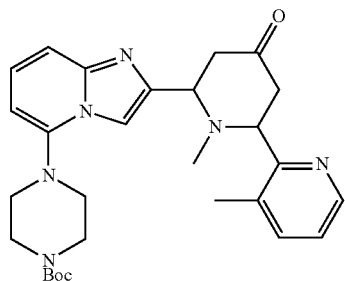

X4-116-A

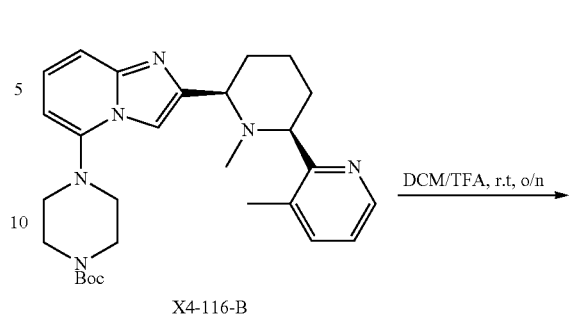

X4-116-B

Following general procedure G, X4-116-A (0.92 g, 24%) was obtained as a yellow solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 92.35%, Rt=1.81 min; MS Calcd.: 504.7, MS Found: 505.7 [M+1]$^+$.

The Synthesis of X4-116-B

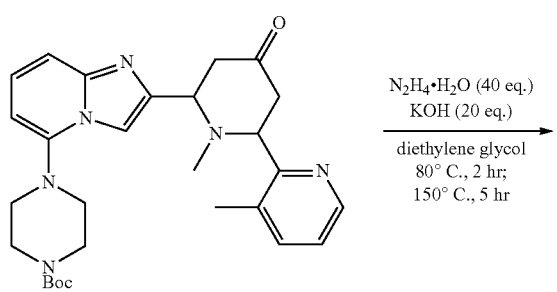

X4-116-A

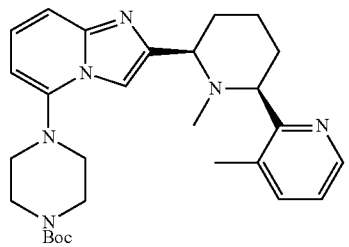

X4-116-B

Following general procedure A, X4-116-B (140 mg, 16%) was obtained as a light yellow solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 93.71%, Rt=1.99 min; MS Calcd.: 490.7, MS Found: 491.7 [M+1]$^+$.

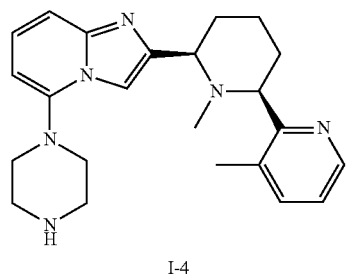

I-4

Following general procedure J, I-4 (110 mg, 99%) was obtained as a light yellow solid. LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Purity: 99.80%, Rt=1.48 min; MS Calcd.: 390.7; MS Found: 391.7 [M+H]$^+$. HPLC (Agilent HPLC 1200, Column: L-column2 ODS (150 mm*4.6 mm*5.0 μm); Column Temperature: 40° C.; Flow Rate: 1.0 ml/min; Mobile Phase: from 95% [water+0.05% TFA] and 5% [$CH_3CN$+0.05% TFA] to 0% [water+0.05% TFA] and 100% [$CH_3CN$+0.05% TFA] in 10 min, then under this condition for 5 min, finally changed to 95% [water+0.05% TFA] and 5% [$CH_3CN$+0.05% TFA] in 0.1 min and under this condition for 5 min). Purity: 98.78%, Rt=4.362 min; MS Calcd.: 390.7; MS Found: 391.7 [M+H]$^+$. $^1$H NMR (400 MHz, CDCl$_3$) δ 8.51 (d, J=3.6 Hz, 1H), 7.63 (s, 1H), 7.43 (d, J=7.2 Hz, 1H), 7.33 (d, J=8.8 Hz, 1H), 7.16-7.12 (m, 1H), 7.07-7.04 (m, 1H), 6.27 (d, J=7.2 Hz, 1H), 3.57 (dd, J=11.2, 2.4 Hz, 1H), 3.47 (dd, J=10.0, 3.6 Hz, 1H), 3.15-3.11 (m, 8H), 2.47 (s, 3H), 2.22 (s, 3H), 1.97-2.06 (m, 4H), 1.75-1.61 (m, 2H).

The Synthesis of I-66

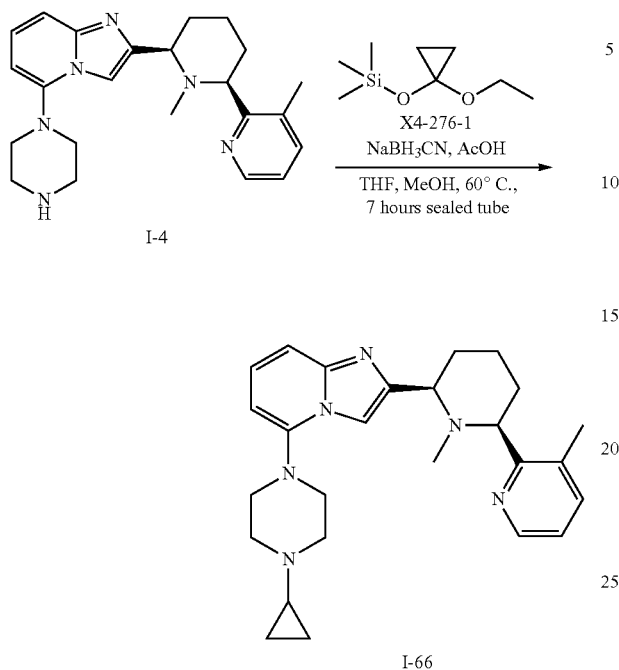

To a solution of I-4 (350.0 mg, 0.90 mmol), X4-276-1 (626.4 mg, 3.6 mmol) in THF (5 mL) and MeOH (5 mL) was added NaBH$_3$CN (223.2 mg, 3.6 mmol) and AcOH (0.05 mL). Then the solution was stirred at 60° C. for 7 hours. After TLC indicated the reaction completed, the mixture was concentrated, quenched with sat. Na$_2$CO$_3$ aq. (20 mL) and extracted with DCM (30 mL×3). The combined organic layers were washed with brine (10 mL), dried over Na$_2$SO$_4$ and filtered. The filtrate was concentrated in vacuum and the residue was purified by prep-HPLC to give I-66 (170 mg, 44%) as off-white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.) Purity: 96.39%. Rt=1.94 min; MS Calcd.: 430.3; MS Found: 431.4 [M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 90% [(total 10 mM AcONH$_4$) H$_2$O/MeCN=900/100 (v/v)] and 10% [total 10 mM AcONH$_4$) H$_2$O/MeCN=100/900 (v/v)] to 15% [total 10 mM AcONH$_4$) H$_2$O/MeCN=900/100 (v/v)] and 85% [total 10 mM AcONH$_4$) H$_2$O/MeCN=100/900 (v/v)] in 5 min, then under this condition for 10 min, finally changed to 90% [(total 10 mM AcONH$_4$) H$_2$O/MeCN=900/100 (v/v)] and 10% [total 10 mM AcONH$_4$) H$_2$O/MeCN=100/900 (v/v)] in 0.1 min and under this condition for 5 min. Purity: 99.9%, Rt=9.61 min. $^1$H NMR (400 MHz, CDCl$_3$) δ 8.51 (d, J=3.6 Hz, 1H), 7.63 (s, 1H), 7.43 (dd, J=7.6, 1.2 Hz, 1H), 7.31 (d, J=8.8 Hz, 1H), 7.14-7.10 (m, 1H), 7.05 (dd, J=7.6, 4.8 Hz, 1H), 6.25 (dd, J=7.2, 0.8 Hz, 1H), 3.59-3.56 (m, 1H), 3.50-3.45 (m, 1H), 3.11 (s, 4H), 2.90 (s, 4H), 2.48 (s, 3H), 2.09-2.05 (m, 2H), 1.97-1.93 (m, 2H), 1.91 (s, 3H), 1.83-1.78 (m, 1H), 1.74-1.61 (m, 2H), 0.57-0.52 (m, 2H), 0.51-0.46 (m, 2H).

Example 19: Synthesis of I-76

Synthetic Scheme for I-76

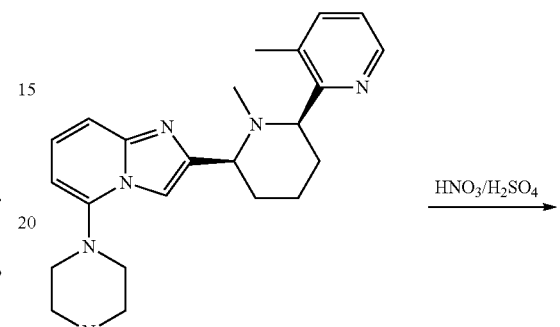

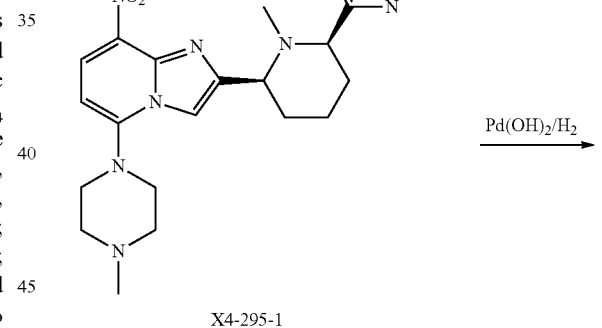

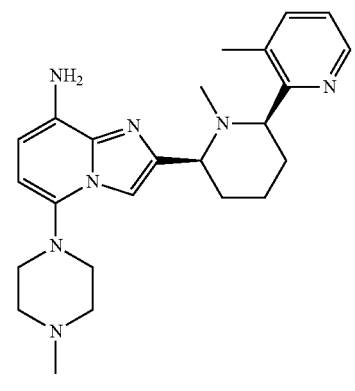

The Synthesis of X4-295-1

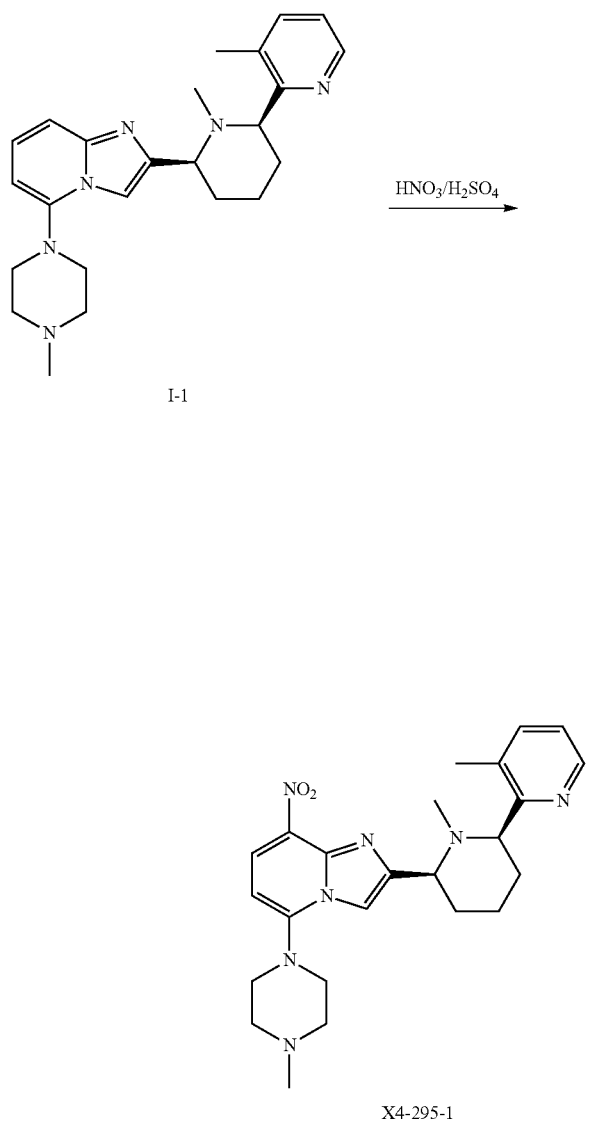

To a solution of I-1 (150 mg, 3.7 mmol) in conc. $H_2SO_4$ (2 ml) was added conc. nitric acid (1.6 mL, 38 mmol) slowly through syringe at 0° C., and the mixture was stirred at room temperature for 1 hour. Then the reaction mixture was poured into cold $NaHCO_3$ aqueous solution and extracted with DCM. The organic layer was concentrated in vacuum and the residue was purified by prep-TLC (DCM/$CH_3OH$=8:1) to provide product X4-295-1 (40 mg, 26% yield) as yellow solid. LCMS (Agilent LCMS 1200-6120, Column: Waters X-Bridge C18 (50 mm*4.6 mm*3.5 μm)); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 50.59%. Rt=1.64 min; MS Calcd.: 449.2; MS Found: 450.4 $[M+H]^+$.

The Synthesis of I-76

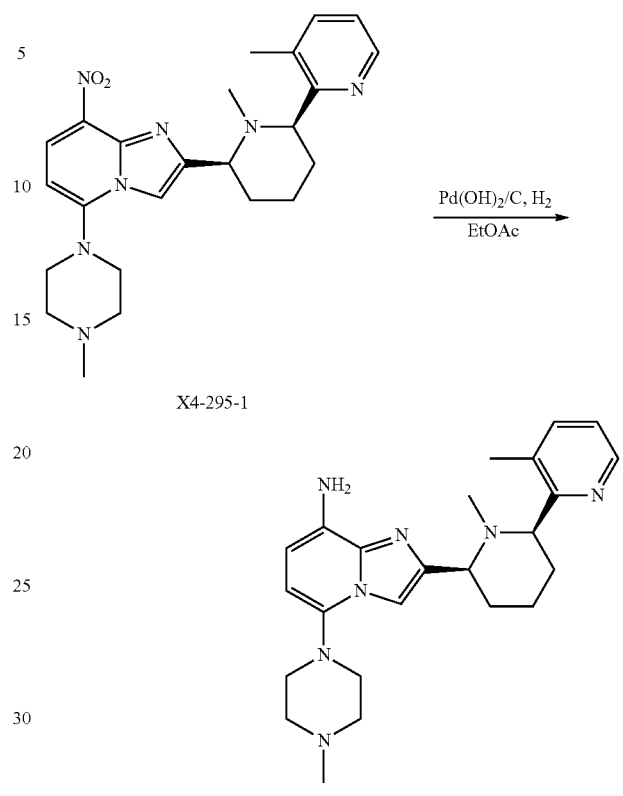

To a solution of X4-295-1 (100 mg, 0.22 mmol) in ethyl acetate (10 ml) was added $Pd(OH)_2/C$ (50 mg), and the mixture was stirred at 25° C. for 36 hours under $H_2$ atmosphere. Then it was filtered through Celite and the filtrate was concentrated in vacuum. The residue was purified by prep-HPLC to give I-76 (80 mg, 87% yield) as off-white solid. LCMS (Agilent LCMS 1200-6120, Column: Waters X-Bridge C18 (50 mm*4.6 mm*3.5 μm)); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min. Purity: 91.83%. Rt=1.66 min; MS Calcd.: 419.6; MS Found: 420.4 $[M+H]^+$. HPLC (Agilent HPLC 1200, Column: Waters X-Bridge C18 (150 mm*4.6 mm*3.5 μm)); Column Temperature: 40° C.; Flow Rate: 1.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 10 min, then under this condition for 5 min, finally changed to 95% [water+10 mM $NH_4HCO_3$] and 5% [$CH_3CN$] in 0.1 min and under this condition for 5 min. Purity: 97.02%. Rt=8.05 min. $^1HNMR$ (400 MHz, $CDCl_3$) δ 8.50 (d, J=3.6 Hz, 1H), 7.55 (1H, s), 7.62 (dd, J=7.6, 1.2 Hz, 1H), 7.32 (dd, J=7.6, 1.2 Hz, 1H), 6.31 (d, J=7.6 Hz, 1H), 6.15 (d, J=7.6 Hz, 1H), 4.30 (brs, 2H), 3.57 (dd, J=10.8, 1.6 Hz, 1H), 3.42 (dd, J=10.8, 1.6 Hz, 1H), 3.05 (s, 4H), 2.66 (s, 4H), 2.44-2.41 (m, 6H), 2.03-1.87 (m, 4H), 1.73-1.59 (m, 5H).

Example 20: Synthesis of I-79

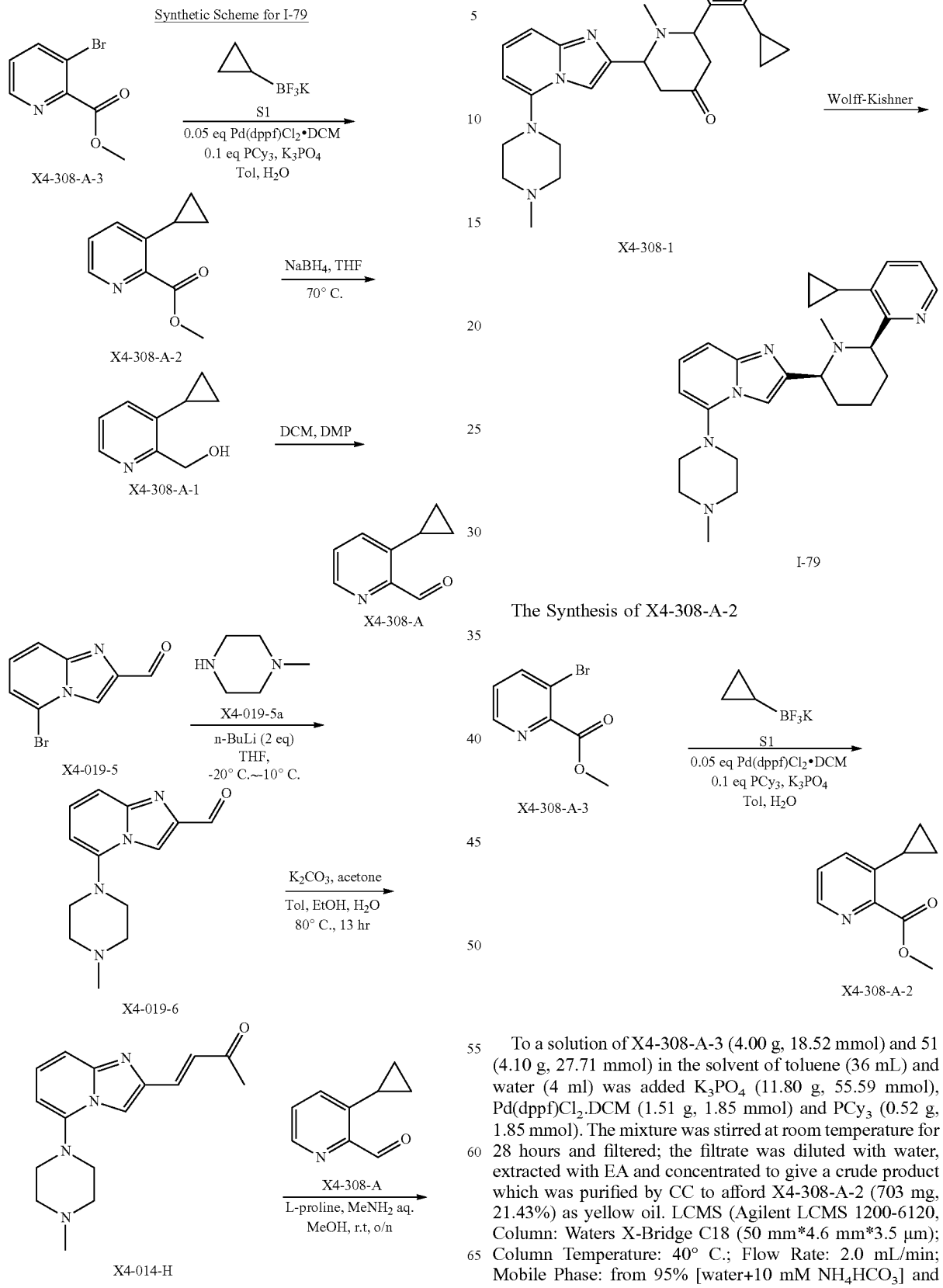

The Synthesis of X4-308-A-2

To a solution of X4-308-A-3 (4.00 g, 18.52 mmol) and 51 (4.10 g, 27.71 mmol) in the solvent of toluene (36 mL) and water (4 ml) was added $K_3PO_4$ (11.80 g, 55.59 mmol), Pd(dppf)$Cl_2$·DCM (1.51 g, 1.85 mmol) and $PCy_3$ (0.52 g, 1.85 mmol). The mixture was stirred at room temperature for 28 hours and filtered; the filtrate was diluted with water, extracted with EA and concentrated to give a crude product which was purified by CC to afford X4-308-A-2 (703 mg, 21.43%) as yellow oil. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100%

[CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 82.76%. Rt=1.51 min; MS Calcd.: 177.1; MS Found: 178.3 [M+H]⁺.

The Synthesis of X4-308-A-1

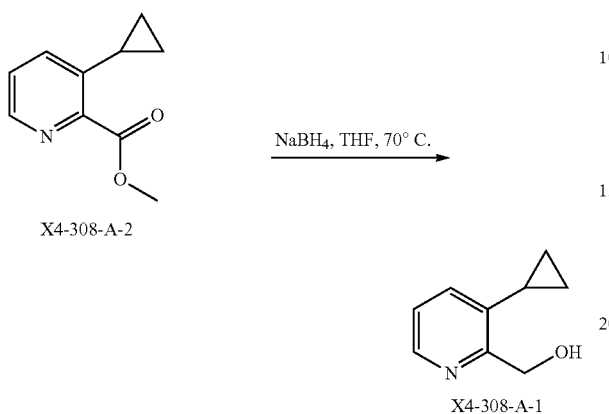

To a solution of X4-308-A-2 (175 mg, 0.99 mmol) in THF (3.5 mL) was added NaBH₄ (150 mg, 3.96 mmol). The mixture was stirred overnight at 70° C., cooled to room temperature, quenched with cooled water, extracted with EA and concentrated to give X4-308-A-1 (120 mg, 81.45%) as yellow oil. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 89.49%. Rt=1.38 min; MS Calcd.: 149.1; MS Found: 150.3 [M+H]⁺.

The Synthesis of X4-308-A

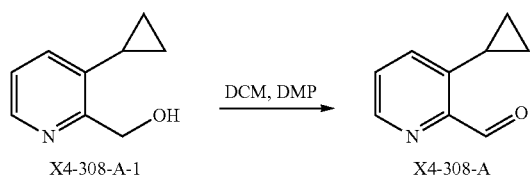 [SMILES: OCc1ncccc1C1CC1 ; O=Cc1ncccc1C1CC1]

To a solution of X4-308-A-1 (550 mg, 3.69 mmol) in DCM (3 ml) was added DMP (1.73 g, 4.08 mmol). Then the reaction mixture was stirred at room temperature for 4 hours. After TLC indicated the reaction completed, the reaction mixture was quenched with NaHCO₃aq. and extracted with DCM. The organic layer was washed with brine, dried over Na₂SO₄ and concentrated to give the crude product, which was purified with CC to give X4-308-A (210 mg, 38.70% yield) as yellow oil. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 98.67%. Rt=1.51 min; MS Calcd.: 147.1; MS Found: 148.3 [M+H]⁺.

The Synthesis of X4-019-6

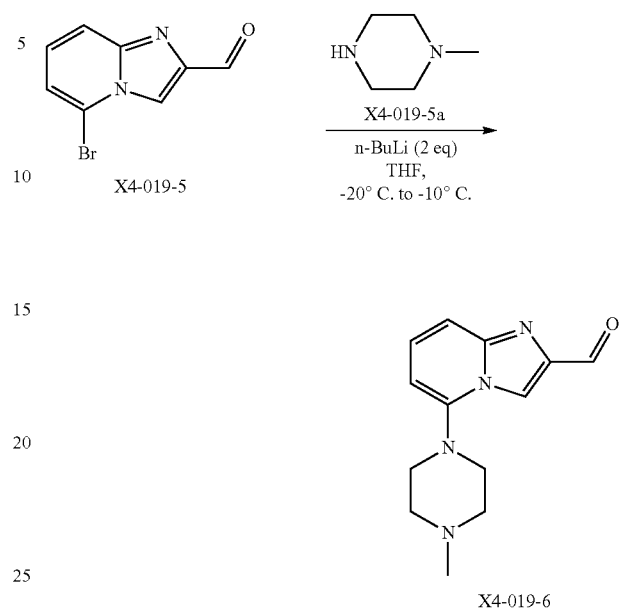

To a solution of X4-019-5a (1.7 g, 16.7 mmol) and THF (10 ml) was added n-BuLi (5.6 ml, 14.1 mmol, 2.5 M in hexanes) dropwise at −20° C. After stirred at −20° C. for 20 min, the mixture was added slurry of X4-019-5 (1.5 g, 6.7 mmol) in THF (30 ml) dropwise at −20° C. and stirred at −10° C. for 7 hours. After quenched with sat NH₄Cl aq. (pH=8), the mixture was extracted with DCM/i-PrOH (10/1). The organic layer was washed with sat NaHCO₃aq., dried over Na₂SO₄, filtered and concentrated in vacuum. The residue was purified by column chromatography to give product X4-019-6 (785 mg, 48%) as yellow oil. LC-MS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 94.5%, Rt=1.31 min; MS Calcd.: 224.13; MS Found: 245.1 [M+H]⁺.

The Synthesis of X4-014-H

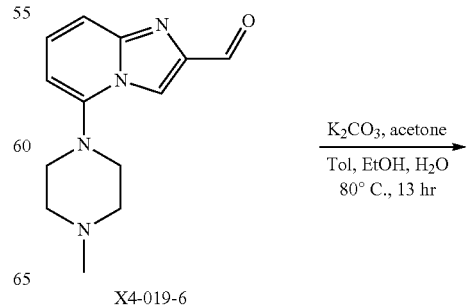

-continued

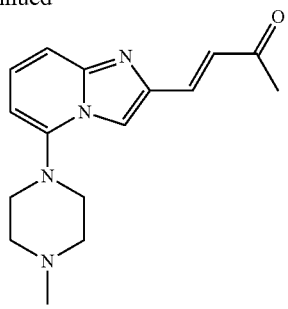

X4-014-H

Following general procedure E, X4-014-H (1.9 g, 41%) was obtained as a yellow foam. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 69.13%; Rt=1.38 min; MS Calcd.: 284.4; MS Found: 285.4 [M+H]$^+$.

The Synthesis of X4-308-1

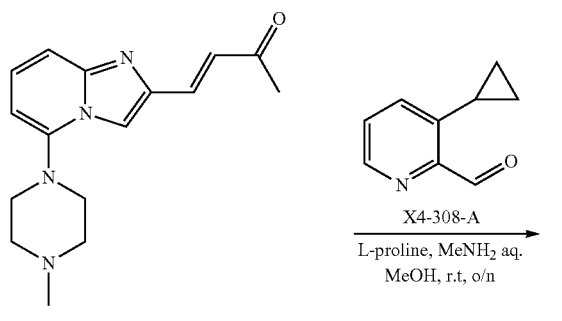

X4-014-H

X4-308-A
L-proline, MeNH$_2$ aq.
MeOH, r.t, o/n

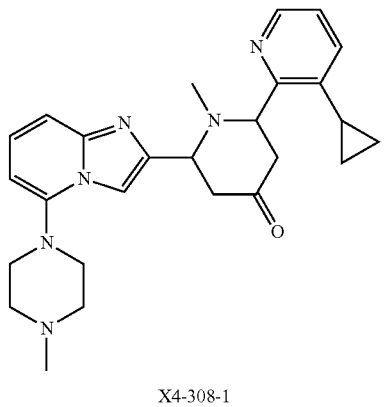

X4-308-1

X4-308-1 (93 mg, 25.86%) was synthesized by reaction of X4-308-A with X4-014-H in the presence of L-proline and methylamine aq. as described above to provide the desired product as as a yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) water/CH$_3$CN=900/100 (v/v)] and 10% [(total 10 mM AcONH$_4$) water/CH$_3$CN=100/900 (v/v)] to 10% [(total 10 mM AcONH$_4$) water/CH$_3$CN=900/100 (v/v)] and 90% [(total 10 mM AcONH$_4$) water/CH$_3$CN=100/900 (v/v)] in 1.6 min, then under this condition for 2.4 min, finally changed to 90% [(total 10 mM AcONH$_4$) water/CH$_3$CN=900/100 (v/v)] and 10% [(total 10 mM AcONH$_4$) water/CH$_3$CN=100/900 (v/v)] in 0.1 min and under this condition for 0.7 min.) Purity: 38.95%. Rt=1.66 min; MS Calcd.: 444.3; MS Found: 445.3 [M+H]$^+$.

The Synthesis of I-79

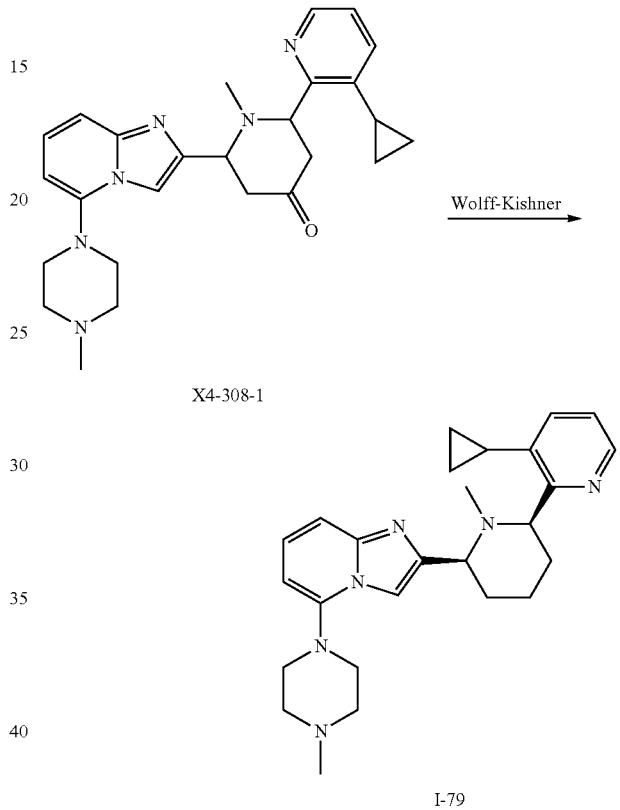

I-79 following General Procedure A, I-79 (12 mg, 13.32%) was synthesized as a light yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min). Purity: 100.00%. Rt=1.756 min; MS Calcd.: 430.3; MS Found: 431.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 98.73%. Rt=8.82 min. $^1$H NMR (400 MHz, CDCl$_3$) δ 8.49 (s, 1H), 7.51 (s, 1H), 7.33-7.27 (m, 2H), 7.14 (dd, J=9.0, 7.0 Hz, 1H), 7.06 (dd, J=8.0, 4.8 Hz, 1H), 6.27 (dd, J=7.2, 0.8, 1H), 3.97 (d, J=8.4 Hz, 1H), 3.48 (dd, J=11.6, 2.4 Hz, 1H), 3.18-3.14 (m, 4H), 2.77-2.70

(m, 4H), 2.43 (s, 3H), 2.13-2.05 (m, 3H), 1.99-1.94 (2H, m), 1.89 (s, 3H), 1.77 (d, J=9.2 Hz, 1H), 1.67-1.62 (m, 2H), 1.07-1.00 (m, 2H), 0.72-0.69 (m, 1H), 0.68-0.51 (m, 1H).
Example 21: Synthesis of I-146
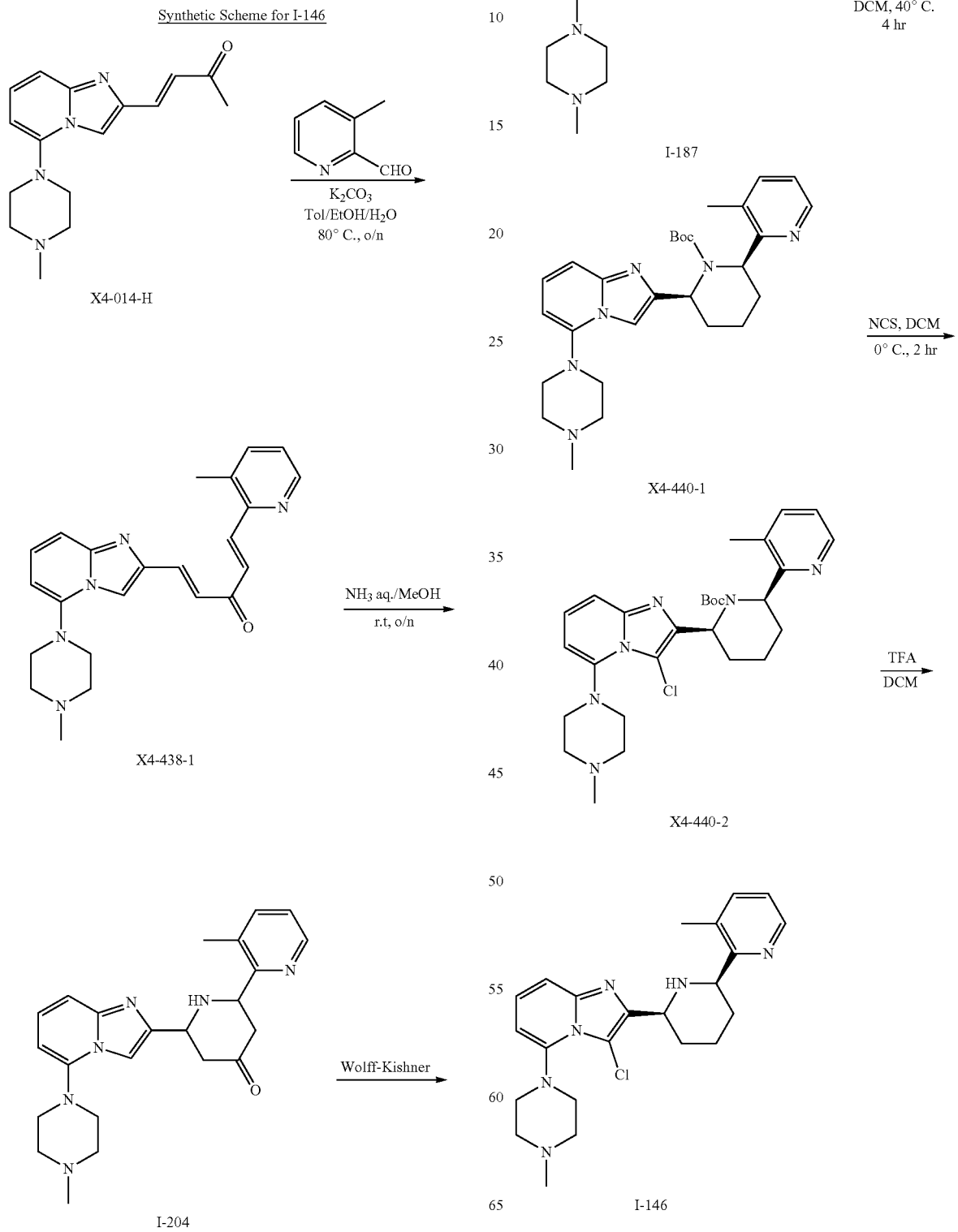

The Synthesis of X4-438-1

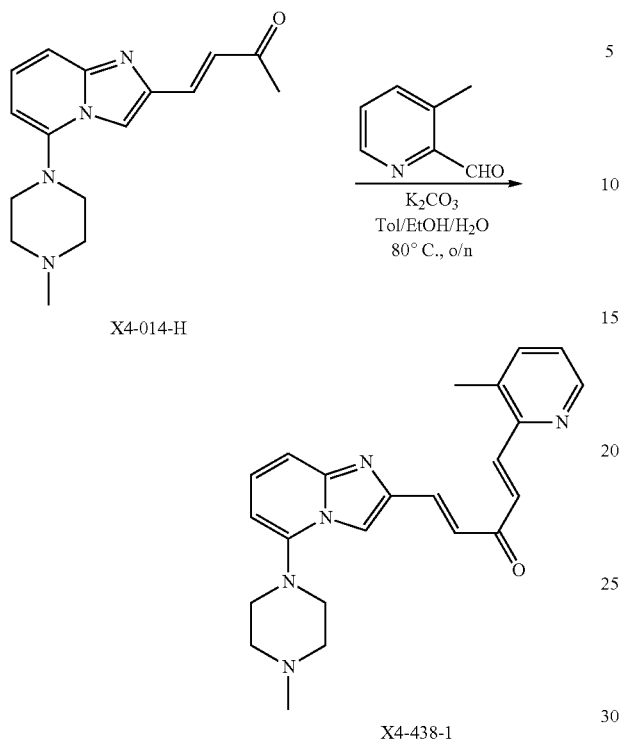

X4-014-H

X4-438-1

A mixture of X4-014-H (2.5 g, 8.8 mmol), 3-methylpicolinaldehyde (1.1 g, 8.8 mmol), K₂CO₃ (1.8 g, 13.2 mmol) in toluene (100 ml)/EtOH (40 ml)/H₂O (20 ml) was stirred at 80° C. overnight. After reaction completed, the mixture was cooled down to room temperature and concentrated in vacuum. The residue was purified by flash silica gel pad (3 cm), eluted with EtOAc:petroleum ether=1:1 to DCM/MeOH=100/1 to give 2.3 g of X4-438-1 as yellow foam (yield: 68%), which was used for the next step directly. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 77.36%; Rt=1.59 min; MS Calcd.: 387.2; MS Found: 388.3 [M+H]⁺.

The Synthesis of I-204

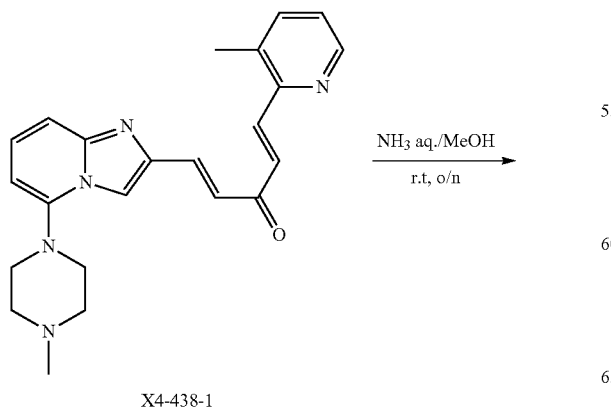

X4-438-1

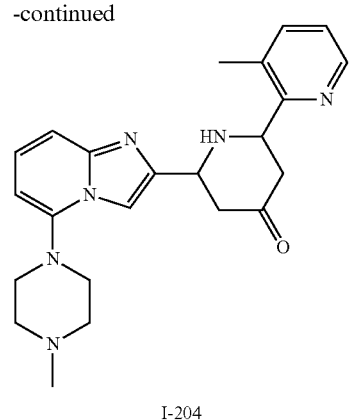

I-204

To a solution of X4-438-1 (2.3 g, 5.9 mmol) in MeOH (120 ml) was added conc. NH₃ aq. (5 ml, 20%, 59 mmol) at room temperature and the mixture was stirred at room temperature overnight. After reaction completed, the mixture was concentrated in vacuum and the residue was purified by flash silica gel pad (3 cm), eluting with DCM/MeOH=60/1 to 30/1 to give 1 g of I-204 as yellow foam (yield: 42%), which was used for the next step directly. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 78.15%; Rt=1.41 min; MS Calcd.: 404.2; MS Found: 405.4 [M+H]⁺.

The Synthesis of I-187

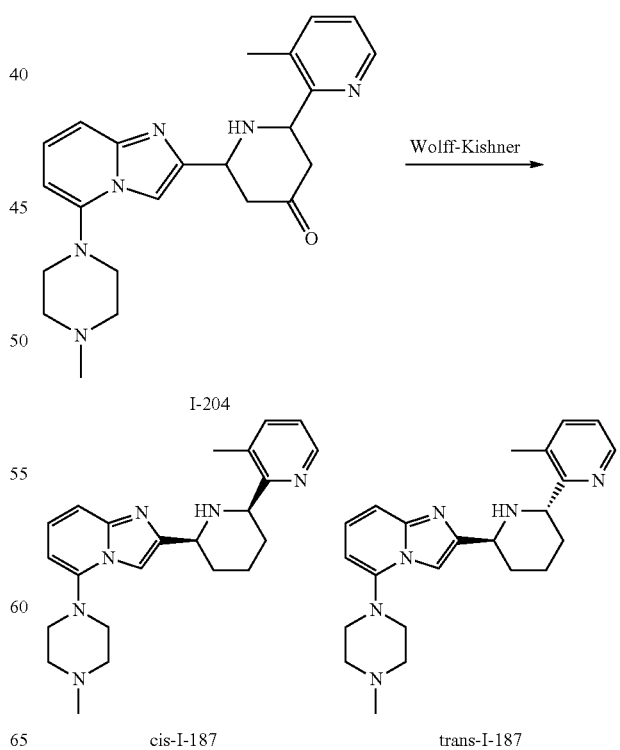

I-204 cis-I-187  trans-I-187

A mixture of I-204 (1 g, 2.5 mmol), KOH (2.8 g, 50 mmol) and $N_2H_4 \cdot H_2O$ (5 g, 100 mmol) in diethylene glycol (30 ml) was stirred at 80° C. for 2 h; then removed $N_2H_4 \cdot H_2O$ in vacuum when heating to 160° C. and stirred at 160° C. for 2 h. After the reaction was completed, the mixture was cooled down to room temperature and quenched with $H_2O$ (90 ml)/DCM (120 ml). The aqueous layer was extracted with DCM (120 ml×3). The combined organic layers were washed with $H_2O$ and brine, dried over $Na_2SO_4$, filtered and concentrated in vacuum. The residue was purified by CC (eluted with DCM/MeOH) to give 220 mg of (racemic) cis-I-187 (220 mg), 400 mg of (racemic) mix of cis/trans-I-187 (400 mg, trans:cis=4:5) and 270 mg of (racemic) trans-I-187 (270 mg). Yield=91%. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM $NH_4HCO_3$] and 5% [$CH_3CN$] to 0% [water+10 mM $NH_4HCO_3$] and 100% [$CH_3CN$] in 1.6 min, then under this condition for 1.4 min, finally changed to 95% [water+10 mM $NH_4HCO_3$] and 5% [$CH_3CN$] in 0.1 min and under this condition for 0.7 min). Cis: Purity: 71.18%; Rt=1.51 min; Trans: Purity: 64.10%; Rt=1.48 min; Mix: Purity: 84.07%; MS Calcd.: 390.3; MS Found: 391.4 $[M+H]^+$.

The Synthesis of X4-440-1

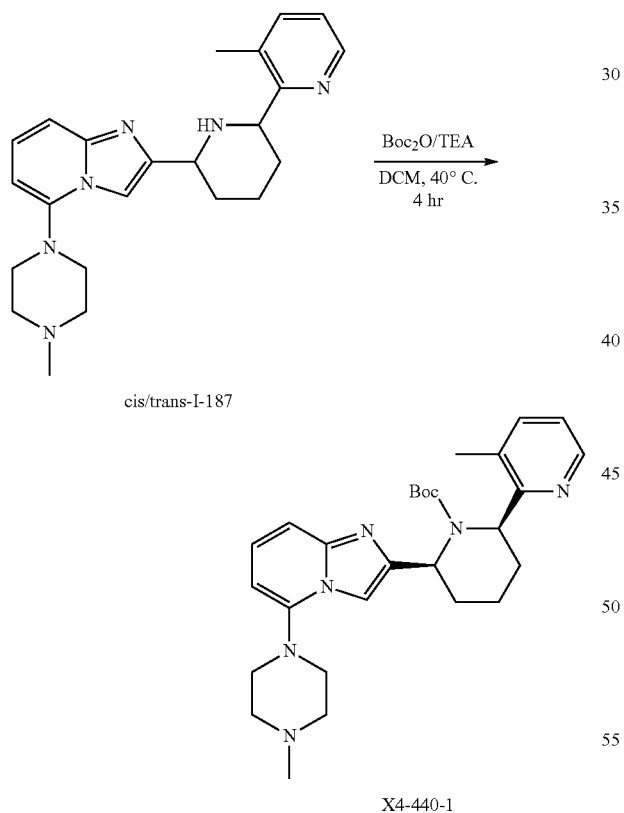

cis/trans-I-187

X4-440-1

To a solution of cis/trans-I-187 (300 mg, 0.77 mmol) in dichloromethane (10 mL) was added triethylamine (233 mg, 2.30 mmol) and di-tert-butyl dicarbonate (252 mg, 1.15 mmol), and the mixture was stirred at 40° C. for 4 h. After reaction was completed, the suspension was diluted with water (10 mL) and dichloromethane (20 mL). The separated organic layer was concentrated by vacuum and the residue was purified by prep-TLC (eluted with ethyl acetate) to give X4-440-1 (100 mg, 27%) as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM $AcONH_4$) $H_2O$/MeCN=900/100 (v/v)] and 10% [(total 10 mM $AcONH_4$) $H_2O$/MeCN=100/900 (v/v)] to 10% [(total 10 mM $AcONH_4$) $H_2O$/MeCN=900/100 (v/v)] and 90% [(total 10 mM $AcONH_4$) $H_2O$/MeCN=100/900 (v/v)] in 1.6 min, then under this condition for 2.4 min, finally changed to 90% [(total 10 mM $AcONH_4$) $H_2O$/MeCN=900/100 (v/v)] and 10% [(total 10 mM $AcONH_4$) $H_2O$/MeCN=100/900 (v/v)] in 0.1 min and under this condition for 0.7 min. Purity: 80.70%, Rt=2.10 min; MS Calcd.: 490.3; MS Found: 491.3 $[M+H]^+$.

The Synthesis of X4-440-2

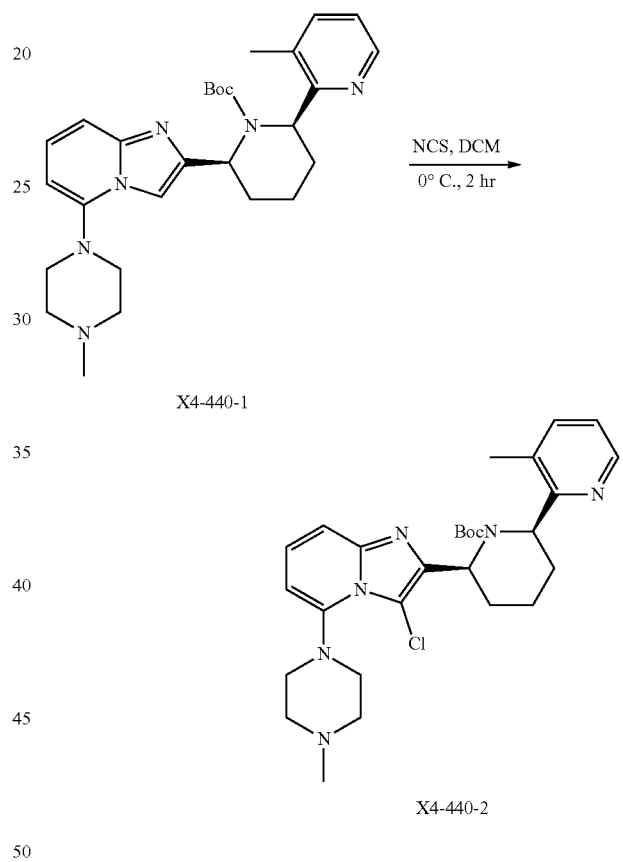

X4-440-1

X4-440-2

Following general procedure K, X4-440-2 (80 mg, 100%) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM $AcONH_4$) $H_2O$/MeCN=900/100 (v/v)] and 10% [(total 10 mM $AcONH_4$) $H_2O$/MeCN=100/900 (v/v)] to 10% [(total 10 mM $AcONH_4$) $H_2O$/MeCN=900/100 (v/v)] and 90% [(total 10 mM $AcONH_4$) $H_2O$/MeCN=100/900 (v/v)] in 1.6 min, then under this condition for 2.4 min, finally changed to 90% [(total 10 mM $AcONH_4$) $H_2O$/MeCN=900/100 (v/v)] and 10% [(total 10 mM $AcONH_4$) $H_2O$/MeCN=100/900 (v/v)] in 0.1 min and under this condition for 0.7 min. Purity: 96.33%, Rt=2.14 min; MS Calcd.: 524.3; MS Found: 525.2 $[M+H]^+$.

The Synthesis of I-146

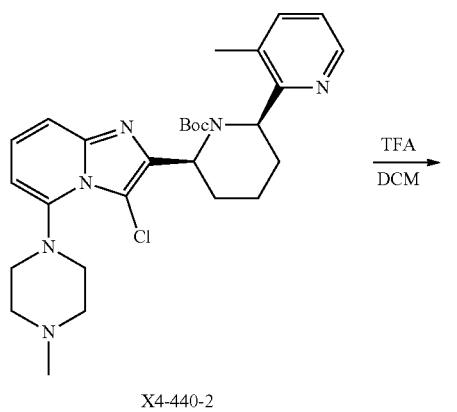

X4-440-2

I-146

Following general procedure J, I-146 (11 mg, 17%) was obtained as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.). Purity: 97.67%; Rt=1.70 min; MS Calcd.: 424.2; MS Found: 425.4[M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min.). Purity: 97.60%, Rt=8.21 min; MS Calcd.: 424.2; MS Found: 425.4[M+H]$^+$. $^1$H NMR (400 MHz, CDCl$_3$) δ 8.40 (dd, J=4.8, 1.2 Hz, 1H), 7.38 (dd, J=7.2, 1.6 Hz, 1H), 7.32 (dd, J=9.2, 1.2 Hz, 1H), 7.08 (dd, J=8.8, 7.2 Hz, 1H), 7.02 (dd, J=8.0, 4.8 Hz, 1H), 6.34 (dd, J=7.2, 0.8 Hz, 1H), 4.25-4.18 (m, 2H), 3.29-3.25 (m, 2H), 2.96-2.78 (m, 4H), 2.53-2.46 (m, 2H), 2.38 (s, 6H), 2.16-2.11 (m, 1H), 1.88-1.80 (m, 4H), 1.72-1.65 (m, 2H).

Example 22: Synthesis of I-149, I-188, I-189, and I-205

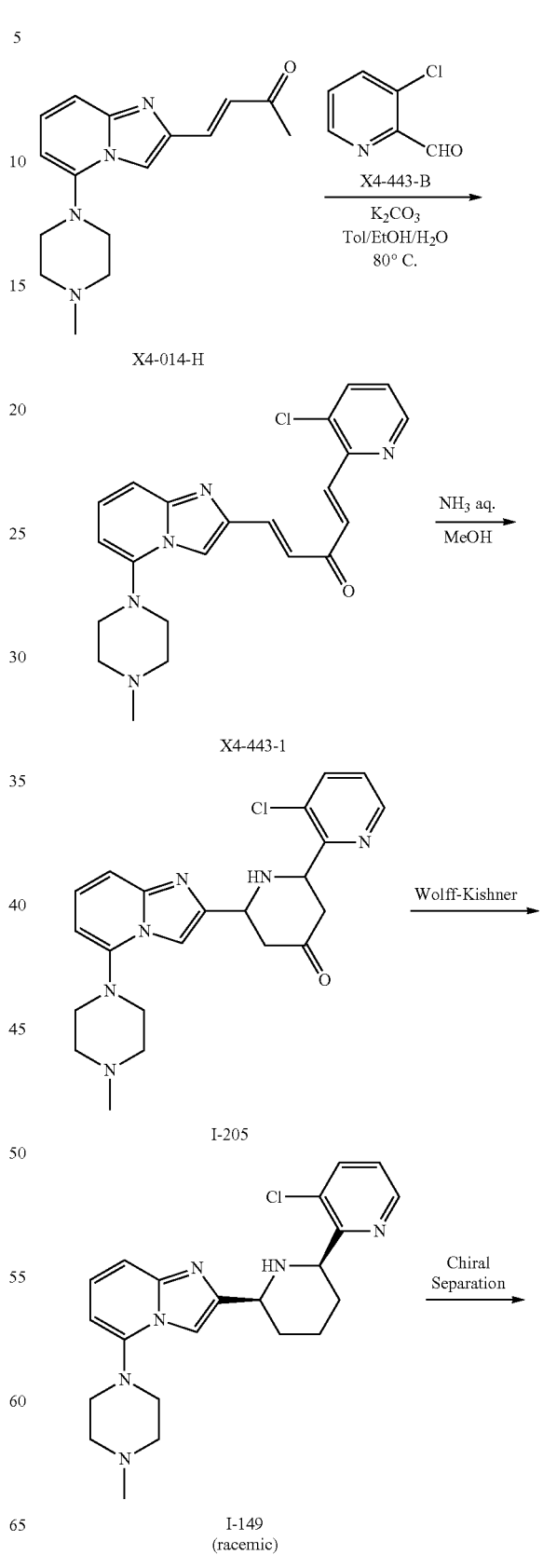

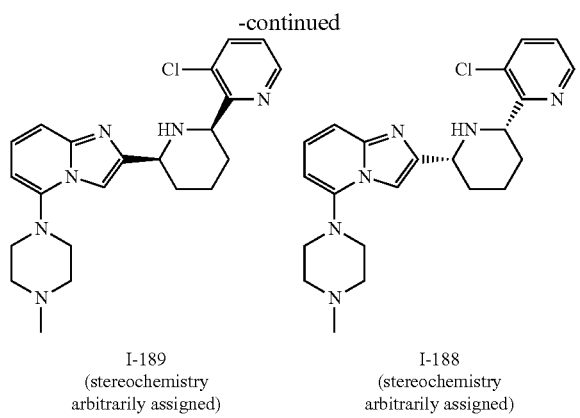

I-189
(stereochemistry
arbitrarily assigned)

I-188
(stereochemistry
arbitrarily assigned)

The Synthesis of X4-443-1

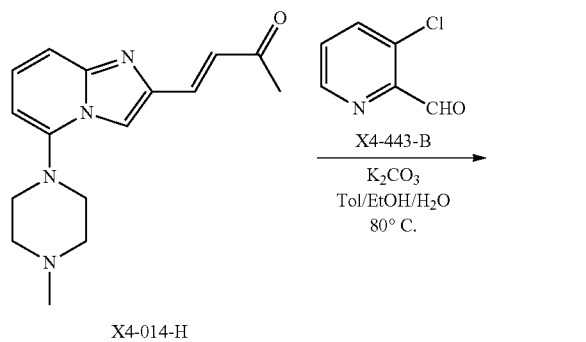

To a solution of X4-014-H (2.0 g, 7.03 mmol), X4-014-B (992.6 mg, 7.01 mmol) in toluene/EtOH/H₂O (5:2:1, 50 mL) was added K₂CO₃ (1.46 g, 10.56 mmol). The mixture was stirred at 80° C. overnight. The reaction mixture was cooled to room temperature, concentrated in vacuum and the residue was purified by column chromatography to give X4-443-1 (2.0 g, 70%) as yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 79.84%. Rt=1.65 min; MS Calcd.: 407.2; MS Found: 408.2 [M+H]⁺.

The Synthesis of I-205

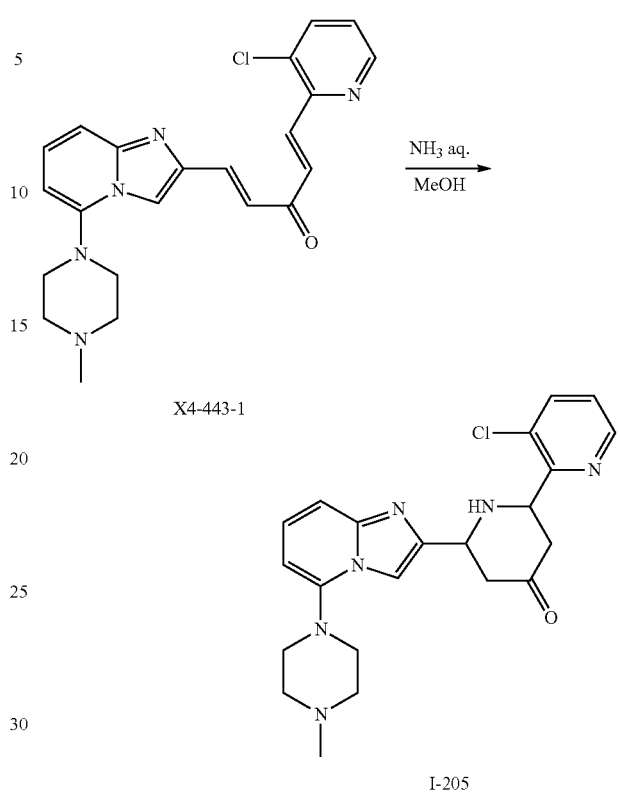

To a solution of X4-443-1 (2.0 g, 4.9 mmol) in MeOH (120 mL) were added NH₃ aq. (20%, 4.2 mL, 49 mmol), and the mixture was stirred at room temperature overnight. Then it was concentrated in vacuum and the residue was purified by column chromatography to give I-205 (600 mg, 29% yield, 65% trans; 25% cis) as yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH₄HCO₃] and 5% [CH₃CN] to 0% [water+10 mM NH₄HCO₃] and 100% [CH₃CN] in 1.6 min, then under this condition for 1.4 min, finally changed to 95% [water+10 mM NH₄HCO₃] and 5% [CH₃CN] in 0.1 min and under this condition for 0.7 min). Purity: 71.43%. Rt=1.44 min, 1.47 min; MS Calcd.: 424.2; MS Found: 425.2 [M+H]⁺.

The Synthesis of I-149, I-188, and I-189

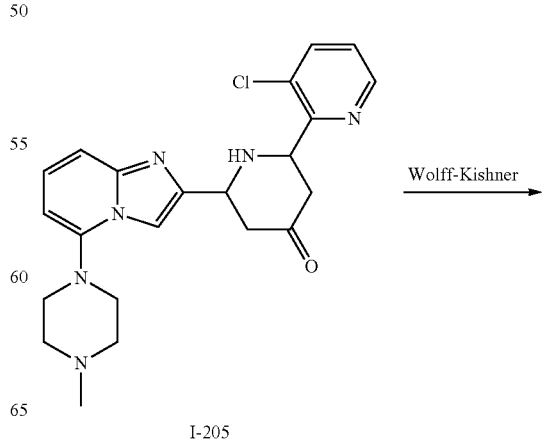

-continued

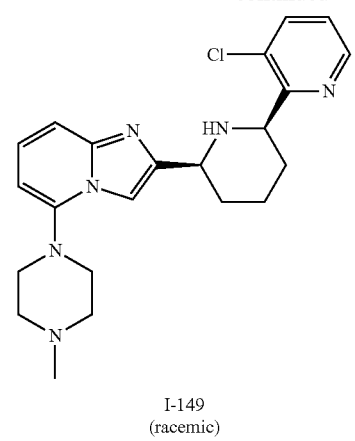

I-149
(racemic)

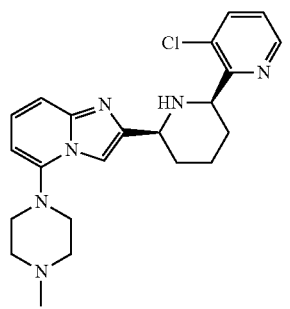

| I-189 | I-188 |
| --- | --- |
| (stereochemistry arbitrarily assigned) | (stereochemistry arbitrarily assigned) |

Following general procedure A, I-149 (30 mg, 22% yield) was obtained as light-yellow solid. The solid was separated by SFC to give I-188 (10 mg) and I-189 (11 mg). LCMS (Agilent LCMS 1200-6120, Column: Waters X-Bridge C18 (50 mm*4.6 mm*3.5 μm); Column Temperature: 40° C.; Flow Rate: 2.0 ml/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.). Purity: 97.24%, Rt=1.60 min; MS Calcd.: 410.2; MS Found: 411.2 [M+H]$^+$. HPLC (Agilent HPLC 1200, Column: L-column2 ODS (150 mm*4.6 mm*5.0 μm); Column Temperature: 40° C.; Flow Rate: 1.0 mL/min; Mobile Phase: from 90% [(total 10 mM AcONH$_4$) H$_2$O/MeCN=900/100 (v/v)] and 10% [total 10 mM AcONH$_4$) H$_2$O/MeCN=100/900 (v/v)] to 15% [total 10 mM AcONH$_4$) H$_2$O/MeCN=900/100 (v/v)] and 85% [total 10 mM AcONH$_4$) H$_2$O/MeCN=100/900 (v/v)] in 5 min, then under this condition for 10 min, finally changed to 90% [(total 10 mM AcONH$_4$) H$_2$O/MeCN=900/100 (v/v)] and 10% [total 10 mM AcONH$_4$) H$_2$O/MeCN=100/900 (v/v)] in 0.1 min and under this condition for 5 min. Purity: >99.00%, Rt=5.63 min. $^1$H NMR (400 MHz, CDCl$_3$) δ 8.59-8.50 (dd, J=4.8, 1.6 Hz, 1H), 7.65-7.63 (m, 1H), 7.51 (s, 1H), 7.32 (d, J=8.8 Hz, 1H), 7.17-7.10 (m, 2H), 6.27 (dd, J=7.2, 0.8 Hz, 1H), 4.52 (dd, J=11.2, 2.4, 1H), 4.20-4.17 (m, 1H), 3.14 (s, 4H), 2.66 (m, 4H), 2.40 (s, 3H), 2.23-2.19 (m, 1H), 2.15-2.11 (m, 1H), 2.02-1.98 (m, 1H), 1.89-1.77 (m, 2H), 1.61-1.54 (m, 1H).

Example 23: Synthesis of I-154 and I-206

Synthetic Scheme for I-154 and I-206

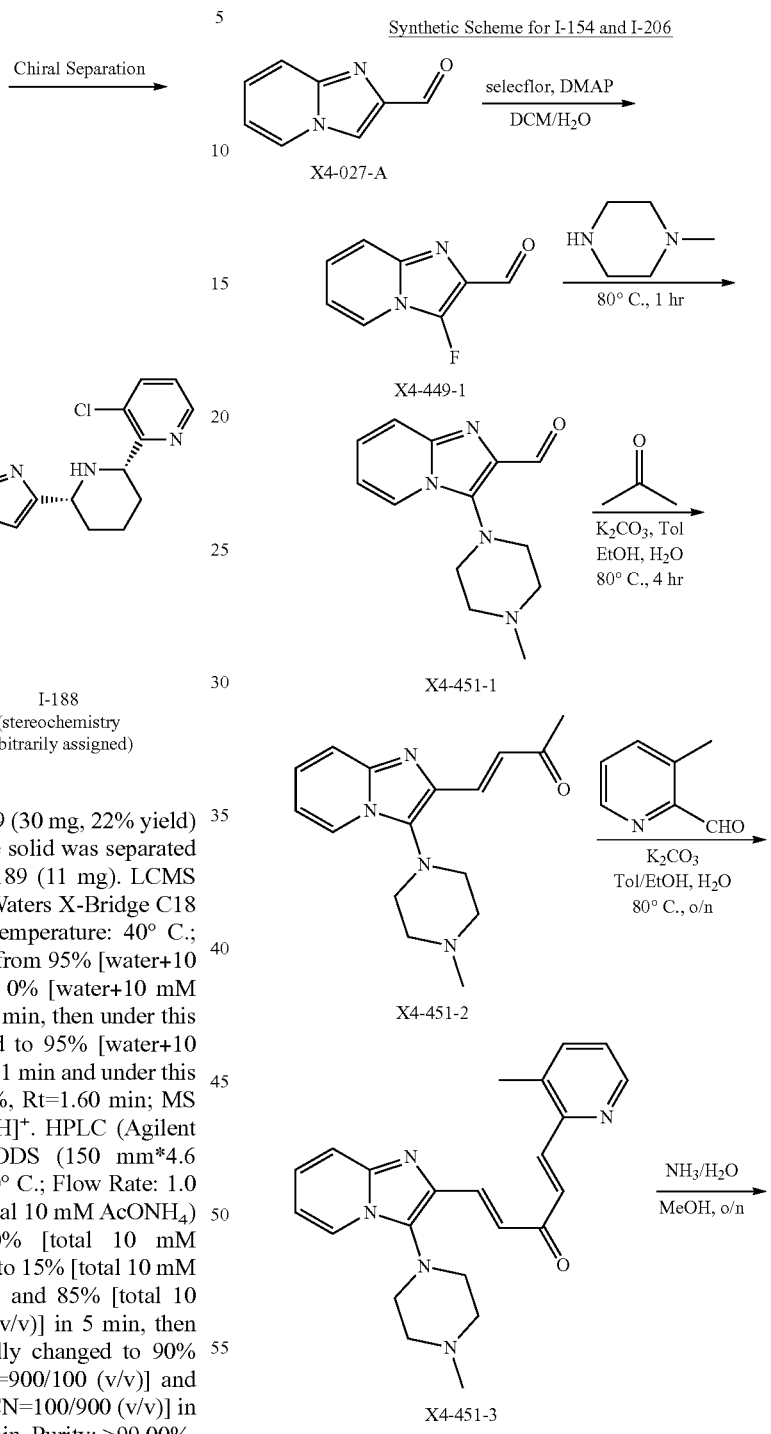

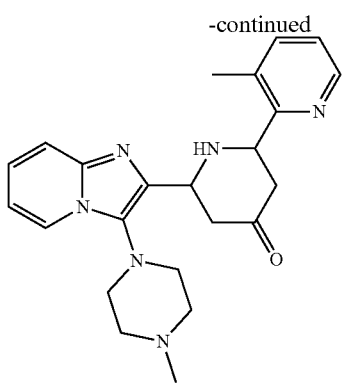

I-206

Wolff-Kishner
80° C., 3 hr
180° C., 2 hr

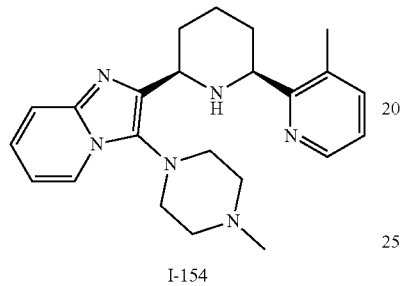

I-154

The Synthesis of X4-449-1

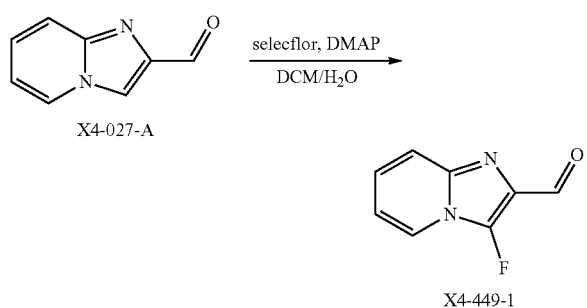

To the solution of X4-027-A (10.0 g, 68.42 mmol) in dichloromethane (60 mL)/water (20 mL) was added selectfluor (10.0 g, 68.42 mmol) and 4-dimethylaminopyridine (10.0 g, 68.42 mmol) in portions at 0° C., and the mixture was stirred at room temperature overnight. After reaction was completed, the suspension was separated and the organics was concentrated by vacuum. The residue was purified by silica gel, eluting with petroleum ether/ethyl acetate 5:1 to give X4-449-1 (6.0 g, 54%) as white solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)] in 0.1 min and under this condition for 0.7 min. Purity: 63.38%, Rt=0.94 min; MS Calcd.: 164.0; MS Found: 165.2 [M+H]$^+$.

The Synthesis of X4-451-1

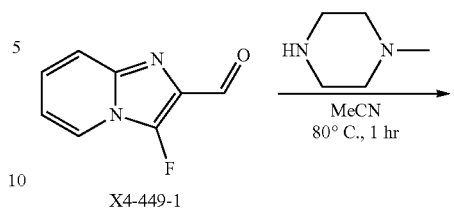

X4-449-1

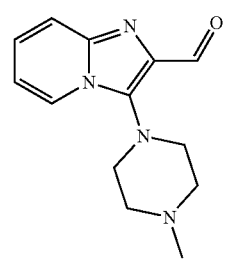

X4-451-1

A mixture of X4-449-1 (1.3 g, 7.92 mmol) and 1-methylpiperazine (1.6 g, 15.84 mmol) in acetonitrile (10 mL) was stirred at 80° C. for 1 hour, then diluted with dichloromethane (60 mL) and water (20 mL). The separated organic layer was concentrated by vacuum, then purified by silica gel, eluting with petroleum ether/ethyl acetate 3:1 to give X4-449-1 (1.5 g, 78%) as pale solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)] in 0.1 min and under this condition for 0.7 min. Purity: 71.35%, Rt=1.02 min; MS Calcd.: 244.1; MS Found: 245.3 [M+H]$^+$.

The Synthesis of X4-451-2

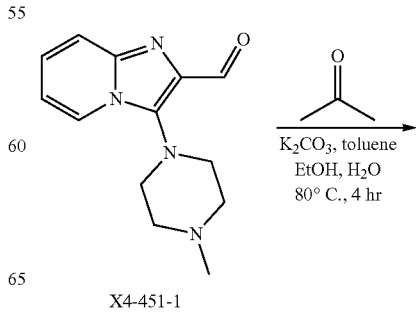

X4-451-1

-continued

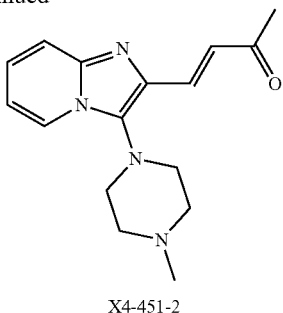

X4-451-2

Following general procedure E, X4-451-2 (580 mg, 33%) was obtained as yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)] in 0.1 min and under this condition for 0.7 min. Purity: 93.40%, Rt=1.27 min; MS Calcd.: 284.2; MS Found: 285.2 [M+H]$^+$.

The Synthesis of X4-451-3

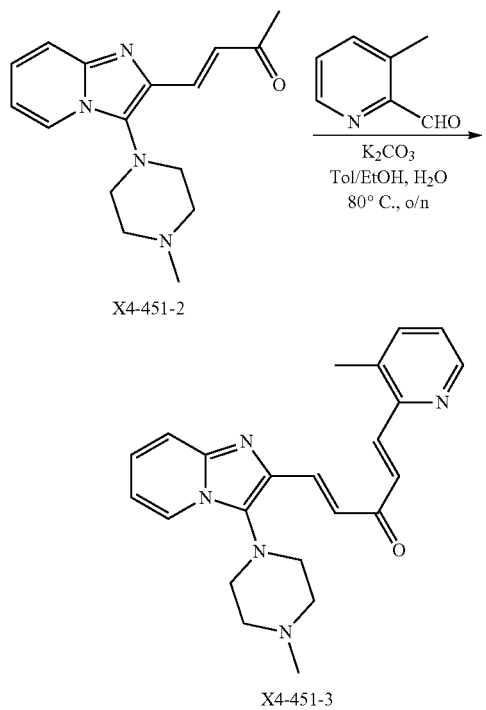

A mixture of X4-451-2 (400 mg, 1.41 mmol), potassium carbonate (293 mg, 2.12 mmol) and 3-methylpicolinaldehyde (188 mg, 1.55 mmol) in toluene (5 mL)/ethanol (2 mL)/water (1 mL) was stirred at 80° C. overnight. The mixture was diluted with dichloromethane (30 mL) and water (10 mL), the separated organics was concentrated by vacuum and purified by flash silica gel column by eluting with dichloromethane/methanol 100:1 to give X4-451-3 (500 mg, 92%) as yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)] in 0.1 min and under this condition for 0.7 min. Purity: 75.42%, Rt=1.65 min; MS Calcd.: 387.2; MS Found: 388.2 [M+H]$^+$.

The Synthesis of I-206

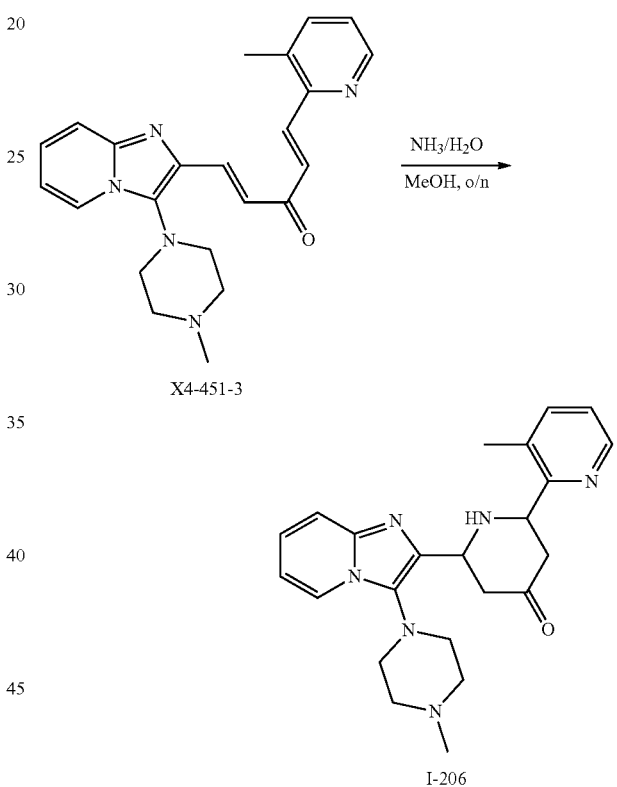

A mixture of X4-451-3 (500 mg, 1.29 mmol) and ammonium hydroxide (878 mg, 12.90 mmol, 25% wt) in menthol (25 mL) was stirred at room temperature overnight. After reaction was completed, the solvent was removed by vacuum, and the residue was purified by silica gel column by eluting with dichloromethane/methanol 80:1 to give I-206 (100 mg, 19%) as light yellow solid. LCMS (Agilent LCMS 1200-6120, Column: Waters X-Bridge C18 (50 mm*4.6 mm*3.5 µm); Column Temperature: 40° C.; Flow Rate: 2.0 mL/min; Mobile Phase: from 90% [(total 10 mM AcONH$_4$) H$_2$O/MeCN=900/100 (v/v)] and 10% [(total 10 mM AcONH$_4$) H$_2$O/MeCN=100/900 (v/v)] to 10% [(total 10 mM AcONH$_4$) H$_2$O/MeCN=900/100 (v/v)] and 90% [(total 10 mM AcONH$_4$) H$_2$O/MeCN=100/900 (v/v)] in 1.6 min, then under this condition for 2.4 min, finally changed to 90% [(total 10 mM AcONH$_4$) H$_2$O/MeCN=900/100 (v/v)] and 10% [(total 10 mM AcONH$_4$) H$_2$O/MeCN=100/900 (v/v)]

The Synthesis of I-154

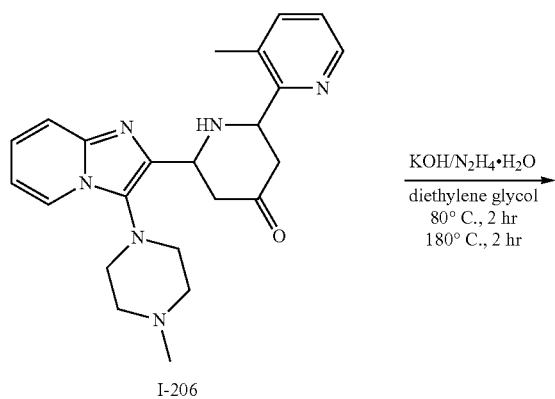

I-206

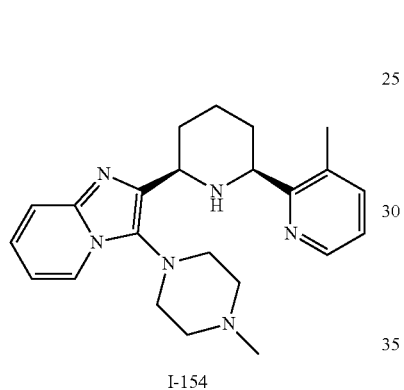

I-154

Example 24: Synthesis of I-187

Synthetic Scheme for I-87

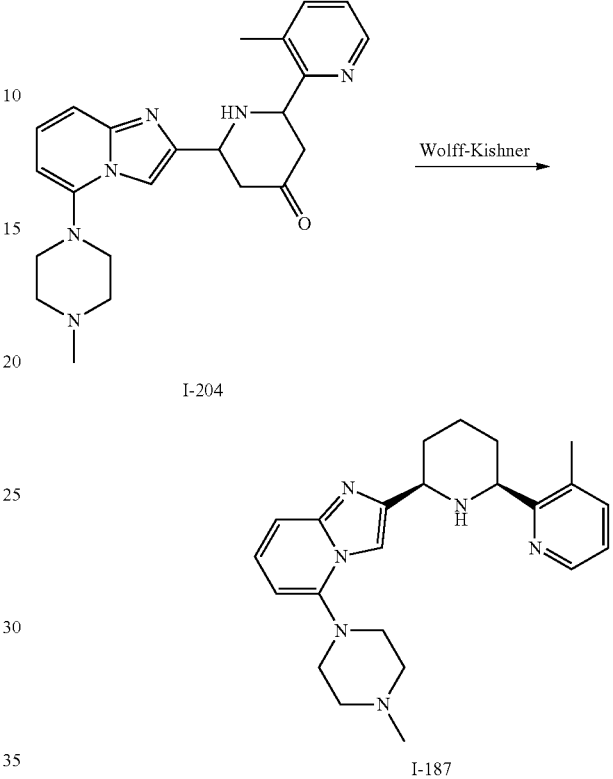

Following general procedure A, I-154 (18 mg, 23%) was obtained as pale solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.). Purity: 99.55%; Rt=1.53 min; MS Calcd.: 390.3; MS Found: 391.3[M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 97.86%, Rt=7.07 min. $^1$H NMR (400 MHz, CDCl$_3$) δ 8.40 (dd, J=4.4, 0.8 Hz, 1H), 8.04 (d, J=6.8 Hz, 1H), 7.49 (d, J=9.2 Hz, 1H), 7.37 (dd, J=7.6, 0.8 Hz, 1H), 7.09-7.05 (m, 1H), 7.00 (dd, J=8.0, 4.8 Hz, 1H), 6.73-6.69 (m, 1H), 4.29-4.23 (m, 1H), 4.16-4.11 (m, 1H), 3.43-3.11 (m, 4H), 3.10-2.72 (m, 4H), 2.41 (s, 3H), 2.36 (s, 3H), 2.14-2.10 (m, 1H), 1.90-1.76 (m, 4H), 1.67-1.59 (m, 2H).

Following general procedure A, 30 mg of I-187 was obtained as white solid from I-204 (1 g, 2.5 mmol). LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.). Cis: Purity: 97.37%; Rt=1.51 min; MS Calcd.: 390.3; MS Found: 391.4 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min.). Purity: 90.65%, Rt=6.95 min. $^1$H NMR (400 MHz, CDCl$_3$) δ 8.43 (dd, J=4.8, 1.2 Hz, 1H), 7.42 (dd, J=7.2, 1.6 Hz, 1H), 7.31 (d, J=9.2 Hz, 1H), 7.13 (dd, J=9.2, 7.2 Hz, 1H), 7.05 (dd, J=7.6, 4.8 Hz, 1H), 6.27 (dd, J=7.2, 1.2 Hz, 1H), 4.24-4.21 (m, 1H), 4.18-4.15 (m, 1H), 3.14 (s, 4H), 2.65 (s, 4H), 2.40 (s, 6H), 2.25-2.22 (m, 1H), 2.15-2.12 (m, 1H), 1.85-1.76 (m, 3H), 1.72-1.65 (m, 2H).

Example 25: Synthesis of I-191

The Synthesis of X4-485-1

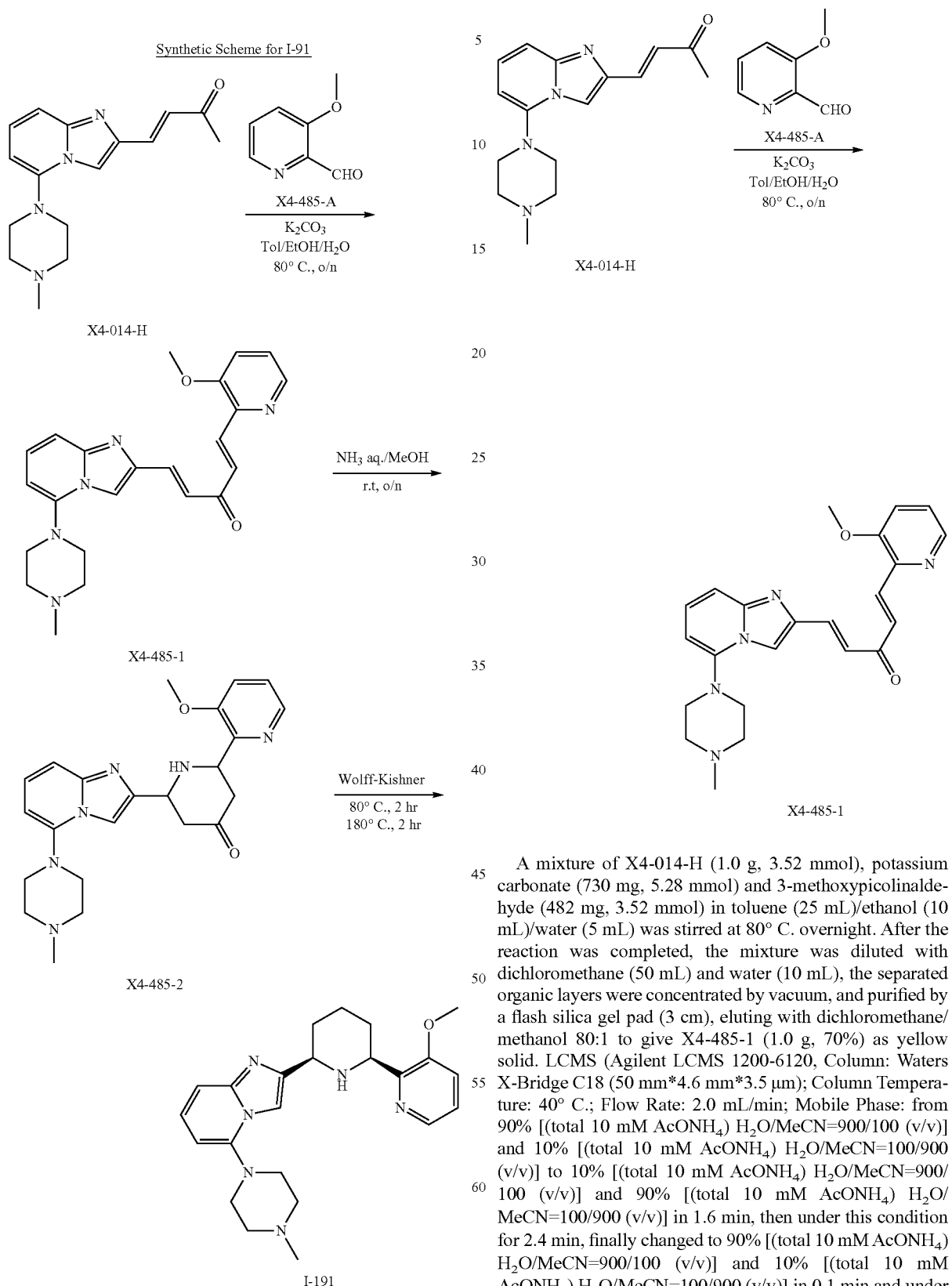

A mixture of X4-014-H (1.0 g, 3.52 mmol), potassium carbonate (730 mg, 5.28 mmol) and 3-methoxypicolinaldehyde (482 mg, 3.52 mmol) in toluene (25 mL)/ethanol (10 mL)/water (5 mL) was stirred at 80° C. overnight. After the reaction was completed, the mixture was diluted with dichloromethane (50 mL) and water (10 mL), the separated organic layers were concentrated by vacuum, and purified by a flash silica gel pad (3 cm), eluting with dichloromethane/methanol 80:1 to give X4-485-1 (1.0 g, 70%) as yellow solid. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM $AcONH_4$) $H_2O$/MeCN=900/100 (v/v)] and 10% [(total 10 mM $AcONH_4$) $H_2O$/MeCN=100/900 (v/v)] to 10% [(total 10 mM $AcONH_4$) $H_2O$/MeCN=900/100 (v/v)] and 90% [(total 10 mM $AcONH_4$) $H_2O$/MeCN=100/900 (v/v)] in 1.6 min, then under this condition for 2.4 min, finally changed to 90% [(total 10 mM $AcONH_4$) $H_2O$/MeCN=900/100 (v/v)] and 10% [(total 10 mM $AcONH_4$) $H_2O$/MeCN=100/900 (v/v)] in 0.1 min and under this condition for 0.7 min. Purity: 82.63%, Rt=1.67 min; MS Calcd.: 403.2; MS Found: 404.2 $[M+H]^+$.

The Synthesis of X4-485-2

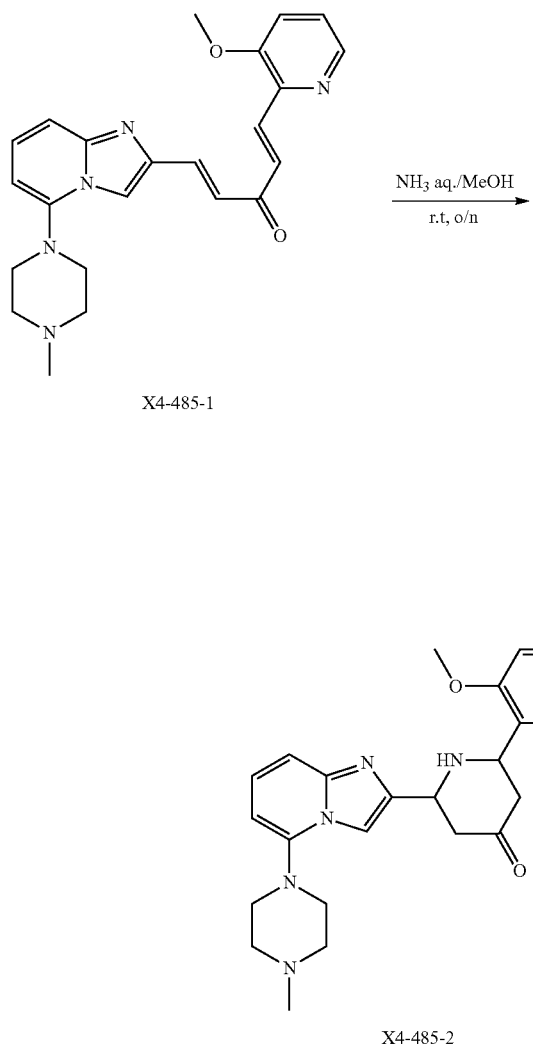

X4-485-1

NH₃ aq./MeOH
r.t, o/n

X4-485-2

A mixture of X4-485-1 (1.0 g, 2.48 mmol) and ammonium hydroxide (1.7 g, 24.78 mmol, 25% wt) in methanol (50 mL) was stirred at room temperature overnight. After the reaction was completed, the organic layer was concentrated and purified by silica gel column by eluting with dichloromethane/methanol 50:1 to give X4-485-2 (600 mg, 58%) as light yellow oil. LCMS (Agilent LCMS 1200-6120, Column: Waters X-Bridge C18 (50 mm*4.6 mm*3.5 μm); Column Temperature: 40° C.; Flow Rate: 2.0 mL/min; Mobile Phase: from 90% [(total 10 mM AcONH₄) H₂O/MeCN=900/100 (v/v)] and 10% [(total 10 mM AcONH₄) H₂O/MeCN=100/900 (v/v)] to 10% [(total 10 mM AcONH₄) H₂O/MeCN=900/100 (v/v)] and 90% [(total 10 mM AcONH₄) H₂O/MeCN=100/900 (v/v)] in 1.6 min, then under this condition for 2.4 min, finally changed to 90% [(total 10 mM AcONH₄) H₂O/MeCN=900/100 (v/v)] and 10% [(total 10 mM AcONH₄) H₂O/MeCN=100/900 (v/v)] in 0.1 min and under this condition for 0.7 min. Purity: 82.42%, Rt=1.35 min; MS Calcd.: 420.2; MS Found: 421.3 [M+H]⁺.

The Synthesis of I-191

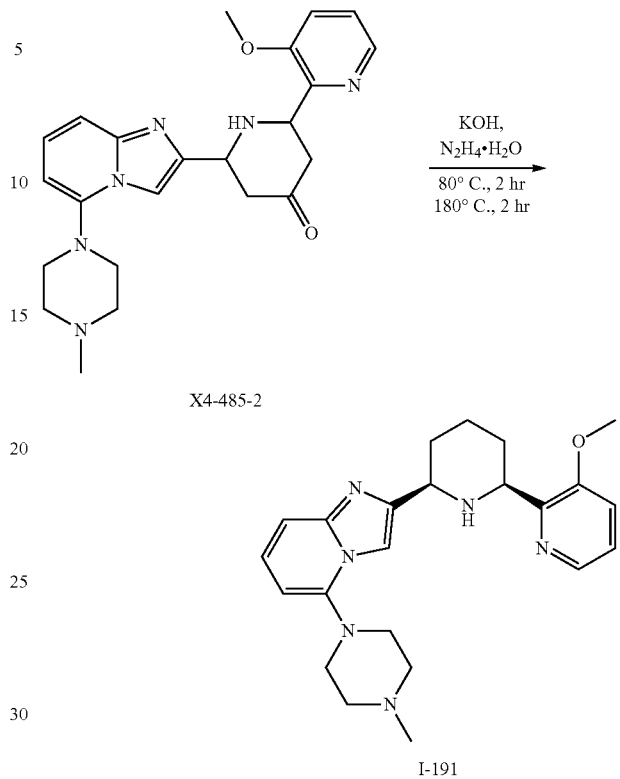

X4-485-2

KOH, N₂H₄·H₂O
80° C., 2 hr
180° C., 2 hr

I-191

Following general procedure A, I-191 (impure, 280 mg, 48%) was obtained as yellow solid, and 140 mg was purified by prep-HPLC to give pure I-191 (80 mg). LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH₄HCO₃] and 10% [CH₃CN] to 5% [water+10 mM NH₄HCO₃] and 95% [CH₃CN] in 0.5 min, then under this condition for 1.5 min, finally changed to 90% [water+10 mM NH₄HCO₃] and 10% [CH₃CN] in 0.1 min and under this condition for 0.7 min. Purity: 100.00%; Rt=1.08 min; MS Calcd.: 406.2; MS Found: 407.1 [M+H]⁺. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH₄HCO₃] and 5% [CH₃CN] to 0% [water+10 mM NH₄HCO₃] and 100% [CH₃CN] in 10 min, then under this condition for 5 min, finally changed to 95% [water+10 mM NH₄HCO₃] and 5% [CH₃CN] in 0.1 min and under this condition for 5 min). Purity: 92.84%, Rt=6.85 min; MS Calcd.: 406.2; MS Found: 407.4 [M+H]⁺. $^1$H NMR (400 MHz, CDCl₃) δ 8.18 (t, J=6.0 Hz, 1H), 7.53 (s, 1H), 7.31 (d, J=9.2 Hz, 1H), 7.15-7.11 (m, 3H), 6.26 (dd, J=7.2, 0.8 Hz, 1H), 4.46 (dd, J=1.6, 1.2 Hz, 1H), 4.19 (d, J=10.0 Hz, 1H), 3.85 (s, 3H), 3.13 (s, 4H), 2.65 (s, 4H), 2.39 (s, 3H), 2.24-2.20 (m, 1H), 2.11-2.07 (m, 1H), 1.95-1.92 (m, 1H), 1.86-1.76 (m, 3H), 1.70-1.63 (m, 1H).

Example 26: Synthesis of Additional Exemplary Compounds

Additional exemplary compounds were prepared following methods substantially similar to those described above and herein. Data for these compounds are provided below.

TABLE 2

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-25 | 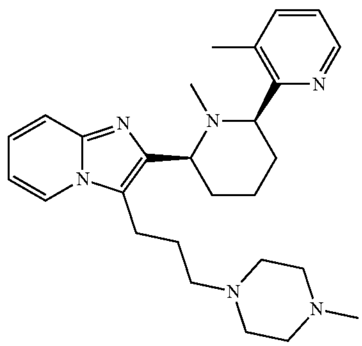 [SMILES: Cc1cccnc1[C@H]1CCC[C@@H](c2nc3ccccn3c2CCCN2CCN(C)CC2)N1C] | 447.4 | 1.56 | 4.45 | (CDCl$_3$) δ 8.42 (s, 1H), 8.35 (d, J = 6.8 Hz, 1H), 7.56 (d, J = 9.2 Hz, 1H), 7.41-7.39 (m, 1H), 7.11-7.03 (m, 2H), 6.77-6.73 (m, 1H), 3.58-3.54 (m, 2H), 3.48-3.45 (m, 2H), 3.11 (brs, 2H), 2.56-2.49 (m, 4H), 2.47-2.45 (m, 4H), 2.44-2.42 (m, 2H), 2.42-2.41 (m, 2H), 2.30 (s, 3H), 2.14-2.04 (m, 2H), 2.03-1.91 (m, 2H), 1.85-1.81 (m, 3H), 1.78 (s, 3H), 1.74-1.59 (m, 2H) |
| I-26 | 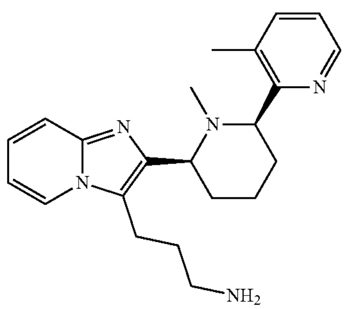 [SMILES: Cc1cccnc1[C@H]1CCC[C@@H](c2nc3ccccn3c2CCCN)N1C] | 364.4 | 1.40 | 6.91 | (CDCl$_3$) δ 8.47 (s, 1H), 7.95 (d, J = 6.8 Hz, 1H), 7.56 (d, J = 8.8 Hz, 1H), 7.41 (d, J = 7.2 Hz, 1H), 7.12-7.03 (m, 2H), 6.77-6.74 (m, 1H), 3.73-3.71 (m, 1H), 3.55-3.41 (m, 1H), 3.13 (brs, 2H), 2.93-2.82 (m, 3H), 2.13-2.00 (m, 2H), 1.97-1.82 (m, 4H), 1.76-1.69 (m, 5H), 1.63-1.22 (m, 2H). |
| I-27 | 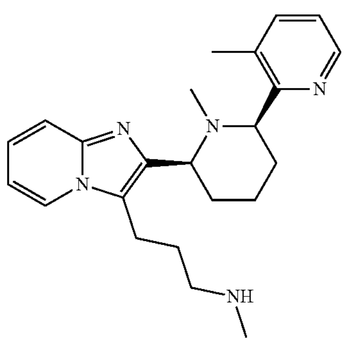 [SMILES: CNCCCc1c([C@@H]2CCC[C@H](c3ncccc3C)N2C)nc2ccccn12] | 378.4 | 1.39 | 4.42 | (CDCl$_3$) δ 8.44 (s, 1H), 7.97 (d, J = 6.8 Hz, 1H), 7.57 (d, J = 8.8 Hz, 1H), 7.41 (d, J = 7.2 Hz, 1H), 7.12-7.03 (m, 2H), 6.78-6.74 (m, 1H), 3.56 (dd, J = 11.6, 2.8 Hz, 1H), 3.47 (dd, J = 11.6, 2.4 Hz, 1H), 3.16-3.08 (m, 2H), 2.74-2.67 (m, 3H), 2.55-2.52 (m, 3H), 2.47 (s, 3H), 2.09-1.99 (m, 2H), 1.94-1.90 (m, 2H), 1.85-1.81 (m, 2H), 1.80 (s, 3H), 1.75-1.55 (m, 2H). |
| I-28 | 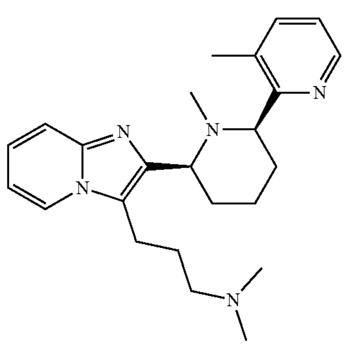 [SMILES: Cc1cccnc1[C@H]1CCC[C@@H](c2nc3ccccn3c2CCCN(C)C)N1C] | 392.3 | 1.59 | 5.71 | (CDCl$_3$) δ 8.46 (s, 1H), 7.98 (d, J = 6.8 Hz, 1H), 7.57 (d, J = 9.2 Hz, 1H), 7.41 (d, J = 6.8 Hz, 1H), 7.12-7.03 (m, 2H), 6.77-6.74 (m, 1H), 3.56 (dd, J = 9.2, 2.8 Hz, 1H), 3.45 (dd, J = 11.6, 2.4 Hz, 1H), 3.06 (s, 2H), 2.71 (s, 6H), 2.49 (s, 2H), 2.37-2.34 (m, 2H), 2.06-2.02 (m, 2H), 1.94-1.91 (m, 2H), 1.82-1.78 (m, 6H), 1.60-1.23 (m, 2H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-29 | 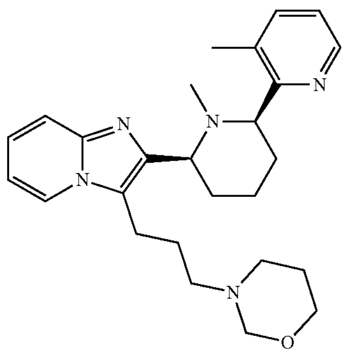 [SMILES: Cc1cccnc1[C@H]1CCC[C@@H](c2nc3ccccn3c2CCCN2CCCOC2)N1C] | 434.3 | 1.87 | 8.15 | (CDCl$_3$) δ 8.46 (s, 1H), 8.01 (d, J = 6.8 Hz, 1H), 7.58 (d, J = 15.4 Hz, 1H), 7.41 (d, J = 8.0 Hz, 1H), 7.12-7.04 (m, 2H), 6.77-6.73 (m, 1H), 3.75-3.73 (m, 4H), 3.56 (dd, J = 11.2, 2.8 Hz, 1H), 3.45 (dd, J = 11.6, 2.4 Hz, 1H), 3.08 (s, 2H), 2.45-2.25 (m, 9H), 2.17-1.95 (m, 2H), 1.94-1.85 (m, 2H), 1.83-1.59 (m, 7H). |
| I-34 | 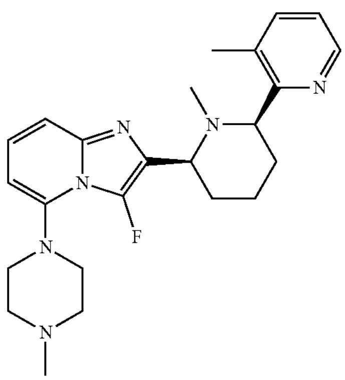 [SMILES: Cc1cccnc1[C@H]1CCC[C@@H](c2nc3cccc(N4CCN(C)CC4)n3c2F)N1C] | 423.2 | 1.96 | 8.85 | (CDCl$_3$) δ 8.47-8.49 (m, 1H), 7.42-7.40 (m, 1H), 7.19-7.16 (m, 1H), 7.07-6.99 (m, 2H), 6.18 (d, J = 7.2 Hz, 1H), 3.58-3.54 (m, 1H), 3.49-3.44 (m, 1H), 3.29-3.24 (m, 2H), 2.98-2.79 (m, 4H), 2.47 (s, 3H), 2.39 (s, 3H), 2.25-2.17 (m, 2H), 2.03-1.90 (m, 2H), 1.85 (s, 3H), 1.66-1.53 (m, 2H), 1.42-1.22 (m, 2H). |
| I-37 | 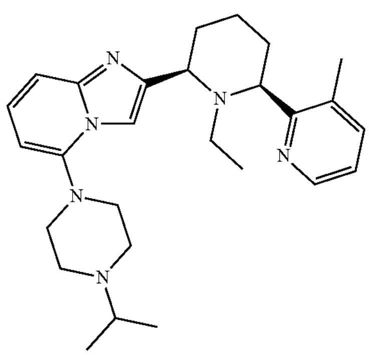 [SMILES: CCN1[C@@H](c2cn3c(N4CCN(C(C)C)CC4)cccc3n2)CCC[C@H]1c1ncccc1C] | 447.4 | 2.67 | 9.97 | (CDCl$_3$) δ 8.43 (d, J = 4.0 Hz, 1H,), 7.59 (brs, 1H), 7.36 (d, J = 7.2 Hz, 1H), 7.24 (d, J = 8.8 Hz, 1H,, 7.06 (t, J = 7.6 Hz, 1H), 6.98 (q, J = 7.2 Hz, 1H), 6.21 (d, J = 7.2 Hz, 1H), 3.91 (brs, 2H), 3.09 (brs, 4H), 2.75 (brs, 5H), 2.44 (brs, 5H), 1.90-1.55 (m, 6H), 1.09 (d, J = 6.4 Hz, 6H), 0.58 (t, J = 6.8 Hz, 3H). |
| I-45 | 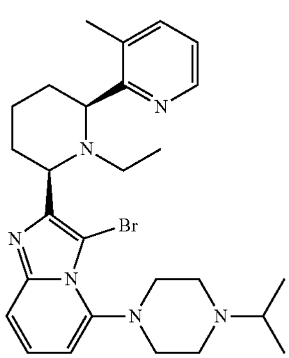 [SMILES: CCN1[C@@H](c2nc3cccc(N4CCN(C(C)C)CC4)n3c2Br)CCC[C@H]1c1ncccc1C] | 525.3 | 3.14 | 11.60 | (CDCl$_3$) δ 8.36 (s, 1H), 7.34-7.31 (m, 2H), 7.06-6.97 (m, 2H), 6.33 (d, J = 6.8 Hz, 1H), 3.99 (brs, 2H), 3.25 (brs, 2H), 2.79 (brs, 6H), 2.45 (brs, 3H), 2.14 (brs, 2H), 1.97-1.82 (m, 2H), 1.70-1.65 (m, 4H), 1.07 (s, 6H), 0.58 (t, J = 6.8 Hz, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-46 | 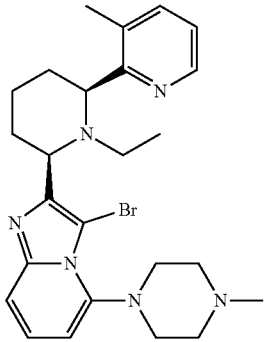 [SMILES: CCN1[C@@H](c2nc3cccc(N4CCN(C)CC4)n3c2Br)CCC[C@H]1c1ncccc1C] | 497.2 | 2.10 | 10.07 | (CDCl$_3$) δ 8.37 (d, J = 3.2 Hz, 1H), 7.45-7.32 (m, 2H), 7.19-6.97 (m, 2H), 6.34 (d, J = 6.8 Hz, 1H), 4.05 (brs, 2H), 3.23 (brs, 2H), 2.90-2.77 (m, 4H), 2.56 (brs, 5H), 2.35 (brs, 5H), 2.04-1.55 (m, 6H), 0.59 (t, J = 6.8 Hz, 3H). |
| I-47 | 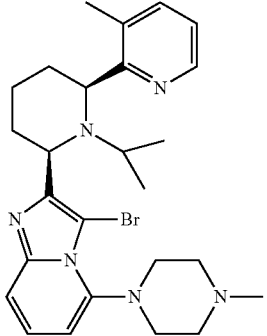 [SMILES: Cc1cccnc1[C@@H]1CCC[C@H](c2nc3cccc(N4CCN(C)CC4)n3c2Br)N1C(C)C] | 511.2 | 2.78 | 10.38 | (CDCl$_3$) δ 8.38 (d, J = 3.6 Hz, 1H), 7.33-7.29 (m, 2H), 7.18-6.96 (m, 2H), 6.32 (tr, J = 7.2 Hz, 1H), 3.20 (d, J = 6.4 Hz, 2H), 3.98 (brs, 2H), 2.87-2.75 (m, 4H), 2.62-2.45 (m, 6H), 2.33 (s, 3H), 2.08-1.62 (m, 6H), 0.62 (d, J = 6.8 Hz, 6H). |
| I-87 | 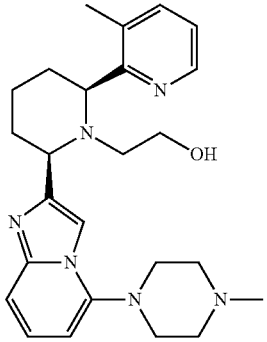 [SMILES: Cc1cccnc1[C@@H]1CCC[C@H](c2cn3c(N4CCN(C)CC4)cccc3n2)N1CCO] | 435.2 | 1.48 | 7.36 | (DMSO-d$_6$) δ 8.41 (d, J = 3.6 Hz, 1H), 7.60 (s, 1H), 7.39 (d, J = 7.6 Hz, 1H), 7.26-7.24 (m, 1H), 7.13-7.01 (m, 2H), 6.24 (d, J = 6.8 Hz, 1H), 3.73 (brs, 1H), 3.17-3.04 (m, 4H), 2.43-2.37 (m, 8H), 2.02-1.90 (m, 4H), 1.74-1.69 (m, 2H). |
| I-49 | 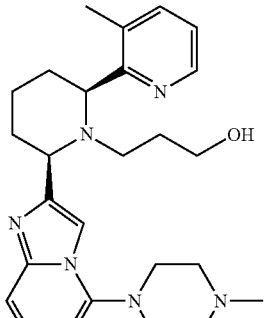 | 449.4 | 2.01 | 7.29 | (CDCl$_3$) δ 8.43 (d, J = 3.2 Hz, 1H), 7.58 (s, 1H), 7.38-7.35 (m, 1H), 7.25-7.20 (m, 1H), 7.11-7.07 (m, 1H), 7.01-6.98 (m, 1H), 6.22 (dd, J = 7.2, 0.8 Hz, 1H), 3.87-3.78 (m, 3H), 3.29-3.03 (m, 6H), 2.63-2.49 (m, 5H), 2.46-2.36 (m, 7H), 2.07-1.69 (m, 8H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-51 | 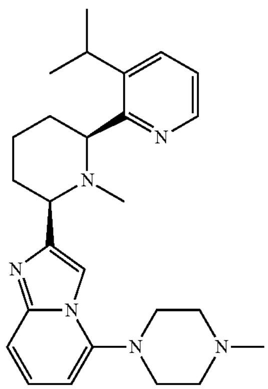 [SMILES: CC(C)c1cccnc1[C@@H]1CCC[C@H](c2cn3c(N4CCN(C)CC4)cccc3n2)N1C] | 433.3 | 0.20 | 9.31 | (CDCl$_3$) δ 8.49 (s, 1H), 7.59 (d, J = 7.6 Hz, 2H), 7.32 (d, J = 9.2 Hz, 1H), 7.16-7.12 (m, 2H), 6.28 (d, J = 6.4 Hz, 1H), 3.67 (d, J = 10.0 Hz, 1H), 3.48-3.46 (m, 1H), 3.16 (d, J = 16.0 Hz, 4H), 2.70 (s, 4H), 2.43 (s, 3H), 2.06-1.90 (m, 6H), 1.76 (s, 4H), 1.27 (t, J = 6.8 Hz, 6H). |
| I-52 | 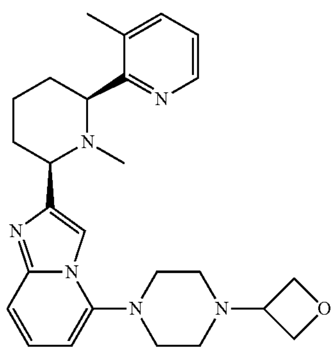 [SMILES: Cc1cccnc1[C@@H]1CCC[C@H](c2cn3c(N4CCN(C5COC5)CC4)cccc3n2)N1C] | 447.3 | 1.59 | 7.61 | (CDCl$_3$) δ 8.51 (d, J = 4.4 Hz, 1H), 7.62 (s, 1H), 7.44-7.42 (m, 1H), 7.33 (d, J = 8.8 Hz, 1H), 7.14 (dd, J = 8.8, 7.2 Hz, 1H), 7.05 (dd, J = 7.6, 4.8 Hz, 1H), 6.30 (dd, J = 7.2, 1.8 Hz, 1H), 4.76 (t, J = 6.4 Hz, 2H), 4.69 (t, J = 6.4 Hz, 2H), 3.71-3.65 (m, 1H), 3.56 (dd, J = 11.6, 2.4 Hz, 1H), 3.47 (t, 1H), 3.19 (s, 4H), 2.63 (s, 4H), 2.47 (s, 3H), 2.08-1.95 (m, 4H), 1.90 (s, 3H), 1.73-1.59 (m, 2H). |
| I-56 | 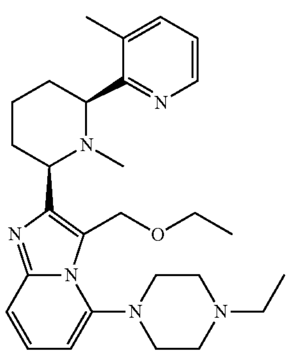 [SMILES: CCOCc1c([C@H]2CCC[C@@H](c3ncccc3C)N2C)nc2cccc(N3CCN(CC)CC3)n12] | 477.4 | 2.66 | 9.83 | (CD$_3$OD) δ 8.46 (brs, 1H), 7.67-7.66 (m, 1H), 7.40-7.26 (m, 3H), 6.83-6.82 (m, 1H), 5.41-5.36 (m, 1H), 5.21-5.18 (m, 1H), 3.78-3.77 (m, 2H), 3.50-3.40 (m, 2H), 3.15-2.95 (m, 5H), 2.65-2.44 (m, 7H), 2.23-1.78 (m, 9H), 1.18-1.31 (m, 7H) |
| I-57 | 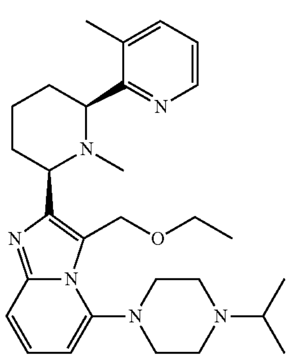 [SMILES: CCOCc1c([C@H]2CCC[C@@H](c3ncccc3C)N2C)nc2cccc(N3CCN(C(C)C)CC3)n12] | 491.4 | 2.03 | 4.63 | (CDCl$_3$) δ 8.35 (d, J = 3.2 Hz, 1H), 7.53 (d, J = 6.8 Hz, 1H), 7.32-7.30 (m, 1H), 7.23-7.14 (m, 2H), 6.67-6.66 (d, J = 6.8 Hz, 1H), 5.20-5.05 (m, 2H), 3.64-3.59 (m, 2H), 3.54-3.44 (m, 2H), 3.18-3.13 (t, 2H), 2.85-2.72 (m, 5H), 2.52-2.46 (m, 5H), 2.02-1.53 (m, 9H), 1.14-1.02 (m, 9H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-58 | 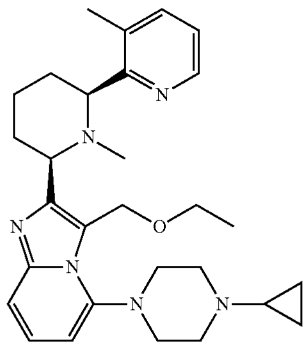 [SMILES: CCOCc1c([C@H]2CCC[C@@H](c3ncccc3C)N2C)nc2cccc(N3CCN(C4CC4)CC3)n12] | 489.4 | 2.09 | 10.85 | (CDCl$_3$) δ 8.46 (s, 1H), 7.42-7.38 (m, 2H), 7.12-7.04 (m, 2H), 6.49 (d, J = 6.8 Hz, 1H), 5.31 (d, J = 11.2 Hz, 1H), 5.12 (d, J = 8.4 Hz, 1H), 3.71-3.65 (m, 2H), 3.59-3.52 (m, 2H), 3.24 (d, J = 9.6 Hz, 2H), 3.07-3.03 (m, 2H), 2.94-2.82 (m, 2H), 2.68-2.61 (m, 2H), 2.52 (s, 3H), 2.17-1.91 (m, 4H), 1.82 (s, 3H), 1.76-1.71 (m, 2H), 1.65-1.59 (m, 1H), 1.25-1.21 (m, 3H), 0.55-0.51 (m, 2H), 0.49-0.46 (m, 2H). |
| I-59 | 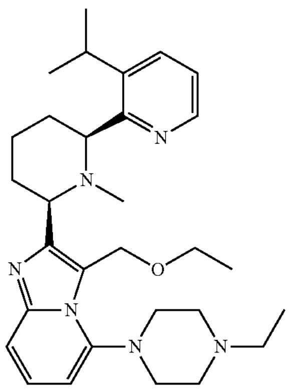 [SMILES: CCOCc1c([C@H]2CCC[C@@H](c3ncccc3C(C)C)N2C)nc2cccc(N3CCN(CC)CC3)n12] | 505.4 | 2.12 | 11.09 | (CDCl$_3$) δ 8.51 (s, 1H), 7.59-7.58 (m, 1H), 7.40 (d, J = 6.4 Hz, 1H), 7.16-7.11 (m, 2H), 6.52 (d, J = 6.8 Hz, 1H), 5.28-5.26 (m, 1H), 5.04-5.02 (m, 1H), 3.71-3.57 (m, 3H), 3.38-3.19 (m, 3H), 3.04-2.90 (m, 4H), 2.53 (q, J = 7.2 Hz, 2H), 2.41-2.34 (m, 2H), 2.28-2.20 (m, 1H), 2.14 (s, 3H), 2.05-2.01 (m, 2H), 1.95-1.92 (m, 2H), 1.79-1.64 (m, 2H), 1.34-1.22 (m, 9H), 1.16 (t, J = 7.2 Hz, 3H). |
| I-60 | 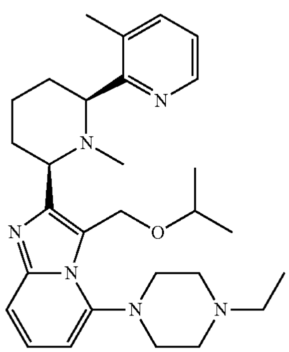 [SMILES: CCN1CCN(c2cccc3nc([C@H]4CCC[C@@H](c5ncccc5C)N4C)c(COC(C)C)n23)CC1] | 491.4 | 2.83 | 10.49 | (CD$_3$OD) δ 8.33 (d, J = 6.4 Hz, 1H), 7.63 (d, J = 8 Hz, 1H), 7.38-7.32 (m, 2H), 7.24-7.21 (m, 1H), 6.79-6.77 (m, 1H), 5.45 (d, J = 10.8 Hz, 1H), 5.16 (d, J = 10.8 Hz, 1H), 4.00 (t, J = 6.0 Hz, 1H), 3.38-3.52 (m, 2H), 3.10-3.04 (m, 3H), 2.93-2.88 (m, 1H), 2.74-2.48 (m, 7H), 2.20-1.67 (m, 10H), 1.30-1.18 (m, 10H). |
| I-61 | 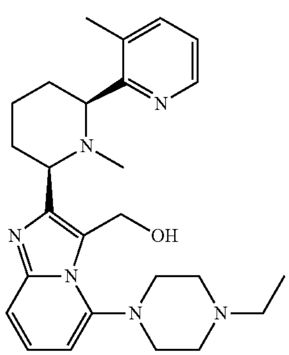 [SMILES: CCN1CCN(c2cccc3nc([C@H]4CCC[C@@H](c5ncccc5C)N4C)c(CO)n23)CC1] | 449.4 | 2.16 | 7.85 | (DMSO-d$_6$) δ 8.36 (s, 1H), 7.56 (d, J = 7.2 Hz, 1H), 7.28 (d, J = 8.4 Hz, 1H), 7.20-7.16 (m, 2H), 6.61 (d, J = 6.4 Hz, 1H), 5.40-5.36 (m, 1H), 5.07 (d, J = 13.2 Hz, 1H), 3.54 (br, 1H), 3.50-3.25 (m, 4H), 3.22-3.20 (m, 1H), 2.95-2.93 (m, 4H), 2.51-2.49 (m, 1H), 2.46 (s, 3H), 2.42-2.33 (m, 2H), 2.21-1.95 (m, 1H), 1.91-1.71 (m, 8H), 1.06 (t, J = 7.2 Hz, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-62 | 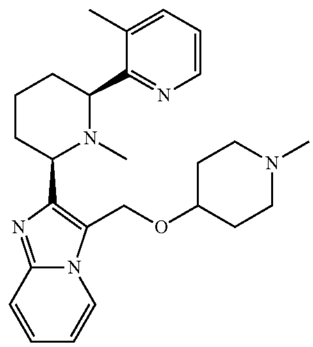 [SMILES: Cc1cccnc1[C@@H]1CCC[C@H](c2nc3ccccn3c2COC2CCN(C)CC2)N1C] | 434.4 | 1.33 | 8.27 | (CDCl$_3$) δ 8.39-8.38 (m, 1H), 8.10-8.09 (m, 1H), 7.57-7.53 (m, 1H), 7.41-7.39 (m, 1H), 7.20-7.17 (m, 1H), 7.07-7.04 (m, 1H), 6.82-6.79 (m, 1H), 5.05-5.02 (m, 2H), 4.80-4.73 (m, 1H), 4.00-3.74 (m, 2H), 2.98-2.82 (m, 3H), 2.58-2.35 (m, 6H), 2.18-1.50 (m, 14H). |
| I-63 | 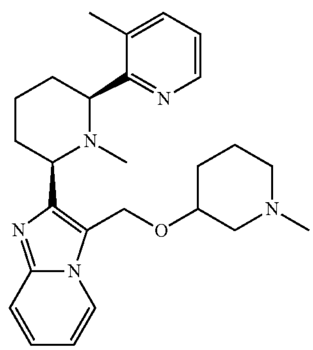 [SMILES: Cc1cccnc1[C@@H]1CCC[C@H](c2nc3ccccn3c2COC2CCCN(C)C2)N1C] | 434.4 | 1.67 | 5.08 | (CDCl$_3$) δ 8.40-8.37 (m, 2H), 7.62-7.52 (m, 2H), 7.39-7.33 (m, 1H), 7.24-7.20 (m, 1H), 7.07-6.97 (m, 1H), 5.50-5.00 (m, 2H), 5.00-4.80 (m, 1H), 3.68-3.50 (m, 3H), 3.34-3.32 (m, 1H), 3.00-2.50 (m, 5H), 2.17 (s, 3H), 2.12-1.50 (m, 13H) |
| I-66 | 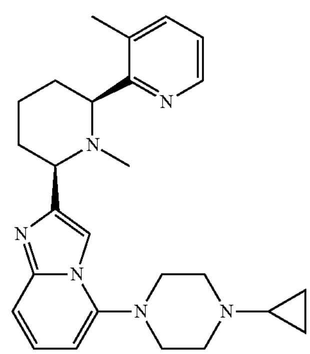 [SMILES: Cc1cccnc1[C@@H]1CCC[C@H](c2cn3c(N4CCN(C5CC5)CC4)cccc3n2)N1C] | 431.4 | 1.94 | 9.61 | (CDCl$_3$) δ 8.51 (d, J = 3.6 Hz, 1H), 7.63 (s, 1H), 7.43 (dd, J = 7.6, 1.2 Hz, 1H), 7.31 (d, J = 8.8 Hz, 1H), 7.14-7.10 (m, 1H), 7.05 (dd, J = 7.6, 4.8 Hz, 1H), 6.25 (dd, J = 7.2, 0.8 Hz, 1H), 3.59-3.56 (m, 1H), 3.50-3.45 (m, 1H), 3.11 (s, 4H), 2.90 (s, 4H), 2.48 (s, 3H), 2.09-2.05 (m, 2H), 1.97-1.93 (m, 2H), 1.91 (s, 3H), 1.83-1.78 (m, 1H), 1.74-1.61 (m, 2H), 0.57-0.52 (m, 2H), 0.51-0.46 (m, 2H). |
| I-67 | 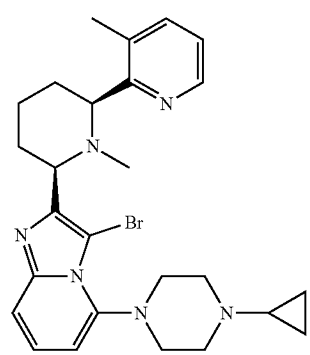 [SMILES: Cc1cccnc1[C@@H]1CCC[C@H](c2nc3cccc(N4CCN(C5CC5)CC4)n3c2Br)N1C] | 509.3 | 2.22 | 7.32 | CDCl$_3$) δ 8.47 (s, 1H), 7.42-7.40 (m, 1H), 7.38 (dd, J = 8.8, 0.8 Hz, 1H), 7.13-7.09 (m, 1H), 7.05 (dd, J = 7.6, 4.8 Hz, 1H), 6.38 (dd, J = 7.2, 0.8 Hz, 1H), 3.63-3.60 (m, 2H), 3.30-3.24 (m, 2H), 3.01-2.98 (m, 2H), 2.88-2.76 (m, 4H), 2.47 (s, 3H), 2.23-1.90 (m, 4H), 1.78 (s, 3H), 1.76-1.70 (m, 2H), 1.65-1.55 (m, 1H), 0.54-0.50 (m, 2H), 0.48-0.44 (m, 2H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-68 | 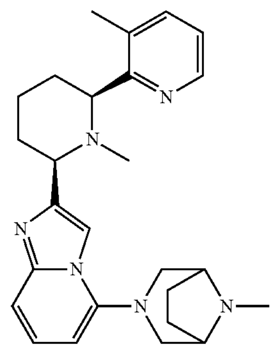 [SMILES: Cc1cccnc1[C@@H]1CCC[C@H](c2cn3c(N4CC5CCC(C4)N5C)cccc3n2)N1C] | 431.4 | 2.28 | 8.44 | (CD$_3$OD) δ 8.47 (d, J = 3.6 Hz, 1H), 7.61 (s, 1H), 7.42 (dd, J = 7.2, 0.8 Hz, 1H), 7.31 (d, J = 9.2 Hz, 1H), 7.13-7.04 (m, 2H), 6.28 (t, J = 3.6 Hz, 1H,), 3.60 (d, J = 9.6 Hz, 1H,), 3.48 (d, J = 7.6 Hz, 1H), 3.29-3.17 (m, 4H), 3.07 (d, J = 10.4 Hz, 1H,), 3.00 (d, J = 10.8 Hz, 1H), 2.52 (s, 3H), 2.38 (s, 3H), 2.21-1.92 (m, 11H), 1.77-1.52 (m, 2H) |
| I-69 | 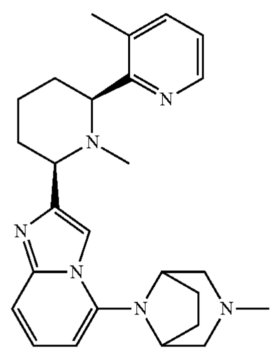 [SMILES: Cc1cccnc1[C@@H]1CCC[C@H](c2cn3c(N4C5CCC4CN(C)C5)cccc3n2)N1C] | 431.4 | 2.53 | 9.29 | (CD$_3$OD) δ 8.49 (d, J = 3.6 Hz, 1H), 7.65 (s, 1H), 7.43 (d, J = 7.2 Hz, 1H), 7.23 (d, J = 8.8 Hz, 1H), 7.10-7.04 (m, 2H), 6.13 (d, J = 6.8 Hz, 1H,), 3.97 (s, 2H), 3.53-3.48 (m, 2H), 2.83 (d, J = 10.4 Hz, 2H), 2.59 (d, J = 10.4 Hz, 2H), 2.50 (s, 3H), 2.38 (s, 3H), 2.04-1.87 (m, 11H), 1.77-1.64 (m, 2H) |
| I-74 | 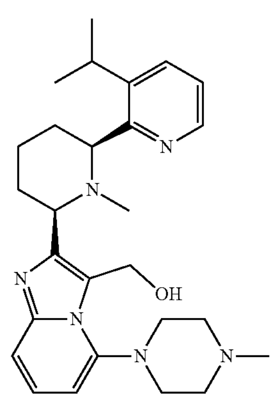 [SMILES: CC(C)c1cccnc1[C@@H]1CCC[C@H](c2nc3cccc(N4CCN(C)CC4)n3c2CO)N1C] | 463.5 | 1.69 | 8.34 | (CDCl$_3$) δ 8.54 (brs, 1H), 7.56 (d, J = 7.2 Hz, 1H), 7.33 (d, J = 8.4 Hz, 1H), 7.14-7.07 (m, 2H,), 6.41 (s, 1H), 5.81 (s, 1H), 5.27 (d, J = 12.8 Hz, 1H), 3.78-3.58 (m, 3H), 3.33 (s, 1H), 3.21 (d, J = 11.2 Hz, 1H), 3.06 (t, J = 11.2 Hz, 1H), 2.93 (d, J = 11.6 Hz, 2H), 2.75 (s, 1H), 2.61-2.56 (m, 1H), 2.51-2.44 (m, 1H), 2.42 (s, 3H), 2.35 (s, 1H), 2.17-2.14 (m, 1H), 2.05-1.93 (m, 3H), 1.87 (s. 3H), 1.78 (d, J = 11.6 Hz, 1H), 1.67-1.58 (m, 1H), 1.26 (d, J = 6.8 Hz, 6H). |
| I-75 | 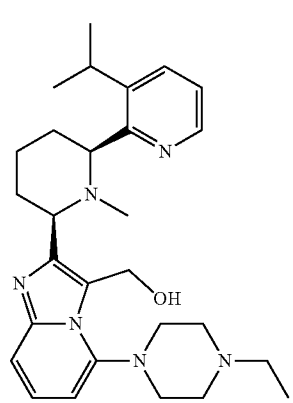 [SMILES: CCN1CCN(c2cccc3nc([C@H]4CCC[C@@H](c5ncccc5C(C)C)N4C)c(CO)n23)CC1] | 477.4 | 1.77 | 4.69 | (CDCl$_3$) δ 8.46-8.44 (s, 1H), 7.52 (s, 1H), 7.28-7.26 (m, 1H), 7.07-7.05 (m, 2H), 6.40-6.36 (m, 1H), 5.75 (brs, 1H), 5.23-5.21 (m, 1H), 3.56-3.23 (m, 3H), 3.24-3.19 (m, 2H), 3.10-2.96 (m, 3H), 2.79-2.72 (m, 1H), 2.60-2.37 (m, 4H), 2.22-2.08 (m, 1H), 2.00-1.94 (m, 3H), 1.87-1.82 (m, 4H), 1.63-1.47 (m, 2H), 1.20 (d, J = 7.2 Hz, 6H), 1.12 (t, J = 7.2 Hz, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-76 | 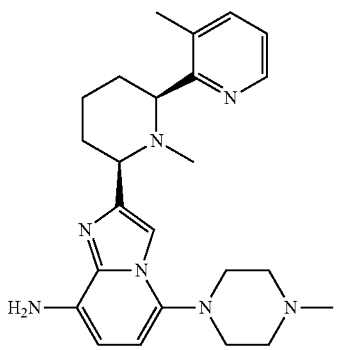 [SMILES: Cc1cccnc1[C@@H]1CCC[C@H](c2cn3c(N4CCN(C)CC4)ccc(N)c3n2)N1C] | 420.4 | 1.66 | 8.05 | (CDCl$_3$) δ 8.50 (d, J = 3.6 Hz, 1H), 7.55 (1H, s), 7.62 (dd, J = 7.6, 1.2 Hz, 1H), 7.32 (dd, J = 7.6, 1.2 Hz, 1H), 6.31 (d, J = 7.6 Hz, 1H), 6.15 (d, J = 7.6 Hz, 1H), 4.30 (brs, 2H), 3.57 (dd, J = 10.8, 1.6 Hz, 1H,), 3.42 (dd, J = 10.8, 1.6 Hz, 1H), 3.05 (s, 4H), 2.66 (s, 4H), 2.44-2.41m, 6H), 2.03-1.87m, 4H), 1.73-1.59 (m, 5H). |
| I-77 | 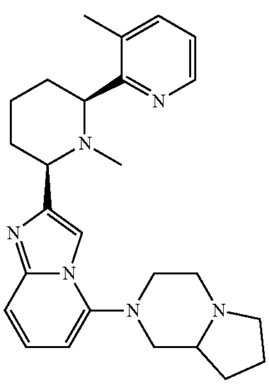 [SMILES: Cc1cccnc1[C@@H]1CCC[C@H](c2cn3c(N4CCN5CCCC5C4)cccc3n2)N1C] | 431.4 | 1.81 | 6.33 | (CDCl$_3$) δ 8.51 (d, J = 3.6 Hz, 1H), 7.63 (s, 1H), 7.43 (dd, J = 7.6, 1.2 Hz, 1H), 7.32 (d, J = 8.8 Hz, 1H), 7.13 (dd, J = 8.8, 7.2 Hz, 1H), 7.05 (dd, J = 7.6, 4.8 Hz, 1H), 6.30 (d, J = 7.2 Hz, 1H), 3.59-3.52 (m, 2H), 3.49-3.42 (m, 2H), 3.21-3.17 (m, 2H), 3.00-2.89 (m, 1H), 2.68-2.55 (m, 2H), 2.48 (s, 3H), 2.41-2.29 (m, 2H), 2.09-2.03 (m, 3H), 1.98-1.93 (m, 4H), 1.87-1.71 (m, 4H), 1.68-1.47 (m, 2H). |
| I-78 | 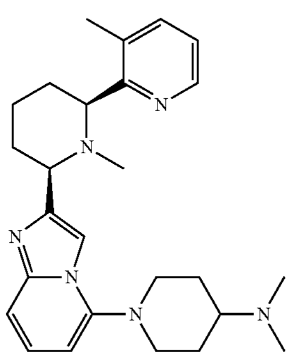 | 433.3 | 1.60 | 6.04 | (CDCl$_3$) δ 8.50 (d, J = 4 Hz, 1H), 7.57 (s, 1H), 7.42 (d, J = 6.8 Hz, 1H), 7.31 (d, J = 6.8 Hz, 1H), 7.12 (dd, J = 8.8, 7.2 Hz, 1H), 7.05 (dd, J = 7.6, 4.8 Hz, 1H), 6.24 (d, J = 6.4 Hz, 1H), 3.58-3.54 (m, 2H), 3.52-3.45 (m, 2H), 2.76-2.68 (m, 2H), 2.48 (s, 3H), 2.45-2.37 (m, 1H), 2.39 (s, 6H), 2.08-1.92 (m, 4H), 1.90 (s, 3H), 1.88-1.85 (m, 2H), 1.77-1.61 (m, 4H). |
| I-79 | 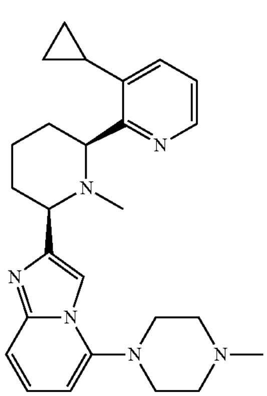 [SMILES: CN1CCN(c2cccc3nc([C@H]4CCC[C@@H](c5ncccc5C5CC5)N4C)cn23)CC1] | 431.4 | 1.76 | 8.82 | (CDCl$_3$) δ 8.49 (s, 1H), 7.51 (s, 1H), 7.33-7.27 (m, 2H), 7.14 (dd, J = 9.0, 7.0 Hz, 1H), 7.06 (dd, J = 8.0, 4.8 Hz, 1H), 6.27 (dd, J = 7.2, 0.8, 1H), 3.97 (d, J = 8.4 Hz, 1H), 3.48 (dd, J = 11.6, 2.4 Hz, 1H), 3.18-3.14 (m, 4H), 2.77-2.70 (m, 4H), 2.43 (s, 3H), 2.13-2.05 (m, 3H), 1.99-1.94 (2H, m), 1.89 (s, 3H), 1.77 (d, J = 9.2 Hz, 1H), 1.67-1.62 (m, 2H), 1.07-1.00 (m, 2H), 0.72-0.69 (m, 1H), 0.68-0.51 (m, 1H). |

TABLE 2-continued

Characterization Data for Additional Exemplary Compounds

| Compound No. | Chemical Structure | M + 1 | Rt (Min) (LCMS) | Rt (Min) (HPLC) | ¹H NMR (400 MHz) |
|---|---|---|---|---|---|
| I-80 | 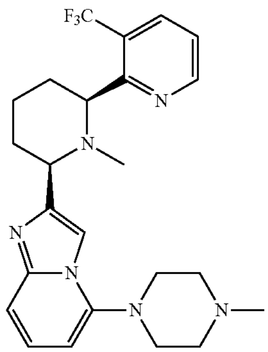 [SMILES: CN1CCN(c2cccc3nc([C@H]4CCC[C@@H](c5ncccc5C(F)(F)F)N4C)cn23)CC1] | 459.3 | 1.83 | 9.16 | (CDCl$_3$) δ 8.90 (d, J = 3.6 Hz, 1H), 7.95 (dd, J = 7.6, 1.2 Hz, 1H), 7.61 (s, 1H), 7.34-7.27 (m, 2H), 7.14 (dd, J = 12.0, 8.0 Hz, 1H), 6.28 (d, J = 6.8 Hz, 1H), 3.73 (d, J = 11.2 Hz, 1H), 3.52 (dd, J = 11.6, 2.4 Hz, 1H), 3.15 (s, 4H), 2.70 (s, 4H), 2.43 (s, 4H), 2.18-1.94 (m, 4H), 1.86 (s, 3H), 1.81-1.78 (m, 1H). |
| I-81 | 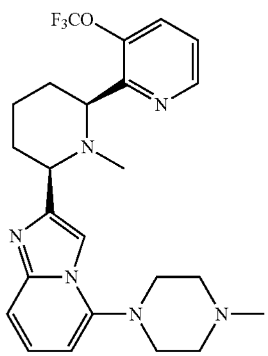 [SMILES: CN1CCN(c2cccc3nc([C@H]4CCC[C@@H](c5ncccc5OC(F)(F)F)N4C)cn23)CC1] | 475.3 | 1.84 | 9.14 | (CDCl$_3$) δ 8.65 (dd, J = 4.4, 1.2 Hz, 1H), 7.59 (s, 1H), 7.58-7.56 (m, 1H), 7.32 (d, J = 8.8 Hz, 1H), 7.25-7.23 (m, 1H), 7.16-7.12 (m, 1H), 6.28 (dd, J = 7.2, 0.8 Hz, 1H), 3.77 (dd, J = 11.2, 2.4 Hz, 1H), 3.49 (dd, J = 11.2, 2.8 Hz, 1H), 3.15 (s, 4H), 2.69 (s, 4H), 2.43 (s, 3H), 2.07-1.93 (m, 3H), 1.88 (s, 3H), 1.73-1.62 (m, 3H). |
| I-82 | 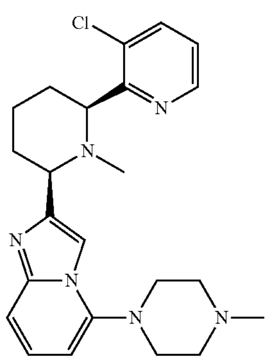 [SMILES: CN1CCN(c2cccc3nc([C@H]4CCC[C@@H](c5ncccc5Cl)N4C)cn23)CC1] | 425.3 | 1.78 | 8.85 | (CDCl$_3$) δ 8.61 (dd, J = 4.4, 1.2 Hz, 1H), 7.67 (dd, J = 8.0, 1.6 Hz, 1H), 7.62 (s, 1H), 7.32 (d, J = 8.8 Hz, 1H), 7.16-7.11 (m, 2H), 6.28 (d, J = 7.2 Hz, 1H), 3.97 (dd, J = 10.8, 2.8 Hz, 1H), 3.53 (dd, J = 11.2, 2.8 Hz, 1H), 3.16 (brs, 4H), 2.70 (s, 4H), 2.43 (s, 3H), 2.10-1.94 (m, 4H), 1.92 (s, 3H), 1.72-1.65 (m, 2H). |
| I-83 | 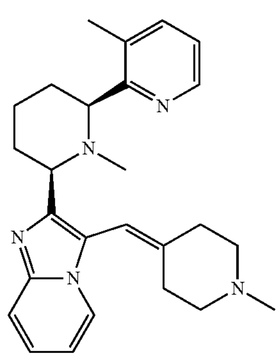 [SMILES: Cc1cccnc1[C@@H]1CCC[C@H](c2nc3ccccn3c2C=C2CCN(C)CC2)N1C] | 416.4 | 1.69 | 8.44 | (CDCl$_3$) δ 8.44 (s, 1H), 7.78 (d, J = 6.8 Hz, 1H), 7.60 (d, J = 8.8 Hz, 1H), 7.41 (d, J = 7.2 Hz, 1H), 7.14 (t, J = 7.6 Hz, 1H), 7.05 (dd, J = 7.6, 4.8 Hz, 1H), 6.77 (t, J = 6.8 Hz, 1H), 6.19 (s, 1H), 3.65-3.49 (m, 1H), 3.48-3.34 (m, 1H), 2.71-2.39 (m, 8H), 2.34 (s, 3H), 2.34-2.25 (m, 1H), 2.16-1.90 (m, 4H), 1.81-1.68 (6H, m), 1.54-1.60 (m, 1H). |

TABLE 2-continued

Characterization Data for Additional Exemplary Compounds

| Compound No. | Chemical Structure | M + 1 (LCMS) | Rt (Min) (LCMS) | Rt (Min) (HPLC) | $^1$H NMR (400 MHz) |
|---|---|---|---|---|---|
| I-85 | 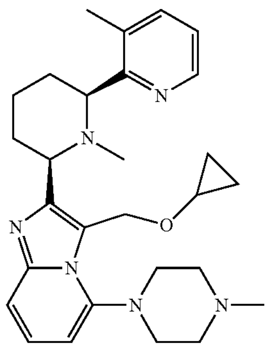 [SMILES: Cc1cccnc1[C@@H]1CCC[C@H](c2nc3cccc(N4CCN(C)CC4)n3c2COC2CC2)N1C] | 475.3 | 2.09 | 6.92 | (CDCl$_3$) δ 8.47 (s, 1H), 7.41 (d, J = 8.8 Hz, 1H), 7.20 (dd, J = 9.2, 7.6 Hz, 1H), 7.05 (dd, J = 7.6, 4.8 Hz, 1H), 6.51 (d, J = 6.8 Hz, 1H), 5.35-5.30 (m, 1H), 5.12 (d, J = 8.8 Hz, 1H), 3.57-3.50 (m, 2H), 3.41 (s, 1H), 3.27-3.20 (m, 2H), 3.01-2.96 (m, 1H), 2.93-2.88 (m, 3H), 2.49-2.43 (m, 4H), 2.17-1.99 (m, 4H), 1.78 (s, 6H), 1.62-1.55 (m, 1H), 1.28-0.88 (m, 2H), 0.65-0.61 (m, 2H), 0.53-0.48 (m, 2H). |
| I-91 | 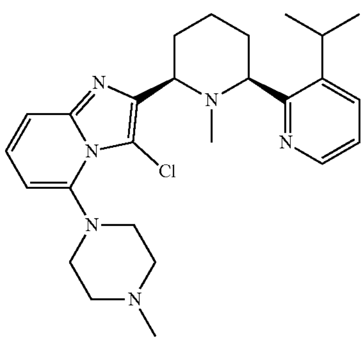 [SMILES: CC(C)c1cccnc1[C@@H]1CCC[C@H](c2nc3cccc(N4CCN(C)CC4)n3c2Cl)N1C] | 467.3 | 2.09 | 10.84 | (CDCl$_3$) δ 8.48 (brs, 1H), 7.58 (d, J = 3.6 Hz, 1H), 7.33 (d, J = 8.8 Hz, 1H), 7.14-7.08 (m, 2H), 6.35 (d, J = 7.2 Hz, 1H), 3.63 (d, J = 50.0 Hz, 2H), 3.30 (t, J = 22.4 Hz, 2H), 2.94 (s, 5H), 2.87-2.84 (m, 3H), 3.55-3.47 (m, 2H), 2.40 (s, 3H), 2.28-2.17 (m, 1H), 2.06 (brs, 1H), 1.96-1.93 (m, 1H), 1.78 (s, 2H), 1.67-1.56 (m, 1H), 1.27-1.23 (m, 6H). |
| I-88 | 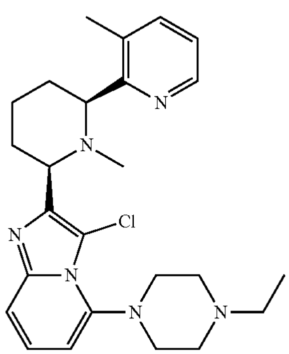 [SMILES: CCN1CCN(c2cccc3nc([C@H]4CCC[C@@H](c5ncccc5C)N4C)c(Cl)n23)CC1] | 453.3 | 2.03 | 7.29 | (CDCl$_3$) δ 8.46 (s, 1H), 7.52-7.32 (m, 2H), 7.12-7.03 (m, 2H), 6.35 (d, J = 7.2 Hz, 1H), 3.61-3.52 (m, 2H), 3.35-3.29 (m, 2H), 2.98-2.87 (m, 7H), 2.24-2.06 (m, 3H), 1.82-1.77 (m, 4H), 1.76-1.61 (m, 2H), 1.16 (t, J = 7.0 Hz, 3H). |
| I-92 | 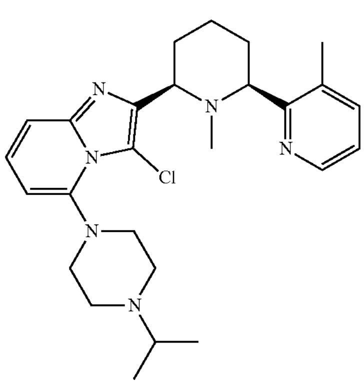 [SMILES: Cc1cccnc1[C@@H]1CCC[C@H](c2nc3cccc(N4CCN(C(C)C)CC4)n3c2Cl)N1C] | 467.4 | 2.15 | 7.57 | (CDCl$_3$) δ 8.42 (s, 1H), 7.41 (d, J = 6.8 Hz, 1H), 7.33 (d, J = 8.8 Hz, 1H), 7.12-7.03 (m, 2H), 6.35-6.33 (m, 1H), 3.61-3.53 (m, 2H), 3.36-3.30 (m, 2H), 2.93-2.83 (m, 4H), 2.78-2.72 (m, 1H), 2.68-2.52 (m, 5H), 2.27-2.17 (m, 1H), 2.07-1.92 (m, 2H), 1.91-1.79 (m, 4H), 1.75-1.31 (m, 2H), 1.12 (d, J = 6.4 Hz, 6H). |

TABLE 2-continued

Characterization Data for Additional Exemplary Compounds

| Compound No. | Chemical Structure | M + 1 | Rt (Min) (LCMS) | Rt (Min) (HPLC) | ¹H NMR (400 MHz) |
|---|---|---|---|---|---|
| I-93 | 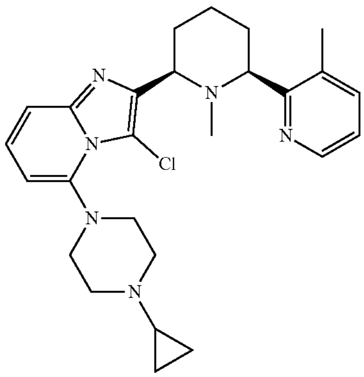 [SMILES: Cc1cccnc1[C@@H]1CCC[C@H](c2nc3cccc(N4CCN(C5CC5)CC4)n3c2Cl)N1C] | 465.3 | 2.22 | 7.34 | (CDCl$_3$) δ 8.47 (s, 1H), 7.41 (dd, J = 7.6, 0.8 Hz, 1H), 7.34 (dd, J = 8.8, 0.8 Hz, 1H), 7.11-7.03 (m, 2H), 6.32 (dd, J = 7.2, 0.8 Hz, 1H), 3.62-3.55 (m, 2H), 3.32-3.25 (m, 2H), 3.03-3.00 (m, 2H), 2.89-2.69 (m, 4H), 2.47 (s, 3H), 2.25-1.92 (m, 4H), 1.79 (s, 3H), 1.77-1.71 (m, 2H), 1.64-1.57 (m, 1H), 0.54-0.50 (m, 2H), 0.48-0.44 (m, 2H). |
| I-89 | 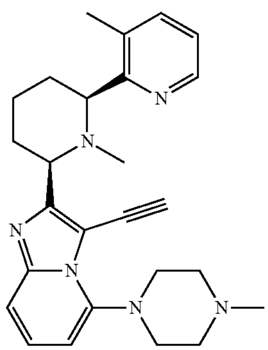 [SMILES: C#Cc1c([C@H]2CCC[C@@H](c3ncccc3C)N2C)nc2cccc(N3CCN(C)CC3)n12] | 429.4 | 1.76 | 5.60 | (CDCl$_3$) δ 8.47 (s, 1H), 7.41-7.38 (m, 2H), 7.21-7.17 (m, 1H), 7.06-7.03 (m, 1H), 6.40 (d, J = 7.2 Hz, 1H), 3.83 (s, 1H), 3.70-3.58 (m, 2H), 3.47-3.38 (m, 2H), 2.98-2.84 (m, 2H), 2.83-2.79 (m, 2H), 2.63-2.54 (m, 2H), 2.52-2.40 (m, 3H), 2.38 (s, 3H), 2.10-2.03 (m, 2H), 1.80 (s, 3H), 1.73-1.61 (m, 2H), 1.58-1.24 (m, 2H). |
| I-104 | 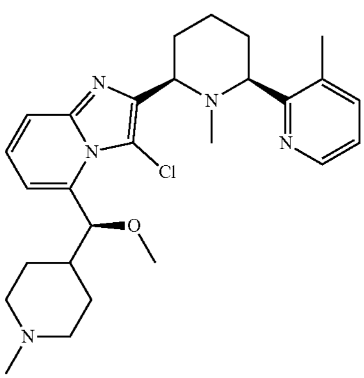 [SMILES: CO[C@H](c1cccc2nc([C@H]3CCC[C@@H](c4ncccc4C)N3C)c(Cl)n12)C1CCN(C)CC1] | 448.4 | 0.59 | 4.41 | (CD$_3$OD) δ 8.45-8.27 (m, 2H), 7.54-7.46 (m, 2H), 7.26-7.23 (m, 1H), 7.15-7.12 (m, 1H), 6.85-6.82 (m, 1H), 4.60-4.30 (m, 1H), 3.03 (s, 3H), 3.00-2.40 (m, 4H), 2.24 (s, 3H), 2.20-1.20 (m, 19H). |
| I-105 | 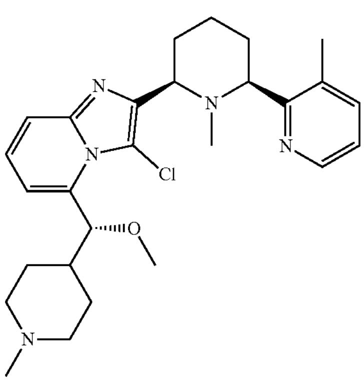 [SMILES: CO[C@@H](c1cccc2nc([C@H]3CCC[C@@H](c4ncccc4C)N3C)c(Cl)n12)C1CCN(C)CC1] | 448.4 | 0.57 | 4.31 | (CD$_3$OD) δ 8.48 (d, J = 6.8 Hz, 1H), 8.23 (br, 1H), 7.53-7.48 (m, 2H), 7.27-7.12 (m, 2H), 6.85-6.81 (m, 1H), 4.60-4.50 (m, 1H), 3.39-3.38 (m, 1H), 3.03 (s, 3H), 3.00-2.50 (m, 4H), 2.25-2.22 (m, 5H), 2.21 (s, 3H), 2.00-1.20 (m, 13H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-106 | 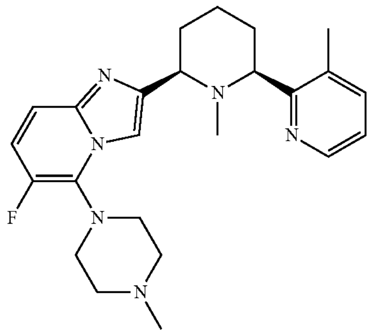 [SMILES: Cc1cccnc1[C@@H]1CCC[C@H](c2cn3c(N4CCN(C)CC4)c(F)ccc3n2)N1C] | 423.4 | 1.73 | 8.43 | (CDCl$_3$) δ 8.51 (d, J = 4.0 Hz, 1H), 7.71 (s, 1H), 7.44-7.42 (m, 1H), 7.32-7.29 (m, 1H), 7.07-7.02 (m, 2H), 4.90-4.30 (m, 2H), 3.58-3.54 (m, 1H), 3.45-3.42 (m, 1H), 3.40-3.25 (m, 4H), 2.92-2.79 (m, 2H), 2.46 (s, 3H), 2.43 (s, 3H), 2.04-1.93 (m, 4H), 1.87 (s, 3H), 1.64-1.60 (m, 2H). |
| I-109 | 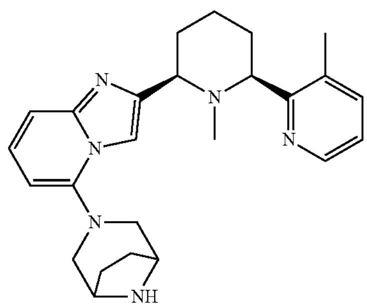 [SMILES: Cc1cccnc1[C@@H]1CCC[C@H](c2cn3c(N4CC5CCC(C4)N5)cccc3n2)N1C] | 417.4 | 2.01 | 4.89 | (CD$_3$OD) δ 8.44 (s, 1H), 7.98 (s, 1H), 7.61 (d, J = 7.2 Hz, 1H), 7.32-7.18 (m, 3H), 6.51 (dd, J = 6.8, 0.8 Hz, 1H), 3.66-3.63 (m, 3H), 3.48-3.44 (m, 1H), 3.32-3.29 (m, 2H), 3.04-2.97 (m, 2H), 2.53 (s, 3H), 2.32-2.27 (m, 2H), 2.02-1.88 (m, 6H), 1.78 (s, 3H), 1.76-1.68 (m, 2H). |
| I-110 | 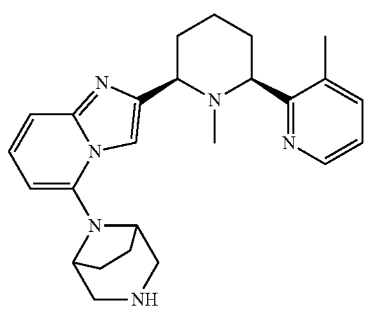 [SMILES: Cc1cccnc1[C@@H]1CCC[C@H](c2cn3c(N4C5CCC4CNC5)cccc3n2)N1C] | 417.4 | 2.00 | 5.61 | (CDCl$_3$) δ 8.41 (d, J = 4.0 Hz, 1H), 7.58 (s, 1H), 7.36-7.34 (m, 1H), 7.18-7.16 (m, 1H), 7.03-6.97 (m, 2H), 6.05 (d, J = 6.8 Hz, 1H), 3.85 (d, J = 3.2 Hz, 2H), 3.53 (dd, J = 11.2, 2.8 Hz, 1H), 3.42 (dd, J = 10.8, 2.8 Hz, 1H), 3..27 (t, J = 11.6 Hz, 2H), 2.814-2.78 (m, 2H), 2.42 (s, 3H), 2.03-1.85 (m, 11H), 1.71-1.57 (m, 2H). |
| I-111 | 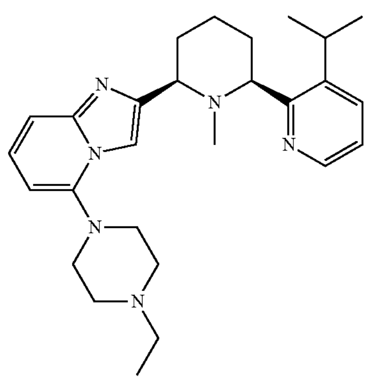 [SMILES: CCN1CCN(c2cccc3nc([C@H]4CCC[C@@H](c5ncccc5C(C)C)N4C)cn23)CC1] | 447.4 | 1.96 | 6.13 | (CDCl$_3$) δ 8.40 (s, 1H), 7.53 (d, J = 7.6 Hz, 2H), 7.25 (d, J = 9.2 Hz, 1H), 7.09-7.05 (m, 2H), 6.21 (d, J = 6.4 Hz, 1H), 3.62-3.60 (m, 1H), 3.58-3.56 (m, 1H), 3.12-3.10 (m, 4H), 2.66 (m, 3H), 2.48 (q, J = 7.2 Hz, 2H), 1.95 (m, 1H), 1.89-1.86 (m, 4H), 1.78 (s, 3H), 1.71-1.53 (m, 2H), 1.26-1.19 (m, 6H), 1.10 (t, J = 7.6 Hz, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-112 | 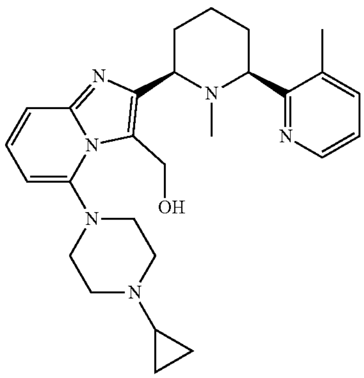 [SMILES: Cc1cccnc1[C@@H]1CCC[C@H](c2nc3cccc(N4CCN(C5CC5)CC4)n3c2CO)N1C] | 461.4 | 1.73 | 8.55 | (CDCl$_3$) δ 8.54 (s, 1H), 7.41 (d, J = 7.2 Hz, 1H), 7.33 (d, J = 8.4 Hz, 1H), 7.11-7.03 (m, 2H), 6.40 (d, J = 2.4 Hz, 1H), 5.82 (s, 1H), 5.29 (d, J = 14.0 Hz, 1H), 3.67-3.61 (m, 2H), 3.55 (s, 1H), 3.21 (d, J = 11.2 Hz, 1H), 3.09 (d, J = 11.6 Hz, 2H), 3.01-2.94 (m, 1H), 2.83-2.67 (m, 3H), 2.40 (s, 3H), 2.17-2.12 (m, 1H), 2.05-1.94 (m, 3H), 1.88 (s, 3H), 1.80-1.78 (m, 3H), 1.66-1.56 (m, 1H), 0.55-0.50 (m, 2H), 0.49-0.44 (m, 2H). |
| I-113 | 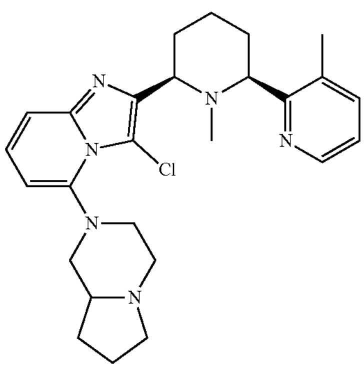 [SMILES: Cc1cccnc1[C@@H]1CCC[C@H](c2nc3cccc(N4CCN5CCCC5C4)n3c2Cl)N1C] | 465.3 | 2.10 | 10.80 | (CDCl$_3$) δ 8.47 (d, J = 2.0 Hz, 1H), 7.41 (dd, J = 7.6, 0.8 Hz, 1H), 7.36-7.33 (m, 1H), 7.12-7.03 (m, 2H), 6.38 (d, J = 7.2 Hz, 1H), 3.61-3.55 (m, 2H), 3.48-3.42 (m, 1H), 3.38-3.31 (m, 1H), 3.18-3.08 (m, 2H), 2.97-2.83 (m, 1H), 2.68-2.55 (m, 2H), 2.46 (s, 3H), 2.44-2.41 (m, 1H), 2.38-2.30 (m, 1H), 2.27-2.14 (m, 2H), 2.07-1.82 (m, 4H), 1.78 (s, 3H), 1.74-1.64 (m, 2H), 1.61-1.42 (m, 2H) |
| I-114 | 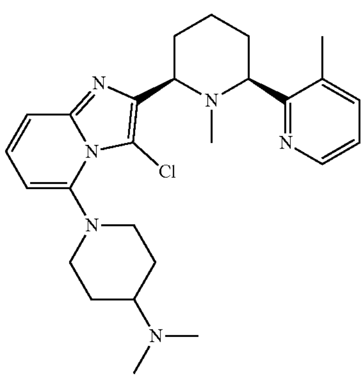 [SMILES: Cc1cccnc1[C@@H]1CCC[C@H](c2nc3cccc(N4CCC(N(C)C)CC4)n3c2Cl)N1C] | 467.3 | 1.81 | 4.97 | (CDCl$_3$) δ 8.38 (s, 1H), 7.34 (d, J = 7.6 Hz, 1H), 7.26 (d, J = 8.4 Hz, 1H), 7.04-6.96 (m, 2H), 6.25-6.23 (m, 1H), 3.60-3.51 (m, 5H), 3.41-3.36 (m, 2H), 2.65-2.55 (m, 2H), 2.43 (m, 2H), 2.36 (s, 9H), 2.14-2.10 (m, 1H), 1.97-1.93 (m, 2H), 1.90-1.80 (m, 2H), 1.74 (s, 3H), 1.56-1.52 (m, 1H). |
| I-115 | 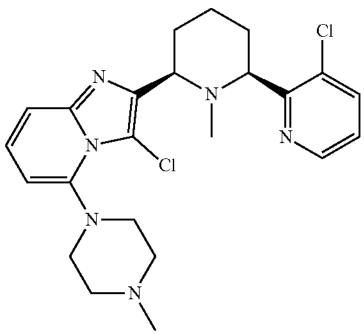 | 459.3 | 2.03 | 10.38 | (CDCl$_3$) δ 8.59 (dd, J = 4.4, 1.2 Hz, 1H), 7.65 (dd, J = 8.0, 1.2 Hz, 1H), 7.34 (dd, J = 8.8, 0.8 Hz, 1H), 7.13-7.08 (m, 2H), 6.35 (dd, J = 7.2, 0.8 Hz, 1H), 3.98 (d, J = 9.2 Hz, 1H), 3.62 (dd, = 14.4, 2.8 Hz, 1H), 3.33-3.26 (m, 2H), 2.98-2.84 (m, 4H), 2.56-2.46 (m, 2H), 2.41 (s, 3H), 2.02-1.93 (m, 2H), 1.82 (s, 3H), 1.78-1.75 (m, 2H), 1.68-1.57 (m, 1H), 1.26 (s, 1H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-116 | 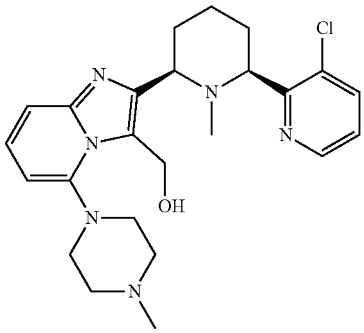 [SMILES: CN1CCN(c2cccc3nc([C@H]4CCC[C@@H](c5ncccc5Cl)N4C)c(CO)n23)CC1] | 455.4 | 1.63 | 7.87 | (CDCl$_3$) δ 8.61 (d, J = 4.0 Hz, 1H), 7.65 (dd, J = 8.0, Hz, 1H), 7.33 (d, J = 8.8 Hz, 1H), 7.14-7.08 (m, 2H), 6.42 (d, J = 7.2 Hz, 1H), 5.80 (s, 1H), 5.25 (d, J = 14.8 Hz, 1H), 4.00 (d, J = 10.0 Hz, 1H), 3.70 (dd, J = 11.2, Hz, 1H), 3.56 (s, 1H), 3.20 (d, J = 9.2 Hz, 1H), 3.10-3.03 (m, 1H), 2.93 (d, J = 12.0 Hz, 2H), 2.77 (t, J = 8.4 Hz, 1H), 2.61-2.54 (m, 1H), 2.50-2.43 (m, 1H), 2.41 (3H, s), 2.19-1.93 (m, 4H), 1.91 (s, 3H), 1.82-1.80 (m, 2H). |
| I-117 | 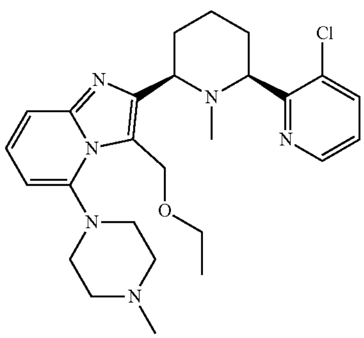 [SMILES: CCOCc1c([C@H]2CCC[C@@H](c3ncccc3Cl)N2C)nc2cccc(N3CCN(C)CC3)n12] | 483.3 | 1.95 | 9.86 | (CDCl$_3$) δ 8.58 (d, J = 4.0 Hz, 1H), 7.65 (dd, J = 8.0 Hz, J = 1.2 Hz, 1H), 7.40 (d, J = 8.0 Hz, 1H), 7.14-7.10 (m, 2H), 6.50 (d, J = 6.8 Hz, 1H), 5.30-5.28 (m, 1H), 5.08 (s, 1H), 3.94 (s, 1H), 3.66 (q, J = 7.2 Hz, 2H), 3.58 (d, J = 12.0 Hz, 1H), 3.26 (t, J = 12.0 Hz, 2H), 3.02-2.87 (m, 4H), 2.40 (s, 3H), 2.19-2.15 (m, 1H), 2..03 (s, 6H), 1.82 (s, 3H), 1.66-1.58 (m, 1H), 1.22 (t, J = 6.8 Hz, 3H). |
| I-119 | 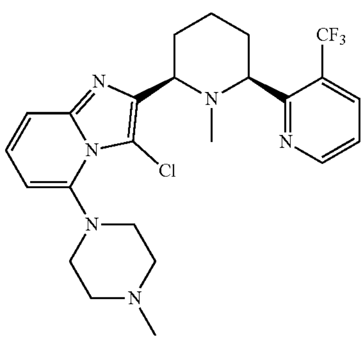 [SMILES: CN1CCN(c2cccc3nc([C@H]4CCC[C@@H](c5ncccc5C(F)(F)F)N4C)c(Cl)n23)CC1] | 493.3 | 2.05 | 10.51 | (CDCl$_3$) δ 8.88 (d, J = 3.2 Hz, 1H), 7.93 (d, J = 6.8 Hz, 1H), 7.35-7.32 (m, 2H), 7.12-7.07 (m, 1H), 6.35 (d, J = 6.4 Hz, 1H), 3.75 (d, J = 10.4 Hz, 1H), 3.64-3.59 (m, 1H), 3.32-3.25 (m, 2H), 2.93-2.83 (m, 4H), 2.52-2.49 (m, 2H), 2.40 (s, 3H), 2.23-2.22 (m, 1H), 1.96-1.78 (m, 2H), 1.76 (s, 3H), 1.64-1.60 (m, 1H). |
| I-123 | 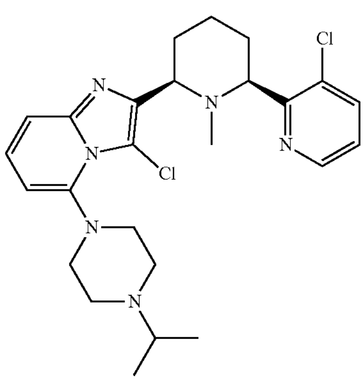 [SMILES: CC(C)N1CCN(c2cccc3nc([C@H]4CCC[C@@H](c5ncccc5Cl)N4C)c(Cl)n23)CC1] | 487.2 | 2.59 | 7.67 | (CDCl$_3$): δ 8.60-8.58 (m, 1H), 7.66-7.64 (m, 1H), 7.35 (d, J = 8.8 Hz, 1H), 7.14-7.09 (m, 2H), 6.39 (d, J = 7.2 Hz, 1H), 4.00-3.97 (m, 1H), 3.64-3.60 (m, 1H), 3.02-2.73 (m, 9H), 1.99-1.94 (m, 3H), 1.81-1.78 (m, 6H), 1.25 (brs, 6H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-125 | 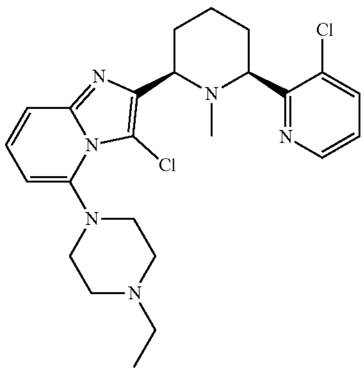 [SMILES: CCN1CCN(c2cccc3nc([C@H]4CCC[C@@H](c5ncccc5Cl)N4C)c(Cl)n23)CC1] | 473.2 | 2.45 | 11.75 | (CDCl$_3$): δ 8.51-8.50 (m, 1H), 7.58-7.56 (m, 1H), 7.27-7.25 (m, 1H), 7.05-7.00 (m, 2H), 6.28 (d, J = 6.8 Hz, 1H), 3.91-3.89 (m, 1H), 3.56-3.52 (m, 1H), 3.28-3.20 (m, 2H), 2.90-2.80 (m, 4H), 2.50-2.36 (m, 4H), 2.23 (brs, 2H), 1.91-1.85 (m, 2H), 1.73 (s, 3H), 1.73-1.66 (m, 2H), 1.10-1.07 (m, 3H). |
| I-126 | 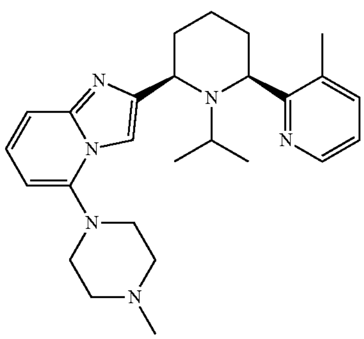 [SMILES: Cc1cccnc1[C@@H]1CCC[C@H](c2cn3c(N4CCN(C)CC4)cccc3n2)N1C(C)C] | 433.4 | 2.27 | 8.52 | (CDCl$_3$) δ 8.34 (d, J = 3.6 Hz, 1H), 7.65 (s, 1H), 7.52-7.48 (m, 1H), 7.24-7.10 (m, 3H), 6.41 (d, J = 6.0 Hz, 1H), 4.08 (dd, J = 11.2 Hz, 1H), 3.86 (t, J = 6.4 Hz, 1H), 3.07 (br, 4H), 2.78-2.73 (m, 1H), 2.67-2.54 (m, 7H), 2.33 (s, 3H), 1.95-1.33 (m, 6H), 0.66 (t, J = 7.2 Hz, 6H). |
| I-127 | 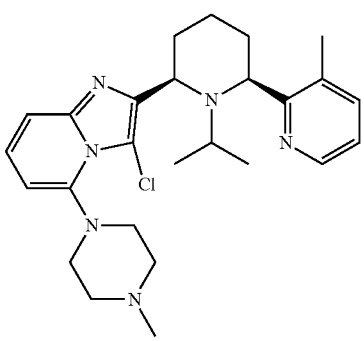 [SMILES: Cc1cccnc1[C@@H]1CCC[C@H](c2nc3cccc(N4CCN(C)CC4)n3c2Cl)N1C(C)C] | 467.3 | 2.78 | 10.37 | (CDCl$_3$) δ 8.38 (d, J = 3.6 Hz, 1H), 7.34-7.28 (m, 2H), 7.19-6.96 (m, 2H), 6.29 (t, J = 7.6 Hz, 1H), 3.99 (br, 2H), 3.24-3.20 (m, 2H), 2.88-2.78 (m, 4H), 2.64-2.45 (m, 6H), 2.33 (s, 3H), 2.09-1.65 (m, 6H), 0.68 (dd, J = 6.8 Hz, 6H). |
| I-132 | 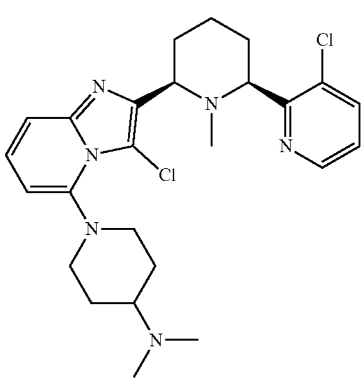 [SMILES: CN(C)C1CCN(c2cccc3nc([C@H]4CCC[C@@H](c5ncccc5Cl)N4C)c(Cl)n23)CC1] | 487.2 | 1.90 | 5.79 | (CDCl$_3$) δ 8.59-8.58 (m, 1H), 7.66-7.64 (m, 1H), 7.32 (d, J = 8.8 Hz, 1H), 7.14-7.07 (m, 2H), 6.31 (d, J = 6.8 Hz, 1H), 4.00-3.97 (m, 1H), 3.63 (dd, J = 11.6, 2.8 Hz, 1H), 3.46-3.40 (m, 2H), 2.72-2.59 (m, 2H), 2.35 (s, 6H), 2.30-2.23 (m, 1H), 2.22-2.10 (m, 1H), 1.98-1.96 (m, 1H), 1.90-1.82 (s, 4H), 1.80 (s, 3H), 1.78-1.74 (m, 2H), 1.68-1.60 (m, 2H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-134 | 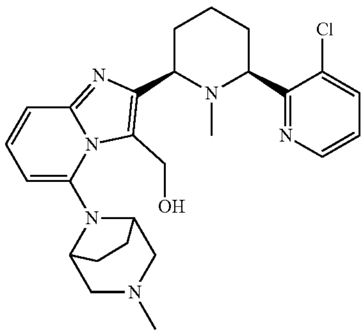 [SMILES: CN1CC2CCC(C1)N2c1cccc2nc([C@H]3CCC[C@@H](c4ncccc4Cl)N3C)c(CO)n12] | 481.3 | 2.40 | 8.75 | (CD$_3$OD): δ 8.60 (d, J = 4.0 Hz, 1H), 7.86-7.84 (m, 1H), 7.32-7.29 (m, 1H), 7.22-7.21 (m, 2H), 6.57-6.56 (m, 1H), 6.00-5.95 (m, 1H), 5.31-5.27 (m, 1H), 4.07-4.00 (m, 3H), 3.66 (d, J = 11.2 Hz, 1H), 2.91-2.84 (m, 2H), 2.77 (d, J = 11.6 Hz, 1H), 2.63 (d, J = 10.4 Hz, 1H), 2.39 (s, 3H), 2.17 (s, 3H), 2.15-2.10 (m, 2H), 2.03-1.99 (m, 2H), 1.96-1.94 (m, 4H), 1.91-1.69 (m, 2H). |
| I-135 | 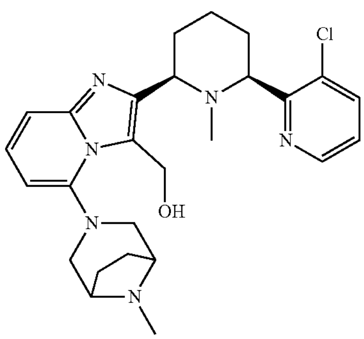 [SMILES: CN1C2CCC1CN(c1cccc3nc([C@H]4CCC[C@@H](c5ncccc5Cl)N4C)c(CO)n13)C2] | 481.4 | 2.19 | 7.89 | (DMSO-d$_6$): δ 8.58 (dd, J = 4.4, 1.2 Hz, 1H), 7.93-7.91 (m, 1H), 7.34 (dd, J = 8.0, 4.8 Hz, 1H), 7.27 (d, J = 7.6 Hz, 1H), 7.15 (dd, J = 8.8, 7.2 Hz, 1H), 6.76 (d, J = 6.4 Hz, 1H), 5.63-5.59 (m, 1H), 5.14 (d, J = 9.2 Hz, 1H), 3.93-3.90 (m, 1H), 3.59-3.56 (m, 1H), 3.22-3.13 (m, 4H), 2.99-2.97 (d, J = 7.6 Hz, 1H), 2.78-2.76 (m, 1H), 2.25 (s, 3H), 2.09-1.97 (m, 4H), 1.90-1.80 (m, 4H), 1.71 (s, 3H), 1.60-1.57 (m, 2H). |
| I-136 | 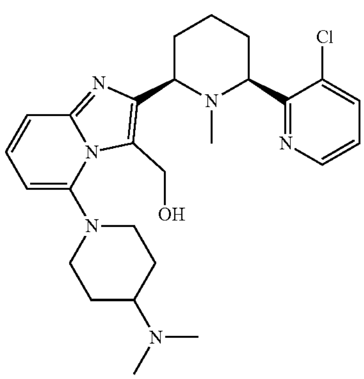 [SMILES: CN(C)C1CCN(c2cccc3nc([C@H]4CCC[C@@H](c5ncccc5Cl)N4C)c(CO)n23)CC1] | 483.3 | 1.56 | 7.67 | (CDCl$_3$) δ 8.62 (d, J = 4.0 Hz, 1H), 7.66-7.64 (m, 1H), 7.28 (d, J = 8.4 Hz, 1H), 7.14-7.07 (m, 2H), 6.40 (d, J = 6.8 Hz, 1H), 5.72 (s, 1H), 5.30-5.21 (m, 1H), 4.00 (s, 1H), 3.70-3.62 (m, 2H), 3.38-3.35 (m, 1H), 2.81 (t, 1H), 2.60-2.57 (m, 1H), 2.45-2.40 (m, 1H), 2.36 (s, 6H), 2.29-2.22 (m, 1H), 2.20-2.10 (m, 1H), 2.01-1.94 (m, 4H), 1.91 (s, 3H), 1.89-1.80 (m, 3H), 1.68-1.54 (m, 2H). |
| I-137 | 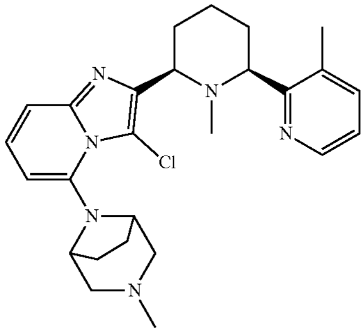 [SMILES: Cc1cccnc1[C@@H]1CCC[C@H](c2nc3cccc(N4C5CCC4CN(C)C5)n3c2Cl)N1C] | 465.4 | 1.94 | 9.78 | (CDCl$_3$) δ 8.47 (s, 1H), 7.42-7.36 (m, 2H), 7.11-7.03 (m, 2H), 6.64 (d, J = 6.8 Hz, 1H), 3.61-3.55 (m, 2H), 3.23-3.05 (m, 6H), 2.47 (s, 3H), 2.36 (s, 3H), 2.29-2.16 (m, 4H), 2.06-1.90 (m, 4H), 1.78 (s, 3H), 1.74-1.64 (m, 1H), 1.61-1.56 (m, 1H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-138 | 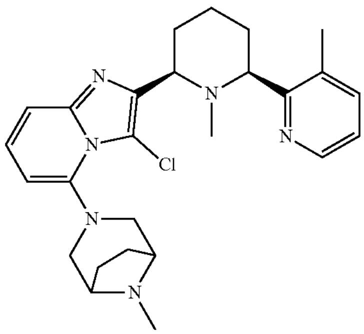 [SMILES: Cc1cccnc1[C@@H]1CCC[C@H](c2nc3cccc(N4CC5CCC(C4)N5C)n3c2Cl)N1C] | 465.4 | 2.12 | 10.81 | (CDCl$_3$) δ 8.45 (s, 1H), 7.41 (dd, J = 7.4, 1.0 Hz, 1H), 7.24 (s, 3H), 7.07-7.00 (m, 2H), 6.23 (d, J = 7.2 Hz, 1H), 3.86 (s, 2H), 3.58 (t, J = 12.6 Hz, 2H), 2.74-2.69 (m, 4H), 2.52 (brs, 3H), 2.32 (s, 3H), 2.23-2.19 (m, 1H), 2.06-1.92 (m, 6H), 1.80 (s, 3H), 1.75-1.71 (m, 2H), 1.62-1.58 (m, 1H). |
| I-139 | 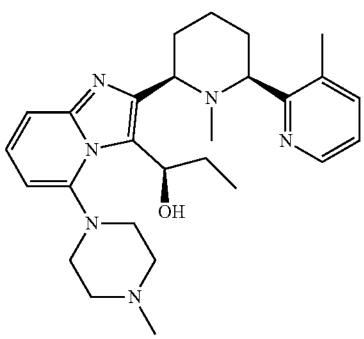 [SMILES: CC[C@@H](O)c1c([C@H]2CCC[C@@H](c3ncccc3C)N2C)nc2cccc(N3CCN(C)CC3)n12] | 463.4 | 1.61 | 8.03 | (CDCl$_3$) δ 8.59 (brs, 1H), 7.42 (d, J = 7.2 Hz, 1H), 7.35 (d, J = 6.4 Hz, 1H), 7.13-7.10 (m, 1H), 7.09-7.04 (m, 1H), 6.51 (brs, 1H), 5.65 (d, J = 4.4 Hz, 1H), 3.74-3.72 (m, 1H), 3.62-3.58 (m, 1H), 3.29-3.27 (m, 1H), 3.18-3.09 (m, 2H), 2.94-2.91 (m, 1H), 2.79 (d, J = 8.8 Hz, 1H), 2.62-2.40 (m, 3H), 2.38 (s, 3H), 2.32 (s, 3H), 2.11-1.92 (m, 4H), 1.92 (s, 3H), 1.70-1.60 (m, 4H), 1.06 (t, J = 7.2 Hz, 3H). |
| I-140 | 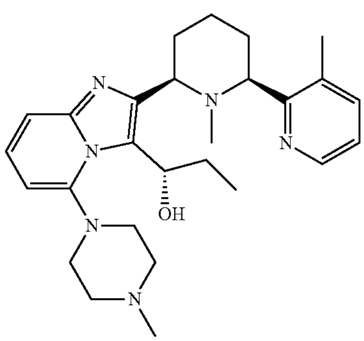 [SMILES: CC[C@H](O)c1c([C@H]2CCC[C@@H](c3ncccc3C)N2C)nc2cccc(N3CCN(C)CC3)n12] | 464.3 | 1.66 | 5.65 | (CDCl$_3$) δ 8.55-8.10 (m, 1H), 7.40 (d, J = 6.4 Hz, 1H), 7.35 (d, J = 8.8 Hz, 1H), 7.10-7.03 (m, 2H), 6.50 (d, J = 6.8 Hz, 1H), 5.32 (s, 1H), 3.70 (d, J = 3.2 Hz, 1H), 3.59 (d, J = 8.0 Hz, 1H), 3.32-3.18 (m, 2H), 3.12-3.08 (m, 1H), 2.93 (d, J = 10.4 Hz, 1H), 2.80 (d, J = 9.6 Hz, 1H), 2.63-2.42 (m, 4H), 2.37 (s, 3H), 2.00 (d, J = 12.8 Hz, 2H), 1.93 (s, 3H), 1.90-1.64 (4H, m), 1.33-1.27 (m, 1H), 1.22 (s, 3H). |
| I-141 | 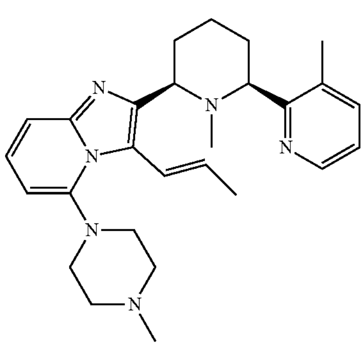 [SMILES: C/C=C/c1c([C@H]2CCC[C@@H](c3ncccc3C)N2C)nc2cccc(N3CCN(C)CC3)n12] | 445.4 | 1.95 | 6.39 | (CDCl$_3$) δ 8.47 (d, J = 2.8 Hz, 1H), 7.39 (dd, J = 7.4, 1.0, 1H), 7.33 (dd, J = 8.8, 0.8 Hz, 1H), 7.09 (dd, J = 15.6, 1.6 Hz, 1H), 7.06-7.01 (m, 2H), 6.28 (dd, J = 7.2, 0.8 Hz, 1H), 6.79-5.72 (m, 1H), 3.56 (dd, J = 11.6, 2.8 Hz, 2H), 3.29 (dd, J = 1.08, 2.2 Hz, 1H), 3.17 (dd, J = 11.0, 2.6 Hz, 1H), 3.01-2.94 (m, 1H), 2.86 (dd, J = 11.2, 2.0 Hz, 1H), 2.79 (dd, J = 11.2, 1.6 Hz, 1H), 2.74-2.67 (m, 1H), 2.48 (brs, 2H), 2.37 (s, 3H), 2.36-2.24 (m, 3H), 2.07-1.93 (m, 4H), 1.86-1.75 (m, 2H), 1.71 (s, 3H), 1.63-1.55 (m, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-142 | 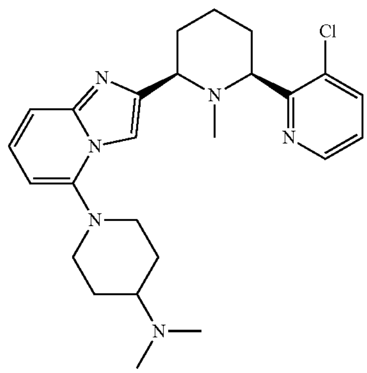 [SMILES: CN(C)C1CCN(c2cccc3nc([C@H]4CCC[C@@H](c5ncccc5Cl)N4C)cn23)CC1] | 453.3 | 1.66 | 8.49 | (CDCl$_3$) δ 8.61-8.60 (m, 1H), 7.66 (dd, J = 8.0, 1.6 Hz, 1H), 7.58 (s, 1H), 7.31 (d, J = 8.8 Hz, 1H), 7.14-7.11 (m, 2H), 6.25-6.23 (m, 1H), 3.98-3.95 (m, 1H), 3.54-3.49 (m, 3H), 2.76-2.68 (m, 2H), 2.45-2.41 (m, 1H), 2.39 (s, 6H), 2.12-2.04 (m, 1H), 2.05-1.96 (m, 4H), 1.92 (s, 3H), 1.86-1.81 (m, 3H), 1.78-1.63 (m, 2H). |
| I-146 | 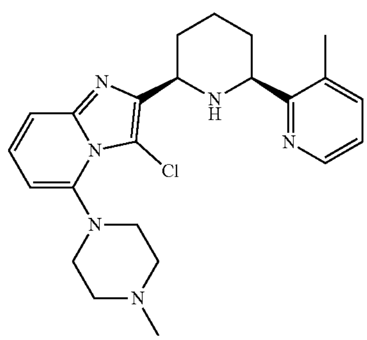 [SMILES: Cc1cccnc1[C@@H]1CCC[C@H](c2nc3cccc(N4CCN(C)CC4)n3c2Cl)N1] | 425.4 | 1.70 | 8.21 | (CDCl$_3$) δ 8.40 (dd, J = 4.8, 1.2 Hz, 1H), 7.38 (dd, J = 7.2, 1.6 Hz, 1H), 7.32 (dd, J = 9.2, 1.2 Hz, 1H), 7.08 (dd, J = 8.8, 7.2 Hz, 1H), 7.02 (dd, J = 8.0, 4.8 Hz, 1H), 6.34 (dd, J = 7.2, 0.8 Hz, 1H), 4.25-4.18 (m, 2H), 3.29-3.25 (m, 2H), 2.96-2.78 (m, 4H), 2.53-2.46 (m, 2H), 2.38 (s, 6H), 2.16-2.11 (m, 1H), 1.88-1.80 (m, 4H), 1.72-1.65 (m, 2H). |
| I-147 | 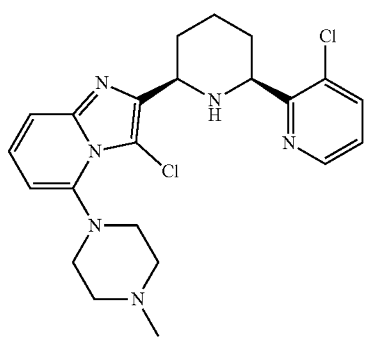 [SMILES: CN1CCN(c2cccc3nc([C@H]4CCC[C@@H](c5ncccc5Cl)N4)c(Cl)n23)CC1] | 445.2 | 3.22 | 9.15 | (CDCl$_3$) δ 8.48 (dd, J = 4.0, 1.6, 1H), 7.63-7.60 (m, 1H), 7.33 (dd, J = 8.8, 1.2 Hz, 1H), 7.11-7.07 (m, 2H), 6.35 (dd, J = 7.2, 0.8 Hz, 1H), 4.52-4.48 (m, 1H), 4.25 (dd, J = 10.0, 3.6 Hz, 1H), 3.31-3.26 (m, 2H), 2.97-2.91 (m, 1H), 2.86-2.79 (m, 3H), 2.54-2.46 (m, 2H), 2.39 (s, 3H), 2.15-2.12 (m, 1H), 2.02-1.98 (m, 1H), 1.93-1.85 (m, 3H), 1.54-1.44 (m, 1H). |
| I-188 | 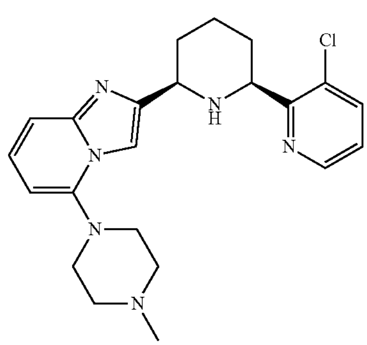 [SMILES: CN1CCN(c2cccc3nc([C@H]4CCC[C@@H](c5ncccc5Cl)N4)cn23)CC1] | 411.2 | 1.60 | 5.63 | (CDCl$_3$) δ 8.59-8.50 (dd, J = 4.8, 1.6 Hz, 1H), 7.65-7.63 (m, 1H), 7.51 (s, 1H), 7.32 (d, J = 8.8 Hz, 1H), 7.17-7.10 (m, 2H), 6.27 (dd, J = 7.2, 0.8 Hz, 1H), 4.52 (dd, J = 11.2, 2.4, 1H), 4.20-4.17 (m, 1H), 3.14 (s, 4H), 2.66 (m, 4H), 2.40 (s, 3H), 2.23-2.19 (m, 1H), 2.15-2.11 (m, 1H), 2.02-1.98 (m, 1H), 1.89-1.77 (m, 2H), 1.61-1.54 (m, 1H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-189 | 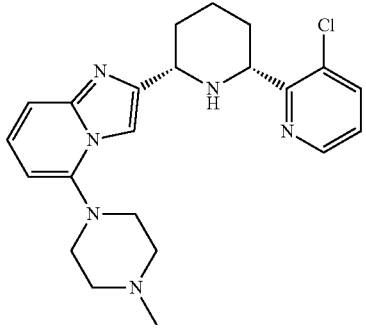 [SMILES: CN1CCN(c2cccc3nc([C@@H]4CCC[C@H](c5ncccc5Cl)N4)cn23)CC1] | 411.2 | 1.60 | 5.63 | (CDCl$_3$) δ 8.59-8.50 (dd, J = 4.8, 1.6 Hz, 1H), 7.65-7.63 (m, 1H), 7.51 (s, 1H), 7.32 (d, J = 8.8 Hz, 1H), 7.17-7.10 (m, 2H), 6.27 (dd, J = 7.2, 0.8 Hz, 1H), 4.52 (dd, J = 11.2, 2.4, 1H), 4.20-4.17 (m, 1H), 3.14 (s, 4H), 2.66 (m, 4H), 2.40 (s, 3H), 2.23-2.19 (m, 1H), 2.15-2.11 (m, 1H), 2.02-1.98 (m, 1H), 1.89-1.77 (m, 2H), 1.61-1.54 (m, 1H). |
| I-150 | 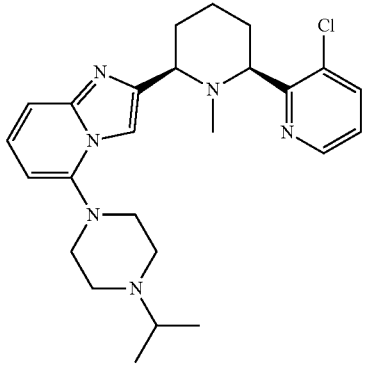 [SMILES: CC(C)N1CCN(c2cccc3nc([C@H]4CCC[C@@H](c5ncccc5Cl)N4C)cn23)CC1] | 453.2 | 2.07 | 6.39 | (CD$_3$OD): δ 8.51-8.50 (m, 1H), 7.93 (s, 1H), 7.77-7.74 (m, 1H), 7.23-7.13 (m, 3H), 6.38-6.36 (m, 1H), 3.92-3.88 (m, 1H), 3.40-3.36 (m, 1H), 3.11 (brs, 4H), 2.80-2.70 (m, 5H), 1.94-1.54 (m, 9H), 1.11-1.04 (m, 6H). |
| I-151 | 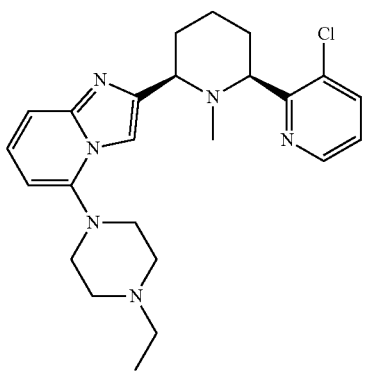 [SMILES: CCN1CCN(c2cccc3nc([C@H]4CCC[C@@H](c5ncccc5Cl)N4C)cn23)CC1] | 439.2 | 1.95 | 6.22 | (CD$_3$OD): δ 8.62 (dd, J = 4.4, 1.6 Hz, 1H), 8.02 (s, 1H), 7.88 (dd, J = 8.2, 1.2 Hz, 2H), 7.35-7.25 (m, 3H), 6.51 (dd, J = 7.2, 1.0 Hz, 1H), 4.04-3.99 (m, 1H), 3.51-3.49 (m, 1H), 3.24 (brs, 4H), 2.84 (brs, 4H), 2.67-2.59 (m, 2H), 2.06-1.67 (m, 9H), 1.66-1.23 (m, 3H). |
| I-154 | 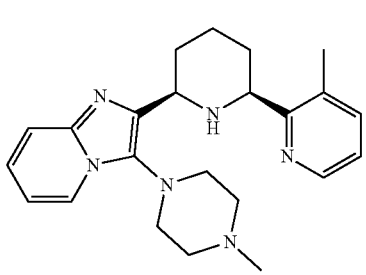 [SMILES: Cc1cccnc1[C@@H]1CCC[C@H](c2nc3ccccn3c2N2CCN(C)CC2)N1] | 391.3 | 1.53 | 7.07 | (CDCl$_3$) δ 8.40 (dd, J = 4.4, 0.8 Hz, 1H), 8.04 (d, J = 6.8 Hz, 1H), 7.49 (d, J = 9.2 Hz, 1H), 7.37 (dd, J = 7.6, 0.8 Hz, 1H), 7.09-7.05 (m, 1H), 7.00 (dd, J = 8.0, 4.8 Hz, 1H), 6.73-6.69 (m, 1H), 4.29-4.23 (m, 1H), 4.16-4.11 (m, 1H), 3.43-3.11 (m, 4H), 3.10-2.72 (m, 4H), 2.41 (s, 3H), 2.36 (s, 3H), 2.14-2.10 (m, 1H), 1.90-1.76 (m, 4H), 1.67-1.59 (m, 2H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-164 | 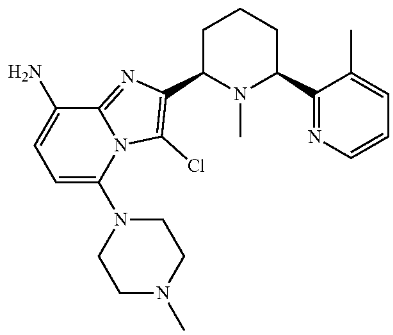 [SMILES: Cc1cccnc1[C@@H]1CCC[C@H](c2nc3c(N)ccc(N4CCN(C)CC4)n3c2Cl)N1C] | 454.4 | 1.89 | 9.55 | (CDCl$_3$) δ 8.48 (d, J = 4.0 Hz, 1H), 7.41 (dd, J = 8.0, 1.6 Hz, 1H), 7.04 (dd, J = 8.0, 1.6 Hz, 1H), 6.30-6.24 (m, 2H), 4.42 (s, 2H), 3.63-3.55 (m, 2H), 3.45-3.31 (m, 2H,), 3.21-3.14 (m, 2H), 3.16-2.80 (m, 3H), 2.70-2.61 (m, 3H,), 2.54-2.42 (m, 2H), 2.10-1.94 (m, 2H), 1.92-1.85 (m, 3H), 1.72-1.65 (m, 2H). |
| I-166 | 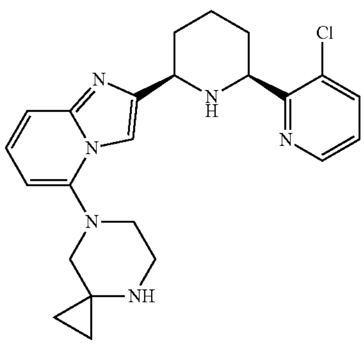 [SMILES: Clc1cccnc1[C@@H]1CCC[C@H](c2cn3c(N4CCNC5(CC5)C4)cccc3n2)N1] | 423.2 | 1.58 | 7.40 | (CDCl$_3$) δ 8.50 (dd, J = 4.8, 1.6 Hz, 1H), 7.65 (dd, J = 8.0, 1.6 Hz, 1H), 7.57 (s, 1H), 7.33 (d, J = 8.8 Hz, 1H), 7.16-7.10 (m, 2H), 6.24 (dd, J = 7.2, 0.8 Hz, 1H), 4.54 (dd, J = 11.2, 2.4 Hz, 1H), 4.20 (dd, J = 11.2, 2.4 Hz, 1H), 3.18 (t, J = 4.8 Hz, 2H), 3.08 (s, 2H), 2.93 (s, 2H), 2.23 (dd, J = 12.4, 2.4 Hz, 1H), 2.16-2.11 (m, 1H), 2.03 (dd, J = 12.8, 2.0 Hz, 1H), 1.92-1.78 (m, 4H), 1.59-1.49 (m, 1H), 0.76 (t, J = 6.0 Hz, 2H), 0.66 (t, J = 4.4 Hz, 2H). |
| I-173 | 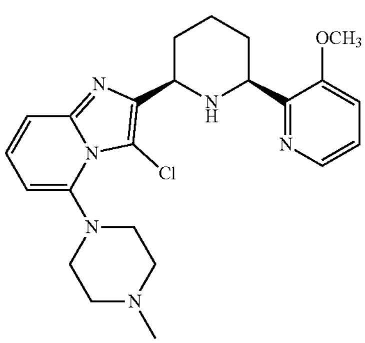 [SMILES: COc1cccnc1[C@@H]1CCC[C@H](c2nc3cccc(N4CCN(C)CC4)n3c2Cl)N1] | 441.3 | 1.68 | 8.09 | (CDCl$_3$) δ 8.16 (dd, J = 4.0, 2.0 Hz, 1H), 7.37 (dd, J = 9.2, 0.8 Hz, 1H), 7.25-7.18 (m, 3H), 6.49 (d, J = 6.4 Hz, 1H), 5.01 (dd, J = 8.4, 3.2 Hz, 1H), 4.85 (dd, J = 3.6, 3.2 Hz, 1H), 3.90 (s, 3H), 3.44-3.12 (m, 6H), 2.91-2.84 (m, 2H), 2.62 (s, 3H), 2.97-2.26 (m, 1H), 2.16-2.00 (m, 4H), 1.93-1.61 (m, 2H). |
| I-175 | 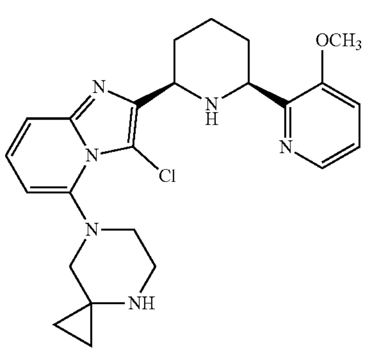 [SMILES: COc1cccnc1[C@@H]1CCC[C@H](c2nc3cccc(N4CCNC5(CC5)C4)n3c2Cl)N1] | 453.3 | 2.20 | 7.80 | (CDCl$_3$) δ 8.15 (t, J = 3.2 Hz, 1H), 7.31 (d, J = 8.8 Hz, 1H), 7.10-7.01 (m, 3H), 6.31-6.27 (m, 1H), 4.45-4.42 (m, 1H), 4.26-4.23 (m, 1H), 3.85 (m, 3H), 3.44-3.20 (m, 3H), 3.02-2.91 (m, 1H), 2.58-2.39 (m, 2H), 2.17-2.10 (m, 1H), 1.92-1.83 (m, 5H), 1.65-1.59 (m, 2H), 0.76-0.63 (m, 3H), 0.57-0.47 (m, 1H). |

TABLE 2-continued

Characterization Data for Additional Exemplary Compounds

| Compound No. | Chemical Structure | M + 1 (LCMS) | Rt (Min) (LCMS) | Rt (Min) (HPLC) | ¹H NMR (400 MHz) |
|---|---|---|---|---|---|
| I-187 | 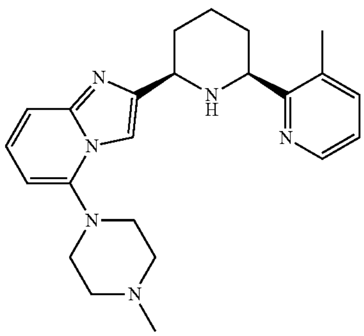 [SMILES: Cc1cccnc1[C@@H]1CCC[C@H](c2cn3c(N4CCN(C)CC4)cccc3n2)N1] | 391.4 | 1.51 | 6.95 | (CDCl₃) δ 8.43 (dd, J = 4.8, 1.2 Hz, 1H), 7.42 (dd, J = 7.2, 1.6 Hz, 1H), 7.31 (d, J = 9.2 Hz, 1H), 7.13 (dd, J = 9.2, 7.2 Hz, 1H), 7.05 (dd, J = 7.6, 4.8 Hz, 1H), 6.27 (dd, J = 7.2, 1.2 Hz, 1H), 4.24-4.21 (m, 1H), 4.18-4.15 (m, 1H), 3.14 (s, 4H), 2.65 (s, 4H), 2.40 (s, 6H), 2.25-2.22 (m, 1H), 2.15-2.12 (m, 1H), 1.85-1.76 (m, 3H), 1.72-1.65 (m, 2H). |
| I-191 | 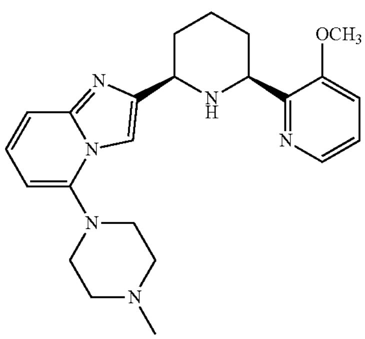 [SMILES: COc1cccnc1[C@@H]1CCC[C@H](c2cn3c(N4CCN(C)CC4)cccc3n2)N1] | 407.1 | 1.08 | 6.85 | (CDCl₃) δ 8.18 (t, J = 6.0 Hz, 1H), 7.53 (s, 1H), 7.31 (d, J = 9.2 Hz, 1H), 7.15-7.11 (m, 3H), 6.26 (dd, J = 7.2, 0.8 Hz, 1H), 4.46 (dd, J = 1.6, 1.2 Hz, 1H), 4.19 (d, J = 10.0 Hz, 1H), 3.85 (s, 3H), 3.13 (s, 4H), 2.65 (s, 4H), 2.39 (s, 3H), 2.24-2.20 (m, 1H), 2.11-2.07 (m, 1H), 1.95-1.92 (m, 1H), 1.86-1.76 (m, 3H), 1.70-1.63 (m, 1H). |
| I-152 | 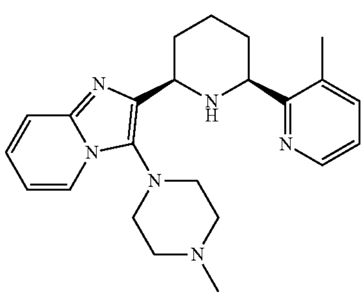 [SMILES: Cc1cccnc1[C@@H]1CCC[C@H](c2nc3ccccn3c2N2CCN(C)CC2)N1] | 405.3 | 1.20 | 7.20 | (CDCl₃) δ 8.46 (s, 1H), 8.05 (d, J = 6.4 Hz, 1H), 7.51 (d, J = 9.2 Hz, 1H), 7.40 (d, J = 6.8 Hz, 1H), 7.11-6.99 (m, 2H), 6.75-6.72 (m, 1H), 3.79-3.55 (m, 2H), 3.54-3.35 (m, 2H), 3.12-2.91 (m, 2H), 2.87-2.76 (m, 2H), 2.59-2.49 (m, 2H), 2.42 (s, 3H), 2.33-2.20 (m, 2H), 2.16 (s, 6H), 2.10-2.00 (m, 1H), 1.94-1.87 (m, 1H), 1.75-1.55 (m, 2H). |
| I-156 | 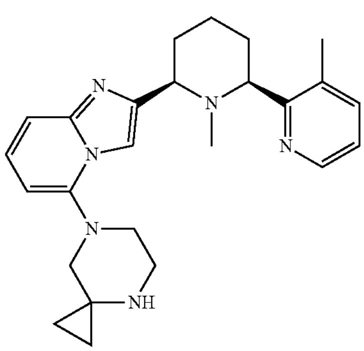 [SMILES: Cc1cccnc1[C@@H]1CCC[C@H](c2cn3c(N4CCNC5(CC5)C4)cccc3n2)N1C] | 417.4 | 2.14 | 7.59 | (CDCl₃) δ 8.49 (d, J = 3.6 Hz, 1H), 7.64 (s, 1H), 7.43 (d, J = 7.6 Hz, 1H), 7.32 (d, J = 8.8 Hz, 1H), 7.13 (dd, J = 8.8, 7.2 Hz, 1H), 7.06 (dd, J = 7.6, 4.8 Hz, 1H), 6.24 (d, J = 7.6 Hz, 1H), 3.58 (dd, J = 11.2, 2.8 Hz, 1H), 3.47-3.43 (m, 1H), 3.23-3.18 (m, 2H), 3.08 (brs, 2H), 2.94-2.91 (m, 2H), 2.51-2.46 (m, 3H), 2.05-1.96 (m, 3H), 1.91 (s, 3H), 1.72-1.58 (m, 3H), 0.79-0.65 (m, 4H). |

TABLE 2-continued

Characterization Data for Additional Exemplary Compounds

| Compound No. | Chemical Structure | M + 1 (LCMS) | Rt (Min) (LCMS) | Rt (Min) (HPLC) | $^1$H NMR (400 MHz) |
|---|---|---|---|---|---|
| I-159 | 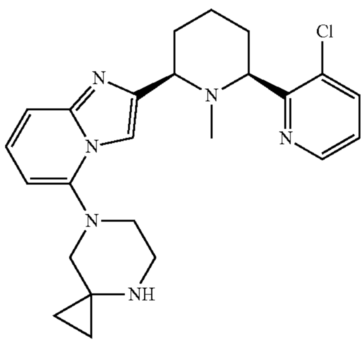 [SMILES: CN1[C@@H](c2cn3c(N4CCNC5(CC5)C4)cccc3n2)CCC[C@H]1c1ncccc1Cl] | 437.3 | 2.30 | 7.20 | (CDCl$_3$) δ 8.61 (dd, J = 4.4, 1.6 Hz, 1H), 7.67 (s, 1H), 7.65 (d, J = 1.6 Hz, 1H), 7.30 (d, J = 8.8 Hz, 1H), 7.15-7.11 (m, 2H), 6.23 (dd, J = 7.2, 1.2 Hz, 1H), 3.96 (dd, J = 11.2, 2.8 Hz, 1H), 3.51 (dd, J = 11.2, 3.2 Hz, 1H), 3.23-3.18 (m, 2H), 3.07 (brs, 2H), 3.00-2.95 (m, 2H), 2.10-1.96 (m, 4H), 1.93 (s, 3H), 1.86-1.61 (m, 3H), 0.78-0.64 (m, 4H). |
| I-160 | 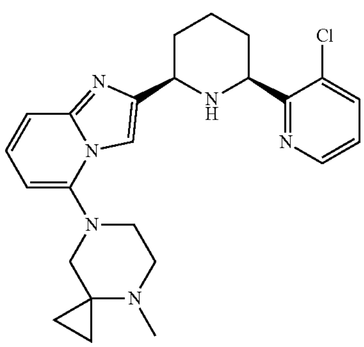 | 437.3 | 2.25 | 8.00 | (CDCl$_3$) δ 8.49-8.48 (d, J = 3.6 Hz, 1H), 7.64 (dd, J = 8, 7.2 Hz, 1H), 7.55 (s, 1H), 7.32 (d, J = 8.8 Hz, 1H), 7.17-7.10 (m, 2H), 6.27 (d, J = 7.2 Hz, 1H), 4.53 (dd, J = 11.2, 8.8 Hz, 1H), 4.20-4.17 (m, 1H), 3.13 (s, 4H), 2.92 (brs, 2H), 2.44 (s, 3H), 2.22-2.19 (m, 1H), 2.03-2.00 (m, 1H), 1.89-1.76 (m, 2H), 1.59-1.52 (m, 1H), 1.26 (brs, 2H), 0.88-0.84 (m, 2H), 0.60-0.57 (m, 2H). |
| I-167 | 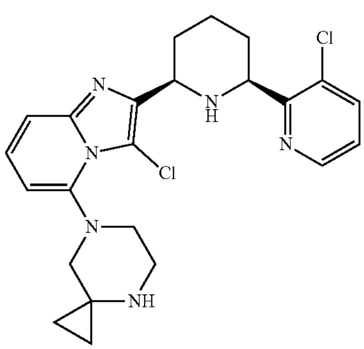 [SMILES: Clc1cccnc1[C@@H]1CCC[C@H](c2nc3cccc(N4CCNC5(CC5)C4)n3c2Cl)N1] | 457.3 | 1.77 | 8.67 | (CDCl$_3$) δ 8.48 (d, J = 4.4 Hz, 1H), 7.63 (dd, J = 8.4, 1.2 Hz, 1H), 7.34 (d, J = 8.8 Hz, 1H), 7.11-7.07 (m, 2H), 6.33 (t, J = 9.6 Hz, 1H), 4.52-4.50 (m, 1H), 4.28-4.26 (m, 1H), 3.44-3.36 (m, 2H), 3.34 (dd, J = 39.2, 11.2 Hz, 1H), 3.01-2.92 (m, 1H), 2.58-2.41 (m, 2H), 2.13-1.88 (m, 3H), 1.54-1.26 (m, 3H), 0.74-0.49 (m, 4H). |
| I-172 | 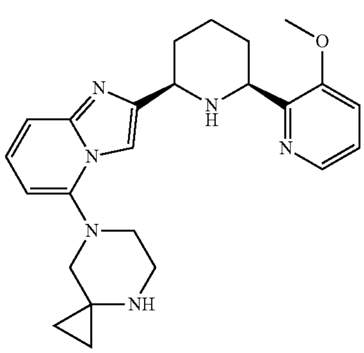 [SMILES: COc1cccnc1[C@@H]1CCC[C@H](c2cn3c(N4CCNC5(CC5)C4)cccc3n2)N1] | 419.3 | 1.91 | 6.72 | (CDCl$_3$) δ 8.18 (t, J = 2.8 Hz, 1H), 7.52 (s, 1H), 7.31 (d, J = 9.2 Hz, 1H), 7.15-7.11 (m, 3H), 6.21 (dd, J = 7.2, 0.8 Hz, 1H), 4.46 (dd, J = 11.2, 2.4 Hz, 1H), 4.17 (dd, J = 11.2, 2.8 Hz, 1H), 3.85 (s, 3H), 3.17-3.15 (m, 2H), 3.08 (brs, 2H), 2.92 (s, 2H), 2.24-2.21 (m, 1H), 2.12-2.08 (m, 1H), 1.96-1.92 (m, 6H), 0.73-0.72 (m, 2H), 0.65-0.63 (m, 2H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-186 | 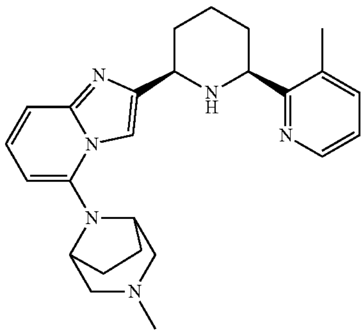 [SMILES: Cc1cccnc1[C@@H]1CCC[C@H](c2cn3c(N4C5CCC4CN(C)C5)cccc3n2)N1] | 417.3 | 2.15 | 7.74 | (CDCl$_3$) δ 8.35 (d, J = 4.0 Hz, 1H), 7.73 (s, 1H), 7.55 (d, J = 7.6 Hz, 1H), 7.22-7.10 (m, 3H), 6.33 (d, J = 7.2 Hz, 1H), 4.46-4.43 (m, 1H), 4.34-4.31 (m, 1H), 3.96 (s, 2H), 2.80-2.77 (m, 2H), 2.50 (d, J = 10 Hz, 2H), 2.34 (s, 3H), 2.26 (s, 3H), 2.21-2.18 (m, 1H), 2.11-2.03 (m, 1H), 1.94 (s, 6H), 1.87-1.80 (m, 1H), 1.63-1.48 (m, 2H). |
| I-190 | 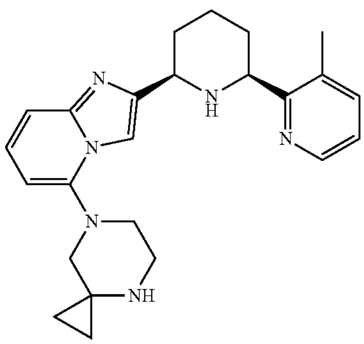 [SMILES: Cc1cccnc1[C@@H]1CCC[C@H](c2cn3c(N4CCNC5(CC5)C4)cccc3n2)N1] | 403.4 | 1.53 | 6.82 | (CDCl$_3$) δ 8.42 (d, J = 4.4 Hz, 1H), 7.58 (s, 1H), 7.42 (d, J = 7.2 Hz, 1 H), 7.32-7.29 (m, 1H), 7.16-7.11 (m, 1H), 7.06 (dd, J = 7.6, 4.8 Hz, 1H), 6.23 (d, J = 7.2 Hz, 1H), 4.26 (d, J = 11.2 Hz, 1H), 4.19 (d, J = 8.8 Hz, 1H), 3.18-3.15 (m, 2H), 3.16 (s, 2H), 2.93 (s, 2H), 2.41-2.22 (m, 1H), 2.16-2.12 (m, 1H), 1.88-1.82 (m, 4H), 1.55-1.52 (m, 2H), 0.75-0.70 (m, 2H), 0.67-0.65 (m, 2 H). |
| I-192 | 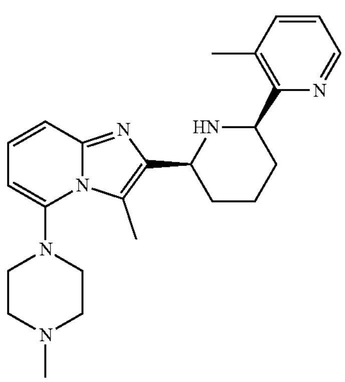 [SMILES: Cc1cccnc1[C@H]1CCC[C@@H](c2nc3cccc(N4CCN(C)CC4)n3c2C)N1] | 405.2 | 2.19 | 7.50 | (CDCl$_3$) δ 8.40 (d, J = 3.6 Hz, 1H), 7.39-7.33 (m, 2H), 7.03-6.99 (m, 2H), 6.36 (d, J = 6.8 Hz, 1H), 4.21-4.18 (m, 1H), 4.13-4.10 (m, 1H), 3.19-3.13 (m, 2H), 2.97-2.91 (m, 1H), 2.89-2.84 (m, 3H), 2.79 (s, 3H), 2.43-2.38 (m, 8H), 2.15-2.13 (m, 1H), 1.98-1.94 (m, 2H), 1.82-1.81 (m, 2H), 1.68-1.62 (m, 1H). |
| I-193 | 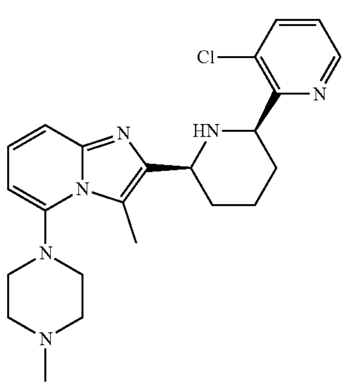 [SMILES: Cc1c([C@@H]2CCC[C@H](c3ncccc3Cl)N2)nc2cccc(N3CCN(C)CC3)n12] | 425.2 | 2.05 | 8.29 | (DMSO-d$_6$) δ 8.54 (dd, J = 4.8, 1.2 Hz, 1H), 7.91 (dd, J = 8.0, 1.2 Hz, 1H), 7.35-7.32 (m, , 1H), 7.26 (d, J = 8.4 Hz, 1H), 7.09 (dd, J = 8.8, 7.6 Hz, 1H), 6.51 (d, J = 6.8 Hz, 1H), 4.39-4.32 (m, 1H), 4.07-4.00 (m, 1H), 3.13-3.08 (m, 2H), 2.84-2.77 (m, 4H), 2.73 (s, 3H), 2.45-2.39 (m, 1H), 2.30-2.24 (m, 5H), 2.03-1.98 (m, 1H), 1.85-1.81 (m, 2H), 1.70-1.59 (m, 2H), 1.30-1.26 (m, 1H). |

TABLE 2-continued

Characterization Data for Additional Exemplary Compounds

| Compound No. | Chemical Structure | M + 1 (LCMS) | Rt (Min) (LCMS) | Rt (Min) (HPLC) | ¹H NMR (400 MHz) |
|---|---|---|---|---|---|
| I-208 | 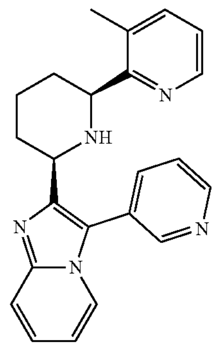 [SMILES: Cc1cccnc1[C@@H]1CCC[C@H](c2nc3ccccn3c2-c2cccnc2)N1] | 370.4 | 1.54 | 7.21 | (CDCl$_3$) δ 8.74 (dd, J = 2.2, 0.6 Hz, 1H), 8.63 (dd, J = 5.2, 1.6 Hz, 1H), 8.33 (dd, J = 4.8, 1.2 Hz, 1H), 7.98-7.95 (m, 1H), 7.85-7.81 (m, 1H), 7.60 (d, J = 9.2 Hz, 1H), 7.44-7.40 (m, 1H), 7.30 (dd, J = 7.8, 1.0 Hz, 1H), 7.15-7.11 (m, 1H), 6.96-6.92 (m, 1H), 6.71-6.66 (m, 1H), 4.04-3.94 (m, 2H), 2.70-2.59 (m, 1H), 2.26 (s, 3H), 2.08-1.94 (m, 2H), 1.83-1.66 (m, 2H), 1.61-1.52 (m, 2H). |
| I-209 | 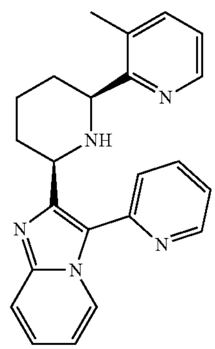 [SMILES: Cc1cccnc1[C@@H]1CCC[C@H](c2nc3ccccn3c2-c2ccccn2)N1] | 370.4 | 1.65 | 7.87 | (CDCl$_3$) δ 9.11 (d, J = 6.8 Hz, 1H), 8.75 (d, J = 4.4 Hz, 1H), 8.41 (d, J = 4.0 Hz, 1H), 7.84-7.82 (m, 2H), 7.66 (d, J = 8.8 Hz, 1H), 7.40 (d, J = 7.6 Hz, 1H), 7.25-7.21 (m, 2H), 7.04-7.01 (m, 1H), 6.80 (t, J = 6.8 Hz, 1H), 4.28-4.20 (m, 2H), 2.40 (s, 3 H), 2.21-2.15 (m, 3H), 1.95-1.68 (m, 4H). |
| I-210 | 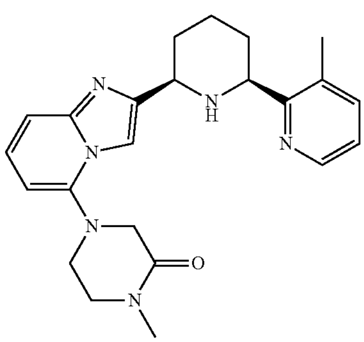 | 405.4 | 1.40 | 6.39 | (CDCl$_3$) δ 8.43 (d, J = 3.6 Hz, 1H), 7.54 (s, 1H), 7.43-7.37 (m, 2H), 7.16 (dd, J = 9.2, 7.2 Hz, 1H), 7.06 (dd, J = 7.6, 4.8 Hz, 1H), 6.27-6.26 (m, 1H), 4.24-4.15 (m, 2H), 3.83 (s, 2H), 3.51-3.49 (m, 2H), 3.43-3.40 (m, 2H), 3.07 (s, 3H), 2.40 (s, 3H), 2.27-2.24 (m, 1H), 2.15-2.11 (m, 1H), 1.86-1.80 (m, 2H), 1.67-1.61 (m, 2H). |
| I-211 | 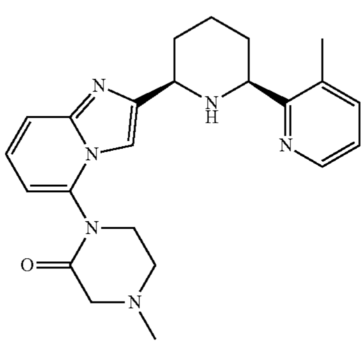 [SMILES: Cc1cccnc1[C@@H]1CCC[C@H](c2cn3c(N4CCN(C)CC4=O)cccc3n2)N1] | 405.4 | 1.35 | 6.08 | (CDCl$_3$) δ 8.43 (d, J = 4.0 Hz, 1H), 7.56 (t, J = 9.2 Hz, 1H), 7.42 (d, J = 6.8 Hz, 2H), 7.21-7.17 (m, 1H), 7.07-7.04 (m, 1H), 6.71 (d, J = 6.8 Hz, 1H), 4.22-4.14 (m, 2H), 3.73-3.70 (m, 2H), 3.48-3.38 (m, 1H), 3.33-3.23 (m, 1H), 2.93-2.80 (m, 2H), 2.45-2.39 (m, 6H), 2.30 2.10 (m, 3H), 1.73-1.58 (m, 3H). |

TABLE 2-continued

Characterization Data for Additional Exemplary Compounds

| Compound No. | Chemical Structure | M + 1 | Rt (Min) (LCMS) | Rt (Min) (HPLC) | $^1$H NMR (400 MHz) |
|---|---|---|---|---|---|
| I-212 | 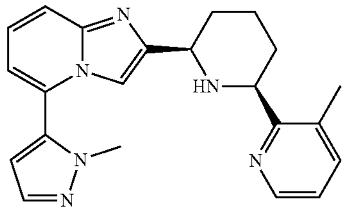 | 373.4 | 1.52 | 7.14 | (CDCl$_3$) δ 8.40 (d, J = 4.4 Hz, 1H), 7.66-7.64 (m, 2H), 7.40 (d, J = 7.6 Hz, 1H), 7.35 (s, 1H), 7.25-7.21 (m, 1H), 7.06-7.03 (m, 1H), 6.77 (d, J = 6.8 Hz, 1H), 6.56 (d, J = 1.6 Hz, 1H), 4.20-4.12 (m, 2H), 3.77 (s, 3H), 2.37 (s, 3H), 2.23-2.21 (m, 1H), 2.13-2.00 (m, 1H), 1.84-1.80 (m, 2H), 1.69-1.57 (m, 2H). |
| I-213 | 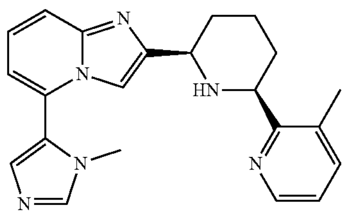 | 373.4 | 1.40 | 6.35 | (CDCl$_3$) δ 8.40 (d, J = 4.4 Hz, 1H), 7.66-7.62 (m, 2H), 7.41 (d, J = 7.2 Hz, 1H), 7.36-7.33 (m, 2H), 7.22 (dd, J = 8.8, 6.8 Hz, 1H), 7.06-7.03 (m, 1H), 6.75 (d, J = 6.8 Hz, 1H), 4.21-4.10 (m, 2H), 3.52 (s, 3H), 2.39 (s, 3H), 2.24-2.21 (m, 1H), 2.13-2.09 (m, 1H), 1.81-1.77 (m, 2H), 1.71-1.57 (m, 2H). |
| I-214 | 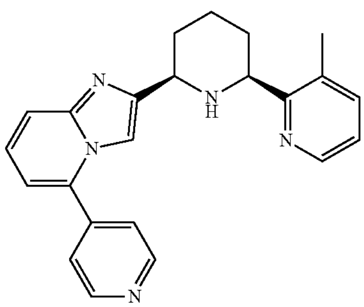 [SMILES: Cc1cccnc1[C@@H]1CCC[C@H](c2cn3c(-c4ccncc4)cccc3n2)N1] | 370.2 | 1.48 | 6.94 | (CDCl$_3$) δ 8.81 (dd, J = 4.4, 1.6 Hz, 2H), 8.40 (d, J = 4.0 Hz, 1H), 7.62 (d, J = 7.6 Hz, 2H), 7.56 (dd, J = 4.4, 1.6 Hz, 2H), 7.41 (d, J = 7.2 Hz, 1H), 7.25-7.23 (m, 1H), 7.06-7.03 (m, 1H), 6.77-6.75 (m, 1H), 4.21-4.13 (m, 2H), 2.37 (s, 3H), 2.26-2.21 (m, 1H), 2.13-2.09 (m, 1H), 1.84-1.81 (m, 2H), 1.69-1.57 (m, 2H). |
| I-215 | 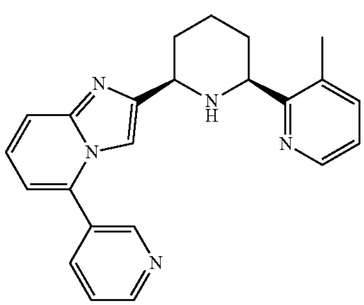 [SMILES: Cc1cccnc1[C@@H]1CCC[C@H](c2cn3c(-c4cccnc4)cccc3n2)N1] | 370.2 | 1.50 | 7.00 | (CDCl$_3$) δ 8.84 (d, J = 0.8 Hz, 1H), 8.75 (d, J = 4.8 Hz, 1H), 8.39 (d, J = 4.4 Hz, 1H), 7.97 (d, J = 7.6 Hz, 1H), 7.61 (d, J = 9.2 Hz, 1H), 7.55 (s, 1H), 7.48 (dd, J = 8.0, 4.8 Hz, 1H), 7.40 (d, J = 7.6 Hz, 1H), 7.26-7.22 (m, 1H), 7.05-7.02 (m, 1H), 6.72 (d, J = 7.2 Hz, 1H), 4.20-4.13 (m, 2H), 2.46 (s, 3H), 2.26-2.22 (m, 1H), 2.13-2.09 (m, 1H), 1.84-1.77 (m, 2H), 1.77-1.57 (m, 2H). |
| I-216 | 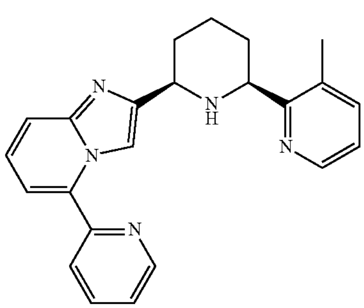 [SMILES: Cc1cccnc1[C@@H]1CCC[C@H](c2cn3c(-c4ccccn4)cccc3n2)N1] | 370.3 | 1.32 | 5.41 | (CDCl$_3$) δ 8.80-8.78 (m, 1H), 8.40-8.39 (m, 1H), 8.32 (s, 1H), 7.88-7.84 (m, 1H), 7.71 (d, J = 7.6 Hz, 1H), 7.63 (d, J = 8.8 Hz, 1H), 7.40-7.37 (m, 2H), 7.26-7.22 (m, 1H), 7.04-7.00 (m, 2H), 4.22-4.16 (m, 2H), 2.38 (s, 3H), 2.28-2.25 (m, 1H), 2.13-2.11 (m, 1H), 1.84-1.66 (m, 3H), 1.26-1.24 (m, 1H). |

TABLE 2-continued
Characterization Data for Additional Exemplary Compounds
| Compound No. | Chemical Structure | M + 1 | Rt (Min) (LCMS) | Rt (Min) (HPLC) | ¹H NMR (400 MHz) |
|---|---|---|---|---|---|
| I-217 | 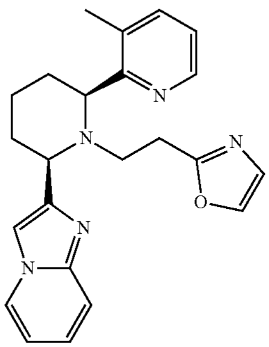 [SMILES: Cc1cccnc1[C@@H]1CCC[C@H](c2cn3ccccc3n2)N1CCc1ncco1] | 388.3 | 1.63 | 7.90 | ¹H NMR (400 MHz, CD₃OD): δ 8.42-8.39 (m, 2H), 7.96 (s, 1H), 7.63 (d, J = 6.80 Hz, 1H), 7.53-7.51 (m, 2H), 7.32-7.27 (m, 1H), 7.25-7.22 (m, 1H), 6.93-6.89 (m, 1H), 6.78 (s, 1H), 4.13 (dd, J = 11.2, 2.80 Hz, 1H), 3.95-3.91 (m, 1H), 2.87-2.67 (m, 3H), 2.65-2.56 (m, 4H), 2.03-1.97 (m, 4H), 1.81-1.66 (m, 2H). |
| I-218 | 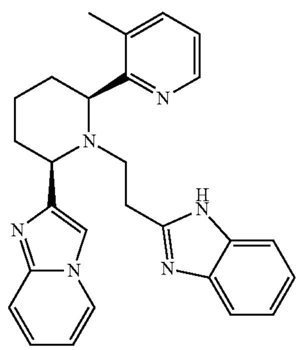 [SMILES: Cc1cccnc1[C@@H]1CCC[C@H](c2cn3ccccc3n2)N1CCc1nc2ccccc2[nH]1] | 437.3 | 1.65 | 8.17 | ¹H NMR (400 MHz, CD₃OD) δ : 8.38 (d, J = 4.0 Hz, 1H), 8.05 (d, J = 6.4 Hz, 1H), 7.63 (s, 1H), 7.54 (d, J = 7.2 Hz, 1H), 7.45 (d, J = 8.0 Hz, 1H), 7.37-7.34 (m, 2H), 7.26-7.22 (m, 1H), 7.19-7.13 (m, 3H), 6.85-6.80 (m, 1H), 4.17-4.12 (m, 1H), 3.95-3.91 (m, 1H), 2.95-2.86 (m, 2H), 2.68-2.62 (m, 1H), 2.58 (s, 3H), 2.45-2.41 (m, 1H), 2.06-1.97 (m, 4H), 1.81-1.68 (m, 2H). |
Example 27: Synthesis of I-207
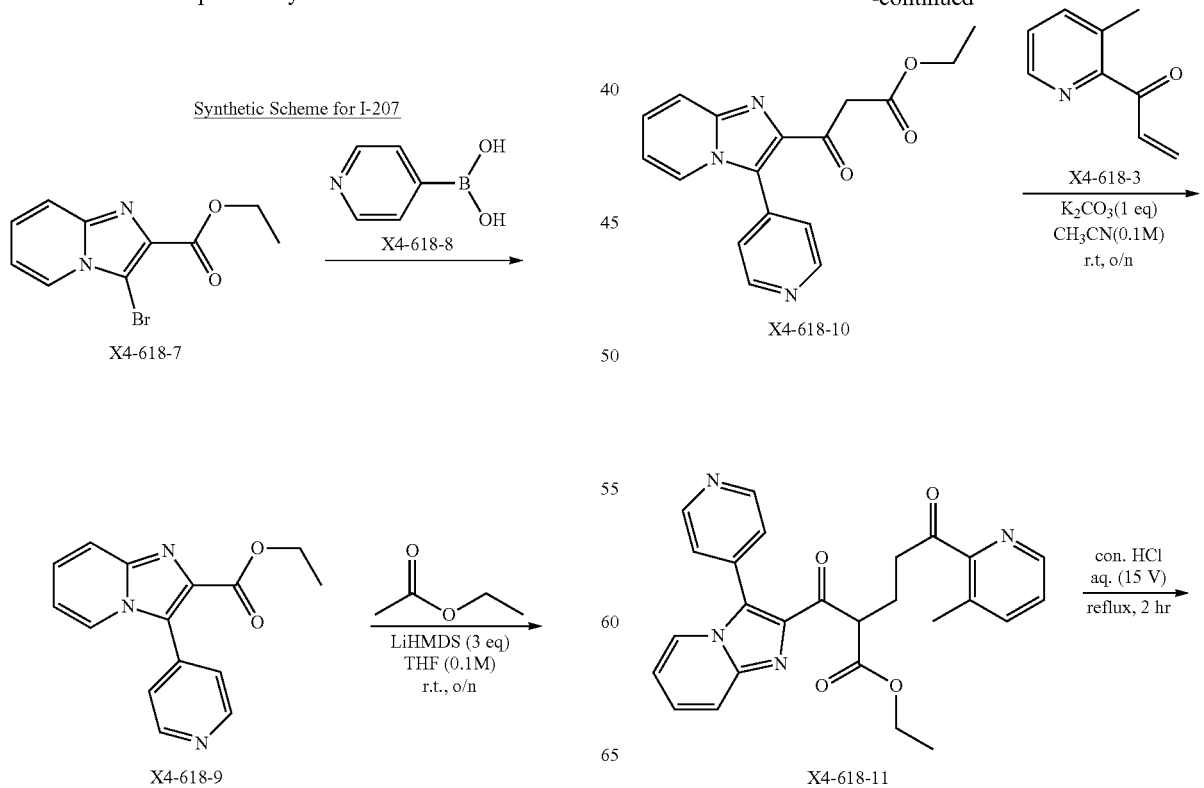
Synthetic Scheme for I-207

-continued

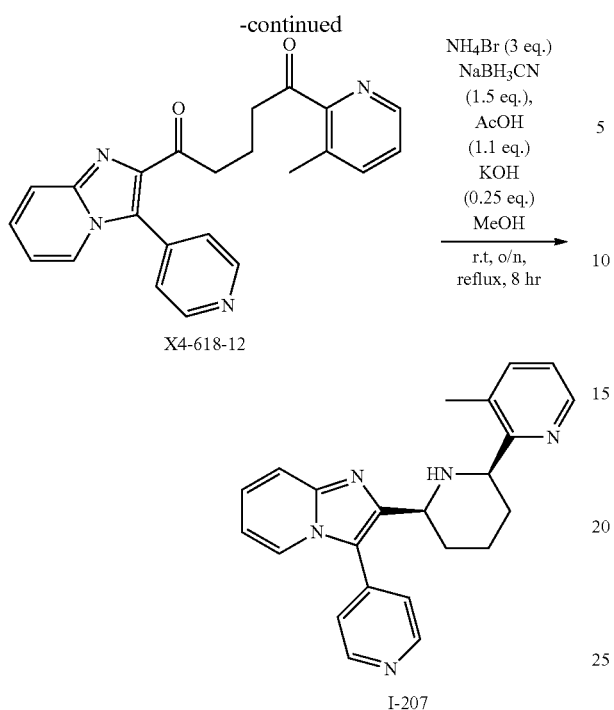

The Synthesis of X4-618-9

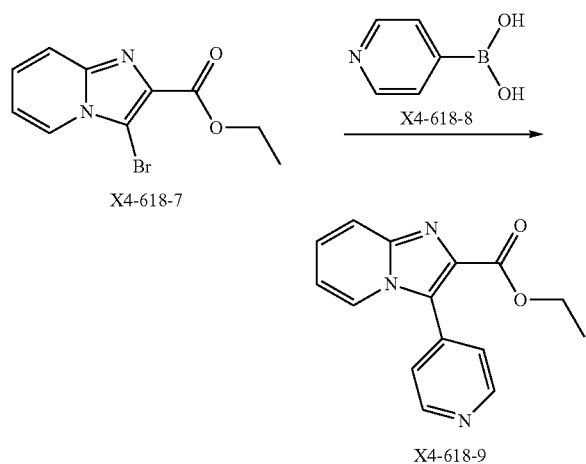

To a solution of X4-618-7 (2.0 g, 7.4 mmol), X4-618-8 (1.4 g, 11.3 mmol), Cs₂CO₃ (4.8 g, 14.7 mmol) in 1,2-dimethoxyethane/H₂O (40 mL/8 mL), were added (Cy)₃P (416.1 mg, 1.5 mmol) and Pd(dppf)Cl₂.CH₂Cl₂ (606.2 mg, 0.7 mmol) under N₂ atmosphere. Then the solution was stirred at 95° C. overnight and the mixture was cooled to room temperature, filtered and extracted with DCM (40 mL×3). The combined organic layers were washed with brine (20 mL×2), dried over anhydrous Na₂SO₄, filtered and concentrated in vacuum. The residue was purified by column chromatography to give X4-618-9 (1.0 g, yield: 50%) as an off-white solid. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH₄HCO₃] and 10% [CH₃CN] to 5% [water+10 mM NH₄HCO₃] and 95% [CH₃CN] in 0.5 min, then under this condition for 1.5 min, finally changed to 90% [water+10 mM NH₄HCO₃] and 10% [CH₃CN] in 0.1 min and under this condition for 0.5 min). Purity: 88.73%, Rt=0.78 min; MS Calcd.: 267.3; MS Found: 268.2 [M+H]⁺.

The Synthesis of X4-618-10

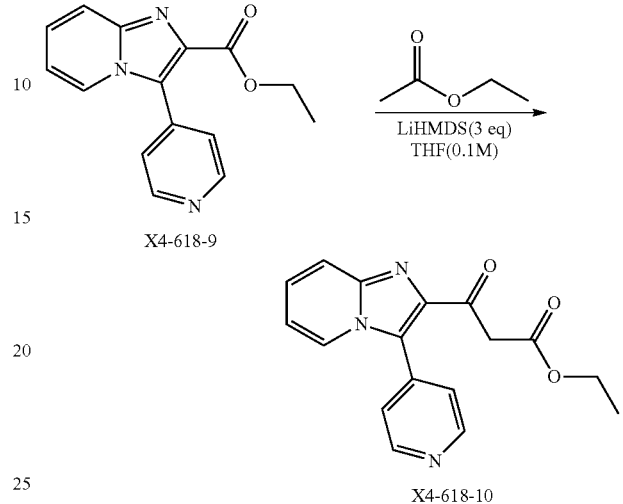

To a solution of X4-618-9 (300 mg, 1.1 mmol), ethyl acetate (593.3 mg, 6.7 mmol) in THF (5 mL) was added LiHMDS (1 M in THF, 3.4 mL, 3.4 mmol) and stirred at room temperature overnight. The reaction was quenched with 2 M HCl (50 mL) solution and washed with MTBE (3×10 mL). Then pH was adjusted to 9 with 40% NaOH (aq.) and extracted with DCM (3×10 mL). The combined organic layers were washed with brine (10 mL×2), dried over anhydrous Na₂SO₄, filtered and concentrated in vacuum to give the crude of X4-619-10 (300 mg, yield: 86%) as brown oil, which was used to the next step without further purification. LCMS (Agilent LCMS 1200-6120, Column: Waters X-Bridge C18 (30 mm*4.6 mm*3.5 μm); Column Temperature: 40° C.; Flow Rate: 2.0 mL/min; Mobile Phase: from 90% [water+10 mM NH₄HCO₃] and 10% [CH₃CN] to 5% [water+10 mM NH₄HCO₃] and 95% [CH₃CN] in 0.5 min, then under this condition for 1.5 min, finally changed to 90% [water+10 mM NH₄HCO₃] and 10% [CH₃CN] in 0.1 min and under this condition for 0.5 min.). Purity: 90.84%, Rt=0.87 min; MS Calcd.: 309.3; MS Found: 310.2 [M+H]⁺.

The Synthesis of X4-618-11

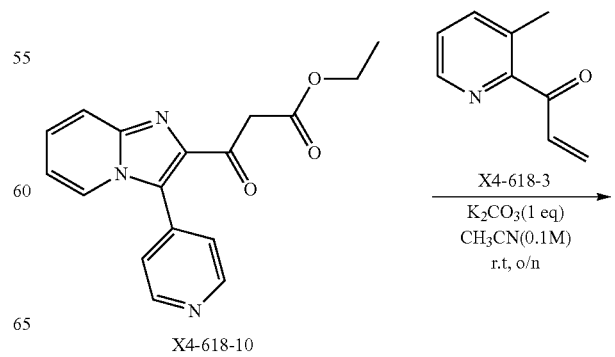

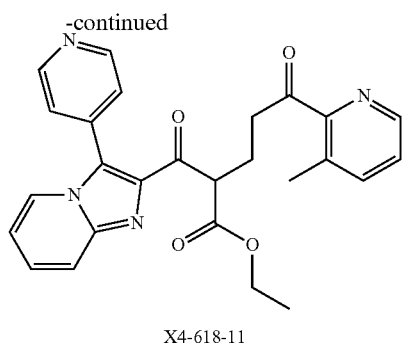

X4-618-11

To a solution of X4-618-10 (200 mg, 0.6 mmol), K$_2$CO$_3$ (82.8 mg, 0.6 mmol) in CH$_3$CN (10 ml) under Ar protection was added X4-618-3 (147 mg, 1.0 mmol). The mixture was stirred at room temperature overnight. Then it was poured into water (30 mL) and extracted with DCM (3×100 mL). The combined organic layers were washed with brine (10 mL×2), dried over anhydrous Na$_2$SO$_4$, filtered and concentrated in vacuum to give the crude of X4-619-11 (90 mg, yield: 30%) as brown oil, which was used to the next step without further purification. LCMS (Agilent LCMS 1200-6120, Column: Waters X-Bridge C18 (30 mm*4.6 mm*3.5 µm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min). Purity: 75.81%, Rt=1.04 min; MS Calcd.: 456.3; MS Found: 457.2 [M+H]$^+$.

The Synthesis of X4-618-12

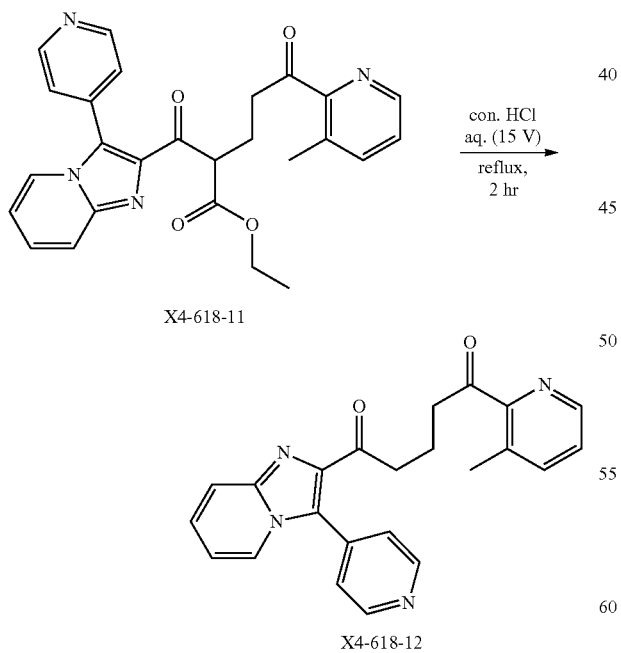

A solution of X4-618-11 (90 mg, 0.2 mmol) in conc. HCl solution (2 mL) was stirred at 100° C. for 2 h. Then it was concentrated in vacuo. The residue was dissolved in H$_2$O (10 mL), neutralized with 20% NaOH aq. to adjust to pH>9, and extracted with DCM (3×10 mL). The combined organic layers were washed with brine (10 mL×2), dried over anhydrous Na$_2$SO$_4$, filtered and concentrated in vacuum to give crude X4-619-12 (70 mg, yield: 92%) as brown semi-solid, which was used to the next step without further purification. LCMS (Agilent LCMS 1200-6120, Column: Waters X-Bridge C18 (30 mm*4.6 mm*3.5 µm); Column Temperature: 40° C.; Flow Rate: 2.0 mL/min; Mobile Phase: from 90% [water+10 mM NH$_4$HCO$_3$] and 10% [CH$_3$CN] to 5% [water+10 mM NH$_4$HCO$_3$] and 95% [CH$_3$CN] in 0.5 min, then under this condition for 1.5 min, finally changed to 90% [water+10 mM NH$_4$HCO$_3$] and 10% [CH$_3$CN] in 0.1 min and under this condition for 0.5 min.). Purity: 78.25%, Rt=0.96 min; MS Calcd.: 384.3; MS Found: 385.2 [M+H]$^+$.

The Synthesis of I-207

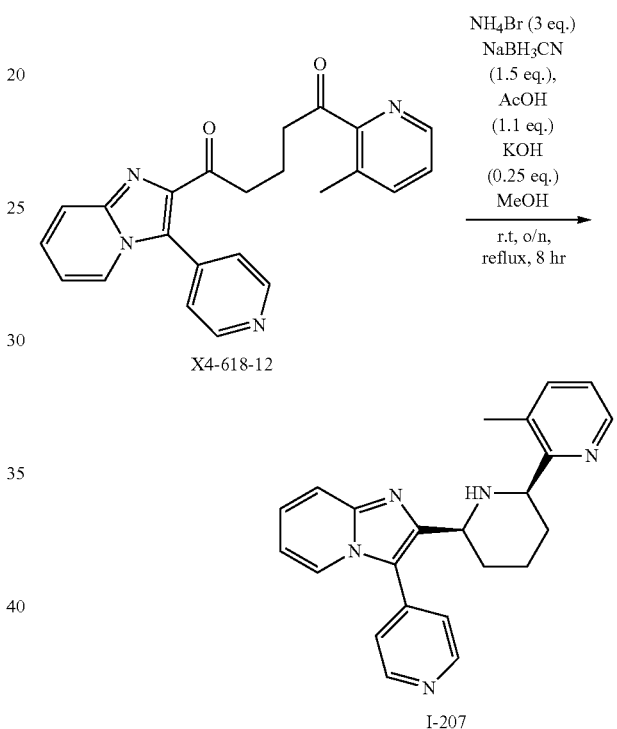

A solution of X4-618-12 (70 mg, 0.2 mmol), NH$_4$Br (53.5 mg, 0.55 mmol), AcOH (12.0 mg, 0.2 mmol), KOH (2.5 mg, 0.05 mmol), and NaBH$_3$CN (17.2 mg, 0.3 mmol) in dry CH$_3$OH (5 ml) under Ar protection was stirred at room temperature overnight, then heated at reflux for 8 h. Then it was cooled to room temperature and quenched with 10 mL of H$_2$O, extracted with DCM (3×20 mL). The combined organic layers were washed with brine (10 mL×2), dried over anhydrous Na$_2$SO$_4$, filtered and concentrated in vacuum. The residue was purified by prep-HPLC to give I-207 (20 mg, yield: 30%) as an off-white solid. LCMS (Agilent LCMS 1200-6120, Column: Waters X-Bridge C18 (50 mm*4.6 mm*3.5 µm)); Column Temperature: 40° C.; Flow Rate: 2.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 1.6 min, then under this condition for 1.4 min, finally changed to 95% [water+10 mM NH$_4$HCO$_3$] and 5% [CH$_3$CN] in 0.1 min and under this condition for 0.7 min.). Purity: 100.00%. Rt=1.53 min; MS Calcd.: 369.3; MS Found: 370.2 [M+H]$^+$. HPLC (Agilent HPLC 1200, Column: Waters X-Bridge C18 (150 mm*4.6 mm*3.5 μm); Column Temperature: 40° C.; Flow Rate: 1.0 mL/min; Mobile Phase: from 95% [water+10 mM NH$_4$HCO$_3$] and 5% [CH$_3$CN] to 0% [water+10 mM NH$_4$HCO$_3$] and 100% [CH$_3$CN] in 10 min, then under this condition for 5 min, finally changed to 95% [water+10 mM NH$_4$HCO$_3$] and 5% [CH$_3$CN] in 0.1 min and under this condition for 5 min). Purity: 95.73%. Rt=7.12 min. $^1$H NMR (400 MHz, CDCl$_3$) δ: 8.78 (d, J=5.6 Hz, 2H), 8.41 (d, J=4.0 Hz, 1H), 8.18 (d, J=7.2 Hz, 1H), 7.68 (d, J=8.8 Hz, 1H), 7.52 (d, J=3.6 Hz, 2H), 7.39 (d, J=7.2 Hz, 1H), 7.24 (d, J=8.0 Hz, 1H), 7.03 (dd, J=7.6, 5.2 Hz, 1H), 6.80 (t, J=6.8 Hz, 1H), 4.12 (s, 2H), 2.36 (s, 3H), 2.16-2.06 (m, 2H), 1.87-177 (m, 5H).

Example 28: REGA Screening Assay

Intracellular CXCL-12-Induced Calcium Mobilization Assay

Intracellular calcium mobilization induced by chemokines or chemokine-derived peptides were evaluated using a calcium responsive fluorescent probe and a FLIPR system. The CXCR-4 transfected U87 cell line (U87.CXCR4) cells were seeded in gelatine-coated black-wall 96-well plates at 20,000 cells per well and incubated for 12 hours. Cells were then loaded with the fluorescent calcium probe Fluo-2 acetoxymethyl at 4 μM final concentration in assay buffer (Hanks' balanced salt solution with 20 mM HEPES buffer and 0.2% bovine serum albumin, pH 7.4) for 45 min at 37° C. The intracellular calcium mobilization induced by the CXCL-12 (25-50 ng/mL) was then measured at 37° C. by monitoring the fluorescence as a function of time in all the wells simultaneously using a fluorometric imaging plate reader (FLIPR Tetra, Molecular Devices). The test compounds were added 15 minutes before the addition of CXCL-12 and monitored to see if compounds induced signals by themselves (agonistic properties).

Chemokine (CXCL12-AF647) Binding Inhibition Assay

Jurkat cells expressing CXCR4 were washed once with assay buffer (Hanks' balanced salt solution with 20 mM HEPES buffer and 0.2% bovine serum albumin, pH 7.4) and then incubated for 15 min at room temperature with the test compounds diluted in assay buffer at dose-dependent concentrations. Subsequently, CXCL12-AF647 (25 ng/mL) was added to the compound-incubated cells. The cells were incubated for 30 min at room temperature. Thereafter, the cells were washed twice in assay buffer, fixed in 1% paraformaldehyde in PBS, and analyzed on the FL4 channel of a FACSCalibur flow cytometer equipped with a 635-nm red diode laser (Becton Dickinson, San Jose, Calif., USA).

The percentages of inhibition of CXCL12-AF647 binding were calculated according to the formula: $[1-((MFI-MFI_{NC})/(MFI_{PC}-MFI_{NC}))]\times 100$ where MFI is the mean fluorescence intensity of the cells incubated with CXCL12-AF647 in the presence of the inhibitor, $MFI_{NC}$ is the mean fluorescence intensity measured in the negative control (i.e., autofluorescence of unlabeled cells), and $MFI_{PC}$ is the mean fluorescence intensity of the positive control (i.e., cells exposed to CXCL12-AF647 alone).

Results of Assays

Table 3 shows the activity of selected compounds of this invention in the assays described above. The compound numbers correspond to the compound numbers in Table 1. Compounds having an activity designated as "A" provided an IC$_{50}$ of 0.01 to 100 nM; compounds having an activity designated as "B" provided an IC$_{50}$ of >100 nm to <1 μM; and compounds having an activity designated as "C" provided an IC$_{50}$ of 1 μM or greater.

TABLE 3

Inhibition of Ca$^{2+}$ Signalling and Inhibition of CXCL12 Binding

| Compound # | IC$_{50}$ CXCL-12 Ca2+ flux U87.CXCR4+ (nM) | IC$_{50}$ CXCL-12 binding Jurkat (nM) |
|---|---|---|
| I-1 | A | A |
| I-2 | B | B |
| I-3 | A | A |
| I-4 | A | A |
| I-5 | B | A |
| I-6 | A | B |
| I-7 | C | B |
| I-8 | A | A |
| I-9 | A | A |
| I-10 | A | A |
| I-11 | A | A |
| I-12 | A | A |
| I-13 | A | A |
| I-14 | B | B |
| I-15 | A | A |
| I-16 | A | A |
| I-17 | A | A |
| I-18 | A | A |
| I-19 | A | A |
| I-20 | B | A |
| I-21 | A | A |
| I-25 | A | A |
| I-26 | B | A |
| I-27 | A | A |
| I-28 | B | A |
| I-29 | B | A |
| I-34 | A | A |
| I-37 | A | A |
| I-38 | A | A |
| I-39 | B | A |
| I-40 | A | A |
| I-45 | C | B |
| I-46 | A | A |
| I-47 | A | A |
| I-48 | B | A |
| I-49 | A | A |
| I-50 | A | A |
| I-51 | B | A |
| I-52 | C | B |
| I-53 | B | A |
| I-54 | A | A |
| I-55 | C | A |
| I-56 | A | A |
| I-57 | A | A |
| I-58 | C | B |
| I-59 | C | B |
| I-60 | A | A |
| I-61 | A | A |
| I-62 | C | B |
| I-63 | B | A |
| I-66 | B | A |
| I-67 | B | A |
| I-68 | A | A |
| I-69 | A | A |
| I-73 | C | B |
| I-74 | C | B |
| I-75 | C | B |
| I-76 | A | A |
| I-77 | A | A |
| I-78 | A | A |
| I-79 | A | A |
| I-80 | B | A |
| I-81 | B | A |
| I-82 | A | A |
| I-83 | B | A |
| I-85 | A | A |
| I-86 | A | A |
| I-87 | A | A |
| I-88 | A | A |
| I-89 | A | A |
| I-91 | C | B |
| I-92 | A | A |
| I-93 | B | A |

TABLE 3-continued

Inhibition of Ca$^{2+}$ Signalling and Inhibition of CXCL12 Binding

| Compound # | IC$_{50}$ CXCL-12 Ca2+ flux U87.CXCR4+ (nM) | IC$_{50}$ CXCL-12 binding Jurkat (nM) |
|---|---|---|
| I-104 | B | A |
| I-105 | C | B |
| I-106 | A | A |
| I-109 | B | A |
| I-110 | A | A |
| I-111 | C | B |
| I-112 | B | A |
| I-113 | A | A |
| I-114 | A | A |
| I-115 | A | A |
| I-116 | A | A |
| I-117 | A | A |
| I-119 | C | A |
| I-123 | C | A |
| I-125 | B | A |
| I-126 | A | A |
| I-127 | A | A |
| I-132 | B | A |
| I-134 | A | A |
| I-135 | A | A |
| I-136 | A | A |
| I-137 | B | A |
| I-138 | A | A |
| I-139 | B | A |
| I-140 | A | A |
| I-141 | B | A |
| I-142 | A | A |
| I-146 | B | A |
| I-147 | B | A |
| I-149 | A | A |
| I-150 | C | A |
| I-151 | B | A |
| I-152 | A | A |
| I-154 | C | B |
| I-156 | A | A |
| I-159 | A | A |
| I-160 | C | B |
| I-164 | A | A |
| I-166 | C | B |
| I-167 | C | B |
| I-172 | C | C |
| I-173 | C | B |
| I-175 | C | C |
| I-179 | A | A |
| I-180 | A | A |
| I-181 | A | A |
| I-182 | C | A |
| I-186 | A | A |
| I-187 | A | A |
| I-188 | A | A |
| I-189 | B | A |
| I-190 | C | B |
| I-191 | B | A |
| I-192 | A | A |
| I-193 | A | A |
| I-207 | C | C |
| I-208 | C | C |
| I-209 | — | C |
| I-210 | C | C |
| I-211 | C | B |
| I-212 | C | C |
| I-213 | C | C |
| I-214 | C | C |
| I-215 | C | C |
| I-216 | C | C |
| I-219 | C | C |

Example 28: Caco-2 Permeability Assay

Assay Procedure

The goal of this assay was to evaluate the intestinal absorption potential of drug candidates using Caco-2 cell lines.

Experimental Procedure
1. Prewarm Prewarm HBSS Buffer in 37° C. water bath
2. Sonicate Take compounds from −20° C., sonicate for a few minutes (no less than 1 minute)
3. Solution Preparation Donor Solution Buffer For A-to-B Direction:
HBSS buffer with 0.3% DMSO and 5 μM LY: add 150 μL DMSO and 50 μL LY (5 mM) into 50 ml HBSS buffer (pH 7.4).
HBSS buffer with 0.1% DMSO and 5 μM LY: add 50 μL DMSO and 50 μL LY (5 mM) into 50 mL HBSS buffer (pH 7.4).
For B-to-A Direction:
HBSS buffer with 0.3% DMSO: add 150 μL DMSO into 50 ml HBSS buffer (pH 7.4).
HBSS buffer with 0.1% DMSO: add 50 μL DMSO into 50 ml HBSS buffer (pH 7.4).
Receiver Solution Buffer:
For A-to-B Direction:
Prepare HBSS buffer with 0.4% DMSO: add 200 μL DMSO into 50 ml HBSS buffer (pH 7.4).
For B-to-A Direction:
Prepare HBSS buffer with 0.4% DMSO and 5 μM LY: add 200 μL DMSO and 50 μL LY (5 mM) into 50 ml HBSS buffer (pH 7.4).

TABLE 4

Preparation of Test Solutions

| Compound | | Stock Solution (in DMSO) | | | | Final DMSO concentration |
|---|---|---|---|---|---|---|
| | | Test cpd | Verapamil | apical Buffer | basolateral buffer | |
| Erythromycin + Metoprolol + Atenolol | A-to-B dosing solution | 10 mM 3 μL | — | 0.1% DMSO HBSS + LY 3 mL | — | 0.4% |
| | A-to-B Receiver solution | — | — | — | 0.4% DMSO HBSS | 0.4% |
| | B-to-A dosing solution | 10 mM 3 μL | — | — | 0.1% DMSO HBSS 3 mL | 0.4% |
| | B-to-A Receiver solution | — | — | 0.4% DMSO HBSS + LY | — | 0.4% |
| cpds | A-to-B dosing solution | 10 mM 3 μL | — | 0.3% DMSO HBSS + LY 3 mL | — | 0.4% |

TABLE 4-continued

Preparation of Test Solutions

| Compound | Stock Solution (in DMSO) | | | | Final DMSO |
|---|---|---|---|---|---|
| | Test cpd | Verapamil | apical Buffer | basolateral buffer | concentration |
| A-to-B Receiver solution | — | — | — | 0.4% DMSO HBSS | 0.4% |
| B-to-A dosing solution | 10 mM 3 μL | — | — | 0.3% DMSO HBSS 3 mL | 0.4% |
| B-to-A Receiver solution | — | — | 0.4% DMSO HBSS + LY | — | 0.4% |

4. Measure TEER Take cell culture plate out of incubator, wash the cell monolayers with HBSS buffer, and then measure TEER values at Rm temperature.
5. Centrifuge Centrifuge the compound solution (from step 3) at 4000 rpm for 5 min before loading to donor chambers.
6. Dosing Add solution based on the volumes listed in the following table (make sure to take extra 100 μL of donor sample for TO as Backup).

TABLE 5

Dosing Parameters

| Position | Transport Direction | Volume added | Final volume |
|---|---|---|---|
| Apical | A--B (Donor chamber) | 600 μL of A-to-B dosing solution (100 μL for LY measurement and 100 μL for Backup) | 400 μL |
| Basolateral | A--B (Receiver chamber) | 800 μL 0.4% DMSO HBSS | 800 μL |
| Basolateral | B--A (Donor chamber) | 900 μL B-to-A dosing solution (100 μL for Backup) | 800 μL |
| Apical | B--A (Receiver chamber) | 500 μL 0.4% DMSO HBSS + LY (100 μL for LY measurement) | 400 μL |

7. Apical LYT0 Samples To determine LY concentration in the apical chamber, take 100 μL sample from apical chambers into an opaque plate for LYT0.
8. Prewarm Prewarm apical and basolateral plates at 37° C. for about 5 min, then begin transport by placing the apical plate onto basolateral plate.
9. Incubation Keep the plates in incubator at 37° C. for 90 min.
10. Standard Curve Preparation Prepare 20× Solution For 300 μM compound solution, add 6 μL of compound stock solution into 192 μL of MeOH/H$_2$O (1:1).

Prepare Working Solution in MeOH/H$_2$O (1:1)

TABLE 6

Solutions for Standard Curve Preparation

| Compound solution (μM) | Solution (μL) | MeOH/H$_2$O (μL) | | Final solution (μM) |
|---|---|---|---|---|
| 300 | 100 | 400 | → | 60 |
| 60 | 100 | 200 | → | 20 |
| 20 | 100 | 400 | → | 4 |

TABLE 6-continued

Solutions for Standard Curve Preparation

| Compound solution (μM) | Solution (μL) | MeOH/H$_2$O (μL) | | Final solution (μM) |
|---|---|---|---|---|
| 4 | 100 | 400 | → | 0.8 |
| 0.8 | 100 | 300 | → | 0.2 |
| 0.2 | 100 | 100 | → | 0.1 |

Prepare 1× Solution

3 μL (20×)+57 μL of 0.4% DMSO HBSS+60 μL ACN with IS (Osalmid or Imipramine) - - - 120 μL (1×)

11. Transport Termination Separate the apical plate from the basolateral plate after 90-min incubation.
12. Measure LY Take 100 μL samples from basolateral plate to an opaque plate as LYT90.
13. Measure LY concentrations for LYT0 and LYT90 by Fluorometer (at excitation of 485 nm/emission of 535 nm).
14. Sample preparation for LC-MS/NIS Donor samples (1:10 diluted): 6 μL of donor sample+54 μL 0.4% DMSO HESS+60 μL ACN with IS (Osalmid or Imipramine) Receiver sample: 60 μL of receiver sample+60 μL ACN with IS (Osalmid or Imipramine)

TABLE 7

Bioanalytical Conditions

| Detection method | LC-MS/MS-014(API4000) |
|---|---|

TABLE 7-continued

| Bioanalytical Conditions | |
|---|---|
| Matrix | HBSS |
| Internal standard (s) | Osalmid or Imipramine |
| MS conditions | Positive ion, ESI |
| Mobile phase | A: $H_2O$ - 0.025% FA-1mM $NH_4OAC$ |
|  | B: MeOH - 0.025% FA-1mM $NH_4OAC$ |
| Column | Ultimate-XB-C18 (2.1 × 50 mm, 5 μm) |

| | 0.60 mL/min | |
|---|---|---|
| | Time (min) | Pump B (%) |
| LC conditions | 0.2 | 2 |
| | 0.4 | 98 |
| | 1.40 | 98 |
| | 1.41 | 2 |
| | 2.50 | stop |

| | compound | Analyte Mass Ranges (Da) | Analyte RT (min) | IS Mass Ranges (Da) | IS RT (min) |
|---|---|---|---|---|---|
| Detection & Retention time (RT) | Erythromycin | 734.300/158.000 Da | 0.90 | 281.100/193.100 Da | 0.91 |
| | Metoprolol | 268.100/133.100 Da | 0.85 | 281.100/193.100 Da | 0.91 |
| | Atenolol | 267.000/145.100 Da | 0.78 | 281.100/193.100 Da | 0.91 |
| | I-11 | 435.299/417.186 Da | 0.85 | 281.100/193.100 Da | 1.00 |
| | I-17 | 484.474/270.000 Da | 0.87 | 281.100/193.100 Da | 1.00 |
| | I-13 | 419.231/175.097 Da | 0.85 | 281.100/193.100 Da | 1.00 |
| | I-14 | 473.400/175.104 Da | 1.01 | 281.100/193.100 Da | 1.01 |
| | I-15 | 433.163/144.300 Da | 0.86 | 281.100/193.100 Da | 1.02 |
| | I-16 | 449.400/157.028 Da | 1.25 | 230.100/121.200 Da | 1.36 |

Results

Study details: Test concentration 10 μM
Reference compounds: Erythromycin, Metoprolol, Atenolol, Lucifer Yellow
Test systems: Caco-2/HBSS solution
Incubation conditions: 0, 90 min at 37° C.
Sample size: Duplicates (n=2)
Bioanalytical method: LC-MS/MS
Calculations Transepithelial electrical resistance (TEER)=(Resistance sample−Resistance blank)×Effective Membrane Area Lucifer Yellow Permeability:

Papp=(VA/(Area×time))×([RFU]accepter−[RFU]blank)/(([RFU]initial,donor−[RFU] blank)×Dilution Factor)×100

Drug Permeability:

Papp=(VA/(Area×time))×([drug]accepter/(([drug]initial,donor)×Dilution Factor)

Where VA is the volume in the acceptor well, area is the surface area of the membrane and time is the total transport time in seconds.

For Millicell-24 Cell Culture Plates: surface area of the membrane=0.7 $cm^2$, VA=0.8 mL (A-to-B) or 0.4 mL (B-to-A)

Results

TEER value of Caco-2 monolayers from randomly selected wells was 357±29 Ω·$cm^2$ (Mean±SD). Note: Cell monolayer is used if TEER value>100 Ω·$cm^2$.

Comments:

1. Papp values were calculated based on calculated concentrations.

2. Most of the Caco-2 monolayers applied in this assay showed intact tight junctions as indicated by TEER values and low permeability for Lucifer Yellow, a low permeability control (data not shown).

3. Metoprolol, a high permeability control, showed both A-to-B and B-to-A permeability >10×$10^{-6}$ cm/sec in Caco-2 cells. Atenolol, a low permeable control, showed both A-to-B and B-to-A permeability less than 5×$10^{-6}$ cm/sec in Caco-2 cells. Erythromycin, an efflux substrate, gave an efflux ratio higher than 116.11 in Caco-2 cells.

4. As summarized in Table 8, compounds showing permeability <5×$10^{-6}$ cm/sec suggest low permeability; compounds showing permeability 5 to 10×$10^{-6}$ cm/sec suggest moderate permeability in A-to-B direction; compounds showing permeability >10×$10^{-6}$ cm/sec suggest high permeability.

Permeability results are shown in Table 8 for selected compounds of the invention. The compound numbers correspond to the compound numbers in Table 1. Compounds having a ratio designated as "A" provided a ratio of 0.1 to 10; compounds having a ratio designated as "B" provided a ratio of >10 to <30; and compounds having a ratio designated as "C" provided a ratio of 30 or greater.

TABLE 8

Caco-Papp Permeability for Selected Compounds

| Compound # | Caco-Papp (A-B) ($10^{-6}$ cm/sec) | Caco-Papp (B-A) ($10^{-6}$ cm/sec) | Efflux ratio (PB-A/PA-B) |
|---|---|---|---|
| I-1 | A | B | A |
| I-3 | A | A | A |
| I-4 | A | B | C |
| I-6 | B | B | A |
| I-9 | B | B | A |
| I-11 | A | B | A |
| I-12 | A | B | A |

TABLE 8-continued

Caco-Papp Permeability for Selected Compounds

| Compound # | Caco-Papp (A-B) ($10^{-6}$ cm/sec) | Caco-Papp (B-A) ($10^{-6}$ cm/sec) | Efflux ratio (PB-A/PA-B) |
|---|---|---|---|
| I-13 | A | B | A |
| I-14 | B | B | A |
| I-15 | A | B | A |
| I-16 | B | B | A |
| I-17 | A | A | A |
| I-18 | A | A | A |
| I-19 | A | A | A |
| I-20 | A | A | A |
| I-21 | A | B | A |
| I-25 | A | B | C |
| I-27 | A | A | B |
| I-28 | A | B | C |
| I-29 | A | B | A |
| I-34 | B | A | A |
| I-37 | A | B | A |
| I-38 | A | C | C |
| I-39 | A | C | B |
| I-40 | A | C | C |
| I-45 | A | A | A |
| I-46 | A | A | A |
| I-47 | A | A | A |
| I-48 | A | B | A |
| I-49 | A | B | A |
| I-50 | A | B | B |
| I-51 | A | B | A |
| I-52 | A | C | B |
| I-53 | A | B | A |
| I-54 | A | A | C |
| I-55 | A | A | A |
| I-56 | A | B | A |
| I-57 | A | B | A |
| I-58 | B | B | A |
| I-60 | A | B | A |
| I-61 | A | B | A |
| I-62 | A | B | C |
| I-63 | A | B | B |
| I-66 | B | B | A |
| I-67 | A | A | A |
| I-68 | A | B | B |
| I-69 | A | B | A |
| I-73 | B | B | A |
| I-75 | A | B | A |
| I-76 | A | B | B |
| I-77 | B | C | A |
| I-78 | A | B | C |
| I-79 | A | B | A |
| I-80 | A | A | A |
| I-81 | B | B | A |
| I-82 | A | B | A |
| I-83 | A | B | B |
| I-85 | A | B | A |
| I-86 | A | B | B |
| I-87 | A | B | B |
| I-88 | A | A | A |
| I-89 | A | A | A |
| I-91 | A | A | A |
| I-92 | A | A | A |
| I-93 | B | A | A |
| I-104 | A | B | C |
| I-105 | A | B | C |
| I-106 | A | B | A |
| I-109 | A | B | C |
| I-110 | A | B | C |
| I-111 | A | A | A |
| I-112 | B | B | A |
| I-113 | A | A | A |
| I-114 | A | A | A |
| I-115 | A | A | A |
| I-116 | A | B | A |
| I-117 | B | B | A |
| I-123 | A | A | A |
| I-125 | A | A | A |
| I-126 | A | B | B |
| I-127 | A | A | A |
| I-132 | A | A | A |
| I-134 | B | B | A |
| I-135 | A | B | A |
| I-136 | A | B | B |
| I-137 | A | A | A |
| I-138 | B | B | A |
| I-139 | A | C | C |
| I-140 | A | B | A |
| I-141 | A | B | A |
| I-142 | A | B | A |
| I-146 | B | B | A |
| I-147 | B | B | A |
| I-149 | B | B | A |
| I-150 | A | B | A |
| I-151 | B | B | A |
| I-152 | A | B | A |
| I-154 | A | B | A |
| I-156 | A | B | A |
| I-159 | B | B | A |
| I-160 | B | B | A |
| I-164 | B | B | A |
| I-166 | B | B | A |
| I-167 | A | A | A |
| I-172 | A | C | C |
| I-173 | A | B | A |
| I-175 | A | B | A |
| I-179 | A | B | A |
| I-180 | B | B | A |
| I-181 | A | B | A |
| I-182 | B | B | A |
| I-186 | A | B | A |
| I-187 | A | B | A |
| I-188 | B | B | A |
| I-189 | B | B | A |
| I-190 | A | C | B |
| I-191 | A | C | B |
| I-192 | A | B | A |
| I-193 | B | B | A |
| I-207 | B | C | A |
| I-208 | B | B | A |
| I-210 | A | B | C |

Example 29: Pharmacokinetics and Brain Penetration Experiment to Determine Brain and Plasma Concentrations of Compounds After IV Administration to Male $CD_1$ Mice or Male SD Rat Mouse Study In-Life Summary:

The study design (9 animals) consisted of administrating the drug (IV: 3 mg/kg (5 mL/kg) via tail vein injection) and collecting samples at terminal bleeding for plasma and brain at 0.083, 0.5 and 1 h. The blood collection was performed as follows: the animal was restrained manually and approximately 150 µL blood/time point was collected into a dipotassium EDTA tube via retro orbital puncture under anesthesia with isoflurane. The blood sample was put on ice and centrifuged to obtain a plasma sample (2000 g, 5 min under 4° C.) within 15 minutes. The brain collection was performed as follows: a mid-line incision was made in the animal's scalp and the skin was retracted. Using small bone cutters and rongeurs, the skull overlying the brain was removed. The brain was removed using a spatula and the brain rinsed with cold saline. The brain was placed in screw-top tubes, and the tubes were stored at −70° C. until analysis. The IV dosing solution was prepared in 50 mM citrate buffer (pH 4.0) at 0.6 mg/mL.

Plasma Sample Preparation:

An aliquot of 30 μL sample was added to 150 μL MeCN containing 50 ng/mL IS (Dexamethasone). The mixture was vortexed for 5 min and centrifuged at 14,000 rpm for 5 min. An aliquot of 5 μL supernatant was injected for LC-MS/MS analysis.

Brain Sample Preparation:

An aliquot of 30 μL brain homogenate (brain:PBS=1:3, w/v) sample was added to 150 μL IS in ACN (Dexamethasone, 50 ng/mL). The mixture was vortexed for 5 min and centrifuged at 14,000 rpm for 5 min. An aliquot of 5 μL supernatant was injected for LC-MS/MS analysis.

Analytical Method:

The sample analysis was performed on LCMS/MS-003 (API4000, triple quadruple) under the following conditions: positive ion, ESI, MRM detection using dexamethasone as internal standard. HPLC conditions: mobile phase A: $H_2O$ (0.025% formic acid (FA) with 1 mM $NH_4OAc$); mobile phase B: MeOH (0.025% FA with 1 mM $NH_4OAc$) on Waters X-Bridge C18 (2.1×50 mm, 2.5 μm) column at 60° C.

Rat Study

In-Life Summary:

The study design consisted of 2 groups (24 animals and 18 animals) and administrating the drug [IV: 3 mg/kg (1.5 mL/kg) via foot dorsal vein], [PO: 10 mg/kg (5 mL/kg) via oral gavage] and collecting samples at terminal bleeding for plasma, brain and CSF at 0.25, 0.5, 1, 4, 8 and 24 hr. The IV and PO dosing solutions were prepared in 50 mM citrate buffer (pH 4.0) at 2 mg/mL. The blood collection was performed as follows: the animal was restrained manually at the designated time points, approximately 150 μL of blood sample was collected via cardiac puncture vein into EDTA-2K tubes. The blood samples were maintained in wet ice first and centrifuged to obtain plasma (2000 g, 4° C., 5 min) within 15 minutes post sampling. The brain collection was performed as follows: a mid-line incision was made in the animal's scalp and the skin was retracted. Using small bone cutters and rongeurs, the skull overlying the brain was removed. The brain was removed using a spatula and rinsed with cold saline. The brain was placed in screw-top tubes and then stored under −70° C. until analysis. The CSF collection was performed as follows: the animal was euthanized under deep anesthesia with air bubble tail vein injection. The CSF was collected by direct puncture of butterfly needle into the *cisterna magna*, using the occipital bone and the wings of the atlas as landmarks. A piece of white paper was used as a background to monitor color change in the sample just above the needle during collection. Upon observation of color change, the PE tubing was quickly clamped off above the color change and cut just above the clamped site. The clear sample was drawn into the syringe.

Plasma Samples Preparation:

An aliquot of 30 μL sample was added with 100 MeCN containing 100 ng/mL IS (Dexamethasone). The mixture was vortexed for 10 min and centrifuged at 5800 rpm for 10 min. An aliquot of 40 μL supernatant was added with 40 μl $H_2O$ and the mixture was vortexed for 5 min. An aliquot of 2 μL supernatant was injected for LC-MS/MS analysis.

Brain Samples Preparation:

The sample was homogenized with 3 volumes (v/w) of PBS. An aliquot of 30 μL sample was added with 100 μL ACN containing 100 ng/mL IS (Dexamethasone). The mixture was vortexed for 10 min and centrifuged at 5800 rpm for 10 min. An aliquot of 40 μL supernatant was added with 40 μl $H_2O$ and the mixture was vortexed for 5 min. An aliquot of 2 μL supernatant was injected for LC-MS/MS analysis.

CSF Samples Preparation:

An aliquot of 10 μL sample was added with 10 μLMeOH/$H_2O$ (1/1) and 404, ACN containing 200 ng/mL IS (Dexamethasone) 120 μL $H_2O$. The mixture was vortexed for 5 min. An aliquot of 2 μL supernatant was injected for LC-MS/MS analysis.

Analytical Method:

The sample analysis was performed on UPLC-MS/MS-02 (Triple Quad 4000) under the following conditions: positive ion, ESI, MRM detection using dexamethasone as internal standard. HPLC conditions: mobile phase A: $H_2O$-0.1% FA, mobile phase B: MeCN-0.1% FA on ACQUITY UPLC HSS T3 (2.1×50 mm, 1.8 μm) column at 60° C.

TABLE 9

Mouse and Rat Brain Uptake Assay Results - 0-1 h, 3 Time Points

Mouse (MBUA, 3 mg/kg, IV)

| Compound # | Cl (L/hr/kg) | $t^{1/2}$ | Fu (p) % | Fu (b) % | AUClast (p) | AUClast (b) | Kp | Kp, uu |
|---|---|---|---|---|---|---|---|---|
| I-6 | 2.9 | 3.6 | | | 531 | 326 | 0.61 | |
| I-18 | 14.7 | 0.344 | 5.4 | 0.2 | 175 | 2063 | 11.78 | 0.43 |
| I-19 | 13.4 | 0.363 | 2.8 | 0.1 | 191 | 1690 | 8.84 | 0.32 |
| I-20 | 10.4 | 0.374 | 2.1 | 0.1 | 241 | 1515 | 6.29 | 0.30 |
| I-114 | 7.01 | 0.72 | 2.8 | 0.3 | 267 | 205 | 0.76 | 0.08 |
| I-146 | 0.433 | 6.02 | 5.3 | 0.6 | 884 | 1643 | 1.86 | 0.21 |
| I-149 | 12.4 | 0.367 | 9.9 | 2.6 | 203 | 295 | 1.45 | 0.38 |
| I-187 | 7.62 | 0.354 | 24.9 | 7.1 | 335 | 76.5 | 0.22 | 0.05 |

Rat (3 mg/kg IV; 10 mg/kg PO)

| Compound # | Cl (L/hr/kg) | $t^{1/2}$ | F % | Fu (p) | Fu (b) | AUClast (p) | AUClast (b) | Kp | Kp, uu |
|---|---|---|---|---|---|---|---|---|---|
| I-146 | 1.46 | 7.89 | 70.1 | 7 | 0.7 | 4276 | 7800 | 1.82 | 0.18 |
| I-149 | 7.63 | 6.7 | 37.9 | 20 | 3.8 | 457 | 3820 | 8.4 | 1.6 |

TABLE 9-continued

| Mouse and Rat Brain Uptake Assay Results - 0-1 h, 3 Time Points | | | | | | | | |
|---|---|---|---|---|---|---|---|---|
| I-188 | 4.46 | 6.87 | 36.9 | 30.8 | 5.7 | 791 | 4472 | 5.65 | 1.04 |
| I-189 | 4.13 | 8.14 | 25.4 | 24.8 | 6.1 | 570 | 2296 | 4.03 | 0.99 |

The following abbreviations are used in Table 9:
Cl: Clearance (L/hr/kg)
$t_{1/2}$: half life (in hours)
Fu (p) %: Fraction of drug unbound to plasma proteins (%)
Fu (b) %: Fraction of drug unbound to brain proteins (%)
F %: oral bioavailability (the total number for protein bound and free fraction)
AUC last(p): Total area under the plasma drug concentration-time curve (time zero to 1 hr after drug administration) (hr*ng/mL)
AUC last(b): Total area under the brain drug concentration-time curve (time zero to 1 hr after drug administration) (hr*ng/mL)
Kp: brain/plasma drug concentration ratio (AUC last(b)/AUC last(p))
Kp uu: unbound brain/unbound plasma drug concentration ratio (calculated as follows: Fu (b)*AUC last (b)/Fu (p)*AUC last (p))

A similar experiment was performed with 4 time points taken from 0-24 h. The results are shown below in Table 10.

TABLE 10

Mouse Brain Uptake Assay Results - 0-24 h, 4 Time Points
Mouse (MBUA, 3 mg/kg, IV)

| Compound # | Cl (L/hr/kg) | $t^{1/2}$ | Fu (p) % | Fu (b) % | AUClast (p) | AUClast (b) | Kp | Kp, uu |
|---|---|---|---|---|---|---|---|---|
| I-6 | 2.9 | 3.6 | | | 1037 | 3173 | 3.05 | |
| I-115 | 2.12 | 3.96 | 2.6 | 0.5 | 1402 | 26886 | 19.17 | 3.68 |
| I-117 | 2.01 | 3.56 | 3.9 | 0.6 | 1480 | 32297 | 21.82 | 3.35 |
| I-146 | 0.433 | 6.02 | 5.3 | 0.6 | 6587 | 34840 | 5.29 | 0.6 |
| I-187 | 1.72 | 4.72 | 24.9 | 7.1 | 1715 | 1358 | 0.79 | 0.22 |
| I-193 | 1.32 | 6.42 | 4.7 | 0.4 | 2131 | 13673 | 6.41 | 0.54 |

Example 30: MTD and Pharmacokinetics and Brain Penetration Experiment to Determine Brain and Plasma Concentration of Compounds after PO Administration to Male C57BL/6 Mice In-Life Summary:

The study was designed with 2 groups (18 animals and 24 animals) consists of administrating the drug [PO-50, 100, 150, 225, 300 mg/kg via oral gavage] and collecting samples at terminal bleeding for plasma, brain and CSF at 0.25, 0.5, 1, 4, 8, and 24 hr. All PO dosing solutions were prepared in 50 mM citrate buffer (pH 4.0).

TABLE 11

| Administration of Compounds Schedule for Two Test Groups | |
|---|---|
| Group 1: Single administration: | PO: 50 mg/kg (10 mL/kg) via oral gavage (N = 18) |
| Group 2: multiple administrations: | PO-day 1: 50 mg/kg (10 mL/kg) via oral gavage (N = 24)<br>PO-day 2: 100 mg/kg (10 mL/kg) via oral gavage (N = 24)<br>PO-day 3: 150 mg/kg (10 mL/kg) via oral gavage (N = 24)<br>PO-day 4: 225 mg/kg (10 mL/kg) via oral gavage (N = 24)<br>PO-day 5: 300 mg/kg (10 mL/kg) via oral gavage (N = 24) |

The blood collection was performed as follows: the animal was restrained manually at the designated time points, approximately 500 μL of blood sample was collected via cardiac puncture vein into EDTA-2K tubes. The whole blood needed to be divided into two parts; one part was placed in the tube containing EDTA-2K for plasma generation and the other was used for the hematology assay, respectively. The blood samples for plasma generation were maintained in wet ice first and centrifuged to obtain plasma (2000 g, 4° C., 5 min) within 15 minutes post sampling. The brain collection was performed as follows: a mid-line incision was made in the animal's scalp and the skin was retracted. Using small bone cutters and rongeurs, the skull overlying the brain was removed. The brain was removed using a spatula and rinsed with cold saline. The brain was placed in screw-top tubes, and then stored at −70° C. until analysis. The CSF collection was performed as follows: a mid line incision was made on the neck. The muscle under the skin was cut to expose the *cisterna magna*. The *cisterna magna* was penetrated with the sharp end of one capillary (Burn one end of capillary to make it sharp). The CSF was sucked spontaneously into the capillary.

Plasma Sample Preparation:

An aliquot of 30 μL sample was added with 100 μL MeCN containing 100 ng/mL IS (Dexamethasone). The mixture was vortexed for 10 min and centrifuged at 5800 rpm for 10 min. An aliquot of 40 μL supernatant was added to 40 μL $H_2O$ and the mixture was vortexed for 5 min. An aliquot of 2 μL supernatant was injected for LC-MS/MS analysis.

Brain Sample Preparation:

An aliquot of 30 μL brain homogenate (brain:PBS=1:3, w/v) sample was added to 100 μL MeCN containing 100 ng/mL IS (Dexamethasone). The mixture was vortexed for 10 min and centrifuged at 5800 rpm for 10 min. An aliquot of 40 μL supernatant was added to 40 μL $H_2O$ and the mixture was vortexed for 5 min. An aliquot of 2 μL supernatant was injected for LC-MS/MS analysis.

CSF Samples Preparation:

An aliquot of 3 μL sample was added to a mixture of 6 CSF, 9 μL MeOH/$H_2O$ (1/1), 40 μL MeCN containing 200 ng/mL IS (Dexamethasone), and 116 μL $H_2O$. The mixture was vortexed for 5 min. An aliquot of 4 μL was injected for LC-MS/MS analysis.

Analytical Method:

The sample analysis was performed on UPLC-MS/MS-02 (Triple Quad 4000) under the following conditions: positive ion, ESI, MRM detection using dexamethasone as internal standard. HPLC conditions: mobile phase A: $H_2O$-0.1% formic acid, mobile phase B: MeCN-0.1% formic acid on: ACQUITY UPLC HSS T3 (2.1×50 mm, 1.8 µm) at 60° C.

TABLE 12

Mouse MTD For Single Administration Group

Mouse (MTD mouse, D1-50 mg/kg, PO)

| | Cl (L/hr/kg) | t½ | Fu (p) % | Fu (b) % | AUClast (p) | AUClast (b) | Kp | Kp, uu |
|---|---|---|---|---|---|---|---|---|
| I-188 | | 1-24 | 14.3 | 5.4 | 23496 | 58553 | 2.49 | 0.94 |

TABLE 13

Mouse MTD For Multiple Administration Group

Mouse (MTD mouse, D5-300 mg/kg, PO)

| | Cl (L/hr/kg) | t½ | Fu (p) | Fu (b) | AUClast (p) | AUClast (b) | Kp | Kp, uu |
|---|---|---|---|---|---|---|---|---|
| I-188 | | 4-72 | 14.3 | 5.4 | 76631 | 430273 | 5.61 | 2.12 |

Example 31: 7-Day Toxicology Study in Mice

Toxicology Summary

A toxicology study may be performed as described in this Example. Overt signs of toxicity after 7 days of repeat dosing up to 100 mg/kg P.O. in terms of clinical observations, body weight or food consumption will be examined. White blood cells will be monitored and internal organs examined after necroscopy.

TABLE 14

Toxicology Study Design

| | |
|---|---|
| Test system | C57BL/6 Mouse, 5 weeks old, 18-20 g, male, N = 12 |
| Food status | Free access to food and water |
| Administration | Group 1: 0 mg/kg/day (10 mL/kg/day) via oral gavage (N = 3) |
| | Group 2: 10 mg/kg/day (10 mL/kg/day) via oral gavage (N = 3) |
| | Group 3: 30 mg/kg/day (10 mL/kg/day) via oral gavage (N = 3) |
| | Group 4: 100 mg/kg/day (10 mL/kg/day) via oral gavage (N = 3) |

Toxicokinetics

Mean plasma, brain and CSF concentration-time profiles of test compounds will be measured after a single PO administration at 30 mg/kg in male C57BL/6 mice (5 weeks old) (N=3/time point). Mean plasma, brain and CSF concentration-time profiles of compounds after repeat PO administrations at 30 mg/kg in male C57BL/6 mice on day 7 (5 weeks old) (N=3/time point) will also be measured.

In-Life Summary:

The study design (36 animals, C57BL/6 mouse) consists of administrating the drug [PO: 30 mg/kg/day (10 mL/kg/day) via oral gavage] and collecting samples at terminal bleeding for plasma, brain and CSF at 0.025, 0.5, 1, 4, 8 and 24 hr. The PO dosing solutions will be prepared in 50 mM citrate buffer (pH 4.0) at 3 mg/mL. The blood collection will be performed as follows: the animal will be anesthetized under isoflurane. Approximately 500 µL blood/time point will be collected into $K_2$EDTA tube via cardiac puncture for terminal bleeding. ~200 µL blood samples will be put on ice and centrifuged to obtain a plasma sample (2000 g, 5 min under 4° C.) within 15 minutes of collection. ~300 blood samples will be used for hematology assay. The brain collection will be performed as follows: a mid-line incision will be made in the animal's scalp and skin retracted. The skull overlying the brain will be removed. The whole brain will be collected, rinsed with cold saline, dried on filtrate paper, weighted, and snap frozen by placing into dry ice. The brain sample will be homogenized for 2 min with 3 volumes of PBS (pH 7.4) by Mini-bead-beater before sample extraction.

Plasma Samples Preparation:

An aliquot of 10 µL sample will be added to 200 µL MeCN containing 10 ng/mL IS (Glipizide). The mixture will be vortexed for 10 min and centrifuged at 6,000 rpm for 10 min. An aliquot of 1 µL constitution will be injected for LC-MS/MS analysis.

CSF Samples Preparation:

An aliquot of 3 µL sample will be added to 70 µL MeCN containing 10 ng/mL IS (Glipizide). The mixture will be vortexed for 2 min and centrifuged at 14,000 rpm for 5 min. An aliquot of 1 µL constitution will be injected for LC-MS/MS analysis.

Tissue Samples Preparation:

The sample will be homogenized with 3 volumes (v/w) of PBS. An aliquot of 10 µL sample will be added to 200 µL MeCN containing 10 ng/mL IS (Glipizide). The mixture will be vortexed for 10 min and centrifuged at 6,000 rpm for 10 min. An aliquot of 1 µL constitution will be injected for LC-MS/MS analysis.

Analytical Method:

The sample analysis will be performed on LCMSMS-28 (Triple Quad 6500+) under the following conditions: positive ion, ESI, MRM detection using glipizide as internal standard. HPLC conditions: mobile phase A: $H_2O$/0.025% FA with 1 mM $NH_4OAc$, mobile phase B: MeOH/0.025% FA with 1 mM $NH_4OAc$ on Waters X-Bridge BEH C18 (2.1×50 mm, 2.5 µm) column at 60° C.

Example 32: Pharmacokinetics of Compounds After Intravenous or Oral Administration to Male Beagle Dogs In-Life Summary:

The study design (9 animals, fasted overnight and fed at 4 h post dosing) consists of administrating the drug [IV: 1 mg/kg via cephalic vein injection], [PO: 3 mg/kg and 10 mg/kg via oral gavage] and collecting samples at serial bleeding for plasma at 0.03, 0.08, 0.25, 0.5, 1, 2, 4, 8, 24, 48 and 72 hr. The IV and PO dosing solutions were prepared in 50 mM citrate buffer (pH 4.0) at 0.5 mg/mL, 1.5 mg/mL and 5 mg/mL, respectively. The blood collection was performed as follows: the animals were restrained manually, and approx. 0.5 mL blood/time point was collected from the cephalic vein into pre-cooled $K_2$EDTA tubes. Blood samples were put on wet ice and centrifuged at 4° C. to obtain plasma within 15 minutes of sample collection. All samples were stored at approximately −70° C. until analysis.

Plasma Samples Preparation:

An aliquot of 30 µL sample was added to 100 MeCN containing 200 ng/mL IS (Dexamethasone). The mixture was vortexed for 10 min and centrifuged at 5,800 rpm for 10 min. An aliquot of 30 µL supernatant was added to 60 µL H$_2$O and the mixture was vortexed for 5 min. An aliquot of 4 µL supernatant was injected for LC-MS/MS analysis.

Analytical Method:

The sample analysis was performed using UPLC-MS/MS-02 (Triple Quad 4000) under the following conditions: positive ion, ESI, MRM detection using dexamethasone as internal standard. HPLC conditions: mobile phase A: H$_2$O-0.1% FA, mobile phase B: ACN-0.1% FA on ACQUITY UPLC HSS T3 (2.1×50 mm, 1.8 µm) column at 60° C.

TABLE 15

Pharmacokinetics of I-188 in Beagle Dogs

| Compound | Species | Dose (mg/kg) | Cmax (ng/mL) | t$_{1/2}$ (hr) | Cl (L/hr/kg) | Vss (L/kg) | AUC p(hr*ng/mL) | % F |
|---|---|---|---|---|---|---|---|---|
| I-188 | dog | IV: 1 | — | 27.3 | 1.19 | 39 | 722 | — |
| | dog | PO: 3 | 46.1 | 27.3 | — | — | 1419 | 65 |
| | dog | PO: 10 | 280 | 23.2 | — | — | 7503 | 97.8 |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:

1. A compound of Formula I:

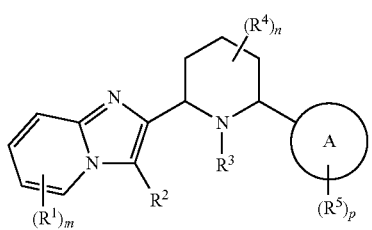

or a pharmaceutically acceptable salt thereof, wherein:

Ring A is a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each R$^1$ is independently —R, halogen, —CN, —OR, —N(R)$_2$, —NO$_2$, —N$_3$, —SR, or -L-R$^6$;

each R is independently hydrogen or an optionally substituted group selected from C$_{1-6}$ aliphatic, a 3-8 membered saturated or partially unsaturated monocyclic carbocyclic ring, phenyl, an 8-10 membered bicyclic aromatic carbocyclic ring, a 4-8 membered saturated or partially unsaturated monocyclic heterocyclic ring having 1-2 heteroatoms independently selected from nitrogen, oxygen, or sulfur, a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur;

each L$^1$ and L$^2$ is independently a covalent bond or a C$_{1-8}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)-, -(R)NC(O)-, —OC(O)N(R)-, —(R)NC(O)O—, —N(R)C(O)N(R)-, —S—, —SO—, —SO$_2$—, —SO$_2$N(R)—, -(R)NSO$_2$—, —C(S)—, —C(S)O—, —OC(S)—, —C(S)N(R)-, -(R)NC(S)-, -(R)NC(S)N(R)-, or -Cy-;

each -Cy- is independently a bivalent optionally substituted 3-8 membered saturated or partially unsaturated monocyclic carbocyclic ring, optionally substituted phenylene, an optionally substituted 4-8 membered saturated or partially unsaturated monocyclic heterocyclic ring having 1-3 heteroatoms independently selected from nitrogen, oxygen, or sulfur, an optionally substituted 5-6 membered monocyclic heteroaromatic ring having 1-4 heteroatoms independently selected from nitrogen, oxygen, or sulfur, an optionally substituted 8-10 membered bicyclic or bridged bicyclic saturated or partially unsaturated heterocyclic ring having 1-5 heteroatoms independently selected from nitrogen, oxygen, or sulfur, or an optionally substituted 8-10 membered bicyclic or bridged bicyclic heteroaromatic ring having 1-5 heteroatoms independently selected from nitrogen, oxygen, or sulfur;

R$^2$ is hydrogen, halogen, —CN, —OR, —N(R)$_2$, —NO$_2$, —N$_3$, —SR, -L$^2$-R$^6$, or optionally substituted C$_{1-8}$ aliphatic;

R$^3$ is hydrogen, optionally substituted C$_{1-6}$ aliphatic, or -L$^3$-R$^6$;

L$^3$ is a C$_{1-6}$ bivalent straight or branched hydrocarbon chain wherein 1, 2, or 3 methylene units of the chain are independently and optionally replaced with —O—, —C(O)—, —C(O)O—, —OC(O)—, —N(R)—, —C(O)N(R)-, -(R)NC(O)-, —S—, —SO—, —SO$_2$—, —C(S)—, or -Cy-;

each R$^4$ is independently hydrogen, deuterium, halogen, —CN, —OR$^6$, or C$_{1-4}$ alkyl, or two R$^4$ groups on the same carbon are optionally taken together to form =NR$^6$, =NOR$^6$, =O, or =S;

each R$^5$ is independently R, halogen, —CN, —OR, —N(R)$_2$, —NO$_2$, —N$_3$, —SR, or -L$^1$-R$^6$, or two R$^5$ groups on the same saturated carbon atom are optionally taken together to form =NR, =NOR, =O, =S, or a spirocyclic 3-6 membered carbocyclic ring;

each R$^6$ is independently hydrogen or C$_{1-6}$ alkyl optionally substituted with 1, 2, 3, 4, 5, or 6 deuterium or halogen atoms;

m is 0, 1, 2, 3, or 4;

n is 0, 1, 2, 3, or 4; and
p is 0, 1, 2, 3, or 4.
2. The compound of claim 1, wherein Ring A is a 5-6 membered monocyclic heteroaromatic ring having 1-4 heteroatoms independently selected from nitrogen, oxygen, or sulfur, or an 8-10 membered bicyclic heteroaromatic ring having 1-5 heteroatoms independently selected from nitrogen, oxygen, or sulfur.
3. The compound of claim 1, wherein Ring A is selected from:
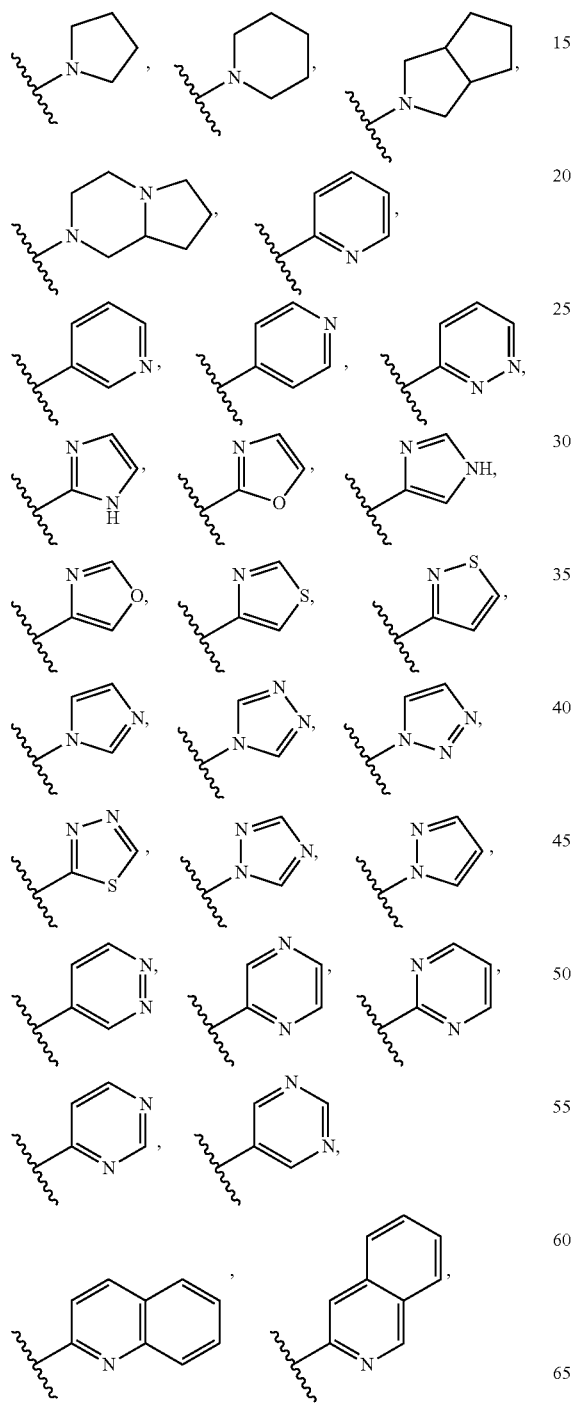
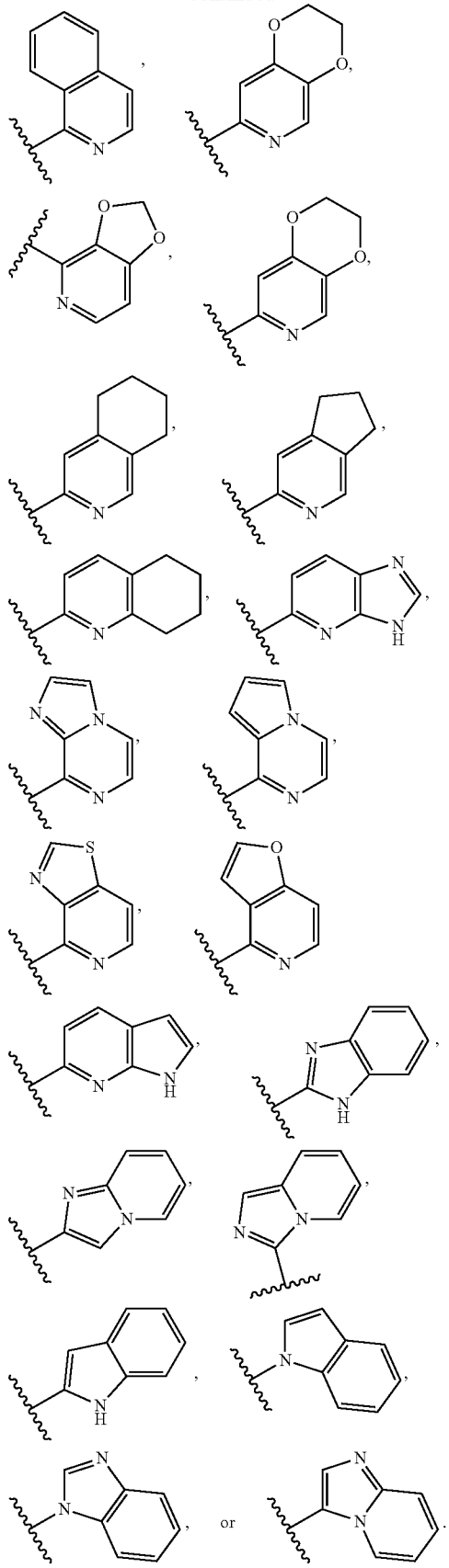

4. The compound of claim 1, wherein Ring A is selected from

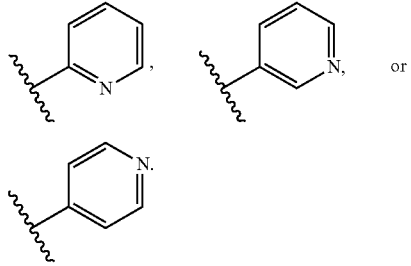

5. The compound of claim 2, wherein $R^1$ is selected from hydrogen, halogen, $C_{1-6}$ alkyl (optionally substituted with 1, 2, or 3 halogens), —CN, —N(R)$_2$, —OR, —SR, —S(O)$R^6$, —SO$_2R^6$, -SO$_2$NH$R^6$,

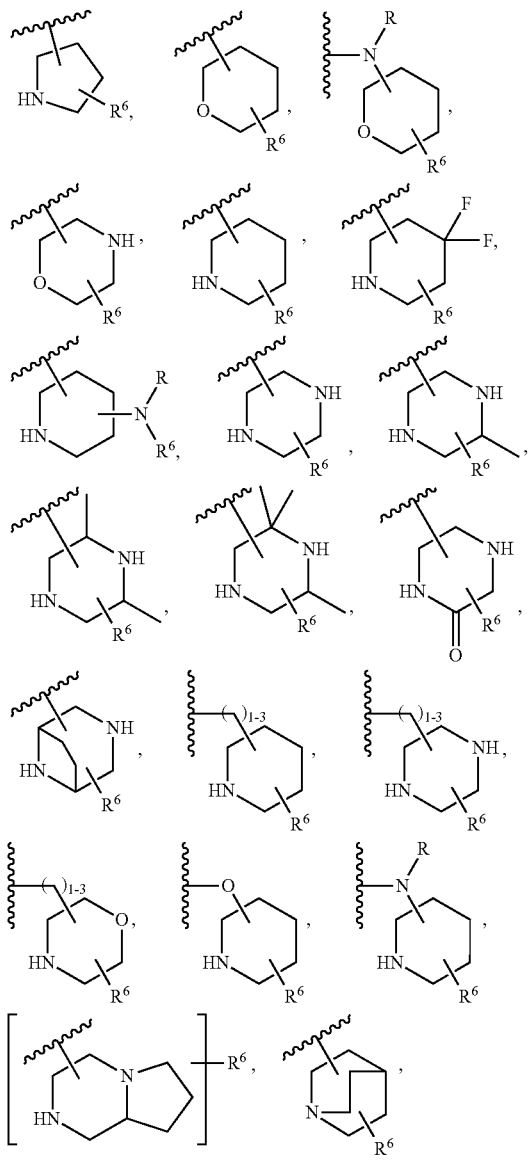

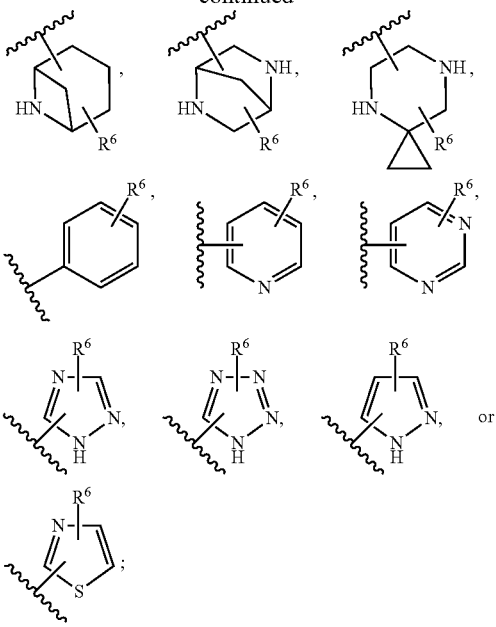

and each R is independently hydrogen, —CH$_2$-phenyl, phenyl, $C_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$.

6. The compound of claim 5, wherein $L^1$ is a $C_{1-6}$ bivalent straight or branched hydrocarbon chain wherein 1, 2, or 3 methylene units of the chain are independently and optionally replaced with —O—, —C(O)—, —N(R)—, —S—, —SO—, —SO$_2$—, —SO$_2$N(R)—, —(R)NSO$_2$—, —C(S)—, or -Cy-, wherein each R is independently hydrogen, —CH$_2$-phenyl, phenyl, $C_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$.

7. The compound of claim 6, wherein $L^2$ is a $C_{1-6}$ bivalent straight or branched hydrocarbon chain wherein 1, 2, or 3 methylene units of the chain are independently and optionally replaced with —O—, —C(O)—, —N(R)—, —S—, —SO—, —SO$_2$—, —SO$_2$N(R)—, —(R)NSO$_2$—, —C(S)—, or -Cy-, and each R is independently hydrogen, —CH$_2$-phenyl, phenyl, $C_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$.

8. The compound of claim 7, wherein -Cy- is

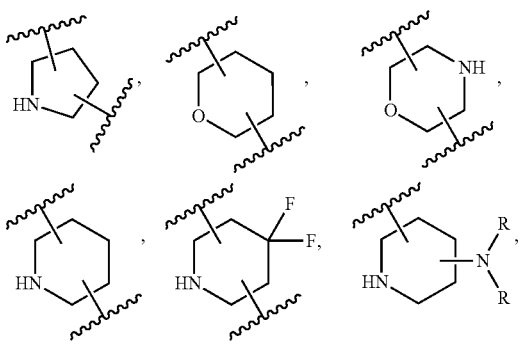

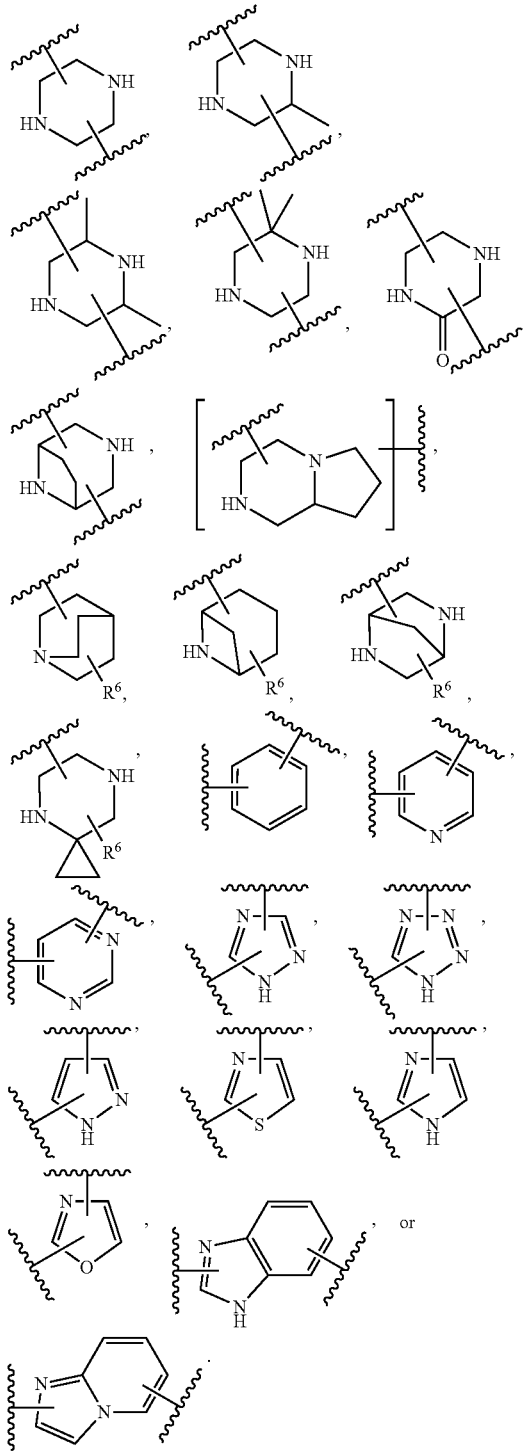

9. The compound of claim 8, wherein R² is hydrogen, halogen, —CN, —OR, —N(R)₂, —SR, optionally substituted C₁₋₆ aliphatic, or -L²-R⁶, wherein L² is a C₁₋₆ bivalent straight or branched hydrocarbon chain wherein 1, 2, or 3 methylene units of the chain are independently and optionally replaced with —O—, —C(O)—, —N(R)—, —S—, —SO—, —SO₂-, —C(S)—, or -Cy-; wherein the C₁₋₆ aliphatic group is optionally substituted with 1, 2, or 3 groups independently selected from halogen, —CN, —N(R)₂, —NO₂, —N₃, =NR, =NOR, =O, =S, —OR, —SR, —SO₂R, —S(O)R, —R, -Cy-R, —C(O)R, —C(O)OR, —OC(O)R, —C(O)N(R)₂, -(R)NC(O)R, —OC(O)N(R)₂, -(R)NC(O)OR, —C(O)N(R)C(O)N(R)₂, —SO₂N(R)₂, -(R)NSO₂R, —C(S)R, or —C(S)OR; wherein each R is independently hydrogen, —CH₂-phenyl, phenyl, C₁₋₆ alkyl, cyclopropyl, cyclobutyl, cyclopentyl, cyclohexyl, —CH₂F, —CHF₂, —CF₃, —CH₂CHF₂, or —CH₂CF₃.

10. The compound of claim 8, wherein R² is hydrogen, halogen, —OR, —N(R)₂, —S(O)R⁶, —SO₂R⁶, —SO₂NHR⁶, —(CH₂)₁₋₆—N(R)R⁶, —(CH₂)₁₋₆-OR⁶,

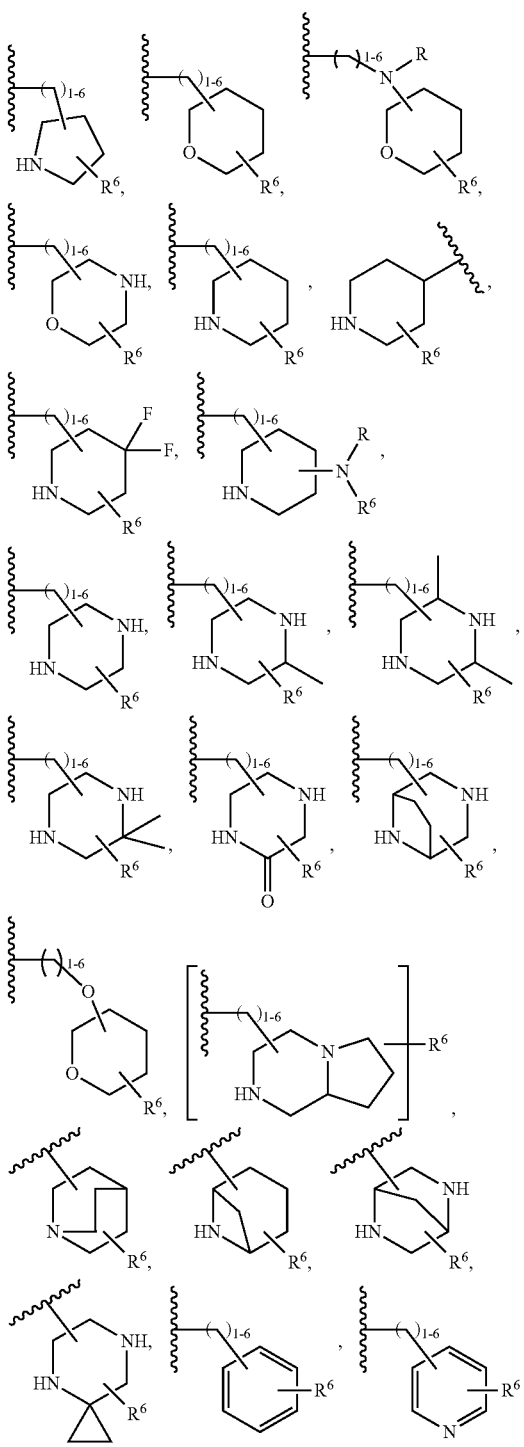

-continued

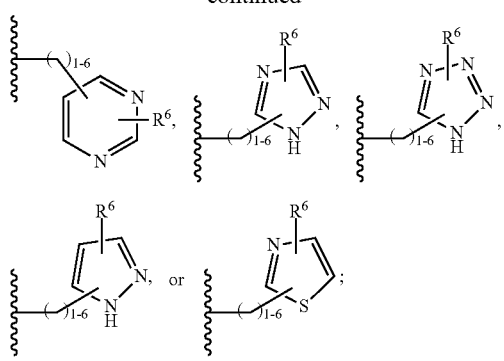

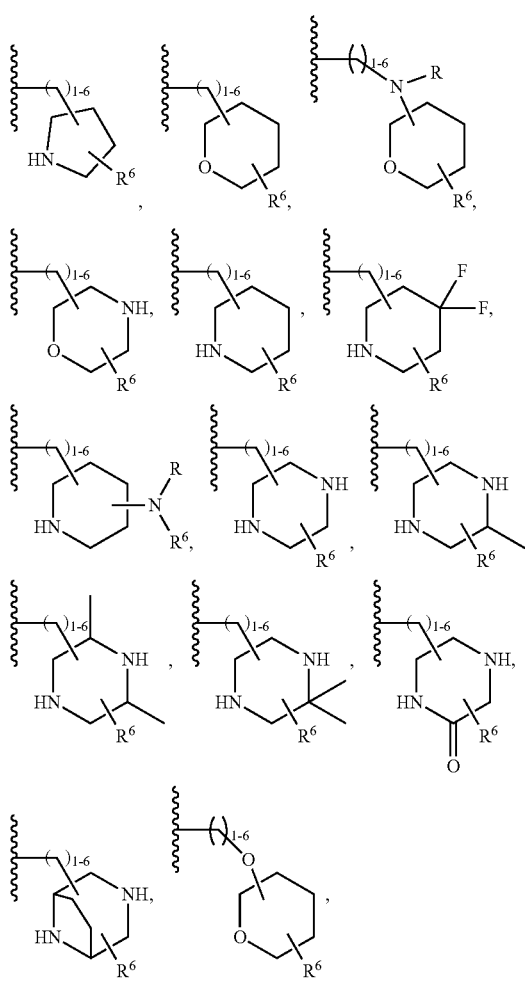

and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$.

11. The compound of claim 8, wherein R$^2$ is hydrogen, —NH$_2$, C$_{2-4}$ alkynyl, F, Cl, Br, or I.

12. The compound of claim 9, wherein R$^3$ is selected from hydrogen, C$_{1-6}$ alkyl (optionally substituted with 1, 2, or 3 deuterium or halogen atoms), —(CH$_2$)$_{1-6}$-CN, —(CH$_2$)$_{1-6}$—N(R)(R$^6$), —(CH$_2$)$_{1-6}$-OR$^6$, -continued

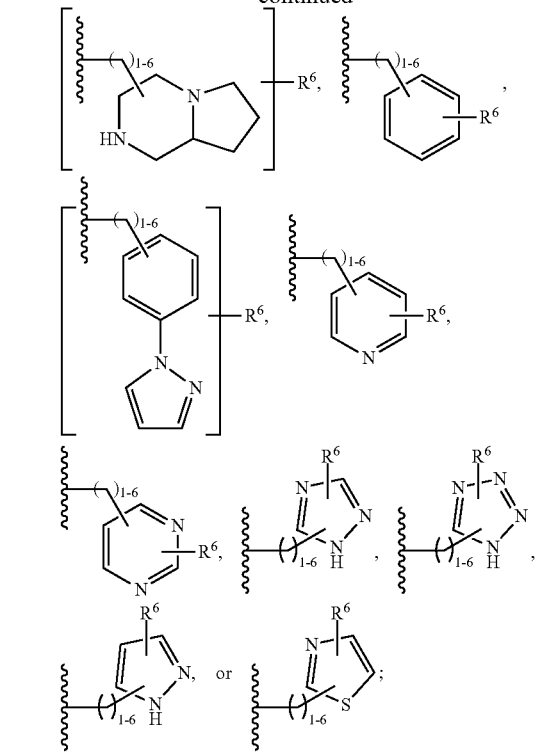

and each R is independently hydrogen, —CH$_2$-phenyl, phenyl, C$_{1-6}$ alkyl, cyclopropyl, cyclobutyl, cyclopentyl, cyclohexyl, —CH$_2$F, —CHF$_2$, —CF$_3$, —CH$_2$CHF$_2$, or —CH$_2$CF$_3$.

13. The compound of claim 9, wherein R$^3$ is C$_{1-4}$ alkyl optionally substituted with

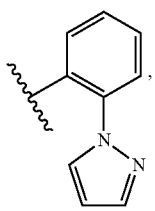 [SMILES: *c1ccccc1-n1cccn1]

pyridyl, —N(R)$_2$, —CN, or 1, 2, or 3 deuterium or halogen atoms, wherein R is hydrogen or C$_{1-3}$ alkyl.

14. The compound of claim 9, wherein R$^3$ is methyl.

15. The compound of claim 12, wherein R$^4$ is hydrogen, deuterium, halogen, —CN, or C$_{1-2}$ alkyl, =O, or =S.

16. The compound of claim 15, wherein R$^5$ is hydrogen, C$_{1-6}$ alkyl, halogen, —CN, —OCF$_3$, cyclopropyl, ethynyl, —OCH$_3$, —CF$_3$, —CD$_3$, or

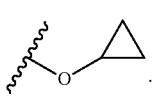 [SMILES: *OC1CC1]

17. The compound of claim 1, wherein the compound is of Formula VII:

VII

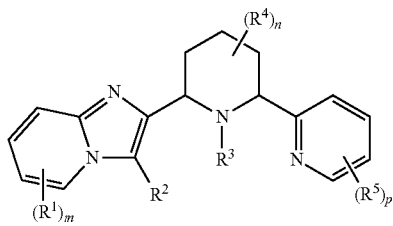

or a pharmaceutically acceptable salt thereof.

18. The compound of claim 1, wherein the compound is of Formulae VIII-a or VIII-b:

VIII-a

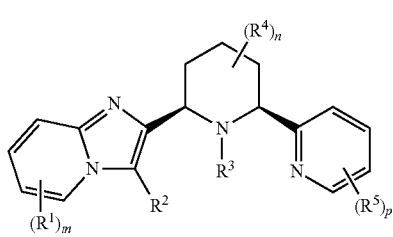

VIII-b

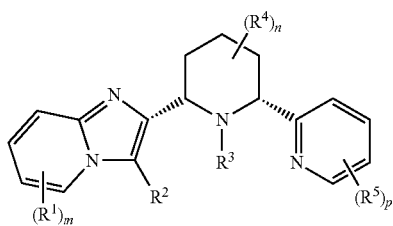

or a pharmaceutically acceptable salt thereof.

19. The compound of claim 1, wherein the compound is of Formulae X-a, X-b, X-c, X-d, or X-e:

X-a

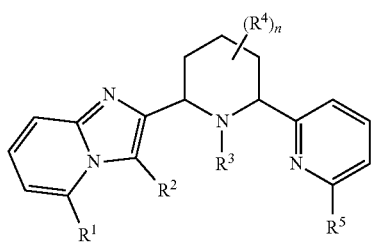

X-b

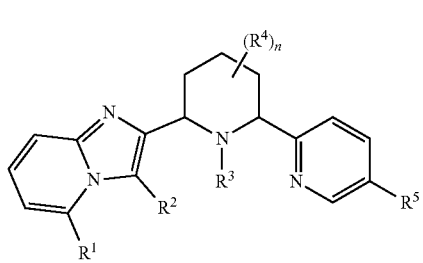

X-c

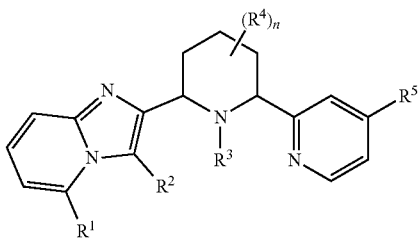

X-d

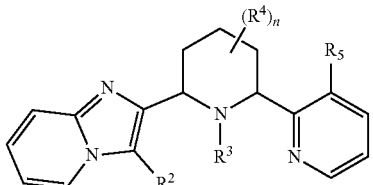

X-e

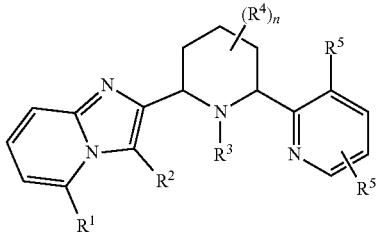

or a pharmaceutically acceptable salt thereof.

20. The compound of claim 1, wherein the compound is of Formulae XIII-a or XIII-b:

XIII-a

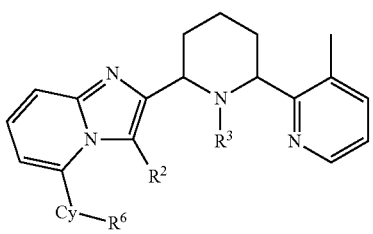

XIII-b

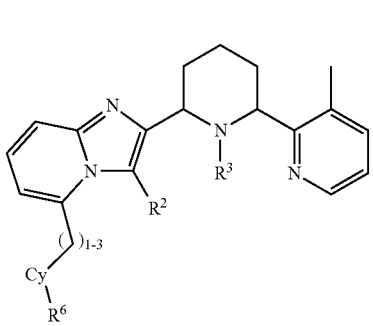

or a pharmaceutically acceptable salt thereof.

21. The compound of claim 1, wherein the compound is selected from one of the following:

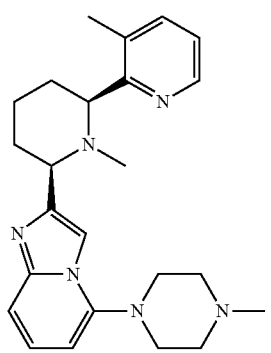
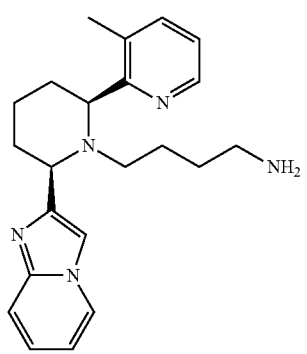
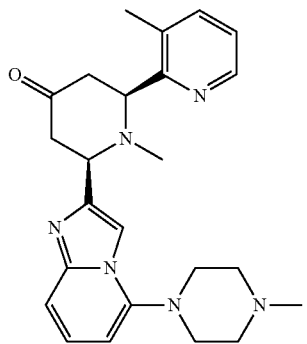
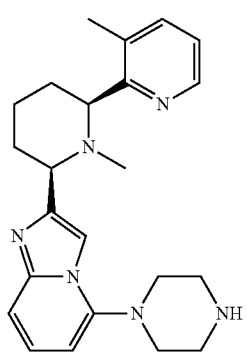
I-1
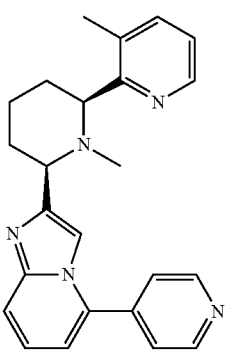
I-2
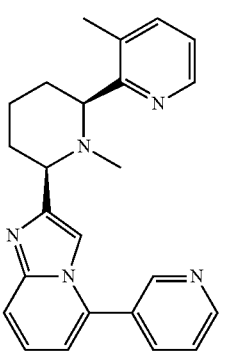
I-3
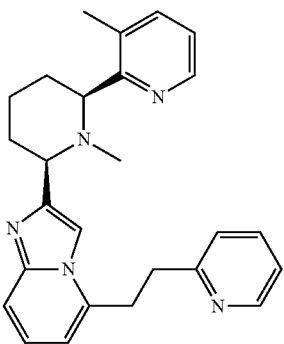
I-4
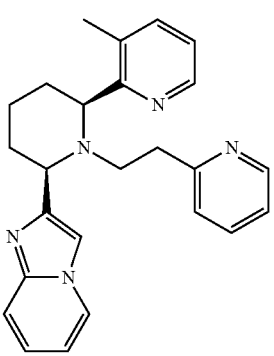
I-5
I-6
I-7
I-8

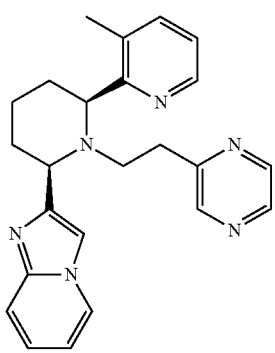
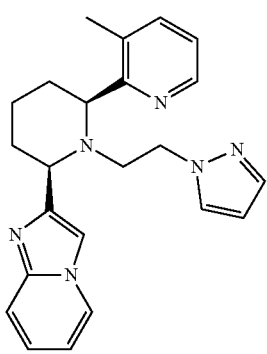
I-9
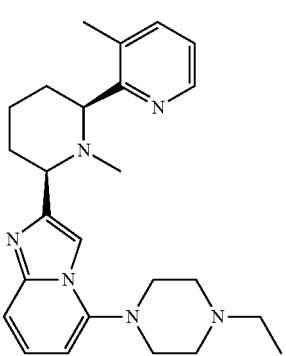
I-10
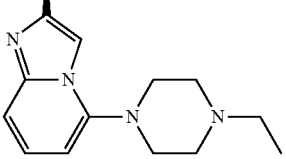
I-11
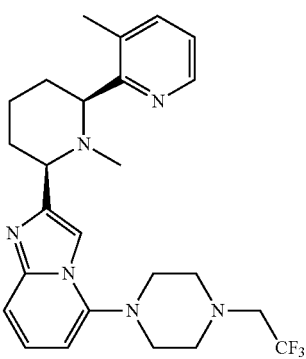
I-12
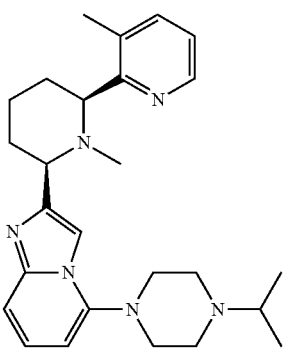
I-13
I-14
I-15
I-16
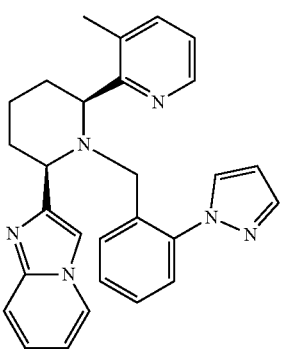

I-17
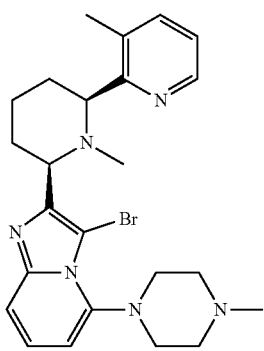
I-18
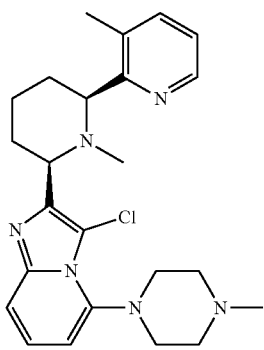
I-19
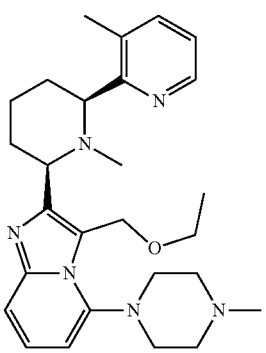
I-20
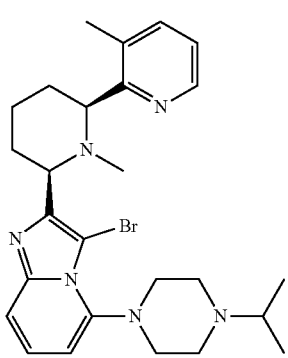
I-21
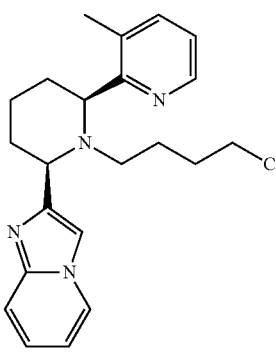
I-22
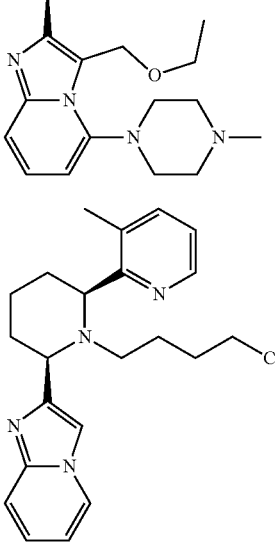
I-23
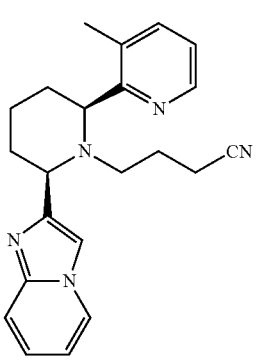
I-24
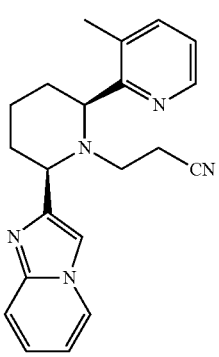

I-25
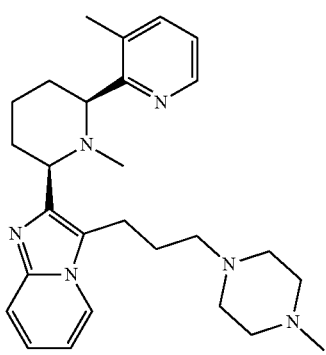
I-26
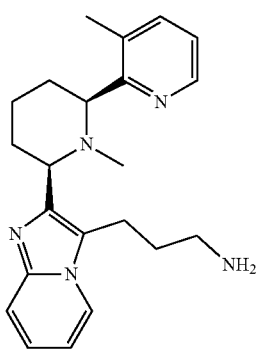
I-27
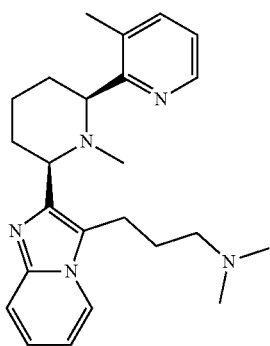
I-28
I-29
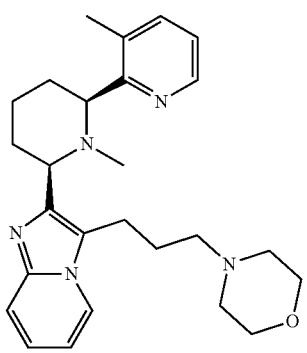
I-30
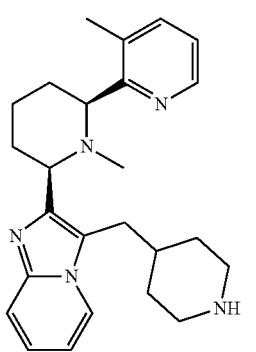
I-31
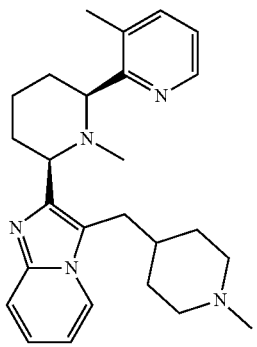
I-32
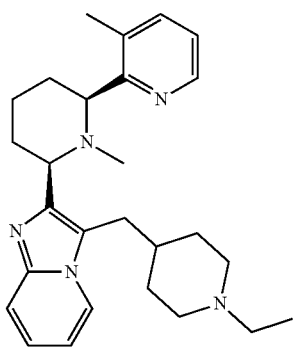

-continued
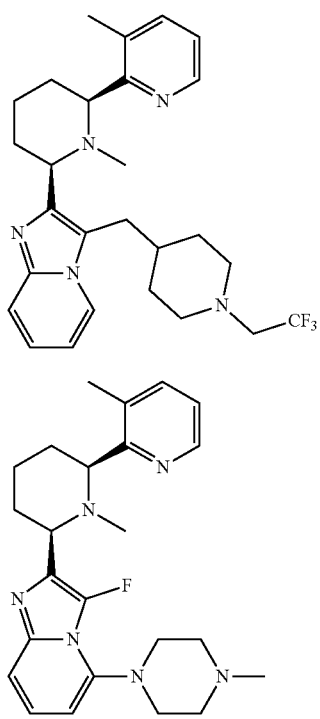
I-33
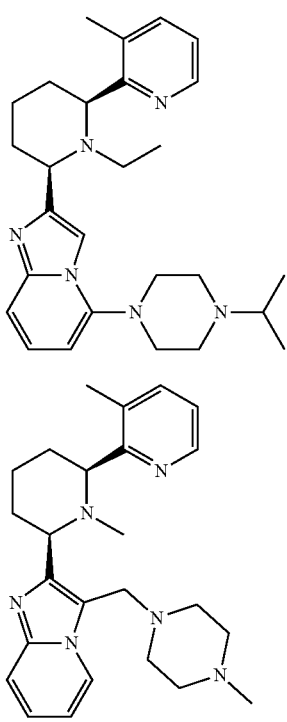
I-37
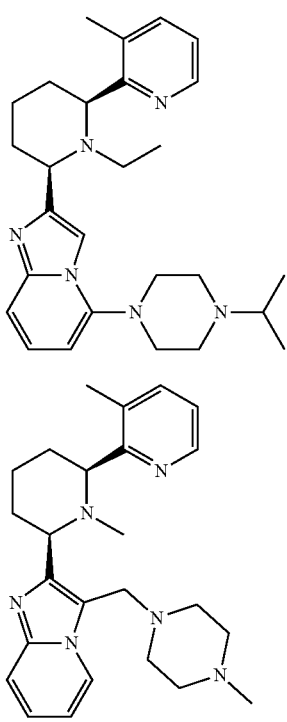
I-34
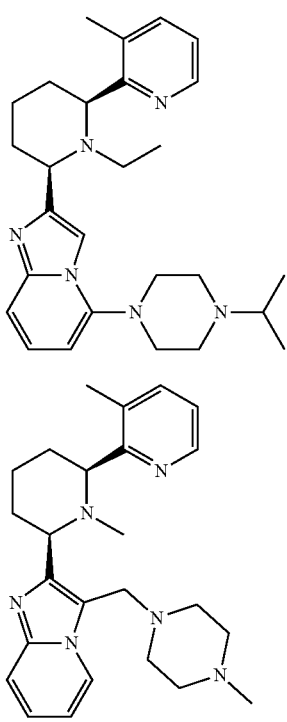
I-38
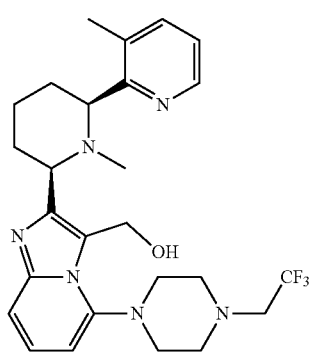
I-35
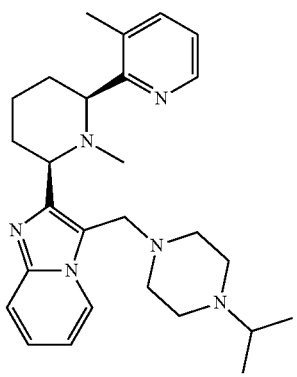
I-39
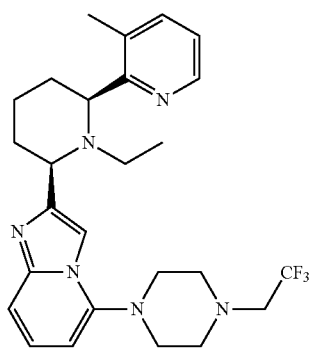
I-36
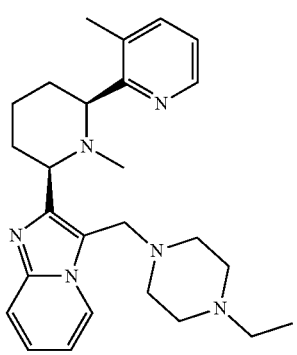
I-40

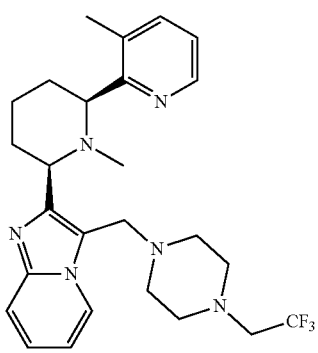
I-41
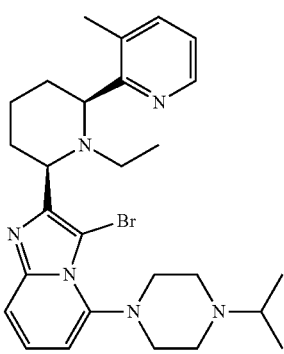
I-45
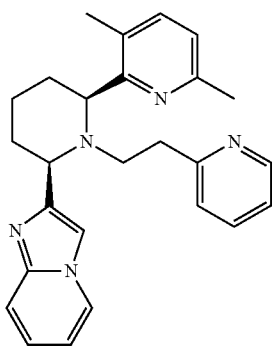
I-42
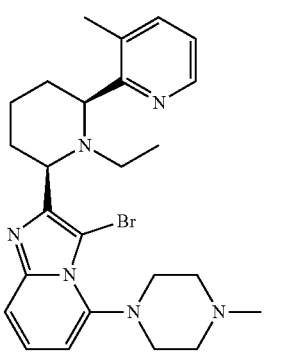
I-46
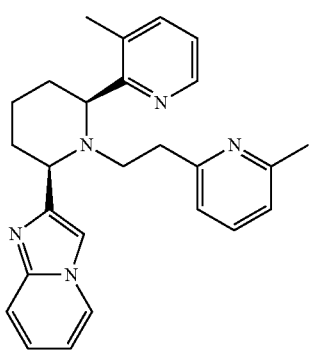
I-43
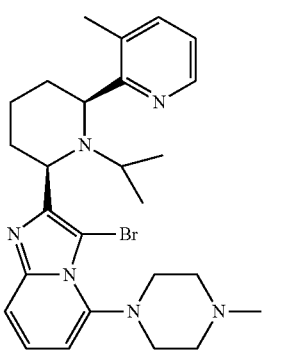
I-47
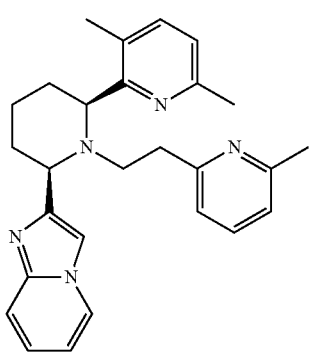
I-44
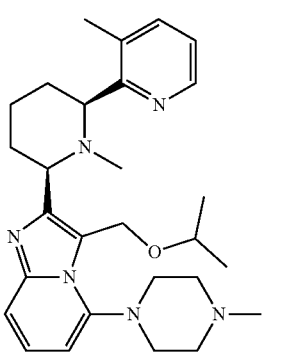
I-48

293
-continued
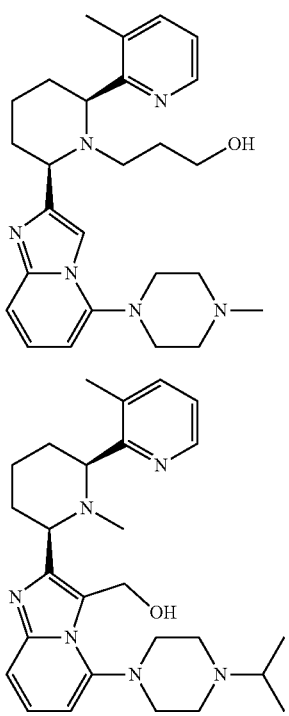
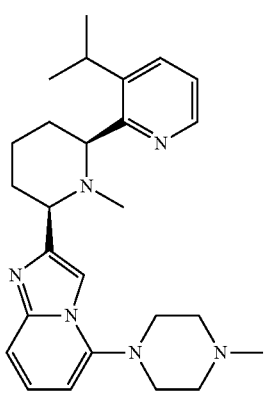
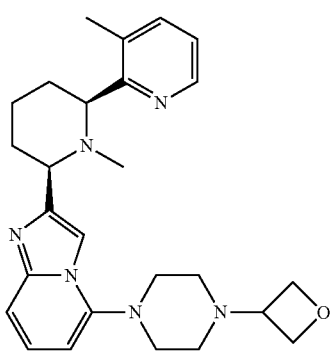
294
-continued
I-49
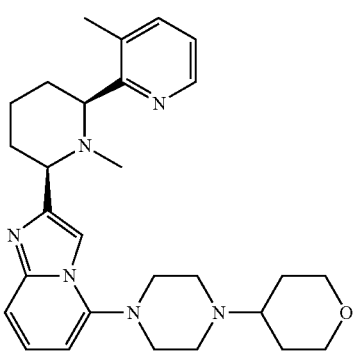
I-50
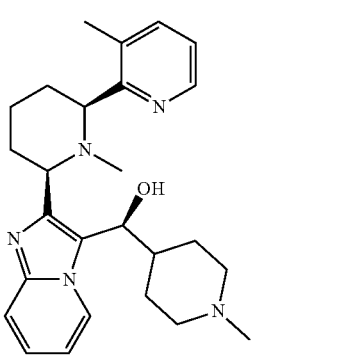
I-51
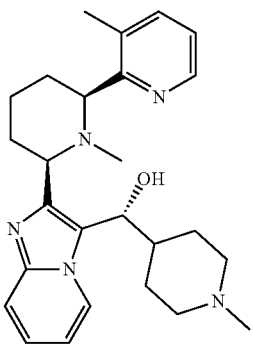
I-52
I-53
I-54
I-55
I-56
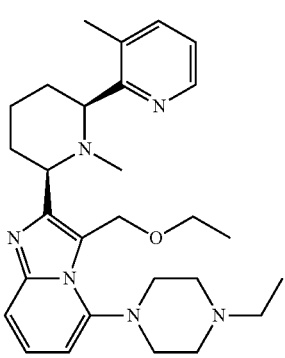

295
-continued
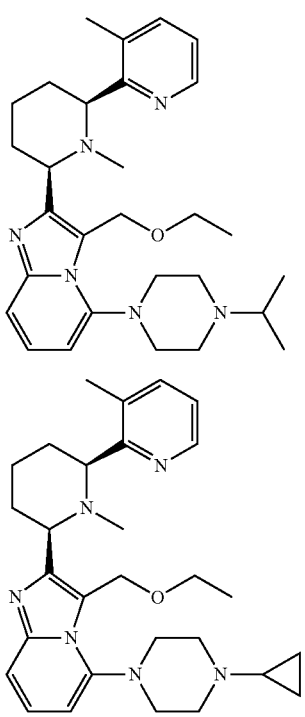
I-57
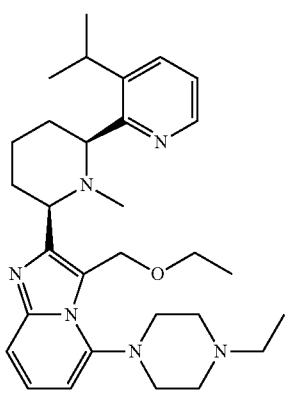
I-58
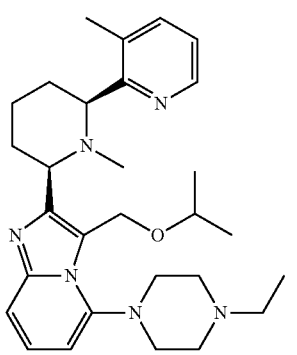
I-59
I-60
296
-continued
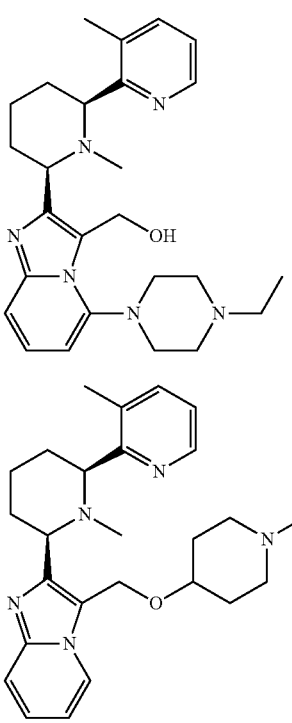
I-61
I-62
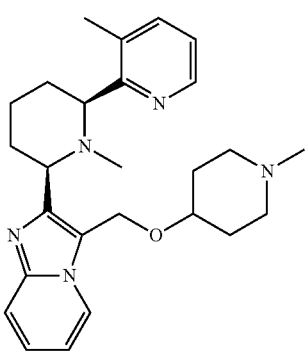
I-63
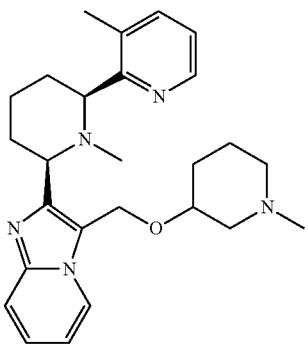
I-64
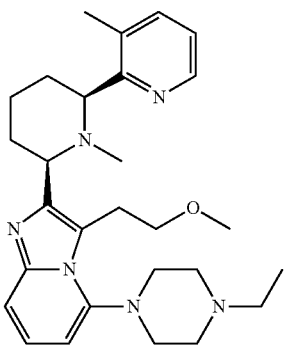

I-65
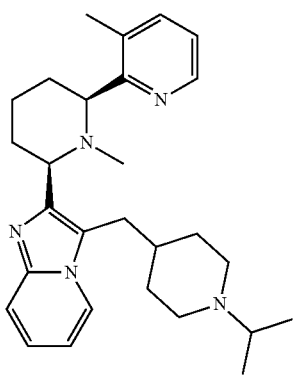
I-66
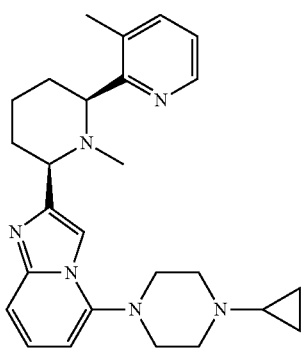
I-67
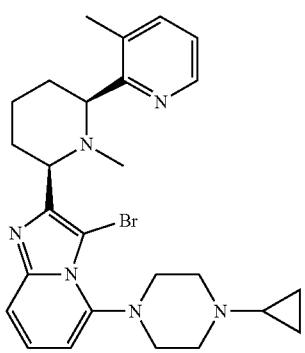
I-68
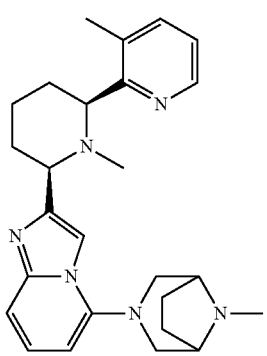
I-69
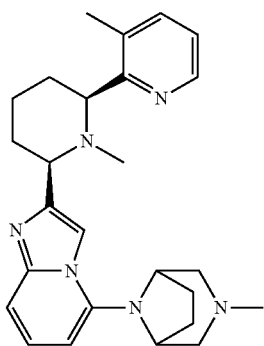
I-70
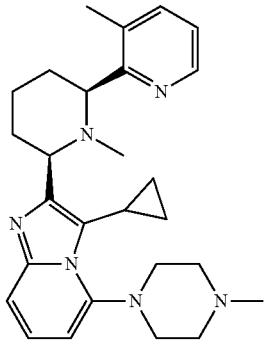
I-71
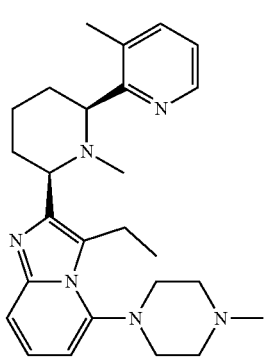
I-72
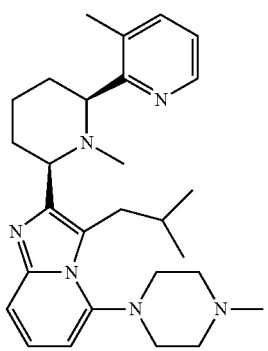

-continued
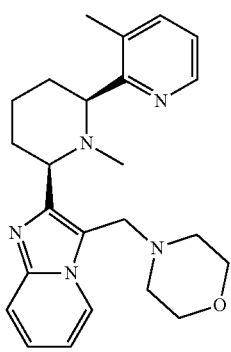
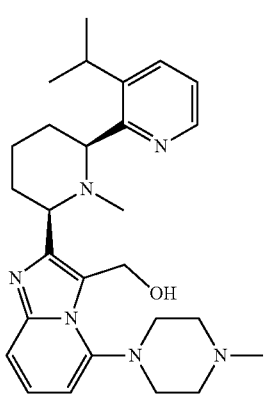
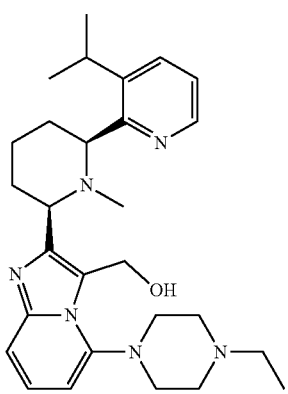
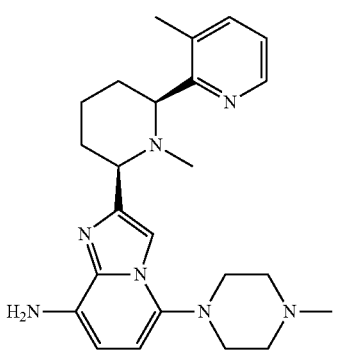
-continued
I-73
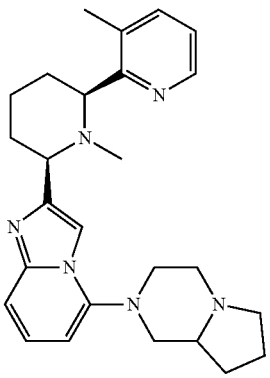
I-74
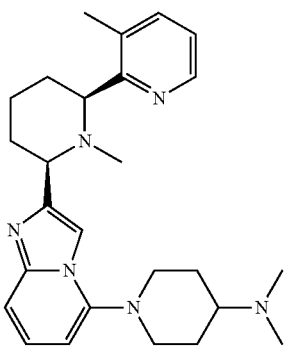
I-75
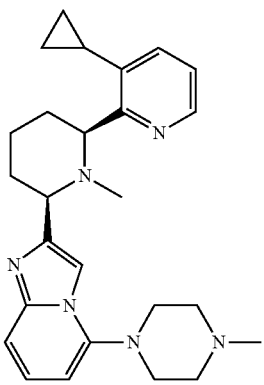
I-76
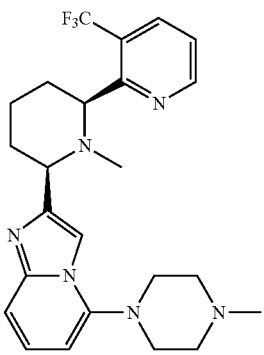
I-77
I-78
I-79
I-80

I-81
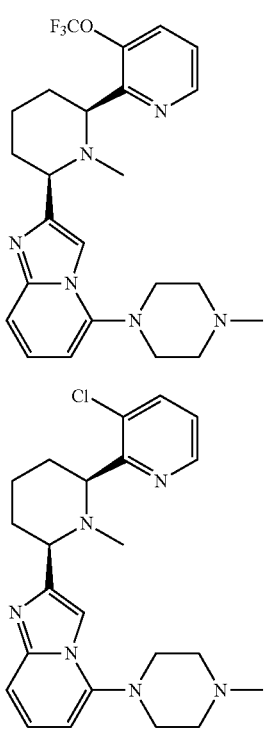
I-82
I-83
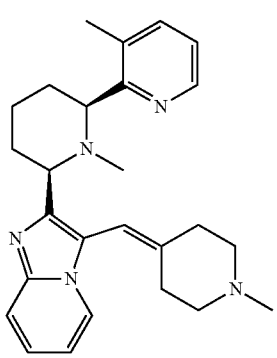
I-84
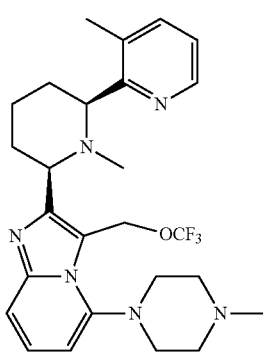
I-85
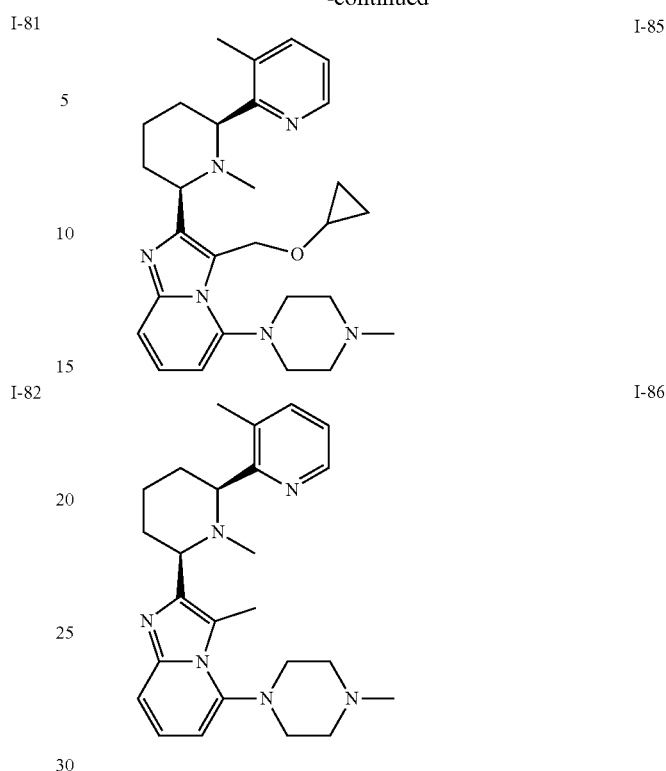
I-86
I-87
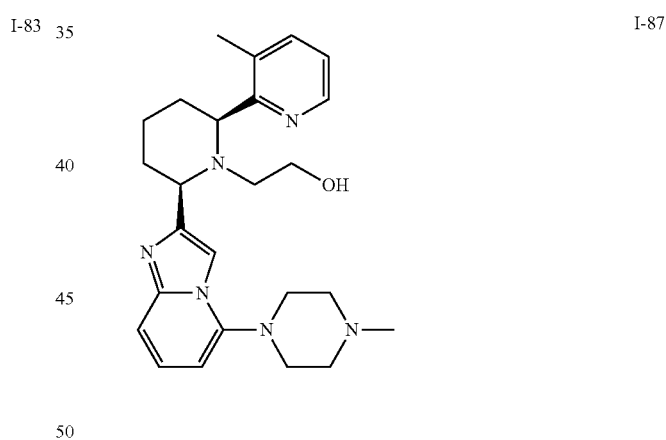
I-88
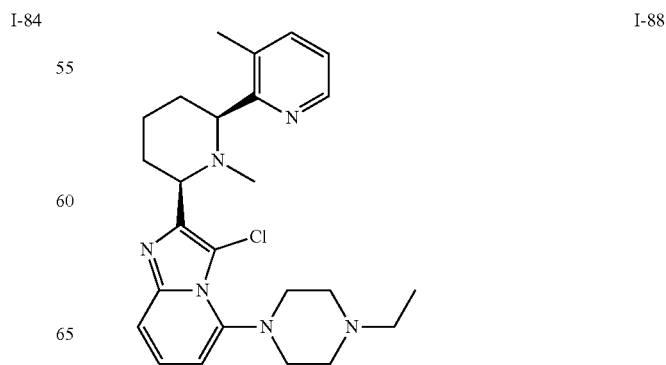

-continued
I-89
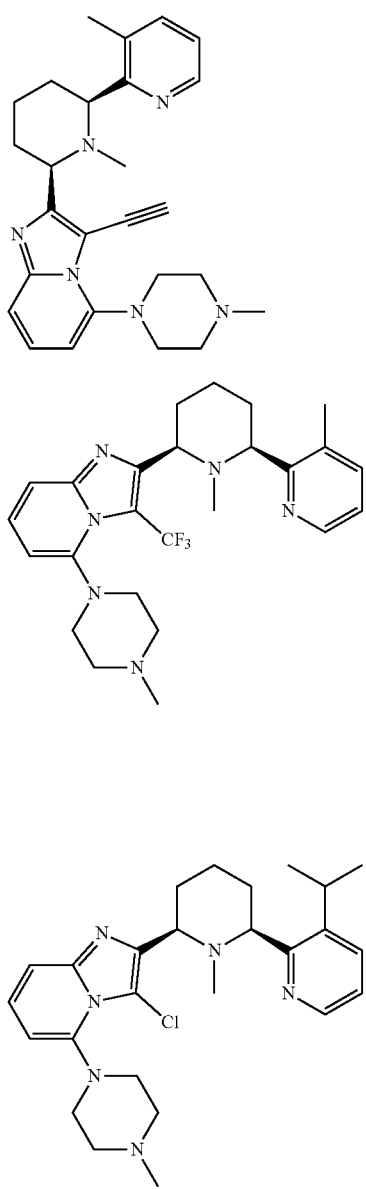
I-90
I-93
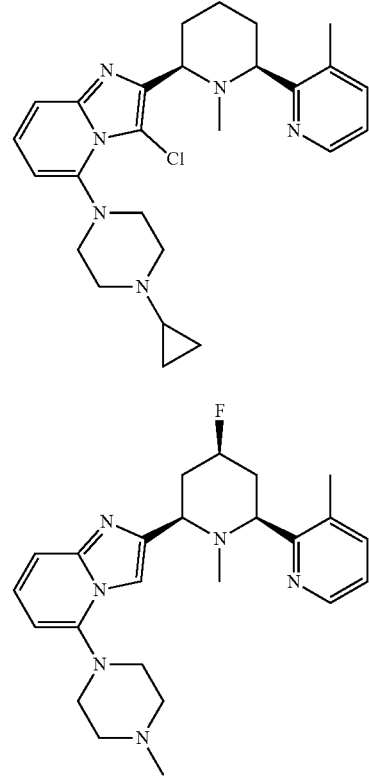
I-94
I-91
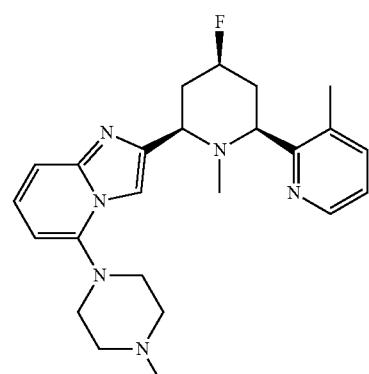
I-95
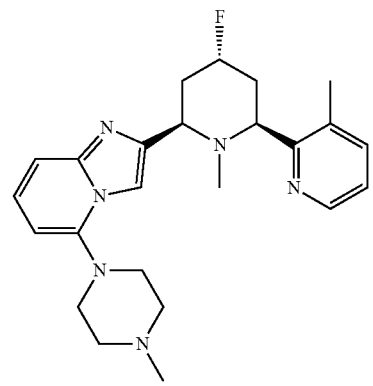
I-92
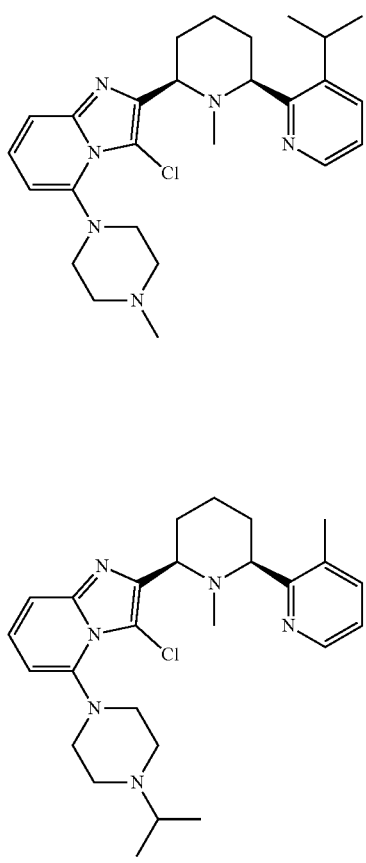
I-96
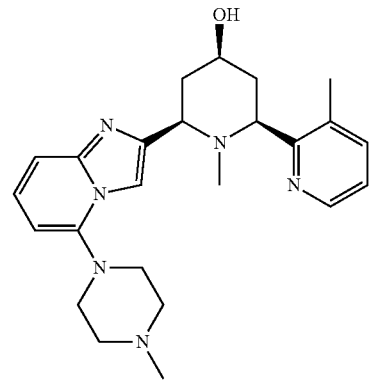

-continued
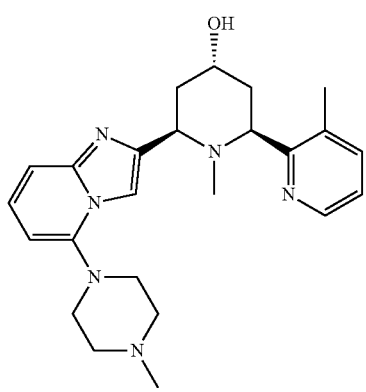
I-97
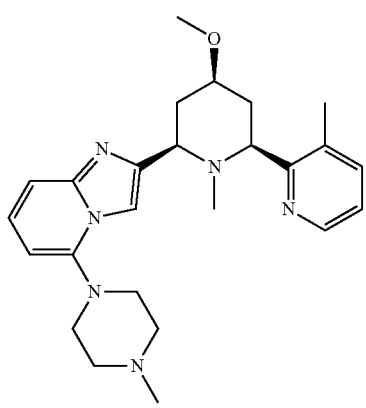
I-98
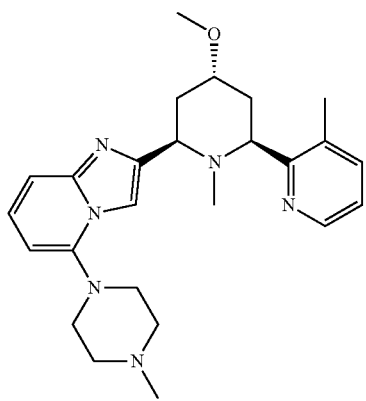
I-99
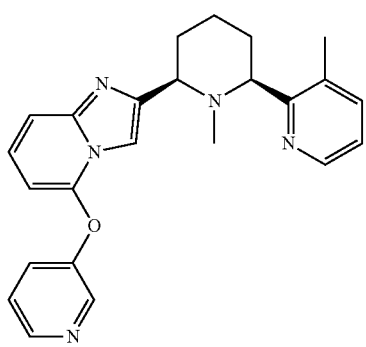
I-100
-continued
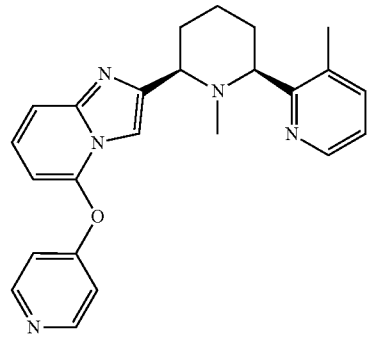
I-101
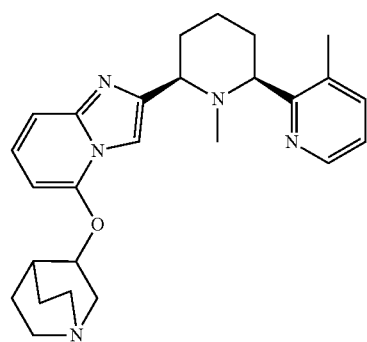
I-102
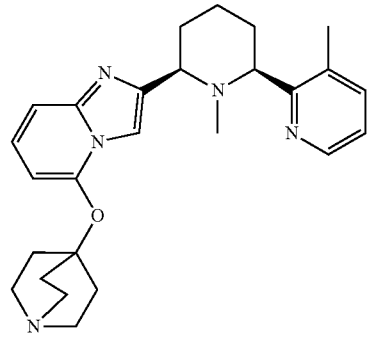
I-103
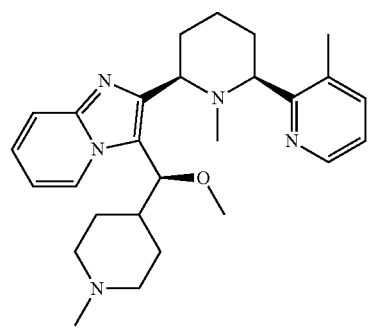
I-104

I-105
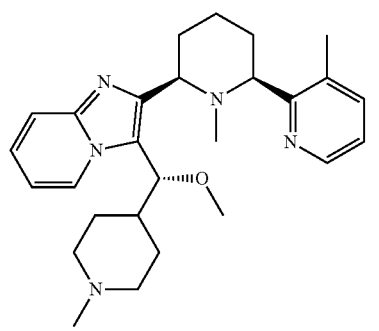
I-106
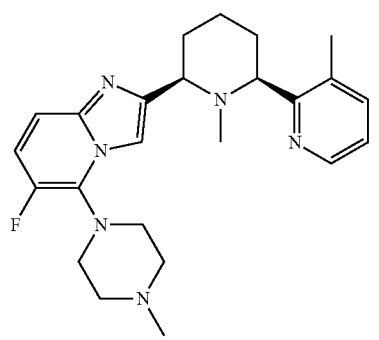
I-107
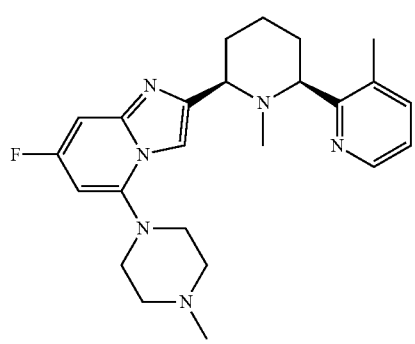
I-108
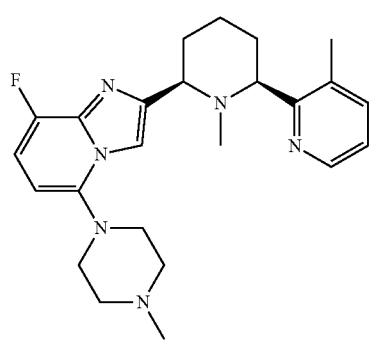
I-109
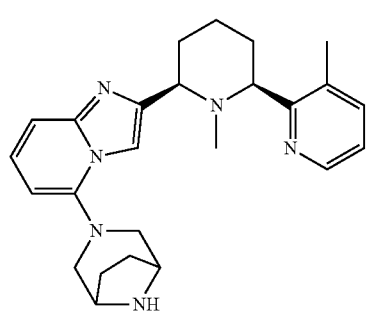
I-110
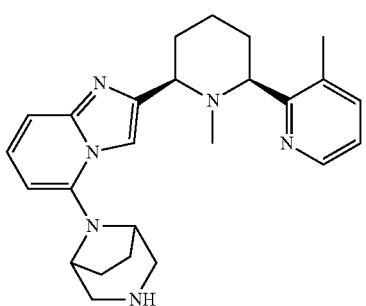
I-111
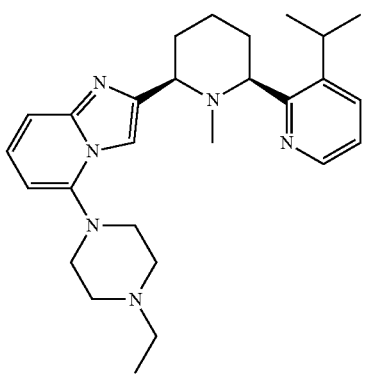
I-112
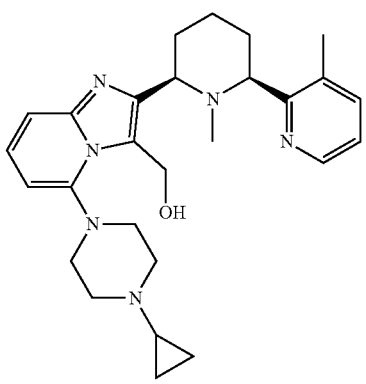
I-113
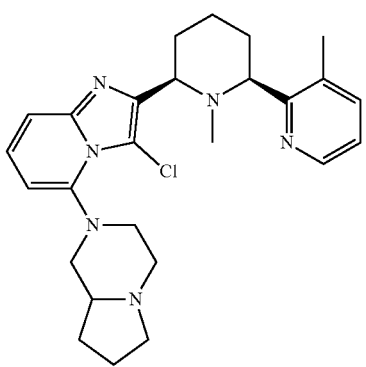

I-114
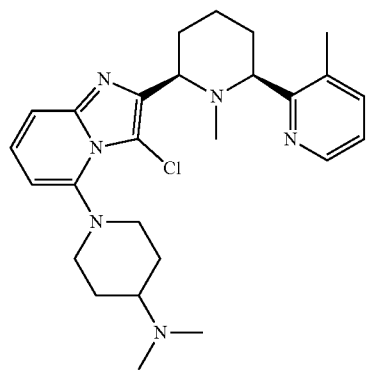
I-115
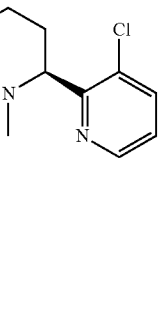
I-116
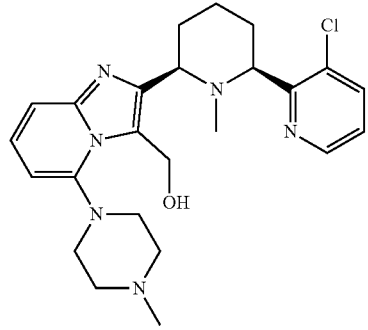
I-117
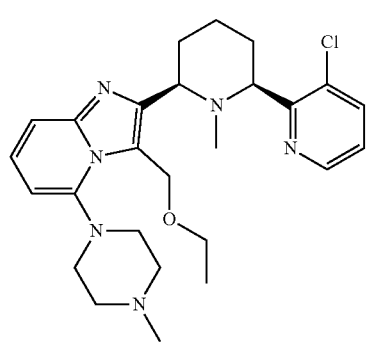
I-118
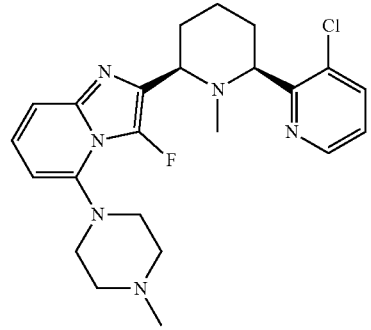
I-119
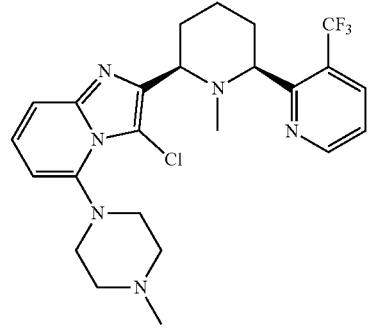
I-120
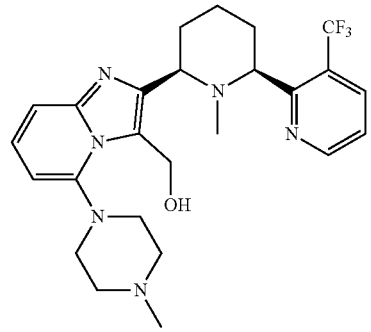
I-121
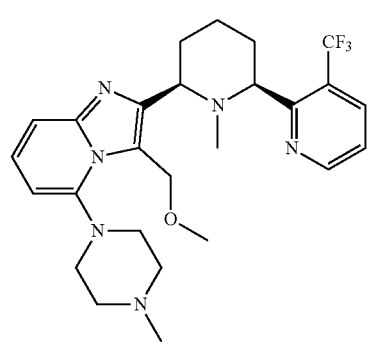

I-122
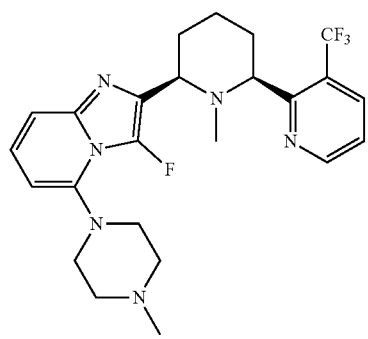
I-123
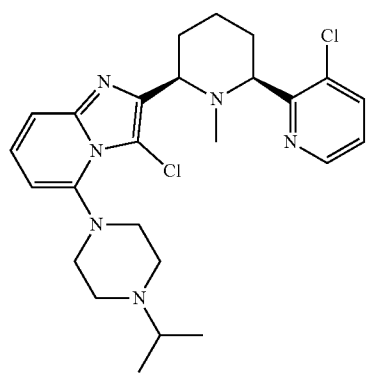
I-124
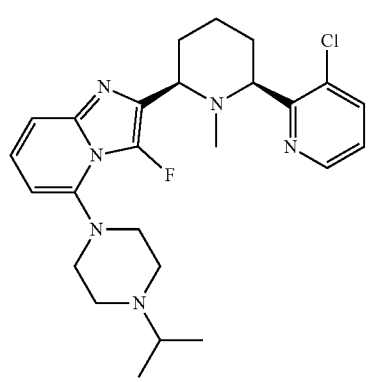
I-125
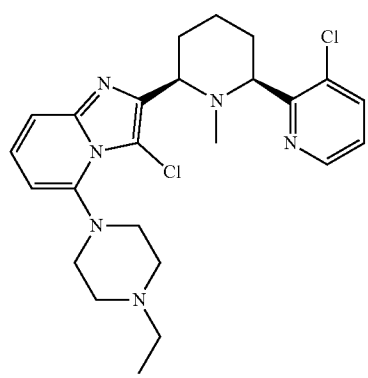
I-126
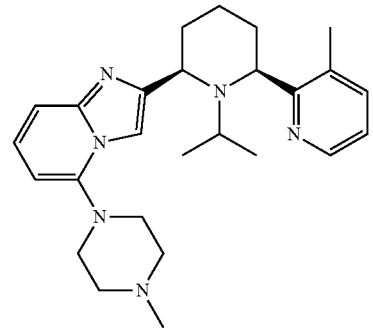
I-127
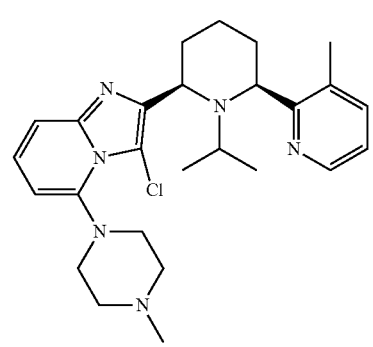
I-128
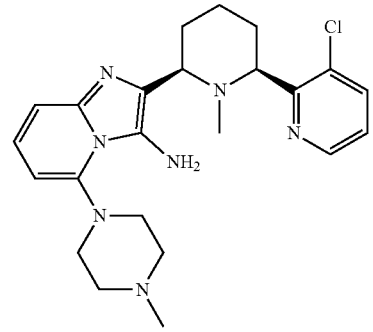
I-129
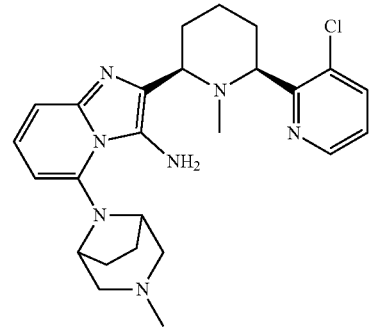

313
-continued
I-130
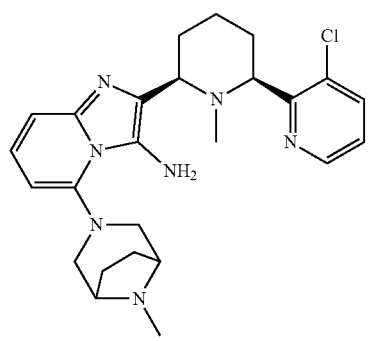
I-131
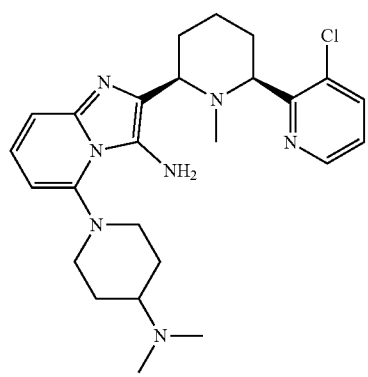
I-132
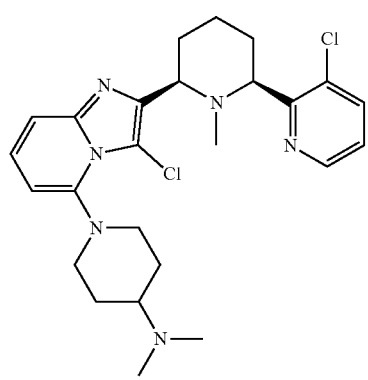
I-133
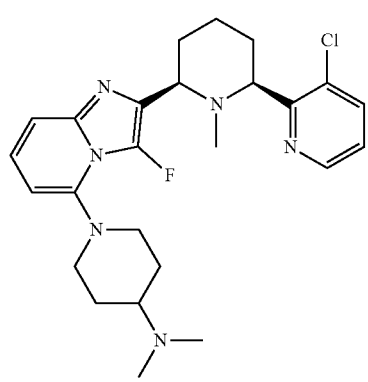
314
-continued
I-134
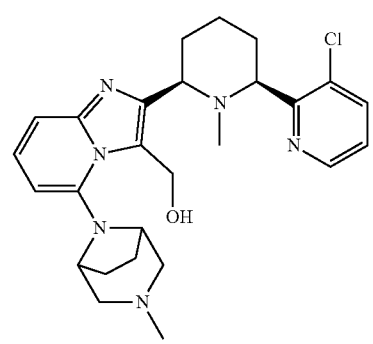
I-135
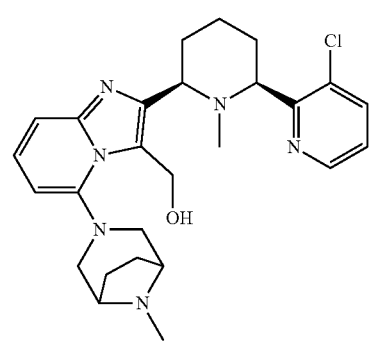
I-136
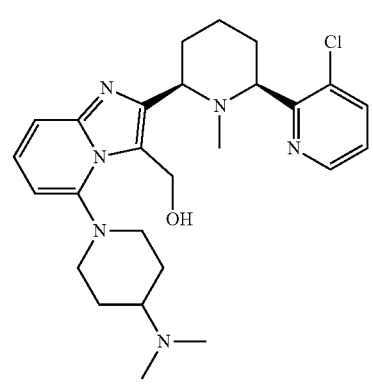
I-137
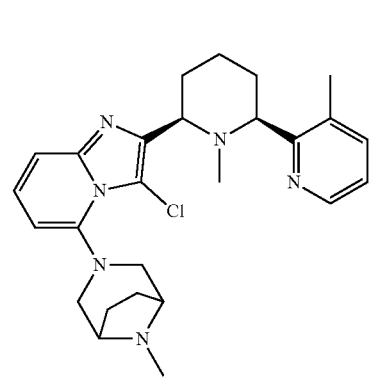

I-138 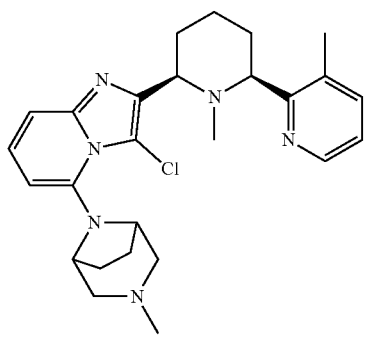
I-139 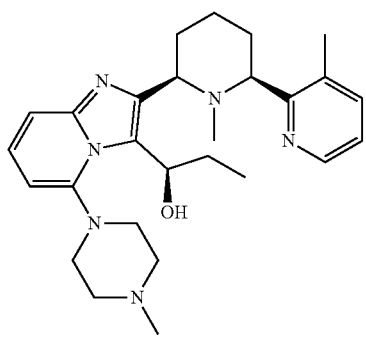
I-140 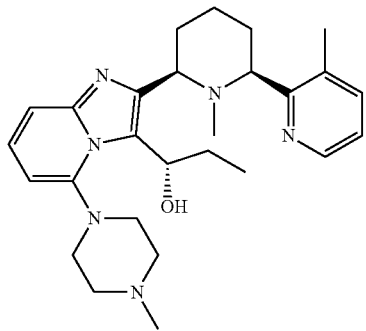
I-141 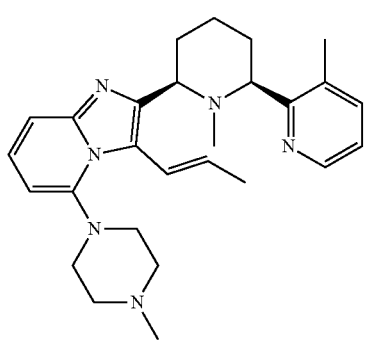
I-142 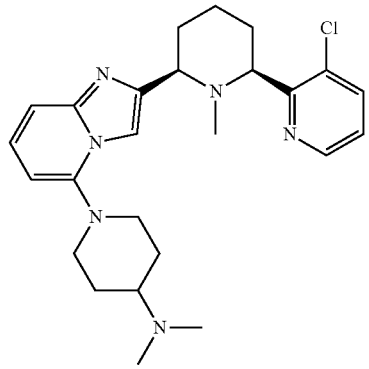
I-143 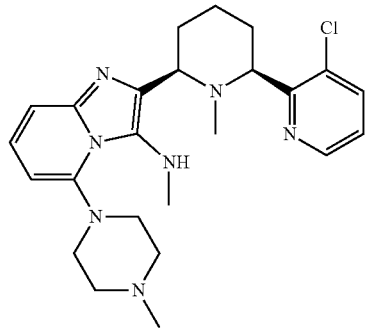
I-144 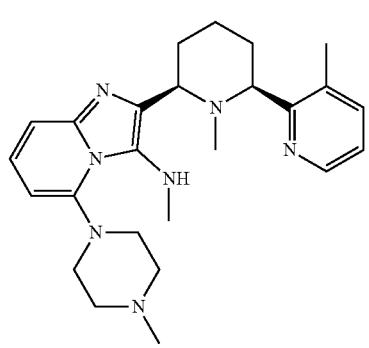
I-145 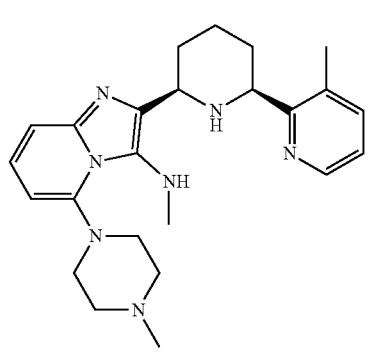

I-146
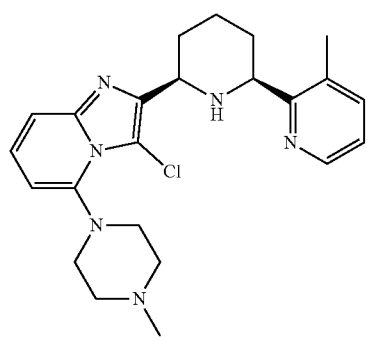
I-147
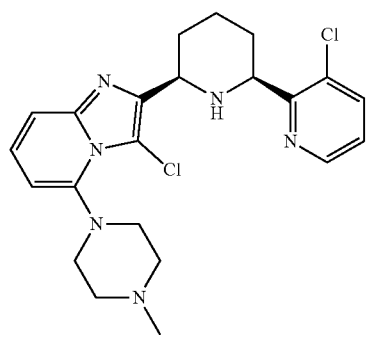
I-148
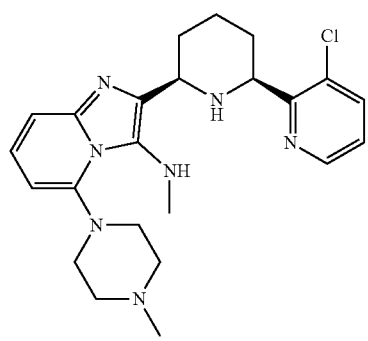
I-149
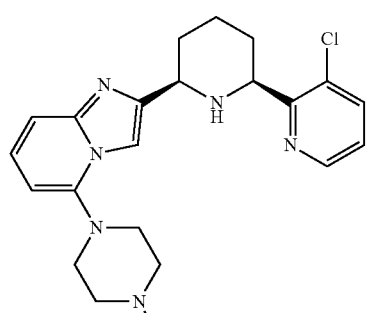
(racemic)
I-150
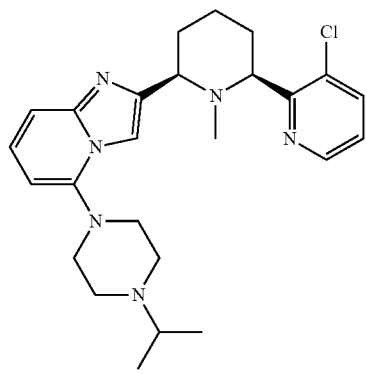
I-151
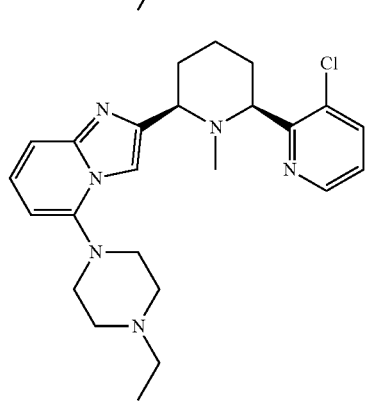
I-152
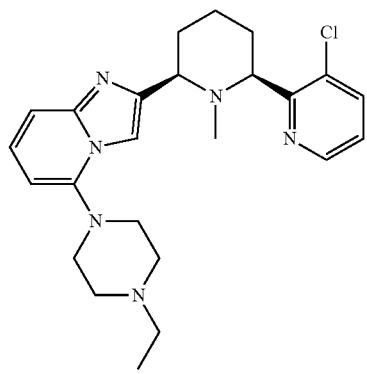
I-153
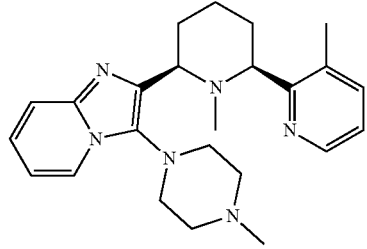
I-154
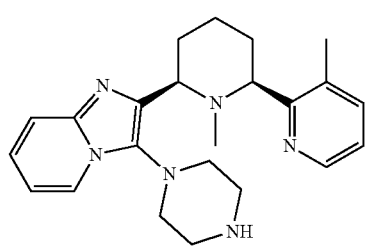

I-155 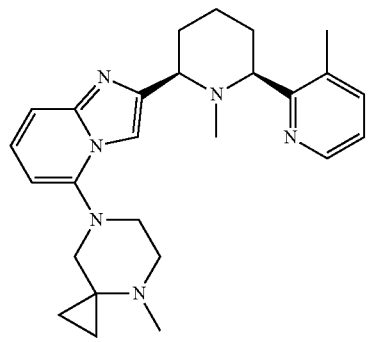
I-156 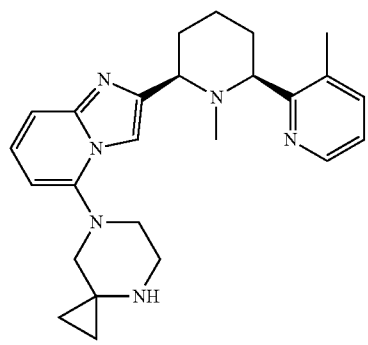
I-157 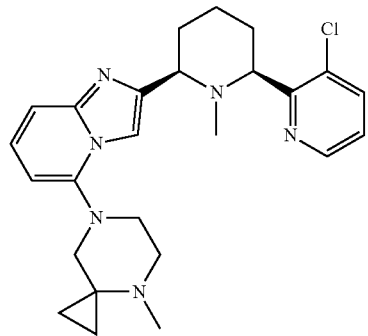
I-158 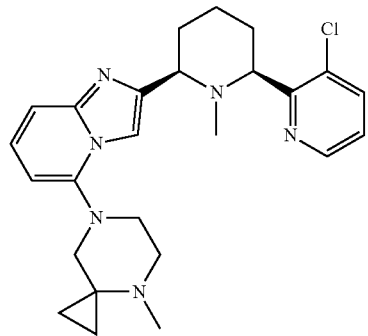
I-159 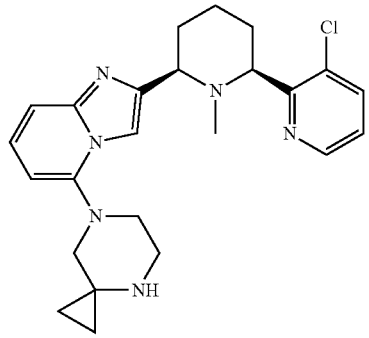
I-160 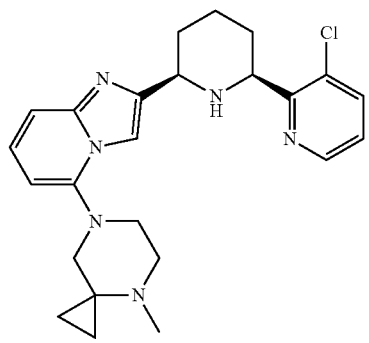
I-161 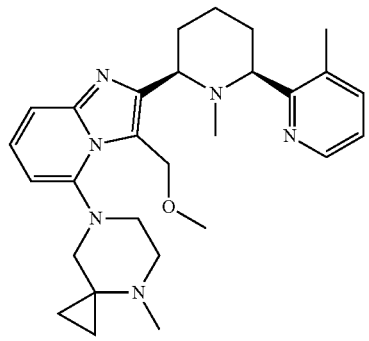
I-162 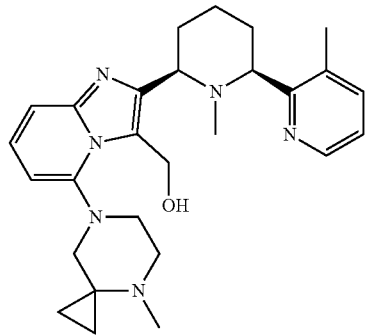

I-163
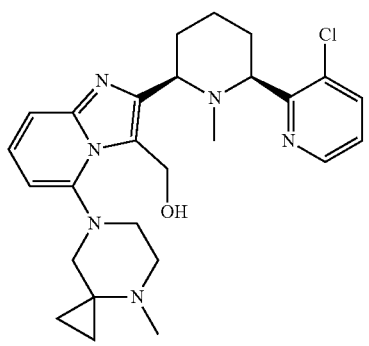
I-164
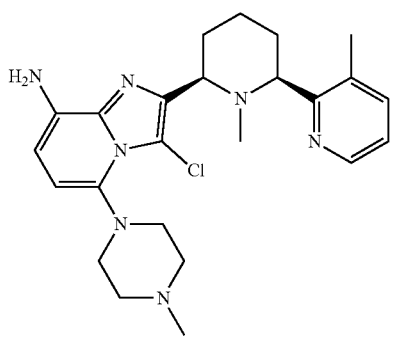
I-165
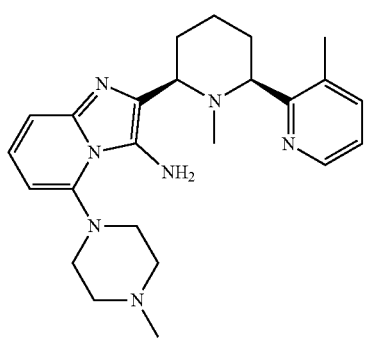
I-166
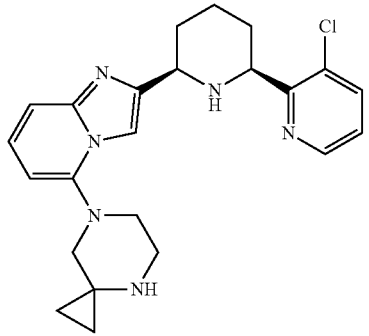
I-167
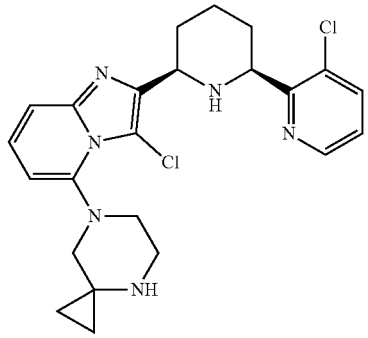
I-168
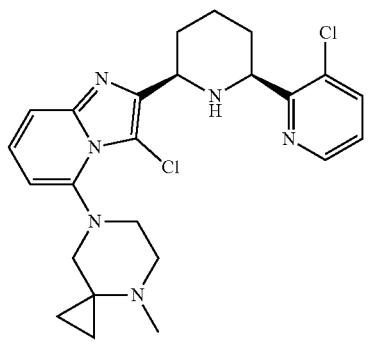
I-169
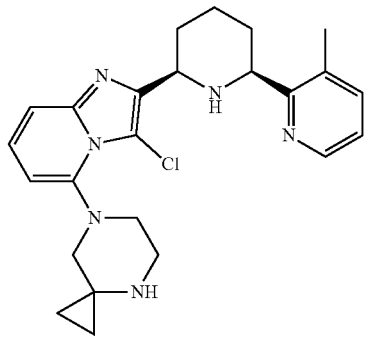
I-170
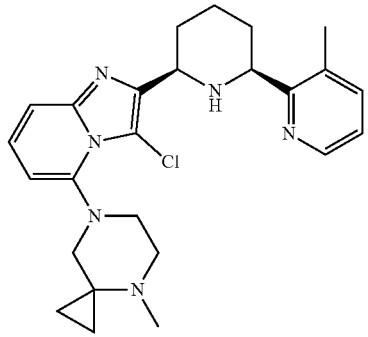

I-171 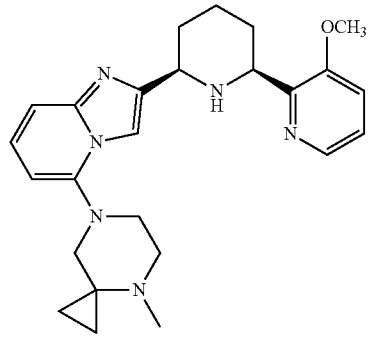
I-172 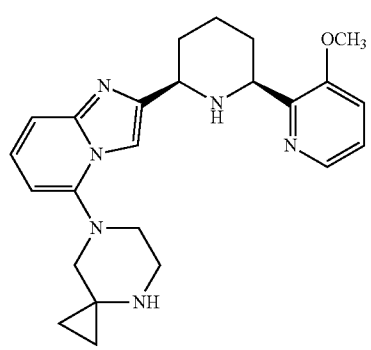
I-173 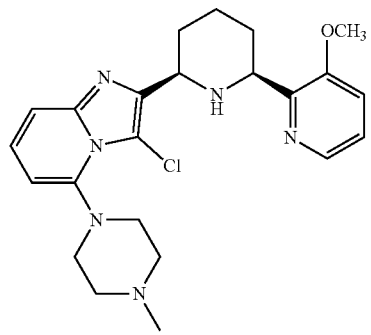
I-174 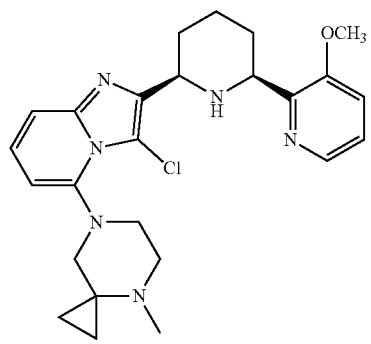
I-175 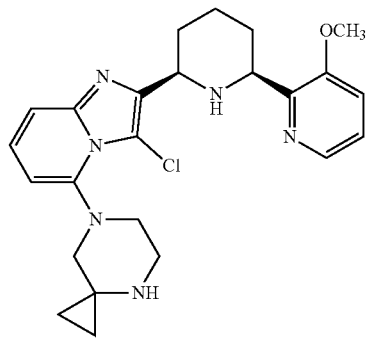
I-176 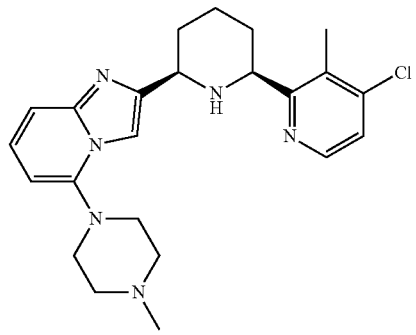
I-177 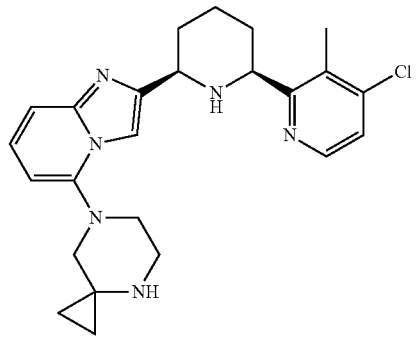
I-178 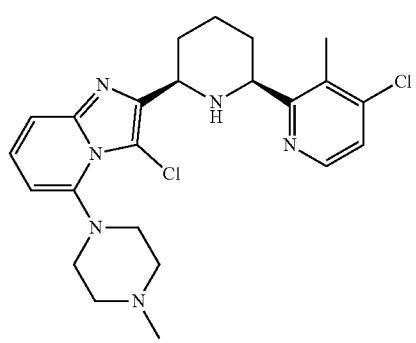

-continued
I-179
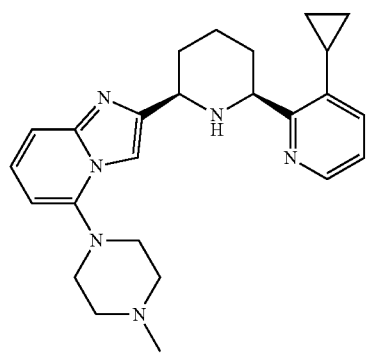
I-180
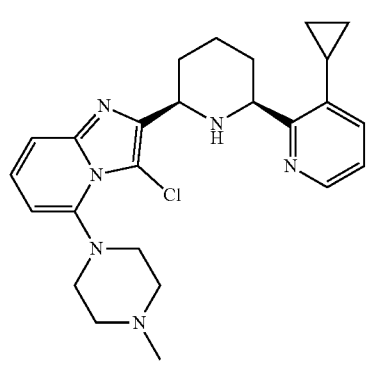
I-181
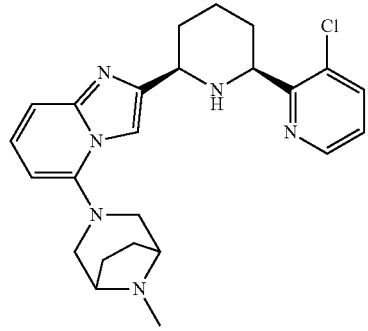
I-182
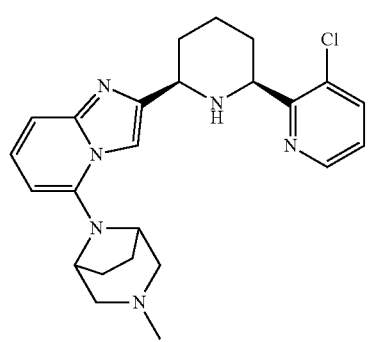
-continued
I-183
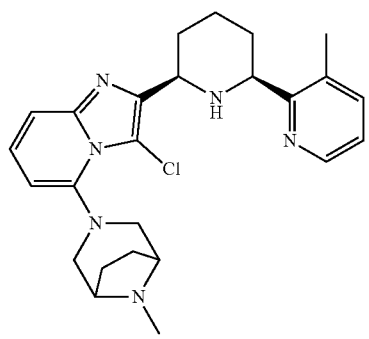
I-184
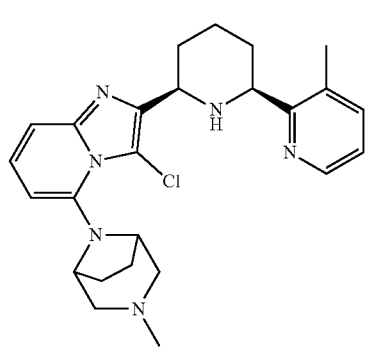
I-185
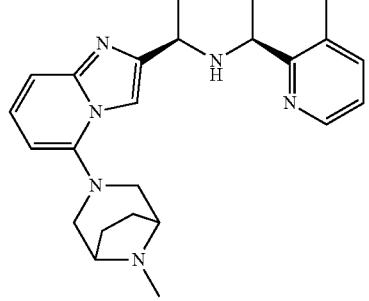
I-186
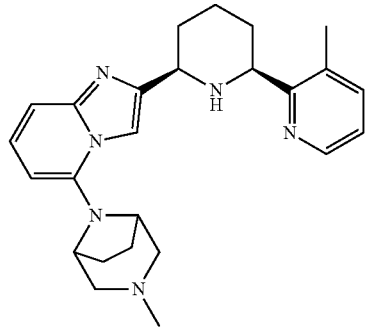

I-187
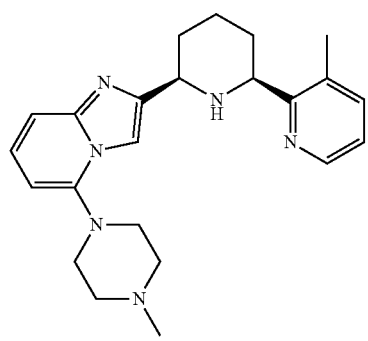
I-188
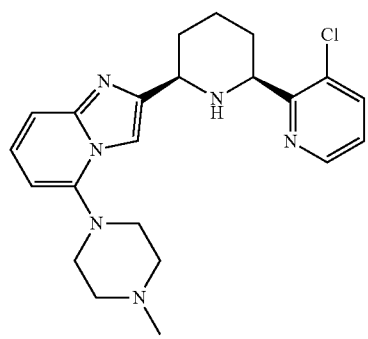
I-189
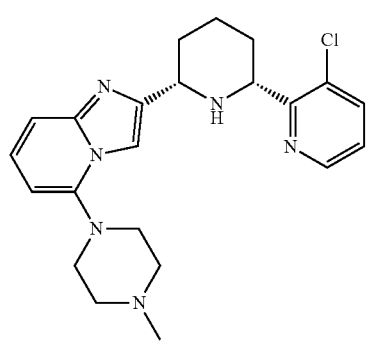
I-190
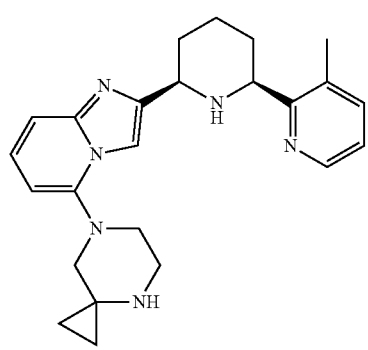
I-191
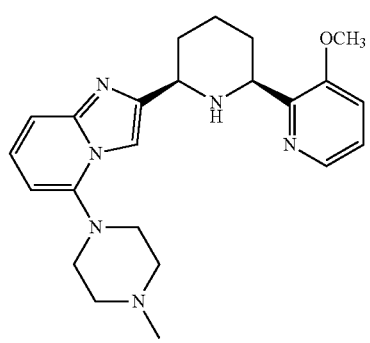
I-192
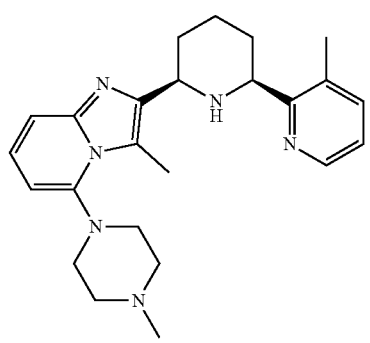
I-193
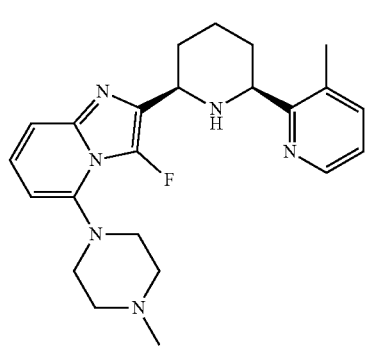
I-194

329
-continued
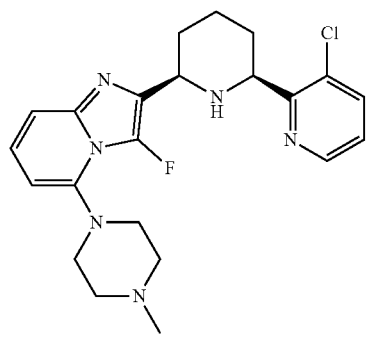
I-195
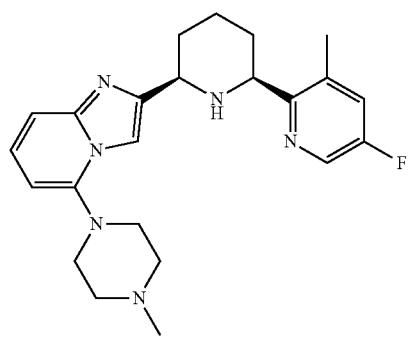
I-196
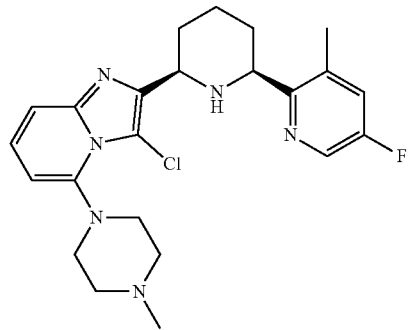
I-197
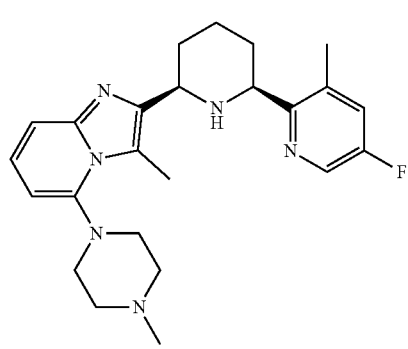
I-198
330
-continued
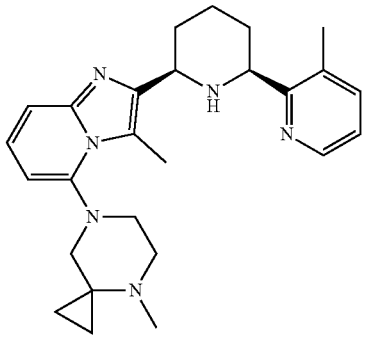
I-199
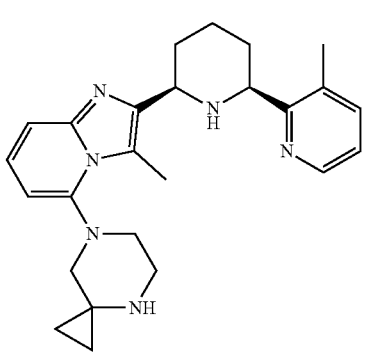
I-200
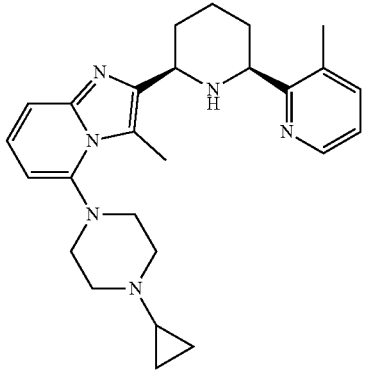
I-201
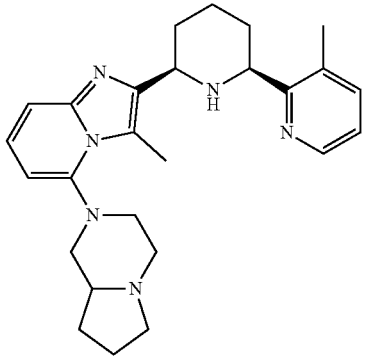
I-202

-continued
I-203 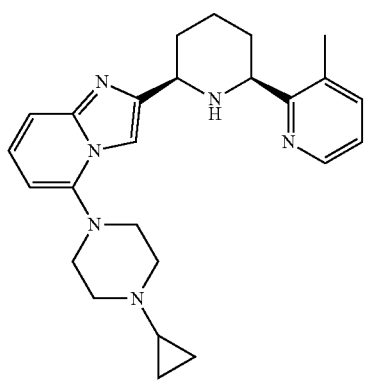
I-204 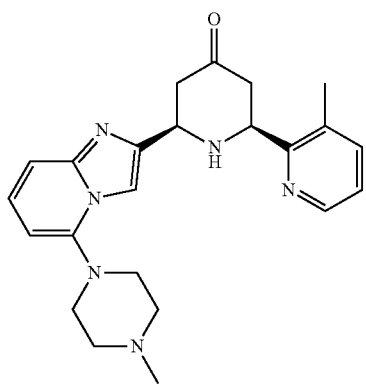
I-205 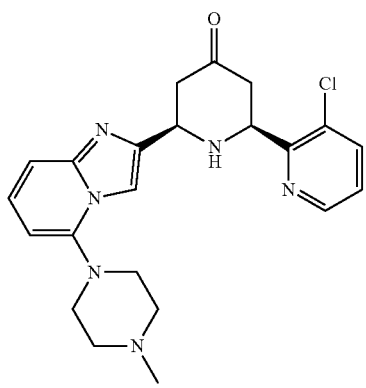
I-206 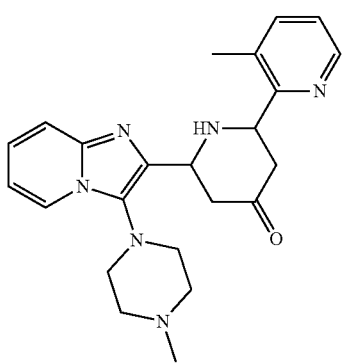
-continued
I-207 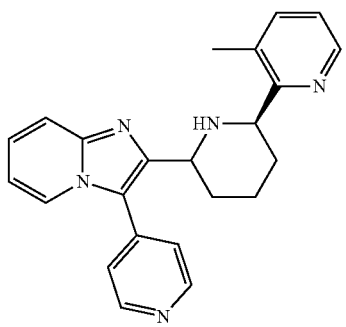
I-208 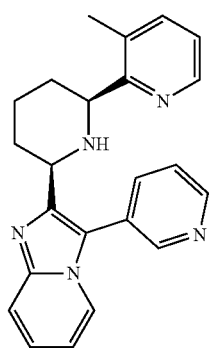
I-209 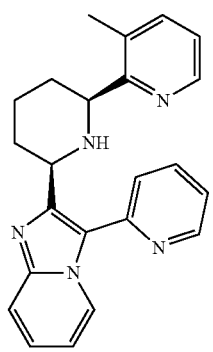
I-210 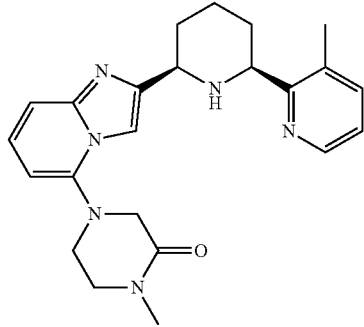

-continued
I-211
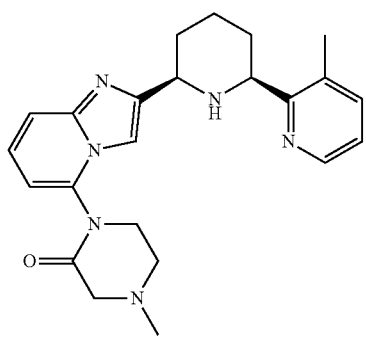
I-212
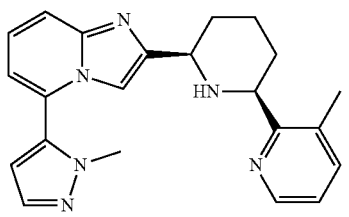
I-213
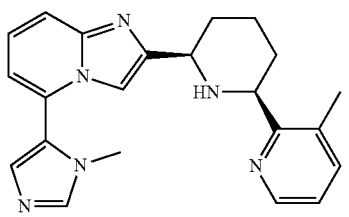
I-214
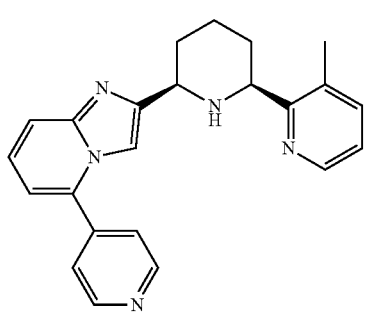
I-215
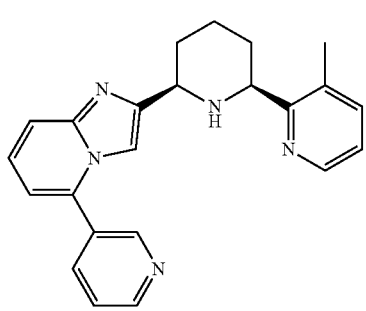
-continued
I-216
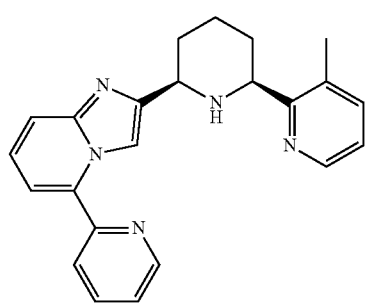
I-217
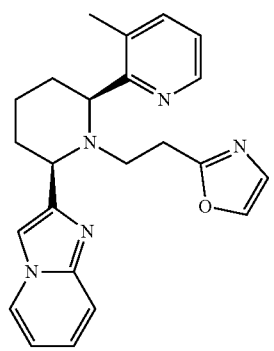
I-218
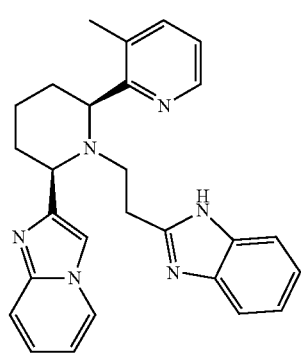
I-219
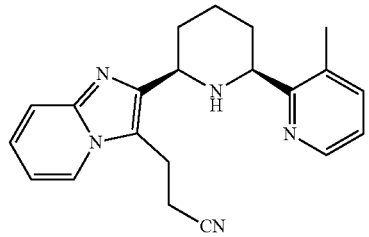
I-220
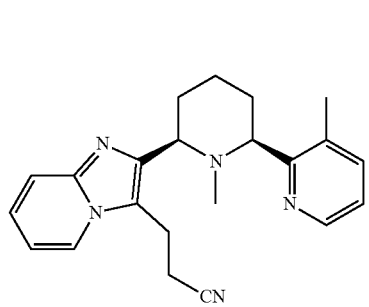

-continued
I-221
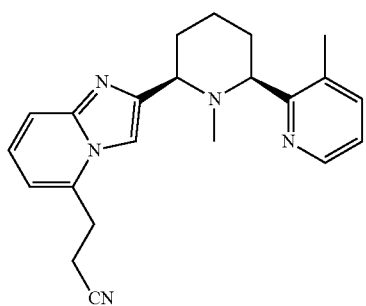
I-222
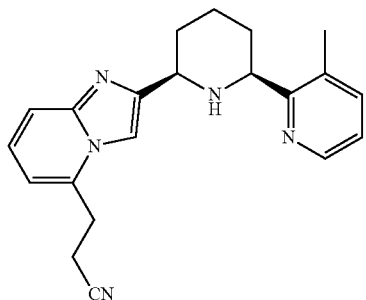
I-223
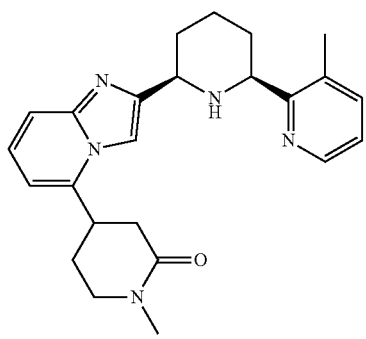
I-224
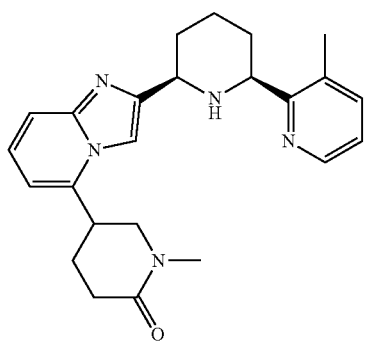
-continued
I-225
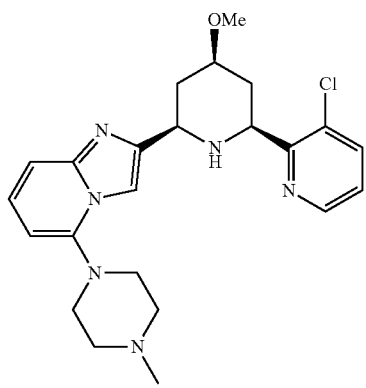
I-226
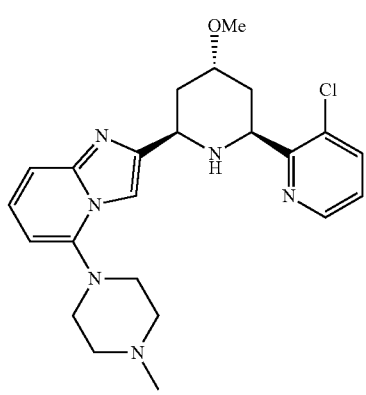
I-227
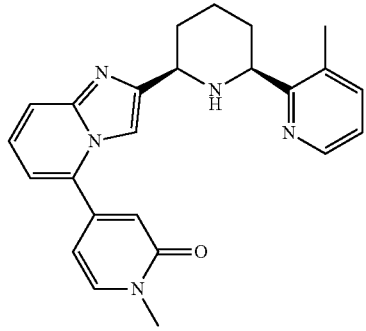
I-228
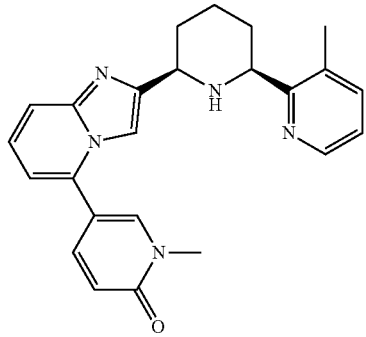 or

I-229

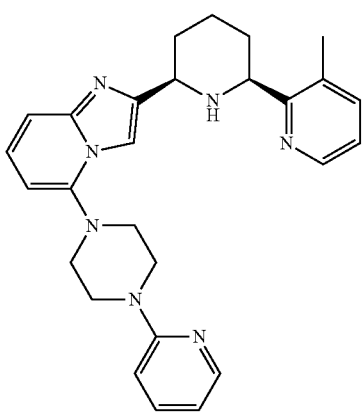

or a pharmaceutically acceptable salt thereof.

22. A pharmaceutical composition comprising a compound of claim 1, or a pharmaceutically acceptable salt thereof, and a pharmaceutically acceptable excipient.

23. A method of treating a cancer selected from the group consisting of glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma, comprising administering to a patient in need thereof an effective amount of a compound of claim 1, or a pharmaceutically acceptable salt thereof.

24. A method of treating a cancer selected from the group consisting of acoustic neuroma, astrocytoma (Grade I—Pilocytic Astrocytoma, Grade II—Low-grade Astrocytoma, Grade III—Anaplastic Astrocytoma, or Grade IV - Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, and schwannoma, comprising administering to a patient in need thereof an effective amount of a compound of claim 1, or a pharmaceutically acceptable salt thereof.

25. A method of treating a cancer selected from the group consisting of brain stem glioma, craniopharyngioma, ependymoma, juvenile pilocytic astrocytoma (JPA), medulloblastoma, optic nerve glioma, pineal tumor, primitive neuroectodermal tumors (PNET), and rhabdoid tumor, comprising administering to a patient in need thereof an effective amount of a compound of claim 1, or a pharmaceutically acceptable salt thereof.

26. The method of claim 23, wherein the patient is an adult human.

* * * * *